(12) United States Patent
Gilbert et al.

(10) Patent No.: US 7,713,534 B2
(45) Date of Patent: May 11, 2010

(54) STREPTOCOCCUS PNEUMONIAE PROTEINS AND NUCLEIC ACID MOLECULES

(75) Inventors: Christophe Francois Guy Gilbert, Villeurbanne cedex (FR); Philip Michael Hansbro, Newcastle (AU)

(73) Assignee: Sanofi Pasteur Limited, Toronto, Ontario (CA)

( * ) Notice: Subject to any disclaimer, the term of this patent is extended or adjusted under 35 U.S.C. 154(b) by 0 days.

(21) Appl. No.: 11/785,513

(22) Filed: Apr. 18, 2007

(65) Prior Publication Data

US 2008/0260768 A1 Oct. 23, 2008

Related U.S. Application Data

(60) Division of application No. 10/873,528, filed on Jun. 23, 2004, now abandoned, which is a division of application No. 09/769,787, filed on Jan. 26, 2001, now Pat. No. 6,936,252, which is a continuation of application No. PCT/GB99/02451, filed on Jul. 27, 1999.

(60) Provisional application No. 60/125,164, filed on Mar. 19, 1999.

(30) Foreign Application Priority Data

Jul. 27, 1998 (GB) ................................. 9816337.1

(51) Int. Cl.
*A61K 39/09* (2006.01)
*C12P 21/04* (2006.01)
*C07H 21/04* (2006.01)
*C07K 14/195* (2006.01)
*C07K 14/315* (2006.01)

(52) U.S. Cl. .............. 424/244.1; 424/190.1; 424/185.1; 424/184.1; 530/300; 530/350; 435/69.1; 435/69.5; 435/69.7; 435/252.3; 435/320.1; 536/23.1; 536/23.5; 536/23.7

(58) Field of Classification Search ........................ None
See application file for complete search history.

(56) References Cited

U.S. PATENT DOCUMENTS

| 6,420,135 B1 | 7/2002 | Kunsch et al. |
| 6,573,082 B1 | 6/2003 | Choi et al. |
| 6,699,703 B1 | 3/2004 | Doucette-Stamm et al. |
| 6,800,744 B1 | 10/2004 | Doucette-Stamm et al. |
| 6,936,252 B2 | 8/2005 | Gilbert et al. |

FOREIGN PATENT DOCUMENTS

| EP | 0622081 | 11/1994 |
| WO | WO 95/06732 | 3/1995 |
| WO | WO 97/09994 | 3/1997 |
| WO | WO 97/37026 | 10/1997 |
| WO | WO 97/43303 | 11/1997 |
| WO | WO 98/18930 | 5/1998 |
| WO | WO 98/18931 | 5/1998 |
| WO | WO 98/26072 | 6/1998 |
| WO | WO 98/31786 | 7/1998 |
| WO | WO 99/15675 | 4/1999 |

OTHER PUBLICATIONS

Houghten et al. (Vaccines, 1986, Edited by Fred Brown: Cold Spring Harbor Laboratory).*
Boslego et al, Chapter 17 in Vaccines and Immunotherapy 1991.*
Li et al (Proc. Natl. Acad. Sci. USA 77:3211-3214, 1980).*
Lederman et al (Molecular Immunology 28:1171-1181, 1991.*
Anderson et al. (1996) "Immune Response in mice following immunization with DNA encoding fragment C of tetanus toxin." Infection and Immunity 64: 3168-3173.
Angel, et al. (1994) "Degradation of C3 by *Streptococcus pneumoniae*." Journal of Infectious Disease 170(3): 600-608.
Alonsodevelasco, et al. (Dec. 1995) "*Streptococcus pneumoniae*: Virulence Factors, Pathogenesis, and Vaccines." Microbiological Reviews 59(4): 591-603.
Breiman et al. (1990) Arch. Intern. Med. 150: 1401.
Breiman et al. (1994) J. Am. Med. Assoc. 271: 1831.
Bowie (1990) Science 257: 1306-1310.
Burgess, et al. (1990) The Journal of Cell Biology 111: 2129-2136.
Donnelly et al. (1997) Ann. Rev. Immunol. 15: 617-648.
Dougall et al. (Sep. 1994) Tibtech 12: 372-379.
Ellis (1988) Vaccines Chapter 29: 568-575.
Greenspan, et al. (1999) Nature Biotechnology 7: 936-937.
Herbert, et al. (1985) The Dictionary of Immunology (Academic Press) 3rd Ed. pp. 58-59.
Holmes, et al. (2001) Exp. Opin. Invest. Drugs 10(3): 511-519.
Jobling et al. (1991) Mol. Microbiol 5(7): 1755-67.
Kohler & Milstein (1975) Nature 256.
Kolkman et al. (1996) 178: 3736-3741.
Kovacevic et al. (1985) J. Bacteriol. 162: 521-528.
Kurar and Splitter (1997) Vaccine 15: 1851-57.
Lange et al. (Sep. 3, 1999) Gene 237(1): 223-234.
Lazar et al. (1988) Molecular and Cellular Biology 8(3): 1247-1252.
Le Loir et al. (1994) J. Bacteriol. 176: 5135-5139.
LeBlanc et al. (1978) PNAS USA 75: 3484-3487.
Li et al. (1997) PNAS 94: 13251-13256.
Liebl et al. (1992) J. Bacteriol. 174: 1854-1861.
Marck (1988) Nucleic Acids Research 16: 1829-1836.
Miller et al. (1987) J. Bacteriol. 169: 3508-3514.
Morrison et al. (1984) PNAS 81: 6851-6855.

(Continued)

*Primary Examiner*—Robert B Mondesi
*Assistant Examiner*—Padma V Baskar
(74) *Attorney, Agent, or Firm*—Hunton & Williams LLP

(57) ABSTRACT

Protein antigens from *Streptococcus pneumoniae* are disclosed, together with nucleic acid sequences encoding them. Their use in vaccines and in screening methods is also described.

5 Claims, 2 Drawing Sheets

OTHER PUBLICATIONS

Nanidwada, et al. (1996) "Genetic Analysis of a C3 degrading proteinase in *Steptococcus pneumoniae*." Abstracts of the General Meeting of the American Society for Microbiology vol. 96 p. 177 (Abstract B-134).

Oultram and Klaenhammer (1985) FEMS Microbiological Letters 27: 129-134.

Pearson et al. (1988) "Improved tools for biological sequence comparison," Proc. Natl. Acad. Sci. USA, vol. 85, 2444-2448.

Poquet et al. (1998) J. Bacteriol. 180: 1904-1912.

Roitt, et al. (1993) Immunology p. 7.7-7.8.

Rudinger et al. (Jun. 1976) "Peptide Hormones" p. 6.

Schappert (1992) Vital and Health Statistics of the Centres for Disease Control/National Centre for Health Statistics 214: 1.

Shortle (1983) Gene 22: 181-189.

Siber (Sep. 1994) "Pneumococcal Disease: Prospects for a New Generation of Vaccines" Science vol. 265, pp. 1385-1387.

Simon and Chopin (1988) Biochimie 70: 559-567.

Stansfield (1987) "Acute respiratory infections in the developing world: strategies for prevention, treatment and control," Pediatric Infect Dis. Journal, vol. 6, 622-629.

Takeda et al. (1985) Nature 314: 452-454.

Taber's Cyclopedic Medical Dictionary (1985) 16th Ed. p. 1354.

van der Vossen, et al. (1985) Applied and Environmental Microbiology 50: 540-542.

Waterfield et al. (1995) Gene 165: 9-15.

Wells and Schoefield (1996) In Current advances in metabolism, genetics, and applications-NATO ASI Series H 98: 37-62.

Wells et al. (1993) J. Appl. Bacteriol. 74: 629-636.

Zhang et al. (1997) Infection and Immunity 176: 1035-1040.

Alonsodevelasco, et al. (Dec. 1995) "*Streptococcus pneumoniae*: Virulence Factors, Pathogenesis, and Vaccines." Microbiological Reviews 59(4): 591-603.

Angel, et al. (1994) "Degradation of C3 by *Streptococcus pneumoniae*." Journal of Infectious Disease 170(3): 600-608.

Nandiwada, et al. (1996) "Genetic Analysis of a C3 degrading proteinase in *Steptococcus pneumoniae*." Abstracts of the General Meeting of the American Society for Microbiology vol. 96 p. 177 (Abstract B-134).

* cited by examiner

STREPTOCOCCUS PNEUMONIAE PROTEINS AND NUCLEIC ACID MOLECULES

This application is a divisional of U.S. patent application Ser. No. 10/873,528, filed Jun. 23, 2004, now abandoned, which is a divisional of U.S. patent application Ser. No. 09/769,787, filed Jan. 26, 2001, now U.S. Pat. No. 6,936,252, which is a continuation of PCT/GB99/02451, filed Jul. 27, 1999, which claims benefit of U.S. Provisional Application No. 60/125,164, filed Mar. 19, 1999, and which also claims benefit of United Kingdom 9816337.1, filed Jul. 27, 1998, the disclosures of which are all hereby incorporated by reference.

The present invention relates to proteins derived from *Streptococcus pneumoniae*, nucleic acid molecules encoding such proteins, the use of the nucleic acid and/or proteins as antigens/immunogens and in detection/diagnosis, as well as methods for screening the proteins/nucleic acid sequences as potential anti-microbial targets.

*Streptococcus pneumoniae*, commonly referred to as the pneumococcus, is an important pathogenic organism. The continuing significance of *Streptococcus pneumoniae* infections in relation to human disease in developing and developed countries has been authoritatively reviewed (Fiber, G. R., *Science*, 265:1385-1387 (1994)). That indicates that on a global scale this organism is believed to be the most common bacterial cause of acute respiratory infections, and is estimated to result in 1 million childhood deaths each year, mostly in developing countries (Stansfield, S. K., *Pediatr. Infect. Dis.*, 6:622 (1987)). In the USA it has been suggested (Breiman et al., *Arch. Intern. Med.*, 150:1401 (1990)) that the pneumococcus is still the most common cause of bacterial *pneumoniae*, and that disease rates are particularly high in young children, in the elderly, and in patients with predisposing conditions such as asplenia, heart, lung, and kidney disease, diabetes, alcoholism, or with immunosuppressive disorders, especially AIDS. These groups are at higher risk of pneumococcal septicaemia and hence meningitis and therefore have a greater risk of dying from pneumococcul infection. The pneumococcus is also the leading cause of otitis media and sinusitis, which remain prevalent infections in children in developed countries, and which incur substantial costs.

The need for effective preventative strategies against pneumococcal infection is highlighted by the recent emergence of penicillin-resistant pneumococci. It has been reported that 6.6% of pneumoccal isolates in 13 US hospitals in 12 states were found to be resistant to penicillin and some isolates were also resistant to other antibiotics including third generation cyclosporins (Schappert, S. M., *Vital and Health Statistics of the Centres for Disease Control/National Centre for Health Statistics*, 214:1 (1992)). The rates of penicillin resistance can be higher (up to 20%) in some hospitals (Breiman et al, *J. Am. Med. Assoc.*, 271: 1831 (1994)). Since the development of penicillin resistance among pneumococci is both recent and sudden, coming after decades during which penicillin remained an effective treatment, these findings are regarded as alarming.

For the reasons given above, there are therefore compelling grounds for considering improvements in the means of preventing, controlling, diagnosing or treating pneumococcal diseases.

Various approaches have been taken in order to provide vaccines for the prevention of pneumococcal infections. Difficulties arise for instance in view of the variety of serotypes (at least 90) based on the structure of the polysaccharide capsule surrounding the organism. Vaccines against individual serotypes are not effective against other serotypes and this means that vaccines must include polysaccharide antigens from a whole range of serotypes in order to be effective in a majority of cases. An additional problem arises because it has been found that the capsular polysaccharides (each of which determines the serotype and is the major protective antigen) when purified and used as a vaccine do not reliably induce protective antibody responses in children under two years of age, the age group which suffers the highest incidence of invasive pneumococcal infection and meningitis.

A modification of the approach using capsule antigens relies on conjugating the polysaccharide to a protein in order to derive an enhanced immune response, particularly by giving the response T-cell dependent character. This approach has been used in the development of a vaccine against *Haemophilus influenzae*. There are issues of cost concerning both the multi-polysaccharide vaccines and those based on conjugates.

A third approach is to look for other antigenic components which offer the potential to be vaccine candidates.

BACKGROUND OF THE INVENTION

In the present application we provide a group of proteins antigens which are secreted/exported proteins.

BRIEF SUMMARY OF THE INVENTION

Thus, in a first aspect the present invention provides a *Streptococcus pneumoniae* protein or polypeptide having a sequence selected from those shown in Table 2 herein.

A protein or polypeptide of the present invention may be provided in substantially pure form. For example, it may be provided in a form which is substantially free of other proteins.

In a preferred embodiment, a protein or polypeptide having an amino acid sequence as shown in Table 3 is provided.

The invention encompasses any protein coded for by a nucleic acid sequence as shown in Table 1 herein.

DETAILED DESCRIPTION OF THE INVENTION

As discussed herein, the proteins and polypeptides of the invention are useful as antigenic material. Such material can be "antigenic" and/or "immunogenic". Generally, "antigenic" is taken to mean that the protein or polypeptide is capable of being used to raise antibodies or indeed is capable of inducing an antibody response in a subject. "Immunogenic" is taken to mean that the protein or polypeptide is capable of eliciting a protective immune response in a subject.

Thus, in the latter case, the protein or polypeptide may be capable of not only generating an antibody response and in addition non-antibody based immune responses.

The skilled person will appreciate that homologues or derivatives of the proteins or polypeptides of the invention will also find use in the context of the present invention, ie as antigenic/immunogenic material. Thus, for instance proteins or polypeptides which include one or more additions, deletions, substitutions or the like are encompassed by the present invention.

In addition, it may be possible to replace one amino acid with another of similar "type". For instance replacing one hydrophobic amino acid with another. One can use a program such as the CLUSTAL program to compare amino acid sequences. This program compares amino acid sequences and finds the optimal alignment by inserting spaces in either sequence as appropriate.

It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In the case of homologues and derivatives, the degree of identity with a protein or polypeptide as described herein is less important than that the homologue or derivative should retain its antigenicity or immunogenicity to *Streptococcus pneumoniae*. However, suitably, homologues or derivatives having at least 60% similarity (as discussed above) with the proteins or polypeptides described herein are provided.

Preferably, homologues or derivatives having at least 70% similarity, more preferably at least 80% similarity are provided. Most preferably, homologues or derivatives having at least 90% or even 95% similarity are provided.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

In an additional aspect of the invention there are provided antigenic fragments of the proteins or polypeptides of the invention, or of homologues or derivatives thereof.

For fragments of the proteins or polypeptides described herein, or of homologues or derivatives thereof, the situation is slightly different. It is well known that is possible to screen an antigenic protein or polypeptide to identify epitopic regions, i.e., those regions which are responsible for the protein or polypeptide's antigenicity or immunogenicity. Methods for carrying out such screening are well known in the art. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties.

Thus, what is important for homologues, derivatives and fragments is that they possess at least a degree of the antigenicity/immunogenicity of the protein or polypeptide from which they are derived.

Gene cloning techniques may be used to provide a protein of the invention in substantially pure form, These techniques are disclosed, for example, in J. Sambrook et al *Molecular Cloning* 2nd Edition, Cold Spring Harbor Laboratory Press (1989). Thus, in a fourth aspect, the present invention provides a nucleic acid molecule comprising or consisting of a sequence which is:
 (i) any of the DNA sequences set out in Table 1 or their RNA equivalents;
 (ii) a sequence which is complementary to any of the sequences of (i);
 (iii) a sequence which codes for the same protein or polypeptide, as those sequences of (i) or (ii);
 (iv) a sequence which is has substantial identity with any of those of (i), (ii) and (iii);
 (v) a sequence which codes for a homologue, derivative or fragment of a protein as defined in Table 1.

In a fifth aspect the present invention provides a nucleic acid molecule comprising or consisting of a sequence which is:
 (i) any of the DNA sequences set out in Table 4 or their RNA equivalents;
 (ii) a sequence which is complementary to any of the sequences of (i);
 (iii) a sequence which codes for the same protein or polypeptide, as those sequences of (i) or (ii);
 (iv) a sequence which is has substantial identity with any of those of (i), (ii) and (iii);
 (v) a sequence which codes for a homologue, derivative or fragment of a protein as defined in Table 4.

The nucleic acid molecules of the invention may include a plurality of such sequences, and/or fragments. The skilled person will appreciate that the present invention can include, novel variants of those particular novel nucleic acid molecules which are exemplified herein. Such variants are encompassed by the present invention. These may occur in nature, for example because of strain variation. For example, additions, substitutions and/or deletions are included. In addition, and particularly when utilising microbial expression systems, one may wish to engineer the nucleic acid sequence by making use of known preferred codon usage in the particular organism being used for expression. Thus, synthetic or non-naturally occurring variants are also included within the scope of the invention.

The term "RNA equivalent" when used above indicates that a given RNA molecule has a sequence which is complementary to that of a given DNA molecule (allowing for the fact that in RNA "U" replaces "T" in the genetic code).

When comparing nucleic acid sequences for the purposes of determining the degree of homology or identity one can use programs such as BESTFIT and GAP (both from the Wisconsin Genetics Computer Group (GCG) software package) BESTFIT, for example, compares two sequences and produces an optimal alignment of the most similar segments. GAP enables sequences to be aligned along their whole length and finds the optimal alignment by inserting spaces in either sequence as appropriate. Suitably, in the context of the present invention compare when discussing identity of nucleic acid sequences, the comparison is made by alignment of the sequences along their whole length.

Preferably, sequences which have substantial identity have at least 50% sequence identity, desirably at least 75% sequence identity and more desirably at least 90 or at least 95% sequence identity with said sequences. In some cases the sequence identity may be 99% or above.

Desirably, the term "substantial identity" indicates that said sequence has a greater degree of identity with any of the sequences described herein than with prior art nucleic acid sequences.

It should however be noted that where a nucleic acid sequence of the present invention codes for at least part of a novel gene product the present invention includes within its scope all possible sequence coding for the gene product or for a novel part thereof.

The nucleic acid molecule may be in isolated or recombinant form. It may be incorporated into a vector and the vector may be incorporated into a host. Such vectors and suitable hosts form yet further aspects of the present invention.

Therefore, for example, by using probes based upon the nucleic acid sequences provided herein, genes in *Streptococcus pneumoniae* can be identified. They can then be excised using restriction enzymes and cloned into a vector. The vector can be introduced into a suitable host for expression.

Nucleic acid molecules of the present invention may be obtained from *S._pneumoniae* by the use of appropriate probes complementary to part of the sequences of the nucleic acid molecules. Restriction enzymes or sonication techniques can be used to obtain appropriately sized fragments for probing.

Alternatively PCR techniques may be used to amplify a desired nucleic acid sequence. Thus the sequence data provided herein can be used to design two primers for use in PCR so that a desired sequence, including whole genes or fragments thereof, can be targeted and then amplified to a high degree. One primer will normally show a high degree of specificity for a first sequence located on one strand of a DNA molecule, and the other primer will normally show a high degree of specificity for a second sequence located on the complementary strand of the DNA sequence and being spaced from the complementary sequence to the first sequence.

Typically primers will be at least 15-25 nucleotides long.

As a further alternative chemical synthesis may be used. This may be automated. Relatively short sequences may be chemically synthesised and ligated together to provide a longer sequence.

In yet a further aspect the present invention provides an immunogenic/antigenic composition comprising one or more proteins or polypeptides selected from those whose sequences are shown in Tables 24, or homologues or derivatives thereof, and/or fragments of any of these. In preferred embodiments, the immunogenic/antigenic composition is a vaccine or is for use in a diagnostic assay.

In the case of vaccines suitable additional excipients, diluents, adjuvants or the like may be included. Numerous examples of these are well known in the art.

It is also possible to utilise the nucleic acid sequences shown in Table 1 in the preparation of so-called DNA vaccines. Thus, the invention also provides a vaccine composition comprising one or more nucleic acid sequences as defined herein. The use of such DNA vaccines is described in the art. See for instance, Donnelly et al, *Ann. Rev. Immunol.*, 15:617-648 (1997).

As already discussed herein the proteins or polypeptides described herein, their homologues or derivatives, and/or fragments of any of these, can be used in methods of detecting/diagnosing *S. pneumoniae*. Such methods can be based on the detection of antibodies against such proteins which may be present in a subject. Therefore the present invention provides a method for the detection/diagnosis of *S. pneumoniae* which comprises the step of bringing into contact a sample to be tested with at least one protein, or homologue, derivative or fragment thereof, as described herein. Suitably, the sample is a biological sample, such as a tissue sample or a sample of blood or saliva obtained from a subject to be tested.

In an alternative approach, the proteins described herein, or homologues, derivatives and/or fragments thereof, can be used to raise antibodies, which in turn can be used to detect the antigens, and hence *S. pneumoniae*. Such antibodies form another aspect of the invention. Antibodies within the scope of the present invention may be monoclonal or polyclonal.

Polyclonal antibodies can be raised by stimulating their production in a suitable animal host (e.g. a mouse, rat, guinea pig, rabbit, sheep, goat or monkey) when a protein as described herein, or a homologue, derivative or fragment thereof, is injected into the animal. If desired, an adjuvant may be administered together with the protein. Well-known adjuvants include Freund's adjuvant (complete and incomplete) and aluminium hydroxide. The antibodies can then be purified by virtue of their binding to a protein as described herein.

Monoclonal antibodies can be produced from hybridomas. These can be formed by fusing myeloma cells and spleen cells which produce the desired antibody in order to form an immortal cell line. Thus the well-known Kohler & Milstein technique (*Nature* 256 (1975)) or subsequent variations upon this technique can be used.

Techniques for producing monoclonal and polyclonal antibodies that bind to a particular polypeptide/protein are now well developed in the art. They are discussed in standard immunology textbooks, for example in Roitt et al, *Immunology* second edition (1989), Churchill Livingstone, London.

In addition to whole antibodies, the present invention includes derivatives thereof which are capable of binding to proteins etc as described herein. Thus the present invention includes antibody fragments and synthetic constructs. Examples of antibody fragments and synthetic constructs are given by Dougall et al in *Tibtech* 12 372-379 (September 1994).

Antibody fragments include, for example, Fab, F(ab')$_2$ and Fv fragments. Fab fragments (These are discussed in Roitt et al [supra]). Fv fragments can be modified to produce a synthetic construct known as a single chain Fv (scFv) molecule. This includes a peptide linker covalently joining $V_h$ and $V_l$ regions, which contributes to the stability of the molecule. Other synthetic constructs that can be used include CDR peptides. These are synthetic peptides comprising antigen-binding determinants. Peptide mimetics may also be used. These molecules are usually conformationally restricted organic rings that mimic the structure of a CDR loop and that include antigen-interactive side chains.

Synthetic constructs include chimaeric molecules. Thus, for example, humanised (or primatised) antibodies or derivatives thereof are within the scope of the present invention. An example of a humanised antibody is an antibody having human framework regions, but rodent hypervariable regions. Ways of producing chimaeric antibodies are discussed for example by Morrison et al in PNAS, 81, 6851-6855 (1984) and by Takeda et al in Nature. 314, 452454 (1985).

Synthetic constructs also include molecules comprising an additional moiety that provides the molecule with some desirable property in addition to antigen binding. For example the moiety may be a label (e.g., a fluorescent or radioactive label). Alternatively, it may be a pharmaceutically active agent.

Antibodies, or derivatives thereof, find use in detection/diagnosis of *S. pneumoniae*. Thus, in another aspect the present invention provides a method for the detection/diagnosis of *S. pneumoniae* which comprises the step of bringing into contact a sample to be tested and antibodies capable of binding to one or more proteins described herein, or to homologues, derivatives and/or fragments thereof.

In addition, so-called AFFIBODIES may be utilised. These are binding proteins selected from combinatorial libraries of an alpha-helical bacterial receptor domain (Nord et al,) Thus, Small protein domains, capable of specific binding to different target proteins can be selected using combinatorial approaches.

It will also be clear that the nucleic acid sequences described herein may be used to detect/diagnose *S. pneumoniae*. Thus, in yet a further aspect, the present invention provides a method for the detection/diagnosis of *S. pneumoniae* which comprises the step of bringing into contact a sample to be tested with at least one nucleic acid sequence as described herein. Suitably, the sample is a biological sample, such as a tissue sample or a sample of blood or saliva obtained from a subject to be tested. Such samples may be pre-treated before being used in the methods of the invention. Thus, for example, a sample may be treated to extract DNA. Then, DNA probes based on the nucleic acid sequences described herein (i.e., usually fragments of such sequences) may be used to detect nucleic acid from *S. pneumoniae*.

In additional aspects, the present invention provides:
(a) a method of vaccinating a subject against *S. pneumoniae* which comprises the step of administering to a subject a protein or polypeptide of the invention, or a derivative, homologue or fragment thereof, or an immunogenic composition of the invention;
(b) a method of vaccinating a subject against *S. pneumoniae* which comprises the step of administering to a subject a nucleic acid molecule as defined herein;
(c) a method for the prophylaxis or treatment of *S. pneumoniae* infection which comprises the step of administering to a subject a protein or polypeptide of the invention, or a derivative, homologue or fragment thereof, or an immunogenic composition of the invention;
(d) a method for the prophylaxis or treatment of *S. pneumoniae* infection which comprises the step of administering to a subject a nucleic acid molecule as defined herein;
(e) a kit for use in detecting/diagnosing *S. pneumoniae* infection comprising one or more proteins or polypeptides of the invention, or homologues, derivatives or fragments thereof, or an antigenic composition of the invention; and
(f) a kit for use in detecting/diagnosing *S. pneumoniae* infection comprising one or more nucleic acid molecules as defined herein.

Given that we have identified a group of important proteins, such proteins are potential targets for anti-microbial therapy. It is necessary, however, to determine whether each individual protein is essential for the organism's viability. Thus, the present invention also provides a method of determining whether a protein or polypeptide as described herein represents a potential anti-microbial target which comprises inactivating said protein and determining whether *S. pneumoniae* is still viable, in vitro or in vivo.

A suitable method for inactivating the protein is to effect selected gene knockouts, ie prevent expression of the protein and determine whether this results in a lethal change. Suitable methods for carrying out such gene knockouts are described in Li et al, *P.N.A.S.*, 94:13251-13256 (1997).

In a final aspect the present invention provides the use of an agent capable of antagonising, inhibiting or otherwise interfering with the function or expression of a protein or polypeptide of the invention in the manufacture of a medicament for use in the treatment or prophylaxis of *S. pneumoniae* infection.

The invention will now be described with reference to the following examples, which should not be construed as in any way limiting the invention. The examples refer to the figures in which:

EXAMPLE 1

Figure 1:
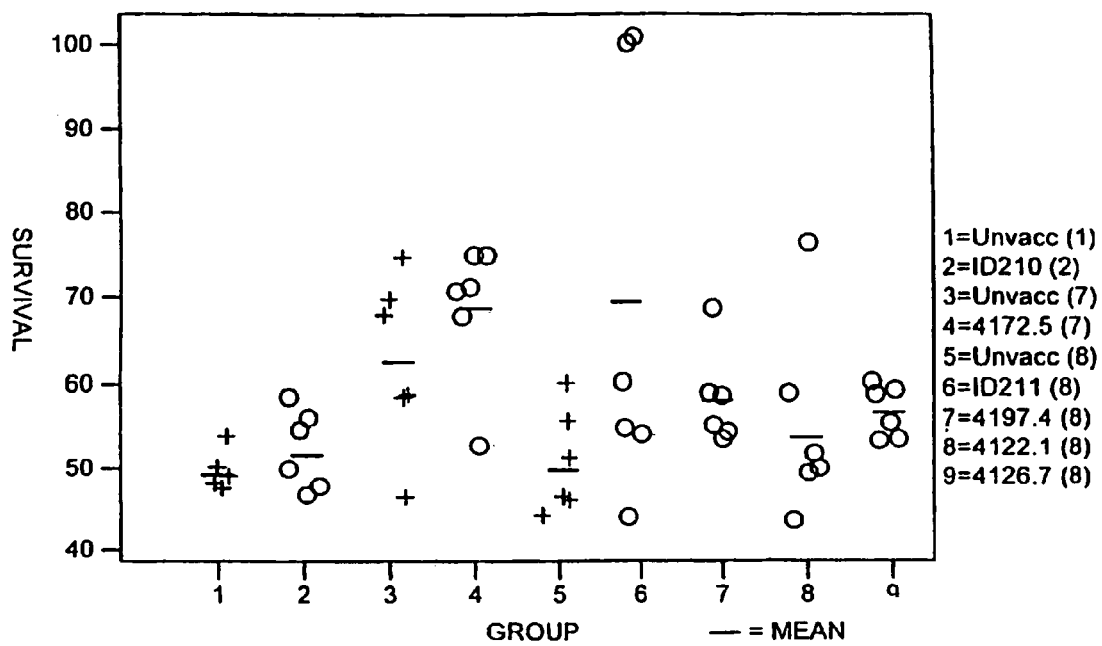
FIG. 1: shows the results of various DNA vaccine trials.

The Genome sequencing of *Streptococcus pneumoniae* type 4 is in progress at the Institute for Genomic Research (TIGR, Rockville, Md., USA). Up to now, the whole sequence has not been completed or published. On Nov. 21, 1997, the TIGR centre released some DNA sequences as contigs which are not accurate reflections of the finished sequence. These contigs can be downloaded from their website. We downloaded these contigs and created a local database using the application GCGToBLAST (Wisconsin Package Version 9.1, Genetics Computer Group (GCG), Madison, USA). This database can be searched with the FastA and TfastA procedures (using the method of Pearson and Lipman (*PNAS USA*, 85:2444-2448 (1988)).

Using FastA and TfastA procedures, the local pneumococcus database was searched for putative leader sequence or anchor sequence features. Relevant sequences were used to interrogate for comparative novel sequences. These were:
(i) already described leader sequences of *Streptococcus pneumoniae* (from proteins NanA, NanB, LytA, PapA, pcpA, PsaA and PspA);
(ii) the leader sequence of Usp45, a secreted protein from *Lactococcus lactis*;
(iii) new hypothetical leader sequences derived from the searches in (i) and (ii);
(iv) the anchor motif LPxTG (SEQ ID NO: 364), a feature common to many Gram-positive bacteria surface proteins which are anchored by a mechanism involving the Sortase complex proteins.

Provided below is an example of this approach, with reference to the sequences derived from the database (see table 1).

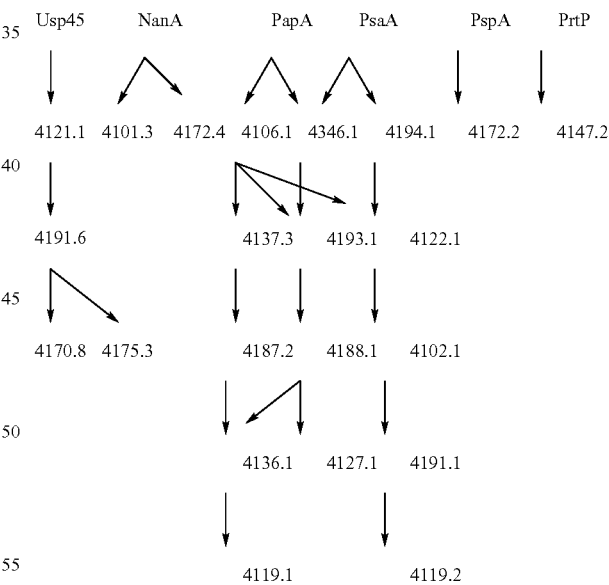

The protein leader sequences of different known exported proteins were used as a starting point for a search of the local pneumococcus database described above. The hypothetical proteins found with this search were then submitted to a Blast search in general databases such as EMBL, Swissprot etc. Proteins remaining unknown in the pneumococcus are kept and annotated. Then the search is performed again using the new potential protein leader sequence as a probe, using the TfastA procedure.

EXAMPLE 2

DNA Vaccine Trials pcDNA3.1+ as a DNA Vaccine Vector pcDNA3.1+

The vector chosen for use as a DNA vaccine vector was pcDNA3.1 (Invitrogen) (actually pcDNA3.1+, the forward orientation was used in all cases but may be referred to as pcDNA3.1 here on). This vector has been widely and successfully employed as a host vector to test vaccine candidate genes to give protection against pathogens in the literature (Zhang, et al., Kurar and Splitter, Anderson et al.). The vector was designed for high-level stable and non-replicative transient expression in mammalian cells. pcDNA3.1 contains the ColE1 origin of replication which allows convenient high-copy number replication and growth in E. coli. This in turn allows rapid and efficient cloning and testing of many genes. The pcDNA3.1 vector has a large number of cloning sites and also contains the gene encoding ampicillin resistance to aid in cloning selection and the human cytomegalovirus (CMV) immediate-early promoter/enhancer which permits efficient, high-level expression of the recombinant protein. The CMV promoter is a strong viral promoter in a wide range of cell types including both muscle and immune (antigen presenting) cells. This is important for optimal immune response as it remains unknown as to which cells types are most important in generating a protective response in vivo. A T7 promoter upstream of the multiple cloning site affords efficient expression of the modified insert of interest and which allows in vitro transcription of a cloned gene in the sense orientation.

Zhang, D., Yang, X., Berry, J. Shen, C., McClarty, G. and Brunham, R. C. (1997) "DNA vaccination with the major outer-membrane protein genes induces acquired immunity to Chlamydia trachomatis (mouse pneumonitis) infection". Infection and Immunity, 176, 1035-40.

Kurar, E. and Splitter, G. A. (1997) "Nucleic acid vaccination of Brucella abortus ribosomal L7/L12 gene elicits immune response". Vaccine, 15, 1851-57.

Anderson, R., Gao, X.-M., Papakonstantinopoulou, A., Roberts, M. and Dougan, G. (1996) "Immune response in mice following immunisation with DNA encoding fragment C of tetanus toxin". Infection and Immunity, 64, 3168-3173.

Preparation of DNA Vaccines

Oligonucleotide primers were designed for each individual gene of interest derived using the LEEP system. Each gene was examined thoroughly, and where possible, primers were designed such that they targeted that portion of the gene thought to encode only the mature portion of the gene protein. It was hoped that expressing those sequences that encode only the mature portion of a target gene protein, would facilitate its correct folding when expressed in mammalian cells. For example, in the majority of cases primers were designed such that putative N-terminal signal peptide sequences would not be included in the final amplification product to be cloned into the pcDNA3.1 expression vector. The signal peptide directs the polypeptide precursor to the cell membrane via the protein export pathway where it is normally cleaved off by signal peptidase I (or signal peptidase II if a lipoprotein). Hence the signal peptide does not make up any part of the mature protein whether it be displayed on the surface of the bacteria surface or secreted. Where a N-terminal leader peptide sequence was not immediately obvious, primers were designed to target the whole of the gene sequence for cloning and ultimately, expression in pcDNA3.1.

Having said that, however, other additional features of proteins may also affect the expression and presentation of a soluble protein. DNA sequences encoding such features in the genes encoding the proteins of interest were excluded during the design of oligonucleotides. These features included:

1. LPXTG (SEQ ID NO: 364) cell wall anchoring motifs.

2. LXXC ipoprotein attachment sites.

3. Hydrophobic C-terminal domain.

4. Where no N-terminal signal peptide or LXXC was present the start codon was excluded.

5. Where no hydrophobic C-terminal domain or LPXTG (SEQ ID NO: 364) motif was present the stop codon was removed.

Appropriate PCR primers were designed for each gene of interest and any and all of the regions encoding the above features was removed from the gene when designing these primers. The primers were designed with the appropriate enzyme restriction site followed by a conserved Kozak nucleotide sequence (in all cases) GCCACC was used. The Kozak sequence facilitates the recognition of initiator sequences by eukaryotic ribosomes) and an ATG start codon upstream of the insert of the gene of interest. For example the forward primer using a BamHI site the primer would begin GCGG-GATCCGCCACCATG (SEQ ID NO: 365) followed by a small section of the 5' end of the gene of interest. The reverse primer was designed to be compatible with the forward primer and with a NotI restriction site at the 5' end in all cases (this site is TTGCGGCCGC) (SEQ ID NO:366).

PCR Primers

The following PCR primers were designed and used to amplify the truncated genes of interest.

```
ID210
Forward Primer
                                          (SEQ ID NO: 367)
5' CGGATCCGCCACCATGTCTTCTAATGAATCTGCCGATG 3'

Reverse Primer
                                          (SEQ ID NO: 368)
5' TTGCGGCCGCCTGTTTAGATTGGATATCTGTAAAGACTT 3'

4172.5
Forward Primer
                                          (SEQ ID NO: 369)
5' CGCGGATCCGCCACCATGGATTTTCCTTCAAATTTGGAGG 3'

Reverse Primer
                                          (SEQ ID NO: 370)
5' TTGCGGCCGCACCGTACTGGCTGCTGACT 3'

ID211
Forward Primer
                                          (SEQ ID NO: 371)
5' CGGATCCGCCACCATGAGTGAGATCAAAATTATTAACGC 3'

Reverse Primer
                                          (SEQ ID NO: 372)
5' TTGCGGCCGCCGTTCCATGGTTGACTCCT 3'

4197.4
Forward Primer
                                          (SEQ ID NO: 373)
5' CGCGGATCCGCCACCATGTGGGACATATTGGTGGAAAC 3'
```

-continued

Reverse Primer
(SEQ ID NO: 374)
5' TTGCGGCCGCTTCACTTGAGCAAACTGAATCC 3'

4122.1
Forward Primer
(SEQ ID NO: 375)
5' CGCGGATCCGCCACCATGTCACAAGAAAAAACAAAAAATGAA 3'

Reverse Primer
(SEQ ID NO: 376)
5' TTGCGGCCGCATCGACGTAGTCTCCGCC 3'

4126.7
Forward Primer
(SEQ ID NO: 377)
5' CGCGGATCCGCCACCATGCTGGTTGGAACTTTCTACTATCAAT 3'

Reverse Primer
(SEQ ID NO: 378)
5' TTGCGGCCGCAACTTTCGTCCCTTTTGG 3'

4188.11
Forward Primer
(SEQ ID NO: 379)
5' CGCGGATCCGCCACCATGGGCAATTCTGGCGGAA 3'

Reverse Primer
(SEQ ID NO: 380)
5' TTGCGGCCGCTTGTTTCATAGCTTTTTTGATTGTT 3'

ID209
Forward Primer
(SEQ ID NO: 381)
5' CGCGGATCCGCCACCATGCTATTGATACGAAATGCAGGG 3'

Reverse Primer
(SEQ ID NO: 382)
5' TTGCGGCCGCAACATAATCTAGTAAATAAGCGTAGCC 3'

ID215
Forward Primer
(SEQ ID NO: 383)
5' CGCGGATCCGCCACCATGACGGCGACGAATTTTC 3'

Reverse Primer
(SEQ ID NO: 384)
5' TTGCGGCCGCTTAATTCGTTTTTGAACTAGTTGCT 3'

4170.4
Forward Primer
(SEQ ID NO: 385)
5' CGCGGATCCGCCACCATGGCTGTTTTTCTTCGCTATCATG 3'

Reverse Primer
(SEQ ID NO: 386)
5' TTGCGGCCGCTTTCTTCAACAAACCTTGTTCTTG 3'

4193.1
Forward Primer
(SEQ ID NO: 387)
5' CGCGGATCCGCCACCATGGGTAACCGCTCTTCTCGTAAC 3'

Reverse Primer
(SEQ ID NO: 388)
5' TTGCGGCCGCGCTTCCATCAAGGATTTTAGC 3'

Cloning

The insert along with the flanking features described above was amplified using PCR against a template of genomic DNA isolated from type 4 *S. pneumoniae* strain 11886 obtained from the National Collection of Type Cultures. The PCR product was cut with the appropriate restriction enzymes and cloned in to the multiple cloning site of pcDNA3.1 using conventional molecular biological techniques. Suitably mapped clones of the genes of interested were cultured and the plasmids isolated on a large scale (>1.5 mg) using Plasmid Mega Kits (Qiagen). Successful cloning and maintenance of genes was confirmed by restriction mapping and sequencing ~700 base pairs through the 5' cloning junction of each large scale preparation of each construct.

Strain Validation

A strain of type 4 was used in cloning and challenge methods which is the strain from which the *S. pneumoniae* genome was sequenced. A freeze dried ampoule of a homogeneous laboratory strain of type 4 *S. pneumoniae* strain NCTC 11886 was obtained from the National Collection of Type Strains. The ampoule was opened and the cultured re suspended with 0.5 ml of tryptic soy broth (0.5% glucose, 5% blood). The suspension was subcultured into 10 ml tryptic soy broth (0.5% glucose, 5% blood) and incubated statically overnight at 37° C. This culture was streaked on to 5% blood agar plates to check for contaminants and confirm viability and on to blood agar slopes and the rest of the culture was used to make 20% glycerol stocks. The slopes were sent to the Public Health Laboratory Service where the type 4 serotype was confirmed.

A glycerol stock of NCTC 11886 was streaked on a 5% blood agar plate and incubated overnight in a CO2 gas jar at 37° C. Fresh streaks were made and optochin sensitivity was confirmed.

Pneumococcal Challenge

A standard inoculum of type 4 *S. pneumoniae* was prepared and frozen down by passaging a culture of pneumococcus 1× through mice, harvesting from the blood of infected animals, and grown up to a predetermined viable count of around $10^9$ cfu/ml in broth before freezing down. The preparation is set out below as per the flow chart.

Streak pneumococcal culture and confirm identity
↓
Grow over-night culture from 4-5 colonies on plate above
↓
Animal passage pneumococcal culture
(i.p. injection of cardiac bleed to harvest)
↓
Grow over-night from animal passaged pneumococcus
↓
Grow day culture (to pre-determined optical density) from over-night of animal passage and freeze down at -70° C. - This is standard minimum
↓
Thaw one aliquot of standard inoculum to viable count
↓
Use standard inoculum to determine effective dose (called VirulenceTesting)
↓
All subsequent challenges- use standard inoculum to effective dose An aliquot of standard inoculum was diluted 500× in PBS and used to inoculate the mice.

Mice were lightly anaesthetised using halothane and then a dose of $1.4 \times 10^5$ cfu of pneumococcus was applied to the nose of each mouse. The uptake was facilitated by the normal breathing of the mouse, which was left to recover on its back.

*S. pneumoniae* Vaccine Trials

Vaccine trials in mice were carried out by the administration of DNA to 6 week old CBA/ca mice (Harlan, UK). Mice to be vaccinated were divided into groups of six and each group was immunised with recombinant pcDNA3.1+ plasmid DNA containing a specific target-gene sequence of interest. A total of 100 μg of DNA in Dulbecco's PES (Sigma) was injected intramuscularly into the tibialis anterior muscle of both legs (50 μl in each leg). A boost was carried using the same procedure 4 weeks later. For comparison, control groups were included in all vaccine trials. These control groups were either unvaccinated animals or those administered with non-recombinant pcDNA3.1+ DNA (sham vaccinated) only, using the same time course described above. 3 weeks after the second immunisation, all mice groups were challenged intranasally with a lethal dose of *S. pneumoniae* serotype 4 (strain NCTC 11886). The number of bacteria administered was monitored by plating serial dilutions of the inoculum on 5% blood agar plates. A problem with intranasal immunisations is that in some mice the inoculum bubbles out of the nostrils, this has been noted in results table and taken account of in calculations. A less obvious problem is that a certain amount of the inoculum for each mouse may be swallowed. It is assumed that this amount will be the same for each mouse and will average out over the course of innoculations. However, the sample sizes that have been used are small and this problem may have significant effects in some experiments. All mice remaining after the challenge were killed 3 or 4 days after infection. During the infection process, challenged mice were monitored for the development of symptoms associated with the onset of *S. pneumoniae* induced-disease. Typical symptoms in an appropriate order included piloerection, an increasingly hunched posture, discharge from eyes, increased lethargy and reluctance to move. The latter symptoms usually coincided with the development of a moribund state at which stage the mice were culled to prevent further suffering. These mice were deemed to be very close to death, and the time of culling was used to determine a survival time for statistical analysis. Where mice were found dead, the survival time was taken as the last time point when the mouse was monitored alive.

Interpretation of Results

A positive result was taken as any DNA sequence that was cloned and used in challenge experiments as described above which gave protection against that challenge. Protection was taken as those DNA sequences that gave statistically significant protection (to a 95% confidence level ($p<0.05$)) and also those which were marginal or close to significant using Mann-Whitney or which show some protective features for example there were one or more outlying mice or because the time to the first death was prolonged. It is acceptable to allow marginal or non-significant results to be considered as potential positives when it is considered that the clarity of some of the results may be clouded by the problems associated with the administration of intranasal infections.

| | | | | | Results for vaccine trials 2, 7 and 8 (see FIG. 1) | | | | |
|---|---|---|---|---|---|---|---|---|---|
| | | | | | Mean survival times (hours) | | | | |
| Mouse number | Unvacc control (2) | ID210 (2) | Unvacc control (7) | 4172.5 (7) | Unvacc control (8) | ID211 (8) | 4197.4 (8) | 4122.1 (8) | 4126.7 (8) |
| 1 | 49.0 | 55.0 | 59.6 | 72.6 | 45.1 | 102.3T | 60.1 | 50.6 | 60.0 |
| 2 | 51.0 | 46.5 | 47.2 | 67.9 | 50.8 | 55.5 | 54.9 | 77.2 | 60.0 |
| 3 | 49.0 | 49.0 | 59.6 | 54.4 | 60.4 | 60.6* | 68.4 | 60.3 | 54.8 |
| 4 | 55.0 | 59.0 | 70.9 | 75.3 | 55.2 | 45.3 | 60.1 | 50.6 | 52.6 |
| 5 | 49.0 | 55.0 | 68.6* | 70.9 | 45.1 | 55.5 | 54.9 | 50.6* | 54.8 |
| 6 | 49.0 | 49.0 | 76.0 | 75.3 | 45.1 | 102.3T | 52.7 | 44.9 | 60 |
| Mean | 50.3 | 52.3 | 63.6 | 69.4 | 50.2 | 70.2 | 58.5 | 55.7 | 57.0 |
| sd | 2.4 | 4.8 | 10.3 | 7.9 | 6.4 | 25.3 | 5.7 | 11.6 | 3.4 |
| p value 1 | — | 0.3333 | — | 0.2104 | — | 0.0215 | 0.0621 | 0.4038 | 0.0833 |

*bubbled when dosed so may not have received full inoculum.

T—terminated at end of experiment having no symptoms of infection.

Numbers in brackets - survival times disregarded assuming incomplete dosing p value 1 refers to significance tests compared to unvaccinated controls Statistical Analyses.

Trial 2 - The group vaccinated with ID210 also had a longer mean survival time than the unvaccinated controls but the results are not statistically significant.

Trial 7 - The group vaccinated with 4172.5 showed much greater survival times than unvaccinated controls although the differences were not statistically significant.

Trial 8 - The group vaccinated with ID211 survived significantly longer than unvaccinated controls. 4197.4, 4122.1 and 4126.7 vaccinated groups showed longer mean survival times than the unvaccinated group but the results were not statistically significant. The 4197.4 and 4126.7 groups also showed a prolonged time to the first death and the 4122.1 group showed 1 outlying result.

Figure 2:
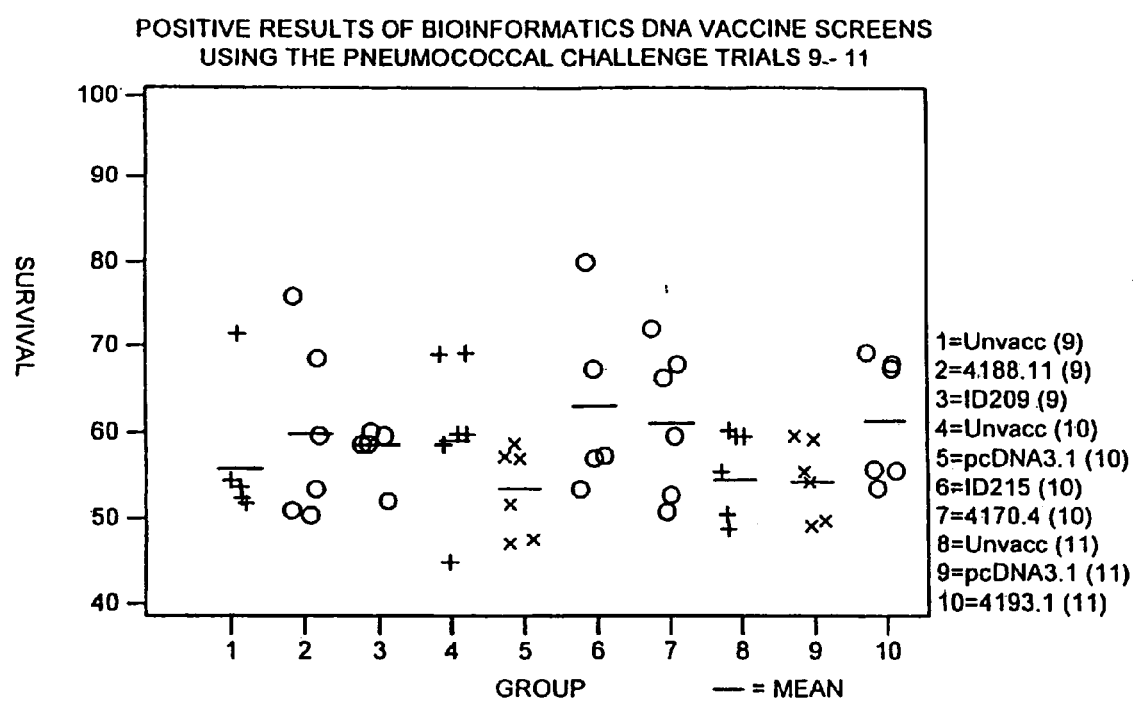
FIG. 2: shows the results of further DNA vaccine trials.

Results of pneumococcal challenge DNA vaccination trials 9-11 (see FIG. 2)

Mean survival times (hours)

| Mouse number | Unvacc control (9) | 4188.11 (9) | ID209 (9) | Unvacc control (10) | pcDNA3.1+ (10) | ID215 (10) | 4170.4 (10) | Unvacc control (11) | pcDNA3.1+ (11) | 4193.1 (11) |
|---|---|---|---|---|---|---|---|---|---|---|
| 1 | (98.5)T | 69.4 | 60.2 | 68.4 | 58.6 | 79.2 | 68.1 | 60.0 | 53.2 | 54.8 |
| 2 | 53.4 | 53.7 | 60.2 | 59.0 | 58.6 | 54.2 | 58.6 | 50.0 | 50.4 | 54.8 |
| 3 | 53.4 | 51.2 | 60.2 | 59.0 | 50.8 | (103.2)*T | 50.9 | 60.0 | 55.4 | 68.7* |
| 4 | 53.4 | 75.0 | (98.0)*T | 45.1* | 58.6 | 58.8 | 72.1 | 55.0 | 60.6 | 54.8 |
| 5 | 70.8 | 51.2 | 60.2 | 68.4 | 46.5 | 68.3 | 68.1 | 60.0 | 50.4 | 68.7 |
| 6 | 53.4 | 61.2 | 52.9 | 59.0 | 48.9 | 58.8 | 54.0 | 50.0 | 60.6 | 68.7* |
| Mean | 56.9 | 60.3 | 58.8 | 59.8 | 53.6 | 63.9 | 62.0 | 55.8 | 55.1 | 61.7 |
| Sd | 7.8 | 10.0 | 3.3 | 8.5 | 5.6 | 10.0 | 8.7 | 5.0 | 4.6 | 7.6 |
| p value 1 | — | 0.3894 | 0.2519 | — | 0.0307 | <30.0 | <39.0 | — | — | 0.1837 |
| p value 2 | — | — | — | — | — | 0.0168 | 0.0316 | — | — | 0.0829 |

*bubbled when dosed so may not have received full inoculum.
T—terminated at end of experiment having no symptoms of infection.
Numbers in brackets - survival times disregarded assuming incomplete dosing
p value 1 refers to significance tests compared to unvaccinated controls
p value 2 refers to significance tests compared to pcDNA3.1+ vaccinated controls
Statistical Analyses.
Trial 9 - Although not statistically significant the groups vaccinated with 4188.11 and ID209 did have noticeably higher mean survival times than unvaccinated controls.
Trial 10 - The unvaccinated control group survived for a significantly longer period than the pcDNA3.1+ vaccinated group. The groups vaccinated with ID215 and 4170.4 showed statistically significant longer survival times compared to the sham vaccinated group (p = 0.0168 and 0.0316) but not compared to the unvaccinated group.
Trial 11 - The group vaccinated with 4193.1 was the most promising and survived an average of 6.5 hours longer than the pcDNA3.1+ vaccinated group and 6 hours longer than the unvaccinated group although the results were not statistically significant.

TABLE 1

4101.1

(SEQ. ID. NO. 208)
ATGGAAGAGTTAGTGACCTTAGATTGTTTGTTTATTGACAGAACTAAGAT
TGAAGCCAATGCCAACAAGTATAGTTTTGTGTGGAAGAAAACGACAGAGA
AATTCTCCGCCAAACTTCAAGAAGCAGATACAGGTCTATTTTCAAGAAGAA
ATCACTCCCCTTCTGATTAAATATGCCATGTTTGATAAGAAACAAAAGAG
AGGGTATAAAGAGTCAGCTAAAAACTTAGCGAATTGGCACTATAATGACA
AGGAGGATAGCTACACACATCCTGATGGCTGGTATTATCGTTTTCACCAT
ACCAAATATCAGAAAACACAGACAGACTTTCAACAAGAAGCTCAAGGTTTA
CTACGCCGACGAACCTGAATCAGCCCCTCAAAAGGGACTGTATATGAACG
AACGCTATCAAAACTTGAAAGCTAAAGAATGTCAGGCGCTTTTATCTCCC
CAAGGTAGACAGATTTTCGCTCAACGCAAGATTGATGTGGAACCTGTCTT
TGGGCAGATAAAGGCTTCTTTGGGTTACAAGAGATGTAATCTGAGAGGGA
AGCGTCAAGTGGAATTGACATGGGATTGGTACTTATGGCCAATAACCTC
CTAAAATATAGTAAAATGAAATAA 4101.3

(SEQ. ID. NO. 209)
ATGGGGAAAGGCCATTGGAATCGGAAAAGAGTTTATAGCATTCGTAAGTT
TGCTGTGGGAGCTTGCTCAGTAATGATTGGGACTTGTGCAGTTTTATTAG
GAGGAAATATAGCTGGAGAATCTGTAGTTTATGCGGATGAAACACTTATT
ACTCATACTGCTGAGAAACCTAAAGAGGAAAAATGATAGTAGAAGAAAA
GGCTGATAAAGCTTTGGAAACTAAAAATATAGTTGAAAGGACAGAACAAA
GTGAACCTAGTTCAACTGAGGCTATTGCATCTGAGAAGAAAGAAGATGAA
GCCGTAACTCCAAAAGAGGAAAAGTGTCTGCTAAACCGGAAGAAAAGC
TCCAAGGATAGAATCACAAGCTTCAAATCAAGAAAAACCGCTCAAGGAAG
ATGCTAAAGCTGTAACAAATGAAGAAGTGAATCAAATGATTGAAGACAGG
AAAGTGGATTTTAATCAAAATTGGTACTTTAAACTCAATGCAAATTCTAA
GGAAGCCATTAAACCTGATGCAGACGTATCTACGTGGAAAAAATTAGATT
TACCGTATGACTGGAGTATCTTTAACGATTTCGATCATGAATCTCCTGCA
CAAAATGAAGGTGGACAGCTCAACGGTGGGGAAGCTTGGTATCGCAAGAC
TTTCAAACTAGATGAAAAGACCTCAAGAAAAATGTTCGCCTTACTTTTG
ATGGCGTCTACATGGATTCTCAAGTTTATGTCAATGGTCAGTTAGTGGGG
CATTATCCAAATGGTTATAGCCAGTTCTCATATGATATCACCAAATACCT
TCAAAAAGATGGTCGTGAGAATGTGATTGCTGTCCATGCAGTCAACAAAC
AGCCAAGTAGCCGTTGGTATTCAGGAAGTGGTATCTATCGTGATGTGACT
TTACAAGTGACAGATAAGGTGCATGTTGAGAAAAATGGGACAACTATTTT
AACACCAAAACTTGAAGAACAACAACATGGCAAGGTTGAAACTCATGTGA
CCAGCAAAATCGTCAATACGGACGACAAAGACCATGAACTTGTAGCCGAA

TATCAAATCGTTGAACGAGGTGGTCATGCTGTAACAGGCTTAGTTCGTAC
AGCGAGTCGTACCTTAAAAGCACATGAATCAACAAGCCTAGATGCGATTT
TAGAAGTTGAAAGACCAAAACTCTGGACTGTTTTAAATGACAAACCTGCC
TTGTACGAATTGATTACGCGTGTTTACCGTGACGGTCAATTGGTTCATGC
TAAGAAGGATTTGTTTGGTTACCGTTACTATCACTGGACTCCAAATGAAG
GTTTCTCTTTGAATGGTGAACGTATTAAATTCCATGGAGTATCCTTGCAC
CACGACCATGGGCGCTTGGAGCAGAAGAAACTATAAAGCAGAATATCG
CCGTCTCAAACAAATGAAGGAGATGGGAGTTAACTCCATCCGTACAACCC
ACAACCCTGCTAGTGAGCAAACCTTGCAAATCGCAGCAGAACTAGGTTTA
CTCGTTCAGGAAGAGGCCTTTGATACGTGGTATGGTGGCAAGAAACCTTA
TGACTATGGACGTTTCTTTGAAAAAGATGCCACTCACCCAGAAGCTCGAA
AAGGTGAAAATGGTCTGATTTTGACCTACGTACCATGGTCGAAAGAGGC
AAAACAACCCTGCTATCTTCATGTGGTCAATTGGTAATGAAATAGGTGA
AGCTAATGGTGATGCCCACTCTTTAGCAACTGTTAAACGTTTGGTTAAGG
TTATCAAGGATGTTGATAAGACTCGCTATGTTACCATGGGAGCAGATAAA
TTCCGTTTCGGTAATGGTAGCGGAGGGCATGAGAAAATTGCTGATGAACT
CGATGCTGTTGGATTTAACTATTCTGAAGATAATTACAAAGCCCTTAGAG
CTAAGCATCCAAAATGGTTGATTTATGGATCAGAAACATCTTCAGCTACC
CGTACACGTGGAAGTTACTATCGCCCTGAACGTGAATTGAAACATAGCAA
TGGACCTGAGCGTAATTATGAACAGTCAGATTATGGAAATGATCGTGTGG
GTTGGGGGAAAACAGCAACCGCTTCATGGACTTTTGACCGTGACAACGCT
GGCTATGCTGGACAGTTTATCTGGACAGGTACGGACTATATTGGTGAACC
TACACCATGGCACAACCAAATCAAACCTCCTGTTAAGAGCTCTTACTTTG
GTATCGTAGATACAGCCGGCATTCCAAAACATGACTTCTATCTCTACCAA
AGCCAATGGGTTTCTGTTAAGAAGAAACCGATGGTACACCTTCTTCCTCA
CTGGAACTGGGAAAACAAAGAATTAGCATCCAAAGTAGCTGACTCAGAAG
GTAAGATTCCAGTTCGTGCTTATTCGAATGCTTCTAGTGTAGAATTGTTC
TTGAATGGAAAATCTCTTGGTCTTAAGACTTTCAATAAAAAACAAACCAG
CGATGGGCGGACTTACCAAGAAGGTGCAAATGCTAATGAACTTTATCTTG
AATGGAAAGTTGCCTATCAACCAGGTACCTTGGAAGCAATTGCTCGTGAT
GAATCTGGCAAGGAAATTGCTCGAGATAAGATTACGACTGCTGGTAAGCC
AGCGGCAGTTCGTCTTATTAAGGAAGACCATGCGATTGCAGCAGATGGAA
AAGACTTGACTTACATCTACTATGAAATTGTTGACAGCCAGGGGAATGTG
GTTCCAACTGCTAACAATCAGTTGCGTTCCAATTGCATGGCCAAGGTCA
ACTGGTCGGTGTAGATAACGGAGAACAAGCCAGCCGTGAACGCTATAAGG
CGCAAGCAGATGGTTCTTGGATTCGTAAAGCATTTAATGGTAAAGGTGTT
GCCATTGTCAAATCAACTGAACAAGCAGGGAAATTCACCCTGACTGCCCA
CTCTGATCTCTTGAAATCGAACCAAGTCACTGTCTTTACTGGTAAGAAAG
AAGGACAAGAGAAGACTGTTTTGGGGACAGAAGTGCCAAAAGTACAGACC

TABLE 1-continued

```
ATTATTGGAGAGGCACCTGAAATGCCTACCACTGTTCCGTTTGTATACAG
TGATGGTAGCCGTCAGAACGTCCTGTAACCTGGTCTTCAGTAGATGTGA
GCAAGCCTGGTATTGTAACGGTGAAAGGTATGGCTGACGGACGAGAAGTA
GAAGCTCGTGTAGAAGTGATTGCTCTTAAATCAGAGCTACCAGTTGTGA
ACGTATTGCTCCAAATACTGACTTGAATTCTGTAGACAAATCTGTTTCCT
ATGTTTTGATTGATGGAAGTGTTGAAGAGTATGAAGTGGACAAGTGGGAG
ATTGCCGAAGAAGATAAAGCTAAGTTAGCAATTCCAGGTTCTCGTATTCA
AGCGACCGGTTATTTAGAAGGTCAACCAATTCATGCAACCCTTGTGGTAG
AAGAAGGCAATCCTGCGGCACCTGCAGTACCAACTGTAACGGTTGGTGGT
GAGGCAGTAACAGGTCTTACTAGTCAAAACCAATGCAATACCGCACTCT
TGCTTATGGAGCTAAGTTGCCAGAAGTCACAGCAAGTGCTAAAAATGCAG
CTGTTACAGTTCTTCAAGCAAGCGCAGCAAACGGCATGCGTGCGAGCATC
TTTATTCAGCCTAAAGATGGTGGCCCTCTTCAAACCTATGCAATTCAATT
CCTTGAAGAAGCGCAAAAATTGCTCACTTGAGCTTGCAAGTGGAAAAAG
CTGACAGTCTCAAAGAAGACCAAACTGTCAAATTGTCGGTTCGAGCTCAC
TATCAAGATGGAACGCAAGCTGTATTACCAGCTGATAAAGTAACCTTCTC
TACAAGTGGTGAAGGGGAAGTCGCAATTCGTAAAGGAATGCTTGAGTTGC
ATAAGCCAGGAGCAGTCACTCTGAACGCTGAATATGAGGGAGCTAAAGAC
CAAGTTGAACTCACTATCCAAGCCAATACTGAGAAGAAGATTGCGCAATC
CATCCGTCCTGTAAATGTAGTGACAGATTTGCATCAGGAACCAAGTCTTC
CAGCAACAGTAACAGTTGAGTATGACAAAGGTTTCCCTAAAACTCATAAA
GTCACTTGGCAAGCTATTCCGAAAGAAAAACTAGACTCCTATCAAACATT
TGAAGTACTAGGTAAAGTTGAAGGAATTGACCTTGAAGCGCGTGCAAAAG
TCTCTGTAGAAGGTATCGTTTCAGTTGAAGAAGTCAGTGTGACAACTCCA
ATCGCAGAAGCACCACAATTACCAGAAAGTGTTCGGACATATGATTCAAA
TGGTCACGTTTCATCAGCTAAGGTTGCATGGGATGCGATTCGTCCAGAGC
AATACGCTAAGGAAGGTGTCTTTACAGTTAATGGTCGCTTAGAAGGTACG
CAATTAACAACTAAACTTCATGTTCGCGTATCTGCTCAAACTGAGCAAGG
TGCAAACATTTCTGACCAATGGACCGGTTCAGAATTGCCACTTGCCTTTG
CTTCAGACTCAAATCCAAGCGACCCAGTTTCAAATGTTAATGACAAGCTC
ATTTCCTACAATAACCAACCAGCCAATCGTTGGACAAACTGGAATCGTAC
TAATCCAGAAGCTTCAGTCGGTGTTCTGTTTGGAGATTCAGGTATCTTGA
GCAAACGCTCCGTTGATAATCTAAGTGTCGGATTCCATGAAGACCATGGA
GTTGGTGTACCGAAGTCTTATGTGATTGAGTATTATGTTGGTAAGACTGT
CCCAACAGCTCCTAAAAACCCTAGTTTTGTTGGTAATGAGGACCATGTCT
TTAATGATTCTGCCAACTGGAAACCAGTTACTAATCTAAAAGCCCCTGCT
CAACTCAAGGCTGGAGAAATGAACCACTTTAGCTTTGATAAAGTTGAAG
CTATGCTGTTCGTATTCGCATGGTTAAAGACAGATAACAAGCGTGGAACGT
CTATCACAGAGGTACAAATCTTTGCGAAACAAGTTGCGGCAGCCAAGCAA
GGACAAACAAGAATCCAAGTTGACGGCAAAGACTTAGCAAACTTCAACCC
TGATTTGACAGACTACTACCTTGAGTCTGTAGATGAAAAGTTTCCGCAG
TCACAGCAAGTGTTAGCAACAATGGTCTCGCTACCCGTCGTTCCAAGCGTT
CGTGAAGGTGAGCCAGTTCGTGTCATCGCGAAAGCTGAAAATGGCGACAT
CTTAGGAGAATACCGTCTGCACTTCACTAAGGATAAGAGCTTACTTTCTC
ATAAACCAGTTGCTGCGGTTAAACAAGCTCGCTTGCTACAAGTAGGTCAA
GCACTTGAATTGCCGACTAAGGTTCCAGTTTACTTCACAGGTAAAGACGG
CTACGAAACAAAAGACCTGACAGTTGAATGGGAAGAAGTTCCAGCGGAAA
ATCTGACAAAAGCAGGTCAATTTACTGTTCGAGGCCGTGTCCTTGGTAGT
AACCTTGCTGAGATCACTGTACGAGTGACAGACAAACTTGGTGAGAC
TCTTTCAGATAACCCTAACTATGATGAAAACAGTAACCAGGCCTTTGCTT
CAGCAACCAATGATATTGACAAAAACTCTCATGACCGCGTTGACTATCTC
AATGACGGAGATCATTCAGAAAATCGTCGTTGGACAAACTGGTCACCAAC
ACCATCTTCTAATCCAGAAGTATCAGCGGGTGTGATTTTCCGTGAAAATG
GTAAGATTGTAGAACGGACTGTTACACAAGGAAAAGTTCAGTTCTTTGCA
GATAGTGGTACGGATGCACCATCTAAACTCGTTTTAGACGCTATGTCGG
TCCAGAGTTTGAAGTGCCAACCTACTATTCAAACATACCAAGCCTACGACG
CAGACCATCCATTCAACAATCCAGAAATTGGGAAGCTGTTCCTTATCGT
GCGGATAAAGACATTGCAGCTGGTGATGAAATCAACGTAACATTTAAAGC
TATCAAAGCCAAAGCTATGAGATGGCGATGGAGCGTAAACAGATAAGA
GCGGTGTTGCGATGATTGAGATGACCTTCCTTGCACCAAGTGAATTGCCT
CAAGAAAGCACTCAATCAAAGATTCTTGTAGATGGAAAAGAACTTGCTGA
TTTCGCTGAAAATCGTCAAGACTATCAAATTACCTATAAAGGTCAACGGC
CAAAAGTCTCAGTTGAAGAAAACAATCAAGTAGCTTCAACTGTGGTAGAT
AGTGGAGAAGATAGCTTTCCAGTACTTGTTCGCCTCGTTTCAGAAAGTGG
AAAACAAGTCAAGGAATACCGTATCCCACTTGACTAAGGAAAAACCAGTTT
CTGAGAGACAGTTGCTGCTGACAAGAAGATCTTCCAAAAATCGAATTT
GTTGAAAAAGATTTGGCATACAAGCAGTTGGAAAAAAAAGATTCAACACT
GTATCTAGGTGAAACTCGTGTAGAACAAGAAGGAAAAGTTGGAAAAGAAC
GTATCTTTACAGCGATTAATCCTGATGGAAGTAAGGAAGAAAAACTCCGT
GAAGTGGTAGAAGTTCCGACAGACCGCATCGTCTTGGTTGGAACCAAAC
AGTAGCTCAAGAAGCTAAAAAACCACAAGTGTCAGAAAAGCAGATACAA
AACCAATTGATTCAAGTGAAGCTAGTCAAACTAATAAAGCCCAGTTACCA
AGTACAGGTAGTGCGGCAAGCCAAGCAGCAGTAGCAGCAGGTTTAACTCT
TCTAGGTTTGAGTGCAGGATTAGTAGTTACTAAAGGTAAAAAAGAAGACT
AG 4101.5
                                       (SEQ. ID. NO. 210)
ATGGATGCAATCTTTGACCTAATCGGAAAGGGTTTTCAATCCCATCTTAGA
AATGGGTGGACCTGTCATCATGTTAATCATTTTGACAGTATTGGCTTTAC
TTTTTGGAGTGAAATTCTCCAAAGCGCTTGAAGGTGGTATCAAACTTGCC
ATCGCTCTTACAGGTATCCGGTGCTATCATCGGTATGCTAAACACTGCTTT
CTCAGCATCACTAGCAAAATTCGTTGAAAACACTGGTATCCAATTGAGTA
TTACCGACGTTGGTTGGGCACCACTTGCTACAATCACTTGGGGTTCTGCT
TGGACACTATACTTCTTGCTCATCATGTTGATTGTCAACATAGTGATGCT
AGCTATGAAGAAACAGATACACTTGATGTCGATATCTTTGATATCTGGC
ACTTGTCTATCACAGGTCTCTTGATTAAATGGTTAGTGCTGATAACAATGGT
GTGAGTCAAGGGGTTTCACTCTTTATTGCTACAGCAGCTATCGTCCTTGT
CGGTGTGTTGAAAATTATCAACTCTGACTTGATGAAACCTACATTTGATG
ACCTTCTTAACGCCCCAAGTTCATCACCAATGACATCAACTCACATGAAC
TACATGATGAACCCAGTTATCATGGTTTTGGATAAGATTTTTGAAAAATT
CTTCCCAGGCCTTGATAAATATGACTTTGATGCTGCTAAATTGAACAAGA
AAATCCGTTTCTGGGGATCTAAATTCTTCATCGGTTTCATCCTTGGTATC
GTTATCGGTATTATGGGAACTCCACATCCAATTGCAGGTGTTGCAGATGC
AGATAAATGCGTCTTGTTATCAAAAGGATGGTTGTCTTGGTTTGACTG
CCGGTGTATCTTTGGAACTCTTCTTCACTTATCGGTTCATGGTTCATCGCA
GCCGTAGAACCACTATCACAAGGTATTACAAACGTTGCTACTAAACGTCT
TCAAGGACGTAAATTCAATATCGGTCTTGACTGGCCATTCATCGCTGGTC
GTGCTGAAATCTGGGCTTGTGCCAACGTACTTGCACCAATCATGTTGATT
GAAGCAGTGCTTCTTTCAAAAGTTGGAAATGGTATCTTGCCACTTGCAGG
TATCATCGCTATGGGTGTTACTCCAGCTCTCTTGGTTGTAACTCGTGGTA
AATTGCTCCGTATGATTATCTTCGGAACACTCTTGTTGCCACTCTTCCTT
CTTTCAGGTACACTTATTGCACCATTTGCAACAGAACTTGCTAAAGGTGT
AGGTGCCTTCCCAGAAGGTGTGAGCCAAACTCAATTGATTACTCACTCTA
CTCTTGAAGGACCAATCGAAAACTTCTTGGTTGGACAATTGGTAACACT
ACAACTGGTGATATCAAAGCAATCCTTGGTCAGTAGTCTTCCTTGTATT
CTATATCGGTATCTTTGCTTGGTACAGAAAACAAATGATCAAACGTAACG
AAGAGTACGCAGCAAAAGCAAATAA
```

4102.1
                                       (SEQ. ID. NO. 211)
```
ATGAAGATTATGAAAAAAAAATATTGGACTTTAGCGATATTATTCTTTG
TTTGTTCAATAATTCTGTTACTGCTCAAGAAATACCTAAAAATCTTGATG
GCAATATAACTCACACTCAGACTAGCGAAAGTTTTTCTGAATCTGATGAA
AACAGGTTGACTATTCAATAAAAATCAAGAAGAAGTAGACCAAAATAAA
TTTCGTATTCAAATCGATAAGACAGAATTATTTGTAACAACAGATAAACA
TTTAGAAAAAAACTGTTGTAAATTGGAACTTGAACCACAAATAAATAACG
ATATTGTTAACTCTGAAAGTAATAATTTACTAGGCGAAGATAATTTAGAT
AATAAAATTAAGGAAATGTTTCTCATCTAGATAATAGAGGAGGAAATAT
AGAGCATGACAAAGATAACTTAGAATCGTCGATTGTAAGAAAATATGAT
GGGATATAGATAAAGTTACTGGTGGAGGCGAAAGTTATAAATTATATTCT
AAAAGTAATTCTAAAGTTTCAATTGCTATTTTAGATTCAGGAGTCGATTT
ACAAAATACTGGATTACTGAAAAATCTTTCAAATCACTCAAAAAACTATG
TCCCCAATAAAGGATATTTAGGAAAAGAGGAGGGAGGAAGGAATAATA
TCAGATATTCAAGATAGATAGGTCATGGTACGGCTGTTGTAGCTCAAAT
TGTAGGGGATGACAATATTAATGGAGTAAATCCTCACGTTAATATTAACG
TCTATAGAATATTTGGTAAGTCGTCAGCTAGTCCAGATTGGATTGTAAAA
GCAATTTTTGATGCTGTAGATATGGCAATGATATTATCAATCTTAGTAC
TGGACAATATTTAATGATTGATGGAATATGAGGACGGAACAAATGATT
TTGAAACATTTTTGAAGTATAAAAAGGCTATTGATTACGCGAATCAAAA
GGAGTAATTATAGTAGCTGCATTAGGGAATGACTCCCTAAATGTATCAAA
TCAGTCAGATTTATTGAAACTTATTAGTTCACGCAAAAAAGTAAGAAAAC
CAGGATTAGTTGATTTGATGTTCCAAGTTATTTCTCATCTACAATTTCGGTC
GGAGGCATAGATCGCTTAGGTAATTTATCAGATTTTAGCAATAAAGGGGA
TTCTGATGCAATATATGCGCCTGCAGGCTCAACATTATCTCTTTCAGAAT
TAGGACTTAATAACTTTATTAATGCAGAAAAATATAAAGAAGATTGGATT
TTTTCGGCACACCATAGGAGGATATACGTATCTTTATGGAAACTCATTTGC
TGCTCCTAAAGTTTCTGGTCGCGATTGCAATGATTATTGATAAATACAAAT
TAAAAGATCAGCCCTATAATTATATGTTTGTAAAAAAATTCTGGAAGAAA
CATTACCAGTAA
```

4106.1
                                       (SEQ. ID. NO. 212)
```
ATGAAGAAAACATGGAAAGTGTTTTTAACGCTTGTAACAGCTCTTGTAGC
TGTTTGTCTTGTGCCTGTGGTCAAGGAACTGCTTCTAAAGACAAGAAG
AGGCAGAACTTAAGAAGGTTGACTTTATCCTAGACTGGACACCAAATACC
AACCACACAGGGCTTTATGTTGCCAAGGAAAAAGGTTATTTCAAAGAAGC
TGGAGTGGATGTTGATTTGAAATTGCCACCAGAAGAAAGTTCTTCTGACT
TGGTTATCAACGGAAAGGCACCATTTGCAGTGTATTTCCAAGACTACATG
GCTAAGAAATTGGAAAAGGAGCAGGAATCACTGCCGTTGCAGCTATTGT
TGAACACAATACATCAGGAATCATCTCTCGTAAATCTGATAATGTAAGCA
GTCCAAAAGACTTGGTTGGTAAGAAATATGGGACATGGAATGACCCAACT
GAACTTGCTATGTTGAAACCTTGGTAGAATCTCAAGGTGGACAGTTTGA
GAAGGTTGAAAAAGTACCAAATAACGACTCAAACTCAATCACACCGATTG
CCAATGGCGTCTTTGATACTGCTTGGATTTACTACGGTTGGGATGGTATC
CTTGCTAAATCTCAAGGTGAGATGCTAACTTCATGTACTTGAAAGACTAT
GTCAAGGAGTTTGACTACTATTCACCAGTTATCATCGCAAACAACGACTA
TCTGAAAGATAACAAAGAAGAAGCTCGCAAAGTCATCCAAGCCATCAAAA
```

TABLE 1-continued

AAGGCTACCAATATGCCATGGAACATCCAGAAGAAGCTGCAGATATTCTC
ATCAAGAATGCACCTGAACTCAAGGAAAAACGTGACTTTGTCATCGAATC
TCAAAAATACTTGTCAAAAGAATACGCAAGCGACAAGGAAAAATGGGGTC
AATTTGACGCAGCTCGCTGGAATGCTTTCTACAAATGGGATAAAGAAAAT
GGTATCCTTAAAGAAGACTTGACAGACAAAGGCTTCACCAACGAATTTGT
GAAATAA 4106.4
(SEQ. ID. NO. 213)
ATGATAAAAAATCCTAAATTATTAACCAAGTCTTTTTTAAGAAGTTTTGC
AATTCTAGGTGGTGTTGGTCTAGTCATTCATATAGCTATTTATTTGACCT
TTCCTTTTTATTATATTCAACTGGAGGGGGAAAAGTTTAATGAGAGCGCA
AGAGTGTTTACGGAGTATTTAAAGACTAAGACATCTGATGAAATTCCAAG
CTTACTCCAGTCTTATTCAAAGTCCTTGACCATATCTGCTCACCTTAAAA
GAGATATTGTAGATAAGCGGCTCCCTCTTGTGCATGACTTGGATATTAAA
GATGGAAAGCTATCAAATTATATCGTGATGTTAGATATGTCTGTTAGTAC
AGCAGATGGTAAACAGGTAACCGTGCAATTTGTTCACGGGGTGGATGTCT
ACAAAGAAGCAAAGAATATTTTGCTTTTGTATCTCCCATATACATTTTTG
GTTACAATTGCTTTTTCCTTTGTTTTTCTTATTTTTATACTAAACGCTTT
GCTCAATCCTCTTTTTTACATTTCAGAAGTGACTAGTAAAATGCAAGATT
TGGATGACAATATTCGTTTTCATCAAACTAGGAAAGATGAAGTTGGTGAA
GTTGGAAAACAGATTAATGGTATGTATGAGCACTTGTTAAAGGTTATTTA
TGAGTTGGAAAGTCTGTAATGAGCAAATTGTAAAATTGCAAAATCAAAAG
GTTTCCTTTGTCCGCGGAGCATCACATGAGTTGAAAACCCCTTTAGCCAG
TCTTAGAATTATCCTAGAGAATATGCAGCATAATATTGGAGATTACAAAG
ATCATCCAAAATATATTGCAAAGAGTATAAATAAGATTGACCAGATGAGC
CACTTATTAGAAGAAGTACTGGAGTCTTCTAAATTCCAAGAGTGGACAGA
GTGTCGTGAGACCTTGACTGTTAAGCCAGTTTTAGTAGATATTTTATCAC
GTTATCAAGAATTAGCTCATTCAATAGGTGTTACAATTGAAAATCAATTG
ACAGATGCTACCAGGGTCGTCATGAGTCTTAGGGCATTGGATAAGGTTTT
GACAAACCTGATTAGTAATGCAATTAAATATTCAGATAAAAATGGGCGTG
TAATCATATCCGAGCAAGATGGCTATCTCTCTATCAAAAATACATGTGCG
CCTCTAAGTGACCAAGAACTAGAACATTTATTTGATATATTCTATCATTC
TCAAATCGTGACAGATAAGGATGAAAGTTCCGGTTTGGGTCTTTACATTG
TGAATAATATTTTAGAAAGCTATCAAATGGATTATAGTTTTCTCCCTTAT
GAACACGGTATGGAATTTAAGATTAGCTTGTAG 4106.6
(SEQ. ID. NO. 214)
ATGTATTTAGGAGATTTGATGGAGAAAGCCGAGTGTGGTCAATTTTCAAT
ACTTTCCTTTCTATTACAAGAGTCTCAGACGACCGTCAAGGCTGTAATGG
AAGAAACAGGATTTTCAAAAGCAACCCTAACCAAATATGTCACCCTGCTC
AATGACAAGGCTTTGGATAGTGGCTTAGAGCTGGCTATTCACTCAGAAGA
TGAAAATCTGCGTCTGTCTATCGGTGCAGCTACCAAGGGGAGAGATATTC
GGAGCTTGTTTTTGGAGAGTGCTGTTAAATACCAGATTTTGGTTTATCTT
CTCTACCACCAACAGTTTTTAGCCCATCAGCTGGCTCAAGAATTGGTGAT
TAGCGAGGCTACGCTTGGTCGTCACTTGGCTGGTTTAAATCAGATTTTGT
CAGAATTTGATTTATCCATCCAAAATGGCCGTTGGCGAGGTCCAGAGCAT
CAGATTCACTATTTCTATTTCTGTCTTTTCCGAAAGGTCTGGTCGAGTCA
GGAATGGGAAGGTCACATGCAGAAACCAGAGAGAAAACAGGAGATTGCCA
ATTTAGAGGAAATCTGCGGTCAAGTTTGTCTGCGGGGCAGAAATTGGAC
TTGGTTCTCTGGGCTCACATCAGTCAACAACGTCTTCGGGTCAATGCTTG
TCAGTTTCAAGTCATAGAAGAGAAAATGCGAGGGTATTTTGACAATATCT
TTTATCTTCGTTTGCTGAGAAAGGTTCCGTCCTTTTTTGCTGGGCAACAT
ATTCCACTAGGAGTTGAGGATGGTGAGATGATAATTCTTCTTCTTTTCT
CCTATCTCATCGCATTCTTCCTCTTCATACTATGGAGTATATTCTTGGTT
TTGGAGGGCAGTTGGCAGATTTACTGACGCAATTGATTCAAGAAATGAAG
AAGGAGGAACTATTGGGGGATTATACAGGAGCCATGTCACCTATGAAGT
CAGTCAGCTTTGTGCTCAAGCTCTATCTCTATAAGGGCTATATTTTACAGT
ATCGCTACAAGTACCAGTTAGAGAATCGTCATCCATATTTACTGATGGAA
CATGATTTTAAAGACACAGCAGAGGAGATTTTTCATGCTCTACCTGCTTT
TCAACAGGGACAGATTTAGATAAGAAGATTCTCTGGGAATTGGCTCCAGT
TAATCGAATATATGGCTGAAAACGGTGGCCAGCATATGCGGATTGGTCTG
GATTTGACATCTGGTTTCTTGTCTTTTCAAGGATGGCAGCCATTTTGAA
ACGGTATTTGGAATACAATCGTTTTATTACCATTGAAGCTTATGACCCTA
GTCGGCATTATGATTTGCTGGTTACCAATAACCCGATTCATAAGAAGGAA
CAGACACCAGTCTATTATTTAAAAAATGACTTGGATATGGAGGATTTGGT
AGCGATTCGCCAGTTATTATTCACTTAA 4106.7
(SEQ. ID. NO. 215)
ATGGAATTTTCAAAAGAAAACACGTGAATTGTCAATTAAAAAAATGCAGG
AACGTACCCTGGACCTCTTGATTATCGGTGGAGGAATCACAGGAGCTGGT
GTAGCCTTGCAGGCGGCAGCTAGCGGTCTTGAGACTGGTTTGATTGAAAT
GCAAGACTTTCAGAAGGAACATCTAGTCGTTCAACAAAATTGGTTCACG
GAGGACTTCGTTACCTCAAACAATTTGACGTAGAAGTGGTCTCAGATACG
GTTTCTGAACGTGCAGTGGTTCAACAAATCGCTCCACACATTCCAAAATC
AGATCCAATGCTCTTACCAGTTTACGATGAAGATGGAGCAACCTTTGCCC
TCTTCCGTCTTAAAGTAGCCATGGACTTGTACGACCTCTTGGCAGGTGTT 4106.8
(SEQ. ID. NO. 216)
ATGATGAATGAATTATTTGGAGAATTTCTAGGGACTTTTAATCCTGATTCT
TCTAGGAAATGGTGTTGTTGCAGGTGTGGTTCTTCCTAAAACCAAGAGCA
ATAGCTCAGGTTGGATTGTGATTACTATGGGTTGGGGATTGCAGTTGCG
GTTGCAGTCTTTGTATCTGGCAAGCTCAGTCCAGCTTATTTAAACCCAGC
TGTGACCATGGTGGCCTTAAAAGGTGGTTTGCCTTGGGCTTCCGTTT
TGCCTTATATCTTAGCCCAGTTCGCAGGGGCCATGCTGGGTCAGATTTTG
GTTTGGTTGCAATTCAAACCTCACTATGAGGCAGAAGAAATGCAGGCAA
TATCCTGGCAACCTTCAGTACTGGACCAGCCATCAAGGATACTGTATCAA
ACTTGATTAGCAAATCCTTGGAACTTTGTTTGTTTTGGTGTTGACAATCTTT
GCTTTGGGTCTTTACGACTTTCAGGCAGGTATCGGAACCTTTGCAGTGGG
AACTTTGATTGTCGGTATCGTCTATCACTAGGTGGGACAACAGGTTATG
CCTTGAACCCAGCTCGTGACCTTGGACCTCGTATCATGCACAGCATCTTG
CCAATTCCAAACAAGGGAGACGGAGACTGGTCTTACGCTTGGATTCCTGT
TGTAGGCCCTGTTATCGGAGCAGCCTTGGCAGTGCTTGTATTCTCACTTTT
TCTAG 4106.10
(SEQ. ID. NO. 217)
ATGAAAAGGACCTGGAGGAACTCATTCGTGACAAATCTTAATACACCTTT
TATGATTGGCAATATTGAGATTCCCAATCGTACCGTTTTAGCGCCTATGG
CTGGCGTGACCAACTCAGCCTTTCGTACTATCGCAAAGGAGCTCGGAGCT
GGACTCGTTGTAATGGAAATGGTCTCTGACAAGGGAATCCAATACAACAA
CGAAAAAACCCTGCACATGCTTCATATCGATGAGGGCGAAAACCCCTGTCT
CTATCCAACTTTTTGGTAGCGATGAAGACAGCCTAGCACGCGCAGCAGAA
TTCATCCAAGAAAACACCAAGACCGATATCGTCGATATCAACATGGGCTG
CCCTGTCAACAAAATCGTGAAGAACGAAGCTGGTGCTATGTGGCTCAAGG
ATCCAGACAAGATTACTCCATCATCAACAAGGTCCAGTCTGTCCTTGAT
ATCCCACTTACTGTCAAAATGCGTACCGGCTGGGCGGACCCATCTCTTGC
AGTAGAAAATGCTCTCGCTGCTGAAGCTGCAGGTGTTTCTGCCCTCGCCA
TGCATGGCCGTACCCGTGACAAGATTATACTGGCCACGCAGACCTTGAG
ACCCTTTACAAGGTTGCCCAAGCTCTAACCAAGATTCCATTCATCGCCAA
CGGTGATATCCGTACTGTCCAAGAAGCCAAGCAACGCATCGAAGAAGTTG
GTGCTGACGCAGTCATGATTGGCCGAGCTGCCATGGGAAATCCTTACCTC
TTCAACCAAATCAACCATTACTTTGAACAGGAGAAATCCTACCTGATTT
GACCTTTGAAGACAAGATGAAGATCGCCTAGGACACTTGAAACGATTGA
TTAACCTCAAAGGAGAAACGTCGCAGTTCGTGAATTCCGCGGTCTCGCT
CCTCACTATCTCCGTGGAACATCTGGCGCTGCCAAATCCGTGGGAGCCAT
TTCCAAGCCAGCACCCTGGCAGAGATTGAAACCCTCTTGCAATTGGAGA
AGGCTTAA 4107.1
(SEQ. ID. NO. 218)
ATGACAAAGAAGAAATTGAGCGTATTTCTGTAATACACCGAGAAAAGAT
TTTATGGCTCAAGTGGTATTTCATGCGAGATAAAGAACAACCTAAGTATA
GTGTCCTTGAGCGTAAAATGTTTGATGCTGCTAAAAATCAAGATATGCTA
GCTTATCAAAAATACGCAACTATCAAGCAGATAACAGATATTAGGGTACA
AACAAGTGAGGCTGACATTTTAGAGGCTGTAAAAGAGGTTTATGTGTACA

TABLE 1-continued

```
ATCACATGAATGTTATCGGAGCTTGTCAGCGGATATTATTTATCAGTCAA
TCACCAGCTTATGATAAGTTAAATAAGTGGTTTAATATCTATTCTGATTT
GTATTTTAGCGTTGTACCCTTGCCCAAAATGGGGTATATCATGAGATGG
TAGGTATCTAG
```

4107.2

(SEQ. ID. NO. 219)

```
ATGAAAAATTCCAACGAGGCTGAGATGAAATTACTTTATACTGATATTCG
GACTTCTTTGACAGAAATTCTAACAAGAGAGGCAGAAGAGCTAGTTGCAG
CTGGCAAGCGGGTCTTCTACATTGCCCCCAACTCTCTTTCTTTTGAAAAG
GAACGCGCCGTGCTGGAATACTTGTCCCAGCAGGCTTCTTTTTCGATTAC
CGTCACGCGCTTTGCTCAAATGGCTCGCTATCTGGTCTTGAATGATTTAC
CAGCTAAAACTACTCTTGATGATATCGGTCTTGGGTTGGCCTTTTACAAA
TGCCTTGCCGAACTCGATCCCAAGGACTTGCGTGTTTATGGCGCTATTAA
GCAGGATCCTCAATTGATCCAGCAGTTAATTGAGCTTTACCATGAGATGA
CCAAATCTCAGATGAGTTTTTTGGACTTGGAGAATTTAACAGATGAGGAT
AAGAGGGCGGATTTACTCTTGATTTTTGAGAAAGTAACAGCCTATCTTAA
TCAAGGTCAGTTAGCCCAGGAAAGTCAGTTGTCCCATTTGATTGAGGCTA
TTGAGAATGACAAGGTAAGTAGTGATTTTAATCAAATCGCCTTGGTCATT
GACGGCTTTACTCGTTTTTGACTTGGACTTGATTGTCGTCAGCTTTACT
TCACGGCAAAGGTGTTGAGATTGTTATCGGGGCTTATGCTAGTAAGAAAG
CCTATACCAGTCCTTTTAGCGAGGGCAATCTCTACCAAGCCAGCGTAAAA
TTTCTCCATCATCTGGCTTCTAAATACCAAACGCCTGCTCAGGACTGTTC
TCAAACTCATGAGAAGATGGATAGTTTTGACAAGGCCTCTCGTTTGTTGG
AGTCTTCTTATGACTTTTCAGAACTCGCTTTGGATGTCGATGAGAAAGAC
CGTGAAAATTTACAAATCTGGTCTTGTTGACGCAAAAGGAGGAGTTGGA
GCTAGTAGCCCGTAGTATTCGTCAGAAATTACATGAGAACTCAGACCTGA
GCTACAAGCATTTTCGTATTCTCTTGGGGATGTAGCTTCTTACCAGTTA
TCTCTCAAAACCATTTTTGACCAGTATCAGATTCCTTTTTATCTTGGTAG
AAGCGAAGCCATGGCTCATCATCCCTTGACTCAGTTTGTCGAGTCTATTT
TAGCTTTAAAACGTTACCGTTTTCGTCAGGAGGATTTGATTAATCTTCTT
AGAACTGATTTGTATACTGACCTCAGTCAGTCTGATATTGATGCTTTTGA
GCAATATATCCGCTATCTTGGTATCAATGGCTTGCCAGCCTTTCAGCAAA
CCTTCACCAAATCCCACCATGGAAAATTTAATCTTGAGCGTTTGAATGTC
CTCCGCCTGAGAATTTTAGCACCTCTTGAAACCCTCTTTGCCAGCCGAAA
ACAAAAGGCTGAAAAACTCCTACAAAAATGGAGTGTCTTTCTAAAAGAAG
GAGCTGTGACCAAGCAGTTACAAGATTTGACAACCATCTTGGAAGCTGA
GAACAGGAAAGACAAGCCGAAGTTTGGAAGGCTTTCTGCCATGTTTTAGA
ACAATTTGCGACTGTTTTTGCTGGTTCACAGGTTAGTCTGGAAGACTTCC
TAGCCTGCTCCATTCTGGAATGAGTTTGTCCCAATACCGTACCATTCCAG
CAACAGTGGACACTGTTCTGGTGCAGCGTTACAGTTTGATTGCACCATTG
ACTGCTGACTTTGTCTATGCTATTGGACTAACTCAGGACATTTACCAAA
AATTTCTCAAAACACCAGTCTTCTGACAGATGAAGAAGGCAAAACCTAA
ACCAAGCGACCGAAGAAGGCGTTCAATTACTGATTGCCAGCAGTGAAAAT
CTCAAGAAAAATCGCTACACTATGCTTTCCTTGCTCAATTCTGCTCGTAA
GCAGTTGTTCTTGTCGGCTCCAAGCCTTTTTAACGAAAGTGAAAGTAAGG
AATCTGCCTATCTTCAAGAGTTGATCCATTTTGGATTTAGGCGGAGAGAG
AAGAGGATGAATCACAAAGGACTGTCTAAGGAGGATATGGGGTCCTATCA
CAGTCTTTTGTCTAGTCTGGTTGCCTATCACCAGCAGGGTGAGATGAGCG
ATACTGAGCAAGATTTGACTTTTGTCAAGGTTCTGTCGCGTGTCATAGGT
AAAAAACTAGATCAGCAAGGTCTGGAAAATCCAGCTATCCCAACCAGTCC
AAGCAGCAAGACCTTAGCCAAGGACACCTTGCAAGCTCTCTATCCTGCCA
AACAGGAGTTTTACCTGTCTACGTCGGGTTTGACAGAGTTTTATCGCAAT
GAATACAGTTATTTCCTACGCTACGTTTTAGGCTTGCAGGAGGAATTACG
TTTGCATCCTGATGCCCGTAGTCACGGGAATTTCTTGCATCGTATCTTTG
AACGCGCCTTACAGTTGCCTAATGAAGATTCCTTTGACCAACGTCTAGAA
CAAGCTATTCAAGAAACCAGTCAAGAACGCGAATTTGAAGCTATTTCA
AGAAACTTTGGAAGCCAGTTTGACCAGAAGTTTTGCTTGATGTTGCAC
GGACAACTGGACATATTCTCCGACACAATCCAGCCATCGAAACCATCAAA
GAAGAAGCAAATTTTGGTGGAAAAGACCAAGCCTTTATTCAATTAGACAA
TGGACGCAGTGTCTTTGTACGAGGCAAGGTGGACCGGATTGACCGTTTGA
AAGCTAATGGAGCGATAGGAGTAGTAGACTACAAATCCAGTCTGACTGA
TTCCAGTTTCCTCATTTCTTTAATGGGCTCAATTCTCAGTTACCAACCTA
TCTTGCTGCCCTAAAAAGAAGGGGAGCAGAACTTTTTCGGCGCCATGT
ACTTGGAAATGGCTGAACCTGTCCAATCTCTGATGGCGGTAAAAAGTCTG
GCAGGAGCAGTGGTAGAGACCGACAAATCTATGAAATCTAACCAAGGGCTCTT
CTTGGAAAAGAAAGCAGTTATTTAGGCGAATTTATAAACAAAAACAAGG
CTAATCAACTGACAGATGAGGAATTCAGCTCCTACTGGACTACAATGCC
TATCTTTACAAGAAAGCTGCTGAGAAGATTTTAGCAGGCCGGTTCGCCAT
CAATCCTTATACTGAAAATGGCAAGCATTGCCCCATACGTCCAGCAAC
ATCAGGCTATTACAGGCTTTGAAGCCAATTACCATCTGGGCCAAGCCCGT
TTCCTAGAAAAGTTGGACCTAGCTGATGGCAAGCGTCTGGTCGGAGAAAA
ACTCAAGCAAGCTTGGCTTGAAAAAATAAGAGAGGAGTTGAATCGATGA
```

4107.3

(SEQ. ID. NO. 220)

```
ATGAAGCTTATTCCCTTTTTAAGTGAGGAGGAGATTCAAAAACTGCAAGA
AGCAGAAGCAAATTCGAGCAAGGAACAGAAGAAAACTGCCGAGCAAATCG
AAGCTATCTACACTTCTGCCCAGAATATCCTGGTCTCAGCATCGGCTGGT
```

```
TCTGGAAAGACCTTTGTCATGGCAGAGCGCATTCTGGACCAATTGGCGCG
TGGTGTCGAAATTTCTCAACTCTTTATCTCAACCTTTACCGTCAAGGCTG
CAACTGAACTTAAAGAACGTTTAGAGAAAAAAATCAGCAAGAAAATCCAA
GAAACAGATGATGTCGACCTCAAACAACACTTGGGTCGCCAGTTGGCAGA
CCTACCCAACGCTGCCATTGGAACCATGGATTCTTTCACACAAAAATTCC
TTGGCAAACATGGTTATCTGCTTGATATTGCACCTAATTTCCGTATTTTA
CAAAACCAAAGCGAGCAACTTATTCTCGAAAACGAAGTCTTTCATGAGGT
CTTTGAAGCGCATTACCAAGGTAAACAGAAAGAGACCTTTAGTCATTTGC
TGAAAAACTTTGCTGGGCGTGGCAAGGACGAACGGGGTCTGCGCCAGCAG
GTCTATAAATCTATGACTTCCTCCAATCCACCAGTAATCCTCAAAAGTG
GCTGAGTGAATCTTTCCTCAAAGGATTTGAGAAAGCTGATTTTACCAGTG
AAAAAGAAAAACTGACCGAGCAAATCAAACAAGCCCTTTGGGATTTGGAA
AGCTTTTTCCGTTACCATCTGGATAACGATGCCAAGGAGTTTGCAAAGGC
TGCCTATTTAGAAAATGTTCAGTTAATTCTGGATGAAATTGGCTCCCTAA
ATCAGGAGTCCGATAGTCAGGCTTATCAGGCAGTGCTTGCGCGTGTTGTC
GCCATCTCTAAGGAGAAAAACGGTCGAGCTCTGACTAATGCCAGCCGTAA
GGCTGATTTGAAGCCCCTGGCTGATGCCTACAACGAAGAGAGAAAGACCC
AGTTTGCTAAACTAGGACAATTATCAGACCAGATAGCGATTCTCGACTAT
CAAGAACGTTATCATGGAGACACTTGGAAACTAGCTAAAACCTTCCAATC
TTTCATGAGCGATTTTGTAGAGGCTTATGTCAGAGAAACGACAGGAAA
ATGCCTTCGAATTCGCTGATATCAGCCATTACACCATTGAGATTTTAGAG
AATTTCCCACAAGTTCGTGAGTCTTATCAGGAGCGCTTCCATGAAGTCAT
GGTCGATGAGTATCAGGATACCAACCATATTCAAGAACGGATGCTGGAAT
TGTTGTCTAATGGCCACAATCGCTTTATGGTGGGAGATATCAAGCAATCC
ATCTATCGTTTCCGTCAGGCAGACCGCAGATTTTCAATGAGAAATTCCA
ACGCTATGCGCAAAATCCCCAAGAAGGCAGGCTCATTATCCTCAAGGAAA
ATTTCCGTAGTAGTTCAGAAGTGCTGTCAGCAACCAATGATGTCTTTGAA
CGTCTCATGGACCAAGAGGTCGGCGAAATCAACTATGATAACAAGCACCA
GCTTGTTTTTGCCAATACCAAACTGACTCCCAATCCAGACAACAAGGCAG
CATTTCTCCTCTACGACAAGGACGATACAGGTGAGGAAGAAGAGAGTCAA
ACAGAAACGAAACTAACAGGCGAAATGCGCTTAGTTATCAAGGAGATTCT
GAAACTTCATCAAGAAAAAGGTGTTGCCTTTAAGGAAATTGCCCTTCTGA
CCTCCAGCCAGTCGTAATGACCAGATTCTCCTCGCCTGTCTGAGTAC
GGAATTCCTGTCAAAACTGACGGAGAGCAAAACAATTATCTCCAATCCT
AGAAGTGCAAGTCATGCTAGACACTCTTCGTGTCATTCACAATCCCTGC
AAGACTACGCCTTGGTTGCCCTTATGAAGTCTCCAATGTTTGGTTTTGAT
GAGGATGAAGCTGACTACAGTTTGTCCCTTCAGAAAGCAGGGATAAAGTCCA
CGAAAATCTCTATGAGAAACTGGTCAATGCACAAAAAAGTGCAAGTAGTC
AAAAAAGGCTTGATTCACACAGCTCTAGCTGAAAAACTAAAGCAATTCATG
GATATCCTAGCTTCTTGGCGCTTGTATGCCAAAACCCACTCTCTCTATGA
CTTGATTTGGAAGATTTACAACGACCGTTTTATTATGACTATGTTGGGG
CTTTGCCGAATGGTCCTGCTAGGCAGGCCAATCTCTATGCCCTAGCACTG
CGTGCTGATCAATTTGAAAAGAGCAATTTCAAAGGTTTGTCGCGTTTTAT
TCGTATGATTGACCAAGTCTTAGAAGCCCAGCACGATTTGGCAAGCGTGG
CCGTCGCACCGCCAAAAGATGCAGTAGAGCTCATGACCATCCACAAGAGT
AAAGGGCTGGAGTTTCCTTACGTCTTTATCCTCAATATGGATCAAGATTT
CAACAAGCAAGACTCTATGTCAGAAGTCATTCTCAGTCGTCAGAATGGTC
TTGGTGTCAAATATATTGCCAAGATGGAGACAGGGGCAGTAGAAGACCAC
TATCCTAAAACCATCAAACTCTCCATTCCTAGTCTGACCTATAGGCAGA
CGAAGAGGAATTACAGCTAGCAAGCTATTCTGAGCAGATGCGTTTGCTGT
ATGTTGCTATGACGCGGGCTGAGAAAAAGCTCTATCTTGTCGGCAAGGGT
TCTCGTGAAAAGCTGGAATCCAAGGAATACCCAGCAGCCAAAAATGGGAA
ACTAAATAGCAATACTAGACTGCAAGCACGGAATTTCCAAGATTGGCTTT
GGGCTATCAGTAAAGTGTTTACTAAGGACAAGCTCAACTTTAGTTATCGT
TTTATTGGCGAAGATCAGTTGACCAGAGAACTTCGGAGAGTTGGAAAC
CAAGAGTCCTCTCCAAGATAGCTCCCAAGCAGACAATCGTCAGTCAGATA
CCATCAAAGAAGCTCTGGAAATGCTGAAGGAGGTGGAAGTTTATAATACT
CTTCACCGCGCAGCTATTGAACTTCCTAGTGTTCAAACCCCAAGTCAGT
CAAGAAATTCTACGAACCAGTTATGGATATGGAAGGTGTCGAGATTGCTG
GTCAAGGTCAGTCAGTAGGCAAGAAAATCAGCTTCGATTTGCCAGATTTT
TCAACCAAAGAAAGGTAACTGGAGCTGAGATTGGTAGTGCTACTCACGA
ACTCATGCAGGAATTGACCTCAGCCAGCAACTAACCCTTGCTAGCCTAA
CAGAAACACTCAAACAAGTTCAAACTAGCCAAGCTGTCAGAGACAAGATC
AATCTTGATAAATTCTTGCTTTCTTTGACACAGTACTCGGTCAGGAAAT
TCTTGCTAATACCGACCATCTTTATCGCGAGCAACCTTTCTCCATGCTCA
AACGAGACCAAGCAGGTCAGGAAGCTTGTTGTCCGTGGTATCCTTGAT
GGCTATCTGCTTTACGAAAACAAAATTGTTCTGTTCGACTACAAGACAGA
CCGCTATGATGAACCAAGTCAACTCGTAGACCGCATCGTGGTCAGTTAG
CTCTATACGAAGAGGCTTTATCACGAGCCTATTCGATTGAAAATATTGAA
AAATACTTGATTTTACTCGGTAAAGACGAGGTTCAAGTTGTAAAGTATA
A
```

4109.1

(SEQ. ID. NO. 221)

```
ATGGAACTTGCTCGCCATGCTGAAACGTTGGGAGTAGATGCTATTGCAA
GATTCCACCAATTTATTTCCGCTTGCCAGGAATACTCAGTTGCCAAATACT
GGAACGATATCAGTTCTGCAGCTCCAAACACAGACTACGTGATTTACAAC
ATTCCTCAATTGGCAGGGGTTGCTTTGACTCCAAGCCTTTACACAGAAAT
GTTGAAAAATCCTCGTGTTATCGGTGTGAAGAACTCTTCTATGCCAGTTC
```

TABLE 1-continued

AAGATATCCAAACCTTTGTCAGCCTTGGTGGAGAAGACCATATCGTCTTT
AATGGTCCTGATGAGCAGTTCCTAGGAGGACGCCTCATGGGGGCTAGGGC
TGGTATCGGTGGTACTTATGGTGCTATGCCAGAACTCTTCTTGAAACTCA
ATCAGTTGATTGCGGATAAGGACCTAGAAACAGCGCGTGAATTGCAGTAT
GCTATCAACGCAATCATTGGTAAACTCACTTCTGCTCATGGAAATATGTA
CGGTGTCATCAAAGAAGTCTTGAAAATCAATGAAGGCTTGAATATTGGAT
CTGTTCGTTCACCATTGACACCAGTGACTGAAGAAGATCGTCCAGTTGTA
GAAGCGGCTGCTGCCTTGATTCGTGAAACCAAGGAGCGCTTCCTCTAA 4110.2
(SEQ. ID. NO. 222)
ATGTATAAGACAAAGTGTTTACGAGAGAAGTTAGTATTATTTTTAAAAAT
TTTCTTCCCAATCCTGATCTACCAATTTGCCAATTATTCTGCCTCTTTTG
TTGATACTGCAATGACAGGTCAATACAACACTATGGACTTGGCTGGTGTA
TCTATGGCAACCAGTATCTGGAATCCTTTCTTTACATTTCTAACAGGGAT
TGTGTCAGCCTTGGTGCCTATCATTGGTCACCATCTTGGTCAGGCAAAA
AGGAAGAAGTTGCGTCTGATTTTTACCAATTTATTTATTTGGCCTTGGGC
CTATCTGTGGTCTTGCTGGGGATGGTACTTTTCTTGGCACCAATAATCTT
GAATCATATTGGGTTAGAAGCAGCAGTAGCGGCAGTAGCGGTTCGCTATC
TTTGTTTTTATCTATCGGGATTATCCCCTTGTTGCTCTTTAGCGTCATT
CGTTCCTTGCTGGATTCGCTGGGCTTGACCAAACTGTCCATGTACCTCAT
GCTTTTCTTACTCCCTCTCAATAGCGGATTTAACTATCTCTTGATTTACG
GTGCCTTTGGTGTTCCACAACTGGGAGGGGCTGGTGCTGGTTTAGGAACA
TCCTTGCCTACTGGGTCTTGCTTGGGATTTCTGTTCTGGTTTTATTTAA
AACAGGAGAAGCTCAAAGCCTTACACCTTGAGAAACGAATTCCACTTAAT
ATGGATAAAATTAAGGAAGGAGTTCGTTTAGGTCTGCCTATTGGGGGAAC
TGTCTTCGCGGAAGTGGCTATCTTTTCAGTGGTTGGCTTGATTATGGCTA
AGTTTTCGCCCTTGATTATAGCTAGTCACCAGTCAGCTATGAACTTTCA
AGTCTTATGTACGCCTTTCCTATGAGTATCTCATCGGCTATGGCTATTGT
CGTTTCCTATGAAGTGGGAGCCAAGCGATTTGATGATGCGAAAACCTATA
TTGGTCTAGGAAGATGGACTGCCCTCATTTTTGCGGCCTTCACCTTAACC
TTCCTTTACATTTTTAGGGGAAATGTGGCCAGTCTTTATGGTAACGACCC
AAAATTTATCGATTTGACAGTGCGTTTTTAACTTATAGTCTTTTCTTCC
AGTTAGCAGATACCTTTCGGCGCCGCTTCAGGGAATTTTGCGGGGGTAT
AAGGATACAGTTATTCCTTTTTACCTTGGTTTGCTTGGTTATTGGGGCGT
AGCAATCCCTGTGTACGCTATTTGA 4112.2
(SEQ. ID. NO. 223)
ATGAGTACTTTAGCAAAAATAGAAGCGCTCTTGTTTGTAGCGGGTGAAGA
TGGGATTCGGGTCCGCCAGTTAGCTGAACTCCTCTCTCTGCCACCGACAG
GCATCCAGCAAAGTTTAGGAAAATTAGCCCAGAAGTATGAAAAGGACCCA
GATTCCAGTTTGGCTTTGATTGAGACAAGTGGTGCTTATAGATTGGTGAC
CAAGCCTCAATTTGCAGAGATTTTGAAGGAATACTCTAAGGCGCCTATCA
ACCAGAGCTTGTCTCGGGCTGCCCTTGAGACCTTGTCCATTATTGCCTAC
AAACAGCCGATTACGCGGATAGAATTGATGCCATCCGTGGAGTTAACTC
GAGTGGAGCCTTGGCAAAGTTGCAGGCTTTTGACCTGATAAAGGAAGACG
GGAAAAAGGAAGTATTGGGGCGCCCCAACCTCTATGTGACTACGGATTAT
TTCCTAGATTACATGGGGATAAACCATTTAGAAGAATTACCAGTGATTGA
TGAGCTTGAGATTCAAGCCCAAGAAAGCCAATTATTTGGTGAAAGGATAG
AAGAAGATGAGAATCAATAA 4113.1
(SEQ. ID. NO. 224)
ATGGATACGATGATTAGTAGATTTTTTCGCCATTTATTTGAAGCCTTAAA
AAGTTTGAAACGAAATGGTTGGATGACAGTAGCTGCTGTCAGTTCAGTCA
TGATTACTTTGACCTTGGTGGCAATATTTGCATCTGTTATTTTCAATACA
GCGAAACTAGCTACAGATATTGAAAATAATGTCCGTGATGTTTATAT
CCGAAAGGATGTGGAAGATAATAGTCAGACAATTGAAAAAGAAGGTCAAA
CTGTTACAAATAATGACTACCACAAGGTATATGATTCTTGAAGAACATG
TCTACGGTTAAAAGTGTTACCTTTTCAAGTAAAGAAGAACAATATGAAAA
ATTAACCGAGATAATGGGAGTAACTGGAAAATCTTTGAAGGAAATCTGA
ATCCTCTCTATGATGCCTATATTGTAGAGGCAAACACTCCAAATGATGTA
AAAACTATAGCCGAAGATGCTAAAAAAATTGAAGGTGTCTCTGAGGTTCA
AGATGGCGGTGCCAATACAGAAAGACTCTTCAAGTTAGCTTCATTTATCC
GTGTTTGGGGACTAGGGATTGCTGTTTGTAAACCTTGGGTAGTAGTTTATAT
TTGATTTCAAATACCATTCGTATTACCATTATTTCCCGCAGTCGCGAAAT
TCAAATCATGCGCTTGGTCGGAGCTAAAAACAGTTATATCCGTGGACCGT
TCTTGTTAGAAGGAGCCTTTATCGGTTTATTGGGAGCTATCGCACCATCT
GTTTTGGTCTTTATTGTTTATCAAATTGTTTACCAATCTGTCAACAAATC
GTTGGTAGGGCAAAATCTATCCATGATTAGTCCAGATTTATTTAGTCCGT
TGATGATTGCCCTACTATTTGTGATTGGGGTTTTCATTGGTTCATTGGGA
TCAGGAATATCCATGCGCCGATTCTTGAAGATTTAG 4117.1
(SEQ. ID. NO. 225)
ATGAAGAAAGTAAGAGATTTATTTTTTTAGCTCTGCTATTTTTCTTAGCTAG
TCCAGAGGGTGCAATGGCTAGTGATGGTACTTGGCAAGGAAAACAGTATC
TGAAAGAAGATGGCAGTCAAGCAGCAAATGAGTGGGTTTTTGATACTCAT

TATCAATCTTGGTTCTATATAAAAGCAGATGCTAACTATGCTGAAAATGA
AATGGCTAAAGCAAGGTGACGACTATTTTTACCTCAAATCTGGTGGCTATA
TGGCCAAATCAGAATGGGTAGAAGACAAGGGAGCCTTTTATTATCTTGAC
CAAGATGGAAAGATGAAAAGAAATGCTTGGGTAGGAACTTCCTATGTTGG
TGCAACAGGTGCCAAAGTAATAGAAGACTGGGTCTATGATTCTCAATACG
ATGCTTGGTTTTATATCAAAGCAGATGGACAGCACGCAGAGAAAGAATGG
CTCCAAATTAAAGGGAAGGACTATTATTTCAAATCCGGTGGTTATCTACT
GACAAGTCAGTGGATTAATCAAGCTATGATGTGAATGCTAGTGGTGCCAAAG
TACAGCAAGGTTGGCTTTTTGACAAACAATACCAATCTTGGTTTTACATC
AAAGAAAATGGAAACTATGCTGATAAAGAATGGATTTTCGAGAATGGTCA
CTATTATTATCTAAATCCGGTGGCTACATGGCAGCCAATGAATGGATTT
GGGATAAGGAATCTTGGTTTTATCTCAAATTTGATGGGAAAATGGCTGAA
AAAGAATGGGTCTACGATTCTCATAGTCAAGCTTGGTACTACTTCAAATC
CGGTGGTTACATGACAGCCAATGAATGGATTTGGGATAAGGAATCTTGGT
TTTATCTCAAATCTGATGGGAAAATAGCTGAAAAAGAATGGGTCTACGAT
TCTCATAGTCAAGCTTGGTACTACTTCAAATCCGGTGGTTACATGACAGC
CAATGAATGGATTTGGGATAAGGAATCTTGGTTTACCTCAAATCTGATG
GGAAAATAGCTGAAAAAGAATGGGTCTACGATTCTCATAGTCAAGCTTGG
TACTACTTCAAATCTGGTGGCTACATGGCGAAAATGAGACAGTAGATGG
TTATCAGCTTGGAAGCGATGGTAAATGGCTTGGAGGAAAAACTACAAGTG
AAAATGCTGCTTACTATCAAGTAGTGCCTGTTACAGCCAATGTTTATGAT
TCAGATGGTGAAAAGCTTTCCTATATATCGCAAGGTAGTGTCGTATGGCT
AGATAAGGATAGAAAAAGTGATGACAAGCGCTTGGCTATTACTATTTCTG
GTTTGTCAGGCTATATGAAAACAGAAGATTTACAAGCGCTAGATGCTAGT
AAGGACTTTATCCCTTATTATGAGAGTGATGGCCACCGTTTTTATCACTA
TGTGGCTCAGAATGCTAGTATCCCAGTAGCTTCCATCTTTCTGATATGG
AAGTAGGCAAGAAATATTATTCGGCAGATGGCCTGCATTTTGATGGTTTT
AAGCTTGAGAATCCCTTCCTTTTCAAAGATTTAACAGAGGCTACAAACTA
CAGTGCTGAAGAATTTGGATAAGGTATTTAGTTTGCTAAACATTAACAATA
GCCTTTTGGAGAACAAGGGCGCTACTTTTAAGGAAGCCGAAGAACATTAC
CATATCAATGCTCTTTATCTCCTTGCCCATAGTGCCCTAGAAAGTAACTG
GGGAAGAAGTAAAATTGCCAAAGATAAGAATAATTTCTTTGGCATTACAG
CCTATGATACGACCCCTTACCTTTCTGCTAAGACATTTGATGATGTGGAT
AAGGGAATTTTAGGTGCAACCAAGTGGATTAAGGAAAATTATATCGATAG
GGAAGAACTTCCTTGGAAACAAGGCTTCTGGTATGAATGTGGAATATG
CTTCAGACCCTTATTGGGCGAAAAAATTGCTAGTGTGATGATGAAAATC
AATGAGAAGCTAGGTGGCAAAGATTAG 4119.2
(SEQ. ID. NO. 226)
ATGAAAAAAGTATTACAAAAATATTGGGCATGGGCTTTTGTGGTCATCCC
CCTCTTGTTACAAGCAATTTTCTTCTATGTGCCGATGTTTCAAGGAGCCT
TTTACAGTTTTACCAACTGGACAGGATTGACTTATAACTACAAATTTGTT
GGCTTAAACAACTTTAAGCTCCTCTTCATGGATCCAAAATTCATGAATGC
GATTGGCTTTACCGCAATCATTGCGATTGCCATGGTGGTTGGTGAGATTG
CACTCGGGATCTTCATTGCGCGTGTCTTGAATTCTAAAATCAAAGGCCAA
ACCTTCTTCCGTGCTTGGTTCTTCTTCCCAGCTGTTTTATCTGGTTTGAC
AGTGGCTTTGATCTTCAAGCAAGTCTTCAACTACGGTCTTCCAGCGATTG
GAAATGCCCTTCATATTGAATTTTTCCAAACCAGTCTTTTAGGGACTAAG
TGGGGAGCAATCTTTGCGGCTGTCTTTGTCCTTCTTGGCAAGGGGTGGC
TATGCCCATCATCATCTTCCTAGCTGGTTTGCAATCTATTCCAACTGAGA
TTACAGAGGCAGCAAGGATTGATGGTGCGACTAGCAAGCAAGTTTTCTGG
AACATTGAATTGCCTTACTTGCTACCAAGTGTCTCTATGGTCTTTATCCT
AGCCTTAAAAGGTGGGCTGACTGCCTTTGACCAAGTCTTTGCCATGACCGG
TGGTGGTCCAAACAATGCCACAACCTCACTTGGGCTCTTGGTTTATAACT
ATGCCTTTAAAAACAACCAATTCGGTTATGCCAATGCCATTGCCGTAATC
TTGTTCTTCTTAATTGTAGTGATTTCGATCATCCAATTGAGAGTATCTAA
GAAATTTGAAATTTAA 4119.3
(SEQ. ID. NO. 227)
ATGATGAAACAAGATGAAAGAAAAGCCCTGATTGGCAAATACATTCTATT
GATTCTAGGATCGGTTCTGATTTTAGTGCCGCTCCTTGCTACCCTCTTTA
GTTCCTTCAAACCCACTAAGGATATTGTAGATAATTTCTTTGGCTTTCCA
ACCAACTTCACATGGGACAACTTTAGCCGTCTCTTAGCTGATGGGATTGG
AGGCTATTATTGGACTCTGTCGTCATCACTGTCTTGTCTTATTTTCAGTG
TAATGATCTTTATCCCTATGGCAGCGTACTTCCATCGCTCGCAATATGAGT
AAAAAGAAAGCCTTTACCATCATGTATACCCTCTTAATCCTCGGAATCTT
CGTACCTTTCCAAGTCATCATGATTCCGATTACGGTTATGATGAGTAAAC
TCGGTTTGCTGTTTTGGTGATTGCTCTACTTGACCTATGCG
ATTCCACAGACCCTCTTTCTCTATGTTGGCTATATCAAAATCTCGATTCC
AGAAAGTCTGGATGAAGCAGCAGAGATCGATGGGCTAATCAATTTACAA
CCTATTTCCGCATCATCTTCCCAATGATGAAACCGATGCATGCGACAACC
ATGATCATCAATGCCCTTTGGTTCTGGAAGTGACTTCATGTTGCCACTCCT
TGTCTTGACCGGGATTCCAAAATGTGGACTCTGCCTTTGTTCCAATACA
ACTACGCAGGCCAATATTTCAACGACTACGGACCAAGCTTTGCCTCTTAC
GTGGTCGGCATTATCAGTATCACCATTGTCTATCTCTTCTTCCAACGCCA
TATCATTTCAGGAATGAGCAACGGGGCAGTGAAGTAA

TABLE 1-continued 4119.4

(SEQ. ID. NO. 228)
ATGAAAAGTATTCTTCAGAAAATGGGGGAGCATCCGATGCTGCTTCTTTT
TCTTAGCTATAGTACTGTTTATATCCATTCTTGCACAAAATTGGATGGGT
CTTGTGGCTTCAGTAGGAATGTTTCTATTTACTATTTTCTTTTTGCACTA
TCAGTCGATTTTATCCCATAAATTCTTTCGATTGATTTTGCAGTTTGTCT
TGTTTGGTAGTGTCTTGTCAGCTGCTTTTGCCAGTTTAGAACATTTCCAA
ATTGTGAAGAACTTTAACTATGCTTTTCTTTCACCCAATATGCAGGTGTG
GCATCAGAACCGGGCAGAAGTGACCTTCTTTAATCCTAATTATTATGGAA
TTATTTGTTGTTTCTGTATTATGATTGCTTTCTATCTGTTTACAACGACG
AAGTTGAATTGGTTGAAAGTATTCTGTGTGATTGCAGGCTTTGTTAATCT
CTTTGGTTTGAACTTTACTCAAAATCGAACTGCCTTTCCTGCTATTATCG
CTGGAGCAATTATCTATCTCTTTACGACTATTAAAACTGGAAGGCCTTT
TGGCTTAGTATTGGGGTCTTCGCGATTGGTTTGAGTTTCCTCTTTTCTAG
TGATTTGGGAGTTCGAATGGGTACTTTAGACTCTTCTATGGAAGAACGCA
TTTCTATCTGGGATGCTGGGATGGCCTTGTTTAAGCAAAATCCTTTTTGG
GGTGAAGGGCCATTGACCTATATGAACTCTTATCCTCGGATACATGCTCC
TTATCATGAACATGCCCACAGTCTTTATATTGATACGATTCTGAGTTACG
GAATTGTGGGACTATTTTATTAGTTTTGTCTTCTGTTGCTCCTGTTCGC
TTGATGATGGATATGAGTCAGGAGTCGGGGAAACGTCCGATTATCGCCT
TTATCTATCTTTCCTTACAGTGGTTGCTGTGCACGGAATTTTTGACTTGG
CTCTCTTCTGGATTCAGTCAGGCTTTATTTTCTTGCTAGTTATGTGCAGT
ATTCCATTGGAGCATCGAATGTTGGTATCGGACATGACGGATTAA 4120.1

(SEQ. ID. NO. 229)
ATGTCAAAGATGGATGTTCAGAAAATCATTGCACCGATGATGAAGTTTGT
GAATATGCGTGGCATTATAGCTCTAAAAGATGGGATGTTAGCAATTTGC
CATTGACAGTAGTTGGTAGTTTGTTCTTGATTATGGGACAATTGCCGTTC
GAAGGATTAAATAAGAGCATTGCTAGTGTTTTGGAGCTAATTGGACAGA
GCCGTTTATGCAAGTATATTCAGGAACTTTTGCTATTATGGGTCTAATTT
CTTGTTTTTCAATTGCCTATTCTTATGCTAAGAATAGCGGCGTAGAGGCT
TTACCAGCTGGACTTCTATCTGTATCTGCATTCTTTATTTTGCTAAGATC
ATCTTATATCCCTAAACAAGGTGAGGCAGTTGGGGACGCTATTAGTAAAG
TTTGGTTTGGAGGCCAAGGAATTATCGGTGCTATCATTATAGGGTTTGTA
GTAGGAAGTATTTATACCTTCTTTATAAAGAGAAAAATTGTTATTAAGAT
GCCAGAACAAGTTCAACATGCTATTGCCAAACAGTTTGAAGCAATGATTC
AGCATTTGTAATTTTCTTATCTTCTATGATTGTATATATTTTAGCGAAG
TCATTGACTAATGGCGGAACATTCATAGAAATGATTTATTCTGCTATTCA
AGTTCCGTTGCAAGGTTTAACTGGATCTTTGTATGGTGCTATTGGAATTG
CATTCTTTTATATCATTTTTGTGGTGGTTTGGTGTTCATGGGCAATCGTA
GTAAATGGAGTAGTGACAGCTCTGCTTTTATCTAATCTTGATGCTAATAA
AGCTATGTTAGCCTCTGCTAATCTATCATTAGAAAATTGGTGCACATATTG
TTACTCAACAATTTTTAGATTCATTTTTAATTCTATCAGGTTCAGGGATT
ACGTTTGGTCTTGTAGTTGCCATGCTTTTTGCAGCAAAATCAAAACAATA
CCAAGCCTTAGGAAAAGTTGCAGCTTTTCCAGCAATATTTAACGTAAATG
AGCCAGTTGTATTTGGATTTCCGATTGTCATGAATCCAGTTATGTTTGTA
CCTTTCATTCTTGTTCCTGTACTTGCAGCTGTGATAGTATATGGAGCTAT
TGCACAGGTTTCATGCAGCCATTCTCAGGGGTAACATTGCCTTGGAGTA
CACCAGCTATTTTATCAGGATTTTTGGTGGGTGGATGGCAAGGAGTTATT
ACTCAGCTGGTGATATTAGCGATGTCTACATTGGTTTATTTTCCATTCTT
TAAAGTACAGGATCGTTTAGCTTACCAAAATGAAATCAAACAATCTTAG 4121.2

(SEQ. ID. NO. 230)
ATGAAGAAAAAGGACTTAGTAGACCAACTAGTCTCAGAGATCGAGACGGG
GAAAGTCAGGACACTGGGAATATACGGTCATGGAGCTTCAGGTAAATCAA
CCTTTGCACAGGAATTGTACCAGCTTTAGATTCTACTACAGTAAATTTG
CTAGAGACAGATCCTTATATCACCTCAGGACGCCATCTGGTACTACCCAA
GGACGCGCCGAATCAAAGGTGACAGCCAGTCTGCCAGTGGCGCATGAAC
TGGAGAGTTTGCAGAGAGATATCCTTgCTTGCAGGCGGGTATGGATGTCT
TGA 4122.1

(SEQ. ID. NO. 231)
ATGAAGAAAAGATACCTAGTCTTGACAGCTTTGCTAGCCTTGAGTCTAGC
AGCTTGTTCACAAGAAAAACAAAAATGAAGATGGAGAAACTAAGACAG
AACAGACAGCCAAAGCTGATGGAACAGTCGGTAGTAAGTCTCAAGGAGCT
GCCCAGAAGAAAGCAGAAGTGGTCAATAAAGGTGATTACTACAGCATTCA
AGGGAAATACGATGAAATCATCGTAGCCAACAAACACTATCCATTGTCTA
AAGACTATAATCCAGGGGAAATCCAACAGCCAAGGCAGAGTTGGTCAAA
CTCACAAAGCGATGCAAGAGGCAGGTTTCCCTATTAGTGATCATTTACA
GTGGTTTTAGAGTTATGAAAACTCAGACCAAGCTCTATCAAGATTATGT
CAACCAAGATGGAAAGGCAGCAGCTGACCGTTACTCTGCCCGTCCTGGCT
ATAGCGAACACCAGACAGGCTGGCCTTTGATGTGATTGGGACTGATGGTG
ATTTGGTGACAGAAGAAAAGCAGCCCAATGGCTCTTGGATCATGCAGCT
GATTATGGCTTTGTTGTCCGTTATCTCAAAGGCAAGGAAAAGGAAACAGG
CTATATGGCTGAAGAATGGCACCTGCGTTATGTAGGAAAAGAAGCTAAAG

TABLE 1-continued

AAATTGCTGCAAGTGGTCTCAGTTTGGAAGAATACTATGGCTTTGAAGGC
GGAGACTACGTCGATTAA 4125.6

(SEQ. ID. NO. 232)
ATGCGTAAATTCTTAATTATTTTGTTGCTACCAAGTTTTTTGACCATTTC
AAAAGTCGTTAGCACAGAAAAGAAGTCGTCTATACTTCGAAAGAAATTT
ATTACCTTTCACAATCTGACTTTGGTATTTATTTTAGAGAAAAATTAAGT
TCTCCCATGGTTTATGGAGAGGTTCCTGTTTATGCGAATGAAGATTTAGT
AGTGGAATCTGGGAAATTGACTCCCAAAACAAGTTTTCAAATAACCGAGT
GGCGCTTAAATAAACAAGGAATTCCAGTATTTAAGCTATCAAATCATCAA
TTTATAGCTGCGGACAAACGATTTTTATATGATCAATCAGAGGTAACTCC
AACAATAAAAAAGTATGGTTAGAATCTGACTTTAAACTGTACAATAGTC
CTTATGATTAAAAGAAGTGAAATCATCCTTATCAGCTTATTCGCAAGTA
TCAATCGACAAGACCATGTTTGTAGAAGGAAGAGAATTTCTACATATTGA
TCAGGCTGGATGGGTAGCTAAAGAATCAACTTCTGAAGAAGATAATCGGA
TGAGTAAAGTTCAAGAAATGTTATCTGAAAAAATATCAGAAAGATTCTTTC
TCTATTTATGTTAAGCAACTGACTACTGGAAAAGAAGCTGGTATCAATCA
AGATGAAAAGATGTATGCAGCCAGCGTTTTGAAACTCTCTTATCTCTATT
ATACGCAAGAAAAAATAAGTAGAGGGTCTTTATCAGTTAGATACGACTGTA
AAATACGTATCTGCAGTCAATGATTTTCCAGGTTCTTATAAACCAGAGGG
AAGTGGTAGTCTTCCTAAAAAAGAAGATAATAAAGAATATTCTTTAAAGG
ATTTAATTACGAAAGTATCAAAAGAATCTGATAATGTAGCTCATAATCTA
TTGGGATATTACATTTCAAACCAATCTGATGCCACATTCAAATCCAAGAT
GTCTGCCATTATGGGAGATGATTGGGATCCAAAAGAAAAATTGATTTCTT
CTAAGATGGCCGGGAAGTTTATGGAAGCTATTTATAATCAAAATGGATTT
GTGCTAGAGTCTTTGACTAAAACAGATTTTGATAGTCAGCGAATTGCCAA
AGGTGTTTCTGTTAAAGTAGCTCTCATAAAATTGGAGATGCGGATGAATTTA
AGCATGATACGGGTGTTGTCTATGCAGATTCTCCATTTATTCTTTCTATT
TCACTAAGAATTCTGATTATGATACGATTTCTAAGATAGCCAAGGATGT
TTATGAGGTTCTAAAATGA 4125.7

(SEQ. ID. NO. 233)
ATGAAAAACAAAATAATGGTTTAATTAAAAATCCTTTTATGGTTATTAT
TTATCTTTTTCCTTGTGACAGGATTCCAGTATTTCTATTCTGGGAATAAC
TCAGGAGGAAGTCAGCAAATCAACTATACTGAGTTGGTACAAGAAATTAC
CGATGGTAATGTAAAAGAATTAACTTACCAACCAAATGGTAGTGTTATCG
AAGTTTCTGGTGTCTATAAAAATCCTAAAACAAGTAAAGAAGAAACAGGT
ATTCAGTTTTTCACGCCATCTGTTACTAAGGTAGAGAAATTTACCAGCAC
TATTCTTCCTGCAGATACTACCGTATCAGAATTGCAAAAACTTGACTTAA
ACCATAAAGCAGAAGTAACTCGTTAAGCATGAAAGTTCAAGTGGTATATGG
ATTAATCTACTCGTATCCATGTGCCATTTGGAATTCTATTCTTCTTCCTA
TTCTCTATGATGGGAAATATGGGAGGAGGCAATGGCCGTAATCCAATGAG
TTTTGGACGTAGTAAGGCTAAAGCAGCAAATAAAGAAGATATTAAAGTAA
GATTTTTCAGATGTTGCTGGAGCTGAGGAAGAAAAACAAGAACTAGTTGAA
GTTGTTGAGTTCTTAAAAGATCCAAAACGATTCACAAAAACTTGGAGCCCG
TATTCCAGCAGGTGTTCTTTTGGAGGGACCTCCGGGGACAGGTAAAACTT
TGCTTGCTAAGGCAGTCGCTGGAGAACAGGAGGTTCCATTCTTTAGTATC
TCAGGTTCTGACTTTGTAGAAATGTTTGTCGGAGTTGGAGCTAGTCGTGT
TCGCTCTCTTTTTGAGGATGCCAAAAAAGCAGCACCAGCTATCATCTTTA
TCGATGAAATTGATGCTGTTGGACGTCAACGTGGAGTCGGTCTCGGCGGA
GGTAATGACGAACGTGAACAAACCTTGAACCACTTTTGATTGAGATGGAT
GGTTTTGAGGGAAATGAAGGGATTATCGTCATCGCTGCGACAAACCGTTC
AGATGTACTTGACCCTGCCCTTTTGCGTCCAGGACGTGTTTGATAGAAAAG
TATTGGTTGGTCGTCCTGATGTTAAAGGTCGTGAAGCAATCTTGAAAGTT
CACGCTAAGAATAAGCCTTTAGCAGAAGATGTTGATTTGAAATTAGTGGC
TCAACAAACTCCAGGCTTTGTTGGTGCTGATTTAGAGAATGTCTTAGTAT
AAGCAGCTTTAGTTGCTGCTCGTCGCAATAAATCGATAATTGATGCTTCA
GATATTGATGAAGCAGAAGATAGAGTTATTGCTGGACCTTCAAGAAAGA
TAAGACAGTTTCACAAAAAGAACGAGAATTGGTTGCTTACCATGAGGCAG
GACACACCATTGTTGGTCTTGTCTTGTCGAATGCTCGCGTTGTCCATAAG
GTTACAATTGTACCACGCGGCCGTGCAGGCGGATACATGATTGCACTTCC
TAAAGAGGATCAAATGCGTTCTATCTAAAGAAGATATGAAAGAGCAATTGG
CTGGCTTAATGGGTGGACGTGTAGCTGAAAGAATTATCTTTAATGTCCAA
ACCACAGGACGTTCAAACGACTTTGAACAAGCGACACAAATGGCACGTGC
AATGGTTACAGATACGGTATGAGTGAAAAACTTGGCCCAGTACAATATG
AAGGAAACCATGCTATGCTTGGTGCACAGAGTCCTCAAAAATCAATTTCA
GAACAAACAGCTTATGAAATTGATGAAGAGGTTCGTTCATTATTAAATGA
GGCACGAAATAAAGCTGCTGAAATTATTCAGTCAAATCGTGAAACTCACA
AGTTAATTGCAGAAGCATTATTGAAATACAGAAACATTGGATAGTACACA
ATTAAAGCTCTTTACGAAACAGGAAAGATGCCTGAAGCAGTAGAAGAGGA
ATCTCATGCACTATCCTATGATGAAGTAAAGTCAAAAATGAATGACGAAA
AATAA 4125.10

(SEQ. ID. NO. 234)
ATGAGGGAACCAGATTTTTTAAATCATTTTCTCAAGAAGGGATATTTCAA
AAAGCATGCTAAGGCGGTTCTAGCTCTTTCTGGTGGATTAGATTCCATGT

TABLE 1-continued

```
TTCTATTTAAGGTATTGTCTACTTATCAAAAAGAGTTAGAGATTGAATTG
ATTCTAGCTCATGTGAATCATAAGCAGAGAATTGAATCAGATTGGGAAGA
AAAGGAATTAAGGAAGTTGGCTGCTGAAGCAGAGCTTCCTATTTATATCA
GCAATTTTTCAGGAGAATTTTCAGAAGCGCGTGCACGAAATTTTCGTTAT
GATTTTTTTCAAGAGGTCATGAAAAAGACAGGTGCGACAGCTTTAGTCAC
TGCCCACCATGCTGATGATCAGGTGGAAACGATTTTTATGCGCTTGATTC
GAGGAACTCGCTTGCGCTATCTATCAGGAATTAAGGAGAAGCAAGTAGTC
GGAGAGATAGAAATCATTCGTCCTTCTTGCATTTTCAGAAAAAAGACTT
TCCATCAATTTTTCACTTTGAAGATACATCAAATCAGGAGAATCATTATT
TTCGAAATCGTATTCGAAATTCTTACTTACCAGAATTGGAAAAGAAAAT
CCTCGATTTAGGGATGCAATCTTAGGCATTGGCAATGAAATTTTAGATTA
TGATTTGGCAATAGCTGAATTATCTAACAATATTAATGTGGAAGATTTAC
AGCAGTTATTTTCTTACTCTGAGTCTACACAAAGAGTTTTACTTCAAACT
TATCTGAATCGTTTCCAGATTTGAATCTTACAAAAGCTCAGTTGCTGA
AGTTCAGCAGATTTTAAAATCTAAAAGCCAGTATCGTCATCCGATTAAA
ATGGCTATGAATTGATAAAAGAGTACCAACAGTTTCAGATTTGTAAAATC
AGTCCGCAGGCTGATGAAAAGGAAGATGAACTTGTGTTACACTATCAAA
TCAGGTAGCTTATCAAGGATATTTATTTTCTTTTGGACTTCCATTAGAAG
GTGAATTAATTCAACAAATACCTGTTTCACGTGAAACATCCATACACATT
CGTCATCGAAAAACAGGAGATGTTTTGATTAAAAATGGGCATAGAAATA
ACTCAGACGTTTATTTATTGATTTGAAAATCCCTATGGAAAAGAGAAACT
CTGCTCTTATTATTGAGCAATTTGGTGAAATTGTCTCAATTTTGGGAATT
GCGACCAATAATTTGAGTAAAAAAACGAAAAATGATATAATGAACACTGT
ACTTTATATAGAAAAAATAGATAGGTAA 4126.1
                                (SEQ. ID. NO. 235)
ATGAAGCGTTCTTCTCTTTTAGTTAGAATGGTTATTTCCATCTTTCTGGT
CTTTCTCATTCTCCTAGCTCTGGTTGGAACTTTCTACTATCAATCAATT
CTTCAGCCATTGAGGCCACCATTGAGGGCAACAGCCAAACGACCATCAGC
CAGACTAGCCACTTTATTCAGTCTTATATCAAAAAACTAGAAACCACCTC
GACTGGTTTGACCCAGCAGACGGATGTTCTGGCCTATGCTGAGAATCCCA
GTCAAGACAAGGTCGAGGGAATCCGAGATTTGTTTTTGACCATCTTGAAG
TCAGATAAGGACTTGAAACTGTTGTGCTGGTGACCAAATCTGGTCAGGT
CATTTCTACAGATGACAGTGTGCAGATGAAACTTCCTCTGATATGATGG
CTGAGGATTGGTACCAAAAGGCCATTCATCAGGGAGCTATGCCTGTTTTG
ACTCCAGCTCGTAAATCAGATAGTCAGTGGGTCATTTCTGTCACTCAAGA
ACTTGTTGATGCAAAGGGAGCCAATCTTGGTGTGCTTCGTTTGGATATTT
CTTATGAAACTCTGGAAGCCTATCTCAATCAACTCCAGTTGGGGCAGCAG
GGCTTTGCCTTCATTATCAATGAAAACCATGAATTTGTCTACCATCCTCA
ACACACAGTTTATAGTTCGTCTAGCAAAATGGAGGCTATGAAACCCTACA
TCGATACAGGTCAGGGTTATACTCCTGGTCACAAATCCTACGTCAGTCAA
GAGAAGATTGCAGGAACTGATTGGACGGTGCTTGGCGTGTCATCATTGGA
AAAGTTAGACCAGGTTCGGAGTCAGCTCTTGTGGACCTTGCTTGGGCCA
GTGTCACATCTCTTCTTGTCTGTCTCTGCTTAGTGTGGTTCAGTCTTAA
CGCTGGATTGCTCCTTTGAAGGATTTGAGAGAAACCATGTTGGAAATTGC
TTCTGGTGCTCAAAATCTTCGTGCCAAGGAAGTTGGTGCCTATGAACTGA
GAGAAGTAACTCGCCAATTTAATGCTATGTTGGATCAGATTGATCAGTTG
ATGGTAGCTATTCGTAGCCAGGAAGAAACGACCCGTCAGTACCAACTTCA
AGCCCTTTCGAGCCAGATTAATCCACATTTCCTCTATAACACTTTGGACA
CCATCATCTGGATGGCTGAATTTCATGATAGTCAGCGAGTGGTGCAGGTG
ACCAAGTCCTTGGCAACCTATTTCCGCTTGGCGCTCAATCAAGGCAAGGA
CTTGATTTGTCTCTCTGACGAAATCAATCATGTCCGCCAGTATCTCTTTA
TCCAGAAACAACGCTATGGAGATAAGCTTGGAATACGAAATTAATGAAGA
TGTTGCCTTTGATAATTTAGTCTTACCCAAGCTGGTCCTACAACCCCTTG
TAGAAAATGCTCTTTACCATGGCATTAAGGAAAAGGAAGGTCAGGGCCAT
ATTAAACTTTCTGTCCAGAAACAGGATTCGGGATTGGTCATCCGTATTGA
GGATGATGGCGTTGGCTTCCAAGATGCTGGTGATAGTAGTCAAAGTCAAC
TCAAACGTGGGGGAGTTGGTCTTCAAAATGTCGATCAACGGCTCAAACTTC
ATTTTGGAGCCAATTACCATATGAAGATTGATTCTAGACCCCAAAAGGG
ACGAAAGTTGAAATATATATAAATAGAATAGAAACTAGCTAA 4126.7
                                (SEQ. ID. NO. 236)
ATGAAGCGTTCTTCTCTTTTAGTTAGAATGGTTATTTCCATCTTTCTGGT
CTTTCTCATTCTCCTAGCTCTGGTTGGAACTTTCTACTATCAATCAATT
CTTCAGCCATTGAGGCCACCATTGAGGGCAACAGCCAAACGACCATCAGC
CAGACTAGCCACTTTATTCAGTCTTATATCAAAAAACTAGAAACCACCTC
GACTGGTTTGACCCAGCAGACGGATGTTCTGGCCTATGCTGAGAATCCCA
GTCAAGACAAGGTCGAGGGAATCCGAGATTTGTTTTTGACCATCTTGAAG
TCAGATAAGGACTTGAAACTGTTGTGCTGGTGACCAAATCTGGTCAGGT
CATTTCTACAGATGACAGTGTGCAGATGAAACTTCCTCTGATATGATGG
CTGAGGATTGGTACCAAAAGGCCATTCATCAGGGAGCTATGCCTGTTTTG
ACTCCAGCTCGTAAATCAGATAGTCAGTGGGTCATTTCTGTCACTCAAGA
ACTTGTTGATGCAAAGGGAGCCAATCTTGGTGTGCTTCGTTTGGATATTT
CTTATGAAACTCTGGAAGCCTATCTCAATCAACTCCAGTTGGGGCAGCAG
GGCTTTGCCTTCATTATCAATGAAAACCATGAATTTGTCTACCATCCTCA
ACACACAGTTTATAGTTCGTCTAGCAAAATGGAGGCTATGAAACCCTAC
ATCGATACAGGTCAGGGTTATACTCCTGGTCACAAATCCTACGTCAGTCA
```

TABLE 1-continued

```
AGAGAAGATTGCAGGAACTGATTGGACGGTGCTTGGCGTGTCATCATTGG
AAAAGTTAGACCAGGTTCGGAGTCAGCTCTTGTGGACCTTTGCTTGGGGC
CAGTGTCACATCTCTTCTTGTCTGTCTCTGCTTAGTGTGGTTCAGTCTTA
AACGCTGGATTGCTCCTTTGAAGGATTTGAGAGAAACCATGTTGGAAATT
GCTTCTGGTGCTCAAAATCTTCGTGCCAAGGAAGTTGGTGCCTATGAACT
GAGAGAAGTAACTCGCCAATTTAATGCTATGTTGGATCAGAGATTCAGTT
GATGGTAGCTATTCGTAGCCAGGAAGAAACGACCCGTCAGTACCAACTTC
AAGCCCTTTCGAGCCAGATTAATCCACATTTCCTCTATAACACTTTGGAC
ACCATCATCTGGATGGCTGAATTTCATGATAGTCAGCGAGTGGTGCAGGT
GACCAAGTCCTTGGCAACCTATTTCCGCTTGGCGCTCAATCAAGGCAAGG
ACTTGATTTGTCTCTCTGACGAAATCAATCATGTCCGCCAGTATCTCTTT
ATCCAGAAACAACGCTATGGAGATAAGCTGGAATACGAAATTAATGAA
ATGTTGCCTTTGATAATTTAGTCTTACCCAAGCTGGTCCTACAACCCCTT
GTAGAAAATGCTCTTTACCATGGCATTAAGGAAAAGGAAGGTCAGGGCCA
TATTAAACTTTCTGTCCAGAAACAGGATTCGGGATTGGTCATCCGTATTG
AGGATGATGGCGTTGGCTTCCAAGATGCTGGTGATAGTAGTCAAAGTCAA
CTCAAACGTGGGGGAGTTGGTCTTCAAAATGTCGATCAACGGCTCAAACT
TCATTTTGGAGCCAATTACCATATGAAGATTGATTCTAGACCCCAAAAAG
GGACGAAAGTTGAAATATATATAAATAGAATAGAAACTAGCTAA 4127.4
                                (SEQ. ID. NO. 237)
ATGTTTTTTAAATTATTAAGAGAAGCTCTTAAAGTCAAGCAGGTTCGATC
AAAAATTTTATTTACAATTTTTATCGTTTTGGTCTTTCGTATCGGAACTA
GCATTACAGTTCCTGGTGTGAATGCCAATAGCTTGAATGCTTTAAGTGGA
TTATCCTTCTTAAACATGTTGAGCTTGGTGTCGGGGAATGCCCTAAAAAA
CTTTTCGATTTTTGCCCTAGGAGTTAGTCCCTATATCACCGCTTCTATTG
TTGTCCAACTCTTGCAAATGGATATTTACCCAAGTTTGTAGAGTGGGGT
AAACAAGGGGAAGTAGGTCGAAGAAAATTGAATCAAGCTACTCGTTATAT
TGCTCTAGTTCTCGCTTTTGTGCAATCTATCGGGATTACAGCTGGTTTTA
ATACCTTGCTGGAGCTCAATTGATTAAAACTGCTTTAACTCCACAAGTT
TTTCTGACGATTGGTATCATCTTAACAGCTGGTAGTATGATTGTCACTTG
GTTGGGTGACAATTACAGATAAGGGATACGGAAACGGTGTTTCCATGA
TTATCTTTGCCGGGATTGTTTCCTCAATTCCAGAGATGATTCAGGGCATC
TATGTGGACTACTTTGTGAACGTCCCAAGTAGCCGTATCACTTCATCTAT
CATTTTCGTAATCATTTTGATTATTACTGTATTGTTGATTATTTACTTTA
CAACTTATGTTCAACAAGCAGATAACAAATTCCAATCCAATATACTAAG
GTTGCACAAGGTGCTCCATCTAGCTCTTACCTTCCGTTAAAAGTAAACCC
TGCTGGAGTTATCCCTGTTATCTTTGCCAGTTCGATTACTGCAGCGCCTG
CGGCTATTCTTCAGTTTTTGAGTGCCACAGGTCATGATTGGGCTTGGGTA
AGGGTAGCACAAGGATTGGCAACTACTTCTCCAACTGGTATTGCCAT
GTATGCTTTGTTGATTATTCTCTTTACATTCTTCTATACGTTTGTACAGA
TTAATCCTGAAAAAGCAGCAGAGACCTACAAAAGAGTGGTGCCTATATCC
ATGGAGTTCGTCCTGGTAAAGGTACAGAAGAATATATGTCTAAACTTCTT
CGTCGTCTTGCAACTGTTGGTTCCCTCTTCCTTGGTGTGA 4127.5
                                (SEQ. ID. NO. 238)
ATGGATATTAGACAAGTTACTGAAACCATCGCCATGATTGAGGAGCAAA
CTTCGATATTAGAACCATTACCATGGGATTCTCTTTTTGGACTGTATCG
ATCCAGATATCAATCGTGCTGCGGAGAAAATCTATCAAAAAATTACGACA
AAGGCGGCTAATTTAGTAGCTGTTGGTGATGAAATTGCGGCTGAGTTGGG
AATTCCTATCGTTAATAAGCGTGTATCGGTGACACCTATTTCTCTGATTG
GGGCAGCGACAGGTGCGGACTACGTGGTTTCTGGCAAAAGCGCCTTGA
TAAGGCTGCGAAAGAGATTGGTGTGGACTTTATTGGTGGTTTTTCTGCCT
TAGTACAAAAAGGTTATCAAAAGGGAGATGAGATTCTCATCAATTCCATT
CCTCGCGCTTTGGCTGAGACGGATAAGGTCTGCTCGTCAGTCAATATCGG
CTCAACCAAGTCTGGTATTAATATGACGGCTGTGGCAGATATGAGGACGAA
TTATCAAGGAAACAGCAAATCTTTCAGATATGGGAGTGGCCAAGTTGGT
TGTATTCGCTAATGCTGTTGAGGACAATCCATTTATGGCGGGTGCCTTTCA
TGGTGTTGGGGAAGCAGATGTTATCATCAATGTCGGAGTTTCTGGTCCTG
GTGTTGTGAACGTGCTTTGGAAAAGTTCGTGGACAGAGCTTTAGTCTA
GTAGCCGAAACAGTTAAGAAACTGCCTTTAAAATCACTCGTATCGGTCA
ATTGGTTGGTCAAATGGCCAGTGAGACTGGGTGTGGAGTTTGGTATTG
TGGACTTGAGTTTGGCACCAACCCCTGCGGTTGGAGACTCTGTGGCACGT
GTCCTTGAGGAATGGCTGGTAGAAACAGTTGGCACGCATGAAGCGACGGC
TGCCTTGGCCCTCTTGAACGACCAAGTTAAAAGGTGGAGTGATGGCCT
GCAACCAAGTCGGTGGTTTATCTGGTGCCTTTATCCCTGTTTCTGAGGAT
GAAGGAATGATTGCTGCAGTGCAAATGGCTCTCTTAATTTAGAAAACT
AGAAGCTATGACGGCTATCTGTTCTGTTGGATTGGATATGATTGCCATC
CAGAAGATACGCCTGTGAAACTATTGCGGCTATGATTGCGGATGAAGCA
GCAATCGGTGTATCAACATGAAAACAACAGCTGTTCGTATCATTCCCAA
AGGAAAAGAAGGCGATATGATTGAGTTTGGTGGTCTATTAGGAACTGCAC
CCGTTATGAAGGTTAATGGGCTTCGTCTGTCGACTTCATCTCTCGCGGT
GGACAAATCCCAGCACCAATTCATAGTTTTAAAAATTAA 4128.1
                                (SEQ. ID. NO. 239)
ATGACACAGATTATTGATGGGAAAGCTTTAGCGGCCAAATTGCAGGGGCA
```

TABLE 1-continued

```
GTTGGCTGAAAAGACTGCAAAATTAAAGGAAGAAACAGGTCTAGTGCCTG
GTTTGGTAGTGATTTTGGTTGGGGACAATCCAGCCAGCCAAGTCTACGTT
CGCAACAAGGAGAGGTCAGCCCTTGCGGCTGGTTTCCGTAGCGAAGTAGT
ACGGGTTCCAGAGACCATTACTCAAGAGGAATTCTTAGACCTGATTGCTA
AATACAATCAGGATCCAGCTTGGCATGGGATTTTGGTTCAGTTGCCATTA
CCAAAACACATTGATGAAGAGGCGGTTCTATTGGCTATTGACCCAGCAAA
AGGATGTGGATGGTTTCCATCCTCTAAACATGGGGCGTCTTTGGTCTGGT
CATCCAGTCATGATTCCTTCGACACCGGCAGGAATTATGGAAATGTTCCA
TGAATATGGGATTGACTGTGGAAGGTAAAAATGCAGTCGTCATCGGTCGA
TCCAATATTGTCGGAAAACCTATGGCCCAGCTTCTTTTGGCAAAGAATGC
AACAGTAACCTTGACTCACTCACGTACTCATAATCTTTCCAAGGTGGCTG
CAAAAGCAGATATTCTGGTTGTTGCAATCGGTCGTGCCAAGTTTGTGACT
GCTGACTTTGTCAAACCAGGTGCGGTAGTCATTGACGTTGGGATGAACCG
CGATGAAATGGTAAGCTCTGGGGATGTTGATTATGAGGCGGTTGCCC
CACTTGCTAGCCACATTACGCCAGTCCCTGGAGGTGTCGGTCCTATGACC
ATTACTATGCTGATGGAGCAAACCTATCAGGCAGCACTTAGGACATTGGA
TAGAAAATAA
```

4128.2
(SEQ. ID. NO. 240)
```
ATGTCTAAATTTAATCGTATTCATTTGGTGGTACTGGATTCTGTAGGAAT
CGGTGCAGCACCAGATGCTAATAACTTTGTCAATGCAGGGGTTCCAGATG
GAGCTTCTGACACACTGGGACACATTTCAAAAACAGTTGGTTTGAATGTC
CCAAACATGGCTAAAATAGGTCTTGGAAATATTCCTCGTGAAACTCCTCT
TAAGACTGTAGCAGCTGAAAGCAATCCAACTGGATATGCTGCAACAAATTAG
AGGAAGTATCTCTTGGTAAGGATACTATGACTGGACACTGGGAAATCATG
GGACTCAACATTACTGAGCCTTTCGATACTTTCTGGAACGGATTCCCAGA
AGAAATCCTGACAAAAATCGAAGAATTCTCAGGACGCAAGGTTATTCGTG
AAGCCAACAACAAACCTTATTCAGGAACGGCTGTTATCTATGATTTGGACCA
CGTCAGATGGAAACTGGAGAGTTGATTATCTATACTTCAGCTGACCCTGT
TTTGCAGATTGCTGCCCACGAAGACATTATTCCTTTGGATGAATTGTACC
GTATCTGTGAATACGCTCGTTCGATTACCCTTGAGCGTCCTGCCCTTCTT
GGTCGCATCATTGCTCGCCCTTATGTAGGTGAACCAGGTAACTTCACTCG
TACGGCAAACCGTCGTGACTTGGCTGTATCTCCATTTTTCCCAACTGTTT
TGGATAAATTGAATGAGGCTGGTATCGATACTTATGCTGTGGGTAAAATC
AACGATATCTTTAACGGTGCTGGTATCAACCATGACATGGGTCACAACAA
GTCAAATAGTCATGGAATTGATACATATTGAAGACTATGAGGTGACTTGCTG
AGTTTGAAAAAGGATTCTCATTCACAAACCTAGTTGACTTTGATGCCCTT
TACGGCCATCGTCGTAATGCTCACGGTTACCGTGATTGCTTGCATGAGTT
TGATGAACGCTTACCTGAAATTATCGCAGCTATGAGAGAGAATGACCTTC
TCTTGATTACTGCGGACCATGGAAATGACCCAACGTTATGCAAGTTCACTG
CACACTCGGGAATATATTCCATTGTTGGCCTATAGCCCTGCCTTTAAAGG
AAATGGTCTCATTCCAGTAGGACATTTTGCAGATATTTCAGCGACTGTTG
CCGATAACTTTGGTGTGGAAACTGCTATGATTGGGGAAAGTTTCTTAGAT
AAATTGGTATAA
```

4129.2
(SEQ. ID. NO. 241)
```
ATGTTTATTTCCATCAGTGCTGGAATTGTGACATTTTTACTAACTTTAGT
AGAAATTCCGGCCTTTATCCAATTTTATAGAAAGGCGCAAATTACAGGCC
AGCAGATGCATGAGGATGTCAAACAGCATCAGGCAAAAGCTGGGACTCCT
ACAATGGGAGGTTTGGTTTTCTTGATTACTTCTGTTTTGGTTGCTTTCTT
TTTCGCCCTATTTAGTAGCCAATTCAGCAATAATGTGGGAATGATTTTGT
TCATCTTGGTCTTGTATGGCTTGGTCGGATTTTTAGATGACTTTCTCAAG
GTCTTTCGTAAAATCAATGAGGGGCTTAATCTAAGCAAAATTAGCTCT
TCAGCTTCTAGGTGGAGTTATCTTCATCTTTTCTATGAGCGCGGTGGCG
ATATCCTGTCTGTCTTTGGTTATCCAGTTCATTTGGGATTTTTCTATATT
TTCTTCGCTCTTTTCTGGCTAGTCGGTTTTTCAAACGCAGAAGATTAGCTG
AGACGGTGTTGACGGTTAGCTAGTATTTCCGTTGTGATTAGTTTGTCTG
CCTATGGAGTTATTGCCTATGTGCCAGGTCAGATGGATATTCTTAGTA
ATTCTTGCCATGATTGGTGGTTTGCTCGGTTTCTTCATCTTTAACCATAA
GCCTGCCAAGGTCTTTATGGGTGATGTGGGAAGTTTGGCCCTAGGTTGGA
TGCTGGCAGCTATCTCTATGGCTCTCCACCAAGAATGGACTCTCTTGATT
ATCGGAATTGTGTATGTTTTGAAACAACTTCTGTTATGATGCAAGTCAG
TTATTTCAAACTGACAGGTGGTAAACGTATTTTCCGTATGACGCCTGTAC
ATCACCATTTTGAGCTTGGGGGGATTGTCTGGTAAAGGAAATCCTTGGAG
CGAGTGGAAGGTTGACTTCTTCTTTTGGGGAGTGGGACTTCTAGCAAGTC
TCCTGACCCTAGCAATTTTATATTTGATGTAA
```

4133.1
(SEQ. ID. NO. 242)
```
TTGTTTAAGAAAAATAAAGACATTCTTAATATTGCATTGCCAGCTATGGG
TGAAAACTTTTTGCAGATGCTAATGGGAATGGTGGACAGTTATTGGTTG
TCATTTAGGATTGATAGCTATTCAGGGGTTTCAGCTGGTGTAATATT
ATCACCATTTTATCAGGCGATTTTCATCGTCTGGGAGCTGCTATTTCCAG
TGTTATTTCAAAAGCATAGGGCAGAAAGACCAGTCGAAGTTGGCCTATC
ATGTGACTGAGGCGTTGAAGATTACCTTACTATTAAGTTTCCTTTTAGGA
TTTTTGTCCATCTTCGCTGGGAAAGAGATGATAGGACTTTTGGGGACGGA
GAGGGATGTAGCTGAGAGTGGTGGACTGTATCTATCTTTGGTAGGCGGAT
```

```
CGATTGTTCTCTTAGGTTTAATGACTAGTCTAGGAGCCTTGATTCGTGCA
ACGCATAATCCACGTCTGCCTCTCTATGTTAGTTTTTTATCCAATGCCTT
GAATATTCTTTTTTCAAGTCTAGCTATTTTTGTTCTGGATATGGGGATAG
CTGGTGTTGCTTGGGGGACAATTGTGTCTCGTTTGGTTGGTCTTGTGATT
TTGTGGTCACAATTAAAACTGCCTTATGGAAGCCAACTTTTGGTTTAGA
TAAGGAACTGTTGACCTTGGCTTTACCAGCAGCTGGAGAGCGACTTATGA
TGAGGGCTGGAGATGTAGTGATCATTGCCTTGGTCGTTTCTTTTGGGACG
GAGGCAGTTGCTGGGAATGCAATCGGAGAAGCTCTTGACCCAGTTAACTA
TATGCCTGCCTTTGGCGTCGCTACGGCAACGGTCATGCTGTTGGCCCGAG
CAGTTGGAGAGGATGATTGGAAAGAGTTGCTAGTTTGAGTAAACAAACC
TTTTGGCTTTCTCTGTTCCTCATGTTGCCCCTGTCCTTTAGTATATATGT
CTTGGGTGTACCATTAACTCATCTCTATACGACTGATTCTCTAGCGGTGG
AGGCTAGTGTTCTAGTGACACTGTTTTTCACTACTTGGGACCCCTATGACG
ACAGGAACAGTCATCTATACGGCAGTCTGGCAGGGATTAGGAAATGCACG
CCTCCCTTTTTATGCGACAAGTATAGGAATGTGGTGTATCCGCATTGGGA
CAGGATATCTGATGGGATTGTGCTTGGTTGGGCGTTGCCTGGTATTTGG
GCAGGGTCTCTCTTGGATAATGGTTTTCGCTGGTTATTTCTACGCTATCG
TTACCAGCGCTATATGAGCTTGAAAGGATAG
```

4135.2
(SEQ. ID. NO. 243)
```
ATGCAAACCAAGAAAAACACTCGCAAGCAGCCGTTCTTGGCTTGCAGCAC
TTACTAGCCATGTACTCAGGATCTATCCTGGTTCCCATCATGATTGCGAC
AGCCCTTGCTATTCAGCTGAGCAGTTGACCTACCTGATTTCTACAGATA
TCTTCATGTGTGGGGTGGCAACCTTCCTCCAACTCCAACTCAACAAATAC
TTTGGGATGGACTCCCAGTCGTTCTTGGAGTTGCATTCCAGTCGGTCGCT
CCCTTGATTATGATTGGGCAAAGCATGGTAGTGGCGCTATGTTGGTGC
CCTTATCGCATCTGGGATTTACGTGGTTCTTGTTTCAGGCATCTTCTCAA
AAGTTGCCAATCTCTTCCCATCTATCGTAACAGGATCTGTTATTACCACG
ATTGGTTTAACCTTGATCCCTGTCGCTATTGGAAATATGGGAAATAACGT
TCCAGAGCCAACTGGTCAAAGTCTCTTGCTTGCAGCTATTACTGTTCTGA
TTATCCTCTTGATCAACATCTTTACCAAAGGATTTATCAAGTCTATCTCT
ATTTTGATTGGTCTGGTTGTTGAACTGCCATTGCTGCTACTATGGGCTT
GGTGGACTTCTCTCCTGTTGCGGTAGCTCCACTTGTCCATGTCCCAACTC
CACTCTACTTTGGGATGCCAACCTTTGAAATCTCATCTATTGTCATGATG
TGTATCATCGCAACGGTGTCTATGGTTGAGTCAACTGGTGTTTATCGGC
CTTGTCTGATATCACAAAAGGAATCCAATCGACAGCCACGCGCCCTTGCAAC
GGATACCGCGCAGAAGGTTTGGCCGTACTTCTCGGAGGAATCTTTAACAC
CTTCCCTTACACCGGATTTTCACAAAACGTTGGTTTGGTTAAATTGTCAG
GCATCAAAAAAGCCTGCCAATCTACTACGCAGCTGGTTTCCTGGTTCTC
CTTGACTGCTTCCTAAGTTTGGCGCCCTTGCCCAAATCATTCCAAGCTC
CGTCCTCGGTGGTGCCATGCTGGTAATGTTTGGTTTTGTATCAATTCAAG
GGATGCAAATCCTCGCCCGTGTTGACTTGCTAACAATGAACAACTTC
CTTATCGCAGCTGTTTCAATCGCTGCAGGTGTCGGTCTCAACAACAGTAA
TCTCTTTGTCAGCATGCCGACAGCCTTCCAAATGTTCTTCTCAAACGGAA
TCGTCTAGCCAGCCTACTCGCTATTGTCCTCAATGCCGTATTAAATCAT
AAAAAAGAAATAA
```

4136.2
(SEQ. ID. NO. 244)
```
ATGAAAGATAGAATAAAAGAATATTTACAAGACAAGGGAAAGGTGACTGT
TGAATGATTTGGCTCAGGCTTGGGAAAAGACAGTTCCAAGGATTTTCGTG
AGTTGATTAAAACCTTGTCCTTAATGGAAAAGAAAGCACCAAATTCGTTTG
AAGAAGATGGTAGTCTGACATTAGAAATTAAGAAAAAACATGAGATTACC
CTCAAGGGGATTTTTCATGCCCATAAAAATGGCTTTGGCTTTGTTAGTCT
GGAAGGCGAGGAGGACGACCTTTTGTAGGGAAAAATGATGTCAACTATG
CTATTGATGGTGATACCGTCGAGGTAGTGATTAAGAAAGTCGCTGACCGC
AATAAGGGACAGCAGCAGAAGCCAAAATTATTGATATCCTAGAACACAG
TTTGACAACAGTTGCGGGCAAATCGTTCTGGATCAGGAAAAACCTAAGT
ATGCTGGCTATATTCGTTCAAAAAATCAGAAATCAGTCAACCGATTTAT
GTTAAGAAACCAGCCCTAAAATTAGAAGGAACAGAAGTTCTCAAAGTCTT
TATCGATAAATACCCAAGCAAGAAAACATGATTTCTTTGTCGCGAGTGTTC
TCGATGTAGTGGGACACTCAACGGATGTCGGAATTGATGTTCTTGAGGTC
TTGGAATCAATGGACATTGTATCCGAGTTTCAGAAGCTGTTGTTAAGGA
AGCAGAAAGTGTGCCTGATGCTCCGTCTCAAAAGGATATGGAAGGTCGTC
TGGATCTAAGAGATGAAATTACCTTTACCATTGACGGTGCGGATGCCAAG
GACTTGGACGATGCAGTCGCATATCAAGGCTCTGAAAAATGCGCAATCTGGA
GTTTGGGGTTCACATCGCAGATGTTTCTTATTATGTGACCGAGGGGTCTG
CCCCTTGACAAGGAAGCCCTTAACCGTGCGACTTCTGTTTACGTGACAGAC
CGAGTGGTGCCAATGCTTCCAGAACGACTATCAAATGGCATCTGCTCTCT
CAATCCCCAAGTTGACCGCCTGACCCAGTCTGCTATTATGGAGATTGATA
AACATGGTCGTGTGGTCAACTATACCATTACACAAACAGTTATCAAGACC
AGTTTTCGTATGACCTATAGCGATGTCAATGATATCCTAGCTGGCGATGA
AGAAAAGAGAAAGAATATCATAAAATTGTATCAAGTATCGAACTCATGG
CCAAGCTTCATGAAACTTTAGAAAACATGCGTGTGAAACGTGGAGCTCTC
AATTTTGATACCAATGAAGCGAAGATTTAGTGTGGATAAACAAGGTAAGCC
TGTTGATATCGTTCTTCGGCAGCGTGGTATTGCCGAGCGGATGATTGAGT
CTTTTATGGTTGATGGCTAATGAAACAGTTGCCGAACATTTCAGCAAGTTG
GATTTGCCTTTTATCTATCGAATTCACGAGGAGCCTAAGGCTGAAAAGGT
```

TABLE 1-continued

TCAGAAGTTTATTGATTATGCTTCGAGTTTTGGCTTGCGCATTTATGGAA
CTGCCAGTGAGATTAGTCAGGAGGCACTTCAAGACATCATGCGTGCTGTT
GAGGGAGAACCTTATGCAGATGTATTGTCCATGATGCTTCTTCGCTCTAT
GCAGCAGGCTCGTTATTCGGAGCACAATCACGGCCACTATGGACTACTG
CTGACTATTATACTCACTTTACCAGTCCAATTCGTCGTTATCCAGACCTT
CTTGTTCACCGTATGATTCGGATTACGGCCGTTCTAAGGAAATAGCAGA
GCATTTTGAACAAGTGATTCCAGAGATTGCGACCCAGTCTTCCAACCGTG
AACGTCGTGCCATAGAGACTGAGCGTGAAGTCGAAGCCATGAAAAAGGCT
GAGTATATGGAAGAATACGTGGGTGAAGAGTATGATGCAGTTGTATCAAG
TATTGTCAAATTCGGTCTCTTTGTCGAATTGCCAAACACAGTTGAAGGCT
TGATTCACATCACTAATCTGCCTGAATTTTATCATTTCAATGAGCGTGAT
TTGACTCTTCGTGGAGAAAAATCAGGTATCACTTTCCGAGTGGGTCAGCA
GATCCGTATCCGTGTTGAAAGAGCGGATAAAATGACTGGAGAGATTGATT
TTTCATTCGTACCTAGTGAGTTTGATGTGATTGAAAAAGGCTTGAAACAG
TCTAGTCGTAGTGGCAGAGGGCGTGATTCAAATCGTCGTTCGGATAAGAA
GGAAGACAAGAGAAAATCAGGACGCTCAAATGATAAGCATGAAGCATTCAC
AAAAAGACAAGAAGAAAAAGGAAAGAAACCTTTTTCACCGGAAGTAGCT
AAGAAAGGAGCCAAGCATGGCAAAGGGCGAGGGAAAGGTCGTCGCACAAA
ATAA 4137.2
(SEQ. ID. NO. 245)
ATGGGCACAACAGGATTTACAATAATTGACTTAATTATCTTGATTGTTTA
TTTACTTGCGGTGTTGGTTGCAGGTATCTATTTCTCTAAAAAAGAGATGA
AAGGAAAAGAGTTCTTTAAAGGAGATGGTTCGGTTCCTTGGTATGTTACT
TCGGTATCCATTTTTGCCACAATGCTCAGTCCGATTTCCTTCTTGGGACT
CGCTGGTAGCTCTTATGCAGGTAGCTGGATTTTATGGTTTGCTCAATTAG
GGATGGTAGTAGCTATTCCACTGACAATTCGTTTTATCTTACCTATCTTT
GCACGGATAGACATCGATACGGCATATTACTTGGATAAACGTTTTAA
TTCTAAAAGCACTTCGTATTATTTCAGCACTCTTGTTTATTATTTATCAA
TTGGGACGTATGTCTATCATTATGTACCTCCCATCAGCTGGTTTATCAGT
ATTGACAGGAATTGACATCAATATTTTGATTATTTTGATGGGTGTAGTTG
CAATTGTTTATTCTTATACTGGTGGTCTAAAATCCGTATTATGGACAAC
TTTATTCAAGGTGTGATTCTGATTAGTGGTGTCGTTTTAGCTTTATTTGT
ACTGATTGCTAATATTAAAGGTGGCTTTGGTGCAGTAGCAGAACATTAG
CAAACGGGAAATTCCTTGCTGCAAATGAAAAACTTTTCGATCCTAACTTG
CTTTCAAACTCCATCTTTTTAATTGTGATGGGTTCAGGCTTTTCAACTCTT
GTCTTCCTATGCTTCATCTCAAGATTTGTTCAACGTTTTACTACAACAC
AAAATATTAAGAAACTTAATAAGATGTTGTTCACAAACGGTGTTTTGTCA
CTTGCAACTGCAACAGTCTTTTACTTGATTGGTACAGGCTTGTACGTATT
CTATCAGTACAAATGCAGATAGTGCAGCTAGCAATATCCCTCAAGACC
AAATCTTTATGTACTTATTGCATACCAGTTACCAGTAGGTATCACAGGT
TTGATCTTGGCAGCGATTTATGCAGCATCTCAATCACTATTTCAACAGG
TTTGAACTCTGTTCAACTTCATGGACATTGGATATTCAAGATGTCATTT
CTAAAAATATGTCAGACAATCGTCGTACGAAAATTCGCACTTCGTATCT
CTAGCAGTAGGTTATTTCAATTGGTGTTTCCATTGTCATGGCTCACTC
AGATATTAAATCTGCATACGAATGGTTCAATAGTTTCATGGGACTTGTAC
TTGGTCTACTTGGTGGTGTATTTATTCTTGGATTTGTTTCTAAAAAAGCA
AATAAACAAGGTGCTTATGCAGCGCTGATTGTATCAACCATCGTCATGGT
ATTTATTAAATACTTCCTTCCTCCAACAGCTGTTAGCTACTGGGCATATT
CATTGATTTCAATCTCTGTATCAGTAGTTTCAGGTTATATTGTATCTGTT
CTTACTGGAAATAAAGTATCTGCACCTAAATATACAACGATTCATGATAT
TACAGAAATTAAAGCGGATTCAAGTTGGGAAGTTCGTCACTAA 4138.1
(SEQ. ID. NO. 246)
ATGAAATTTAGTAAAAAATATATAGCAGCTGGATCAGCTGTTATCGTATC
CTTGAGTCTATGTGCCTATGCACTAAAACAGCATCGTTCGCAGGAAAATA
AGGACAATAATCGTGTCTCTTATGTGGATGGCAGCCAGTCAAGTCAGAAA
AGTGAAAACTTGACACCAGACCAGGTTAGCCAGAAAGAAGGAATTCAGGC
TGAGCAAATTGTAATCAAAATTACAGATCAGGGCTATGTAACGTCACACG
GTGACCACTATCATTACTATAATGGGAAGTTCCTTATGATGCCCTATTT
AGTGAAGAACTCTTGATGAAGGATCCAAACTATCAACTTAAAGACGCTGA
TATTGTCAATGAAGTCAAGGGTGGTTATATCATCAAGGTCGATGGAAAT
ATTATGTCTACCTGAAAGATGCAGCTCATGCTGATAATGTTCGAACTAAA
GATGAAATCAATCGTCAAAAACAAGACATGTCAAAGATAATGAGAGGTT
TAACTCTAATGTTGCTAGCAAGGTCTCAGGGACGATATACGACAAATG
ATGGTTATGTCTTTAATCCAGCTGATATTATCGAAGATACGGGTAATGCT
TATATCGTTCCTCATGGAGGTCACTATCACTACATTCCCAAAAGCGATTT
ATCTGCTAGTGATTAGCAGCAGCTAAAGCACATCTGGTGAAAAATA
TGCAACCGAGTCAGTTAAGCTATTCTTCAACAGCTAGTGACAATAACACG
CAATCTGTAGCAAAAGGATCAACTAGCAAGCCAGCAAATAAATCTGAAAA
TCTCCAGAGTCTTTTGAAGGAACTCTATGATTCACCTAGCGCCCAACGTT
ACAGTGAATCAGATGGCCTGCTTTTGACCCTGCTGACCGACCATTACCACTTTATTCC
TTACAGCAAGCTTTCTGCCTTAGAAGAAAAGATTGCCAGAATGGTGCCTA
TCAGTGGAACTGGTTCTACAGTTTCTACAAATGCAAAACCTAATGAAGTA
GTGTCTAGTCTAGGCAGTCTTTCAAGCAATCCTTCTTCTTTAACGACAAG
TAAGGAGCTCTCTTCAGCATCTGATGGTTATATTTTAATCCAAAAGATA

TCGTTGAAGAAACGGCTACAGCTTATATTGTAAGACATGGTGATCATTTC
CATTACATTCCAAAATCAAATCAAATTTGGGCAACCGACTCTTCCAAACAA
TAGTCTAGCAACACCTTCTCCATCTCTTCCAATCAATCCAGGAACTTCAC
ATGAGAAACATGAAGAAGATGATCGGATTTGATGCTAATCGTATTATC
GCTGAAGATGAATCAGGTTTTGTCATGATCACGGAGACCACAATCATTA
TTTCTTCAAGAAGGACTTGACAGAAGAGCAAATTAAGGTGCGCAAAAACA
TTTAG 4139.1
(SEQ. ID. NO. 247)
ATGAAAAAAGAGCAATAGTGGCAGTCATTGTACTGCTTTTGATTGGGCT
GGATCAGTTGGTCAAATCCTATATCGTCCAGCAGATTCCACTGGGTGAAG
TGCGCTCCTGGATCCCCAATTTCGTTAGCTTGACCTACCTGCAAAATCGA
GGTGCAGCCTTTTCTATCTTACAAGATCAGCAGCTGTTATTCGCTGTCAT
TACTCTGGTTGTCGTGATAGGTGCCATTTGGTATTTACATAAAACACATG
GAGGACTCATTCTGGATGGTCTTGGGTTTGACTCTAATAATCGCGGGTGG
TCTTGGAAACTTTATTGACAGGGTCAGTCAGGGCTTTGTTGTGGATATGT
TCCACCTTGACTTTATCAACTTTGCAATTTTCAATGTGGCAGATAGCTAT
CTGACGGTTGGAGTGATTATTTTATTGATTGCAATGCTAAAAGAGGAAAT
AAATGGAAATTAA 4139.5
(SEQ. ID. NO. 248)
ATGAATACAAATCTTGCAAGTTTTATCGTTGGACTGATCATCGATGAAA
CGACCGTTTTTACTTTGTGCAAAAGGATGGTCAAACCTATGCTCTTGCTA
AGGAAGAAGGCCAACATACAGTAGGGGATACGGTCAAAGTTTTGCATAC
ACGGATATGAAGCAAAAACTCCGCCTGACAACCTTAGAAGTGACTGCCAC
TCAGGACCAATTTGTTGGGGACGTGTCACAGAGGTTCGTAAGGACTTGG
GTGTCTTTGTGGATACAGGCCTTCCTGACAAGGAAATCGTTGTGTCACTC
GATATTCTCCCTGAGCTCAAGGAACTCTGGCCTAAGAAGGGCGACCAACT
CTACATCCGTCTTGAAGTGGATAAGAAAGACCGTATCTGGGCGTCTTGG
CTTATCAAGAAGACTTCCAACGTCTTGCTCGTCCTGCCTACAACAACATG
CAGAACCAAAACTGGCCAGCCATTGTTTACCGTCTCAAGCTGTCAGGAAC
TTTTGTTTACCTACCAGAAATAATATGCTTGGTTTTATTCATCCTAGCG
AGCGTTACGCAGAGCCACGTTGGGCAAGTATTAGATGCGCGTTATTG
GTTTCCGTAAGTGGACCGCACTCTGAACCTCTCCCTCAAACCACGCTCCT
TTGAAATGTTGGAAAACGATGCTCAGATGATTTTGACTTATTTGGAAAGC
AATGGCGGTTTCATGACCTTAAATGACAAGTCATCTCCAGACGACATCAA
GGCAACCTTTGGCATTTCTAAAGGTCAGTTCAAGAAAGCTTTAGGTGGTC
TTATGAAGGCTGGTAAAATCAAGCAGGACCAGTTTGGGACAGAGTTGATT
TAG 4139.8
(SEQ. ID. NO. 249)
ATGAAAGATGTTAGTCTATTTTTATTGAAAAAAGTTTTCAAAAGCCGCTT
AAACTGGATTGTCTTAGCTTTATTTGTATCTGTACTCGGTGTTACCTTTT
ATTTAAATAGTCAGACTGCAAACTCACACAGCTTGGAGAGCAGGTTGGAA
AGTCGCATTGCAGCCAACGAGAGGGCTATCAATGAAAATGAAGAGAAACT
CTCCCAAATGTCTGATACCAGCTCGGAGGAATACCAGTTTGCTAAAAATA
ATTTAGACGTGCAAAAAAATCTTTTGACGCGAAAGACAGAAATTCTGACT
TTATTAAAAGAAGGGCGCTGGAAAGAAGCCTACTATTTGCAGTGGCAAGA
TGAAGAGAAGAATTATGAATTTGTATCAAATGACCCGACTGCTAGCCCTG
GCTTAAAAATGGGGGTTGACCGCGAACGAAGATTTACCAAGCCCTGTAT
CCCTTGAACATAAAAGCACATACATTTGGAGTTTCCGACCCACGGATTGA
TCAGATTGTCTGGATTTTAGAGGGTTATCATCCCAAGTTTGTTTGTGGTTG
CTATTATTTTTATGCTAACACAACTATTTGCAGAAAGATATCAAATCAT
CTGGACACAGCTCACTTATATCCTGTTTCAAAAGTGACATTTGCAATATC
CTCAGTTGGAGTTGGAGTGGGAAGTCTGATAAGGTGTTTATCGGAATCT
GTGGCTTTCTTTTCTAGTGGGAAGTCTGATAAGGTGTTTTTGGACAGTTA
GATTATCCCTACCCAATTTATAGCTTAGTGAATCAAGAAGTAACTATTGG
GAAAATACAAGATGTATTATTTCCTGGCTTGCTCTTAGCTTTCTTAGCCT
TTATCGCATTGTGGAAGTTGTGTACTTGATTGCTTACTTTTTCAAGCAA
AAAATGCCTGTCCTCTTTCTTTCACTCATTGGGATTGTTGGCTTATTGTT
TGGTATCCAAACCATTCAGCCTCTTCAAAGGATTGCACATCTGATTCCCT
TTACTTACTTGCGTTCAGTGGAGATTTTATCTGGAAGATTACCTAAGCAG
ATTGATAATGTCATCAAAGAACATGTTGGAGCATGGAATGGTCTTACTTCCTTG
CCTGATTATCTTTTTTGCTATTGGGAATTCTATTTATTGAAAGATGGGGAA
GTTCACAGAAAAAGAATTTTTAATAGATTCTAG 4141.1
(SEQ. ID. NO. 250)
ATGATGAAGTTCATATTGGATATTGTTAGTACACCAGCTATTTTAGTAGC
TTTAATTGCAATCTTAGGATTAGTTCTTCAGAAGAAGAAATTACCTGATA
TTATTAAAGGTGGAATTAAGACCTTTGTTGGTTTCGTTAGTTGTATCTGGT
GGTGCAGGAATTGTACAAAATTCTTTAAATCCATTTGGTACCATGTTTGA
GCATGCTTTTCATTTATCTGGCGTTGTGCCGAATAATGAAGCAATTGTAG
CTGTAGCTTTAACAACATATGGCTCAGCTACTGCAATGATTATGTTTGCA
GGCATGGTGTTCAATATCTTAATCGCTCGTTTTACTCGATTTAAATATAT
TTTTTTAACAGGGCACCACACTCTATATATGGCATGTATGATTGCGGTCA

TABLE 1-continued

TTTTATCAGTTGCTGGCTTTACTAGCTTGCCTCTCATCTTACTAGGAGGA
TTAGCACTCGGTATTATTATGAGTATTTCCCCAGCATTTGTGCAAAAATA
TATGGTTCAATTAACTGGAAATGACAAGGTAGCTTTAGGTCATTTCAGTT
CTTTGGGATATTGGTTGAGTGGTTTTACTGGTAGCCTTATCGGTGACAAA
TCAAAATCAACAGAGGACATTAAATTTCCAAAGAGTTTAGCTTTTTTACG
TGATAGTACTGTTAGTATTACTTTATCCATGGCAGTTATTTACATTATTG
TAGCTATCTTTGCAGGGTCAGAATATATAGAAAAAGAAATCAGTAGTGGT
ACAAGTGGTCTAGTTTATGCTTTACAATTAGCAGGTCAATTTGCAGCAGG
GGTATTTGTTATTTTAGCAGGTGTTCGCCTTATTTTGGGCGAAATTGTTC
CAGCCTTTAAAGGTATTTCAGAGCGTCTTGTACCTAATTCAAAACCTGCT
TTGGATTGTCCGATTGTTTATACTTATGCACCCAATGCAGTTCTAATTGG
ATTTATCTCTAGTTTTGTTGGTGGTTTAGTAAGTATGGTAATTATGATTG
CTTCAGGAACGGTTGTTATCTTACCAGGTGTTGTGCCTCATTTCTTCTGT
GGGAGCGACTGCAGGTGTCATTGGGAATGCATCTGGTGGTGTTCGTGAGC
CACTATTGGAGCATTTTTACAAGGTATTTTAATCAGTTTTCTTCCAGTCT
TTTTAATGCCAGTTTTGGGAGGACTTGGTTTCCAAGGATCAACTTTCTCA
GATGCAGATTTTGGTCTATCAGGAATTATTTTAGGAATGTTAAATCAATT
TGGCTCACAAGCAGGCATTGTGATTGGTCTTGTTCTTATTCTAGCAGTTA
TGTTTGGAGTATCCTTTATTAAAAAGCCATCTGCAACGGAGGAATAA 4142.3

(SEQ. ID. NO. 251)
ATGATTAAAACATTTCTCTCTGCCCTTTCGGTCATTCTCTTTTCTATCCC
TATCATAACTTATTCTTTTTTCCCATCTTCTAATCTTAACATTTGGCTAT
CTACCCAACCTATCTTGGCACAGTTATGCCTTCCCCTTAGCTACTGCA
ACTATGGCTGCTATTTTAAGTTTCTTATTTTTTTCCTATCTTTTTACAA
GAAAAATAAACAAATACGGTTTTACTCTGGCATTTTGCTCTTACTATCGC
TCATATTACTATTATTCGGAACAGATAAAACCCTTTCTTCTGCATCAAAT
AAGACTAAAAACTTAAAATTAGTAACTTGGAACGTCGTAATCAAATAGA
AGCACAACATATTGAGCGAATTTTTAGCCATTTTGACGCCGATATGGCTA
TATTCCCTGAACTAGCTACCAATATCAGAGGTGAGCAAGAAACCAGAGA
ATCAAACTATTGTTTCATCAAGTTGGACTTTCTATGGCCAACTATGATAT
TTTCACTTCTCCACCTACCAATAGTGGAATAGCTCCTGTGACTGTGATTG
TCAAGAAAAGTTATGGTTTCTATACAGAAGCTAAAACTTTTCATACAACA
CGGTTCGGGACAATTGTATTACATTCGAGAAAACAAAATATACCAGATAT
CATTGCCTTGCATACTGCGCCTCCTCTGCCAGGTTTAATGGAAATCTGGA
AGCAAGACTTAAACATCATTCATAATCAATTGGCTTCAAAATATCCAAAG
GCTATTATTGCAGGTGATTTAATGCAACTATGCGTCATGGAGCACTTGC
AAAAAATAAGCTCTCATAGGGACGCATTAAATGCACTGCCACCTTTTGAAA
GAGGAACTTGGAATAGCCAAAGTCCAAAACTTTTTAATGCAACAATAGAT
CATATTTTATTGCCTAAAAACCACTACTATGTTAAAGATTTAGACATTGT
AAGTTTTCAAAACTCTGATCATAGATGTATTTTTACAGAAATCACATTTT
AA 4142.4

(SEQ. ID. NO. 252)
ATGAATCCAATCCAAAGATCTTGGGCTTATGTCAGCAGAAAGCGACTGAG
AAGTTTTATTTTATTTCTGATTTTATTGGTCTTATTGGCCGGAATTTCAG
CCTGTTTGACTCTGATGAAGTCCAACAAAACAGTAGAAAGCAATCTTTAT
AAATCACTCAATACATCTTTTTCTATTAAGAAGATAGAGAATGGTCAGCA
ATTCAAGTTGTCAGACCTAGCATCTGTAAGCAAGATTAAGGGGCTGGAAA
ATGTCTCTCCTGAACTTGAGACGGTCGCAAAACTAAAAGACAAGGAAGCA
GTGACTGGCGAGCAGAGCGTGGAGCGTGATGATTTATCAGCTGCAGACAA
TAACTTGGTTAGCTTAACGGCTCTTGAGGATTCATCCAAGGATGTAACCT
TTACCAGTTCGGCTTTCAATCTAAAAGAAGGGCGACACCTTCAAAAAGGG
GATTCCAAGAAAATCCTTATCCACGAAGAATTGGCTAAGAAGAACGGTCT
TTCGCTTCATGACAAGATTGGCTTGGATGCTGGTCAGTCTGAATCTGGAA
AAGGACAAACAGTAGAGTTTGAGATTTGAGCATCTTTTCTGGTAAAAGAA
CAAGAGAAATTCACAGGCTTGTCTTCGACTTCAGTGAAAATCAAGTCTT
TACAGACTATGAAAGTAGCCAAACCCTTTTGGGCAATAGTGAAGCTCAAG
TCAGTGCAGCACGCTTCTATGTAGAAAATCCTAAGGAAATGGACGGACTC
ATGAAGCAGGTAGAAAACTTGGCCTTGGAAAATCAAGGCTACCAAGTCGA
AAAGGAAAACAAGGCTTTTGAACAAATCAAAGACTCAGTTGCAACTTTCC
AAACCTTCCTGACCATCTTCCTTTATGGGATGTTGATAGCAGGAGCTGGA
GCCTTAATTCTGGTTTTGTCTCTCTGGTTGAGAGAACGGGTCTATGAAGT
GGGGATTTTACTTGCACTTGGAAAAGGCAAGACTCGATCTTCCTACAAT
TCTGTTTAGAGGTAGTTTTGGTATCTCTTGGAGCTTTGCTTCCAGCATTT
GTTGCAGGAAACGCAATCACAACTTACCTACTCCAAACTCTACTAGCAAG
TGGAGATCAGGCAAGCTTACAAGATACACTAGCCAAAGCAAGCAGTTTAT
CAACTAGCATCTTATCTTTTGCAGAATCCTATGTTTTTCTAGTTCTGCTT
AGTTGCTTATCTGTAGCCCTTTGTTTCCTATTCTTATTTAGAAAATCACC
GAAAGAAATTTTATCATCTATTAGTTAA 4142.5

(SEQ. ID. NO. 253)
ATGTTACACAACGCATTTGCCTATGTTACAAGGAAGTTTTTCAAATCGAT
TGTCATCTTCCTGATTATTCTCCTCATGGCGAGCTTGAGTTTGGTCGGCT
TGTCAATCAAGGGAGCTACTGCCAAGGCTTCTCAGGAGACCTTTAAAAAT
ATCACCAATAGCTTCTCCATGCAAATCAATCGTCGCGTCAACCAAGGAAC

TABLE 1-continued

GCCTCGTGGTGCTGGGAATATCAAGGGTGAAGACATCAAAAAAATCACCG
AAAACAAGGCCATTGAGTCTTATGTCAAACGTATCAACGCTATCGGAGAT
TTGACTGGATATGACCTGATTGAAACGCCAGAAACCAAGAAGAATCTCAC
TGCTGATCGTGCCAAGCGTTTTGGAAGTAGCTTGATGATTACAGGTGTCA
ATGACTCCTCTAAAGAAGAACAAGTTTGTCTCTGGTTCTTATAAACTAGTC
GAAGGAGAGCACTTAACCAACGACGACAAGGATAAAATCCTCTTGCACAA
GGACTTGGCAGCCAAACACGGCTGGAAAGTAGGGGACAAGGTTAAACTGG
ACTCTAATATCTACGATGCAGATAATGAAAAAGGAGCCAAGGAAACAGTT
GAAGTGACAATCAAGGGACTCTTTGATGGTCATAATAAGTCAGCAGTAAC
CTACTCACAAGAACTTTACGAAAACACAGCTATTACAGACATTCACACTG
CTGCAAAACTTTATGGATACACAGAAGACACAGCCATTTATGGGGACGCA
ACCTTCTTTGTAACAGCAGACAAGAACTTGGATGATGTTATGAAAGAGTT
GAATGGCATCAGTGGTATCAACTGGAAGAGCTACACACTCGTCAAGAGCT
CCTCTAACTACCCAGCTCTTGAGCAATCTATCTCTGGTATGTACAAGATG
GCCAACCTCCTCTTCTGGGGTAGCTTGAGCTTCTCAGTTCTCCTCCTTGC
CCTCTTGCTCAGCCTTTGGATCAACGCCCGTCGCAAGGAAGTGGGAATTC
TCCTCTCTATCGGCCTCAAGCAGGCAAGTATCTTGGGTCAATTCATCACC
GAATCTATCTTGATTGCTATCCCTGCTCTAGTTTCTGCTTACTTCCTAGC
TAATTACACTGCCCGTGCAATTGGAAACACTGTCCTTGCCAATGTGACTT
CAGGTGTTGCCAAACAGGCTAGTAAGGCGGCTCAAGCCTCTAACCTTGGT
GGTGGTGCAGAAGTAGATGGCTTTAGCAAGACCTTGTCGAGCCTAGACAT
TTCCATTCAGACATCAGACTTTATCATCATTTTTGTCCTTGCCTTGGTTC
TAGTGGTTCTCGTTATGGCGCTTGCTTCAAGCAATCTCCTTAGAAAACAA
CCAAAAGAGCTCTTGCTGGATGGTAATAA 4144.1

(SEQ. ID. NO. 254)
ATGTCACAGGATAAACAAATGAAAGCTGTTTCTCCCCTTCTGCAGCGAGT
TATCAATATCTCATCGATTGTCGGTGGGGTTGGGAGTTTGATTTTCTGTA
TTTGGGCTTATCAGGCTGGGATTTTACAATCCAAGGAAACCCTCTCTGCC
TTTATCCAGCAGGCAGGCATCTGGGGTCCACCTCTCTTTATCTTTTTACA
GATTTTACAGACTGTCGTCCCTATCATTCCAGGGGCCTTGACCTCGGTGG
CTGGGGTCTTTATCTACGGGACACATCATCGGGACTATCTACAACTATATC
GGCATCGTGATTGGCTGTGCCATTATCTTTATCTAGTGCGCCTATACGG
AGCTGCCTTTGTCCAGTCTGTCGTCAGCAAGCGCACCTACGACAAGTACA
TCGACTGGCTAGATAAGGGCAATCGTTTTGACCGCTTCTTTATTTTTATG
ATGATTTGGCCCATTAGCCCAGCTGACTTTCTCTGTATGCTGGCTGCCCT
GACCAAGATGAGCTTCAAGCGCTACATGACCATCATCATTCTGACCAAAC
CCTTTACCCTCGTGGTTTATACCTACGGTCTGACCTATATTATTGACTTT
TTCTGGCAAATGCTTTGA 4144.2

(SEQ. ID. NO. 255)
ATGAGAAATATGTGGGTTGTAATCAAGGAAACCTATCTTCGACATGTCGA
GTCATGGAGTTTCTTCTTTATGGTGATTTCGCCGTTCCTCTTTTTAGGAA
TCTCTGTAGGAATTGGGCATCTCCAAGGTTCTTCTATGGCTAAAAATAAT
AAAGTGGCAGTAGTGACAACAGTGCCATCTGTAGCAGAAGGACTGAAGAA
TGTAAATGGTGTTAACTTCGACTATAAAGACGAAGCAAGTGCCAAAGAAG
CAATTAAAGAAGAAAATTAAAAGGTTATTTGACCATTGATCAAGAAGAT
AGTGTTCTAAAGGCGTTTATCATGGCGAAACATCGCTTGAAAATGGAAT
TAAATTTGAGGTTACAGGTACACTCAATGAACTGCAAAATCAGCTTAATC
GTTCAACTGCTTCCTTGTCTCAAGAGCAGGAAAAACGCTTAGCGCAGACA
ATTCAATTCACAGAAAAGATTGATGAAGCCAAGGAAAATAAAAAGTTTAT
TCAAACAATTGCAGCAGGTCGCTTAGGATTTCTTTCTTTATATGATTCTGA
TTACCTATGCGGGTGTAACAGCTCAGGAAGTTGCCAGTGAAAAAGGCACC
AAAATTATGGAAGTCGTTTTTTCTAGCATAAGGGCAAGTCACTATTTCTA
TGCGCGGATGATGGCTCTGTTTCTAGTGATTTTAACGCATATTGGGATCT
ATGTTGTAGGTGGCTGGCTGCCGTTTTGCTCTTTAAAGATTTGCCATTC
TTGGCTCAGTCTGGTATTTTGGATCACTTGGGAGATGCTATCTCACTGAA
TACCTTGCTCTTTATTTTGATCAGTCTTTTCATGTACGTAGTCTTGGCAG
CCTTCCTAGGATCTATGGTTTCTCGTCCTGAGGACTCAGGGAAAGCCTTG
TCGCCTTTGATGATTTTGATTATGGGTGGTTTTTTTGGAGTGACAGCTCT
AGGTGCAGCTGGTGCAATCTTCCTCTTGAAGATTGGTTCTTATATTCCCT
TTATTTCGACCTTCTTTATGCCGTTTCGAACGATTAATGACTATGCGGGG
GGAGCAGAAGCATGGATTTCACTTGCTATTACAGTGATTTTTGCGGTGGT
AGCAACAGGATTTATCGGACGCATGTATGCTAGTCTCGTTCTTCAAACGG
ATGATTTAGGGATTTGGAAAACCTTTAAACGTGCCTTATCTTATAAATAG 4144.3

(SEQ. ID. NO. 256)
ATGACAGAAACCATTAAATTGATGAAGGCTCATACTTCAGTGCGCAGGTT
TAAAGAGCAAGAAATTCCCCAAGTAGACTTAAATGAGATTTTGACAGCAG
CCCAGATGGCATCATCTTGGAAGAATTTCCAATCCTACTCTGTGATTGTG
GTACGAAGTCAAGAGAAGAAAGATGCCTTGATATGAATTGGTACCTCAAGA
AGCCATTCGCCAGTCTGCTCGTGTTTCCTTCTCTTTTGTCGGAGATTTGAACC
GAGCAGAAAAGGGAGCCCGACTTCATACCGACACCTTCCAACCCCAAGGT
GTGGAAGGTCTCTTGATTAGTTCGGTCGATGCAGCTCTTGCTGGACAAAA
CGCCTTGTTGGCAGCTGAAAGCTTGGGCTATGGTGGTGTGATTATCGGTT
TGGTTCGATACAAGTCTGAAGAAGTGGCAGAGCTCTTTAACCTACCTGAC

TABLE 1-continued

TACACCTATTCTGTCTTTGGGATGGCACTGGGTGTGCCAAATCAACATCA
TGATATGAAACCGAGACTGCCACTAGAGAATGTTGTCTTTGAGGAAGAAT
ACCAAGAACAGTCAACTGAGGCAATCCAAGCTTATGACCGTGTTCAGGCT
GACTATGCTGGGGCGCGTGCGACCACAAGCTGGAGTCAGCGCCTAGCAGA
ACAGTTTGGTCAAGCTGAACCAAGCTCAACTAGAAAAAATCTTGAACAGA
AGAAATTATTGTAG 4146.1

(SEQ. ID. NO. 257)
ATGTTAAAACTTATTGCTATTGTTGGAACAAATTCAAAACGTTCTACAAA
CCGTCAATTGCTTCAATACATGCAAAAACACTTTACTGACAAAGCTGAAA
TTGAACTTGTTGAAATCAAGGCCATTCCTGTCTTCAACAAACCAGCTGAC
AAGCAAGTACCTGCTGAAATATTGGAAATTGCTGCTAAAATCGAAGAGGC
AGATGGCGTTATTATCGGTACTCCTGAGTATGATCACTCTATTCCAGCTG
TTTTTGATGAGCGCTCTTGCTTGGTTGTCTTATGGTATTTACCCACTTTTG
AACAAACCAATCATGATTACAGGTGCTTCTTACGGTACGCTTGGTTCATC
TCGTGCCCAATTGCAACTTCGTCAAATCTTGAATGCTCCTGAAATCAAGG
CAAATGTTCTTCCAGATGAATTCTTGCTCTCACACTCTCTTCAAGCATTT
AACCCAAGTGGCGACTTGGTTGACCTTGATGTTATCAAGAAATTGGATGC
CATCTTTGATGACTTCCGTATCTTTGTAAAAATCACAGAAAAATTACGTA
ATGCACAAGAATTACTTCGCAAAGATGCTGAAGACTTTGACTGGGAAAAT
TTGTAA 4146.2

(SEQ. ID. NO. 258)
ATGAATACCTATCAATTAAATAATGGAGTAGAAATTCCAGTATTGGGATT
TGGAACTTTTAAGGCTAAGGATGGAGAAGAAGCCTATCGTGCAGTGTTAG
AAGCCTTGAAGGCTGGTTATCGTCATATTGATACGGCGGCGATTTATCAG
AATGAAGAAAGTGTTGGTCAAGCAATCAAAGATAGCGGAGTTCCACGTGA
AGAAATGTTCGTAACTACCAAGCTTTGGAATAGTCAGCAAACCTATGAGC
AAACTCGTCAAGCTTTGGAAAAATCTATAGAAAACTGGGCTTGGATTAT
TGACGCATGGAAAACTCACTGCGGAAGTTTGGAGAGCGATGGAAGACC
TCTATCAAGAAGGGAAATCCGTGCTATCGGCGTTAGCAATTTTCTTCCC
CATCATTTGGATGCCTTGCTTGAAACTGCAACTATCGTTCCTGCGGTCAA
TCAAGTTCGCTTGGCGCCAGGTGTGTATCAAGATCAAGTCGTAGCTTACT
GTCGTGAAAAGGGAATTTTATTGGAAGCTTGGGGGCCTTTTGGACAAGGA
GAACTGTTTGATAGCAAGCAAGTCCAAGAAATAGCAGCAAATCACGGAAA
ATCGGTTGCTCAGATAGCCTTGGCCTGGAGCTTGGCAGAAGGATTTTTAC
CACTTCCAAAATCTGTCACAACCTCTCGTATTCAAGCTAATCTTGATTGC
TTTGGAATTGAACTGAGTCATGAGGAGAGAGAAACCTTAAAACGATTGC
TGTTCAATCGGGTGCTCCACGAGTTGATGATGTGGATTTCTAG 4147.1

(SEQ. ID. NO. 259)
ATGAGGTGCAAAATGCTTGATCCAATTGCTATTCAACTAGGACCCCTAGC
CATTCGTTGGTATGCCTTATGTATTGTGACAGGCTTGATTCTTGCGGTTT
ATTTGACCATGAAAGAAGCACCTAGAAAGAAGATCATACCAGACGATATT
TTAGATTTTATCTTAGTAGCCTTTCCCTTGGCTATTTTAGGAGCTCGTCT
CTACTATGTTATTTTCCGATTTGATTACTATAGTCAGAATTTAGGAGAGA
TTTTTGCCATTTGGAATGGTGGTTTGGCCATTTACGGTGGTTTGATAACT
GGGGCTCTTGTGCTCTATATCTTTGCTGACCGTAAACTCATCAATACTTG
GGATTTTCTAGATATTGCGGCGCCTAGCGTTATGATTGCTCAAAGTTTGG
GGCGTTGGGTAATTTCTTTAACCAAGAAGCTTATGGTGCAACAGTGGAT
AATCTGGATTATCTACCTGGCTTTATCCGTGACCAGATGTATATTGAGGG
GAGCTACCGTCAACCGACTTTCCTTTATGAGTCTCTATGGAATCTGCTTG
GCTTTGCCTTGATTCTGATTTTTAGACGGAAATGGAAGAGTCTCAGACGA
GGTCATATCACGGCCTTTTACTTGATTTGCTATGGTTTCGGTCGTATGGT
TATCGAAGGTATGCGAACAGATAGTCCATGTCTTCGGCTTTCGAGTGT
CCCAATGCTGTCAGTTGTCCTTATCGGTCTCGGTATAATGATCGTTATT
TATCAAAATCGAAAGAAGGCCCCTTACTATATTACAGAGGAGGAAAACTA
A 4147.2

(SEQ. ID. NO. 260)
ATGGGTAAATTATCCTCAATCCTTTTAGGAACCGTTTCAGGTGCAGCTCT
TGCCTTGTTTTTAACAAGTGATAAGGGCAAACAAGTTTGCAGTCAGGCTC
AAGATTTTCTAGATGATTTGAGAGAAGATCCGGATGTATGCCAAGGAGCAA
GTCTGTGAAAAACTGACAGAAGTTAAGGAGCAGGCTACAGATTTTGTTCT
GAAAACAAAAGAACAGGTTGAGTGCAGGTGAAATCACTGTGGACAGTATAC
TTGCTCAAACTAAATCCTATGCTTTTCAAGCGACAGAAGCATCAAAAAAT
CAATTAAATAATCTCAAGGAGCAATGGCAAGAAAAAGCCGAAGCTCTTGA
TGACTCAGAAGAGATTGTGATTGATATAACAGAAGAATAA 4147.3

(SEQ. ID. NO. 261)
ATGAAAACTAAATTGATCTTTTGGGGCTCTATGCTCTTTCTCCTCTCCCT
CTCCATCCTTCTGACCATTTATCTGGCTTGATTTTCTATCCTATGGAGAT
TCAGTGGCTAAACTTAACGAATCGAGTCTATCTAAAACCAGAAACCATTC

AATACAATTTTCATATCTTGATGAATTATCTGACCAATCCTTTTAGTCAG
GTCTTACAGATGCCTGATTTTCGTTCGTCAGCAGCTGGTCTGCACCATTT
CGCAGTGGTCAAGAATCTCTTTCATTTGGTTCAGCTAGTAGCTCTAGTGA
CACTGCCAAGTTTCTATGTCTTTGTCAATAGGATTGTGAAAAAGGACTTT
TTGTCTCTTTATCGAAAAAGTCTCCTGGCTCTAGTAGTCTTACCTGTGAT
GATTGGACTTGGGGGAGTTTTCATTGGTTTTGACCAATTCTTTACTCTTT
TCCATCAAATTCTCTTTGTGGGAGATGATACCTGGCTTTTTGATCCAGCC
AAGGATCCTGTTATTATGATTTTGCCAGAGACCTTCTTTCTTCATGCCTT
CCTCCTCTTTTTTGCCCTCTATGAAAACTTCTTTGGCTATCTGTATCTGA
AAAGTCGTAGGAAGTGA 4149.1

(SEQ. ID. NO. 262)
ATGACTTATCATTTTACTGAAGAATACGATATTATTGTAATTGGTGCGGG
ACACGCTGGGGTTGAGGCTTCCTTGGCCGCTAGCCGTATGGGCTGTAAGG
TCCTGCTTGCGACCATCAATATTGAAATGCTGGCTTTCATGCCTTGTAAT
CCCTCTATCGGTGGTTCTGCCAAGGGGATTGTCGTGCGTGAAGTCGATGC
CCTCGGTGGCGAGATGGCCAAAACCATTGACAAGACTTACATCCAGATGA
AGATGCTAAACACAGGGAAGGGGCCAGCTGTCCGTGCCCTTCGTGCGCAG
GCTGACAAGGAACTTTACTCTAAGGAGATGCGCAAGACGGTTGAAAACCA
AGAAAATCTGACCCTTCGTCAAACCATGATTGATGAGATTTTGGTGGAAG
ATGGCAAGGTTGTCGGTGTGCGTACAGCCACCCATCAAGAATATGCTGCT
AAGGCTGTTATTGTGACGACAGGGACTGCTCTCCGTGGGGAAATTATCAT
CGGAGACCTCCAAGTACTCATCAGGTCCTAACCACAGCTTGGCTTCTATTA
ACCTAGCTGACAATCTCAAGGAACTGGGTCTCGAAATCGGTCGTTTCAAG
ACAGGACCCCTCCACGTGTCAAGGCTTCTTCTATCAATTACGATGTGACA
GAAATTCAGCCAGGAGACGAAGTGCCTAATCATTTCTCATACACTTCACG
TGATGAGGATTATGTCAAGGACCAAGTACCATGCTGGTTGACCTATACCA
ATGGTACCAGTCATGATGATTATCCAAAACAACCTCCACCGTGCGCCTATG
TTTACAGGTGTGGTCAAGGGAGTGGGGCCTCGTTACTGTCCGTCGATTGA
AGACAAGATTGTGCGCTTTGCGGACAAGGAACGTCACCAACTCTTCCTTG
AGCCAGAAGGGCGCATTACTGAGGAAGTCTATGTGCAAGGACTTTCAACC
AGTCTGCCTGGCGATGTCCAGCGTGACTTGGTGCATTCCATCAAAGGTTT
GGAAAATGCAGAGATGATGCGGACAGGTTATGCTATTGAGTATGATATGG
TCTTGCCTCATCAGTTGCGTGCGACTTTGGAAACCAAGAAATCTCAGGT
CTCTTCACTGCTGGTCAGACAAATGGAACATCAGGTTACGAAGAGGCAGC
AGGCCAAGGGATTATCGCGGGTATCAATGCGGCTCTGAAAATCCAAGGCA
AGCCTGAATTGATTTTGAAGCGCAGTGATGGTTATATCGGGGTGATGATC
GACGACTTGGTGACCAAGGGAACCATTGAACCCTACCGTCTCTTGACCAG
TCGTGCTGAATACCGTCTCATTCTTCGTCATGACAATGCTGATATGCGCT
TGACTGAGATGGGACGCAGGATTGGCCTTGTGGACGATGAACGCTGGGCT
CGTTTTGAAATCAAGAAAAATCAATTTGATAATGAGATGAAGCGCCTAGA
CAGTATCAAACTCAAGCCAGTCAAGGAAACAATGCCAAGGTTGAGGAGA
TGGGCTTCAAACCCTTGACCGATGCAGTGACAGCCAAGGAATTCCTTCGC
CGTCCAGAAGTTCTTACCAAGATGTGGTGGCCTTCATCGGACCAGCTGC
AGAAGACTTGGATGACAAGGATTATCGAATTGATTGAAACAGAAATCAAGT
ATGAAGGCTATATTTCCAAAGCCATGGACCAGGTTGCCAAGATGAAACGC
ATGGAAGAAAAACGCATTCCGGCCAATATCGACTGGGATGACATTGATTC
TATCGCAACCGAACGCCCGTCAGAAGTTCAAACTCATCAATCCAGAAACCA
TCGGCCAAGCCAGCCGTATTTCGGGAGTAAACCCAGCAGATATTTCTATT
TTGATGGTGTATCTGGAAGGTAAAAATCGTAGTATTTCTAAAACTCTTCA
AAAAATCAAAATGA 4149.2

(SEQ. ID. NO. 263)
ATGAAAGTATTAGCTTTTGATACGTCCAGCAAGGCTCTTTCTCTGGCTAT
TTTAGAGGATAAGCAGGTTCTTGCCGAGACGACGATTAATATTAAGAAAA
ATCACAGTTACTCTTATGCTGCCATCGATTTTTTGATGGCAAGTTTG
GATTGGACACCCAAGGATTGGACCGAATCGTGTAGCTGAAGGGCCGGG
TAGCTATACAGGCTTGCGAATTGCGGTAGCAACTGCTAAGACCTTAGCTC
ACACCCTGAACATCGAGTTGGTTGGTATGTCGAGTCTCTTGGCTCTGGTG
CCCCATCAACAAGAAGGTTTGTTTGTCCCCTTGATGGATGCGCGTCGCAA
TAATGTTTATGCAGGATTTTATGAAAATGCCAAACCTGTCATGGCAGAAG
CGCACCTATCTTTTGAAGAGGTGCTAGAAAAAGTCAAGGGTACTAGTCAG
GTAACCTTTGTCGGAGAAGTTGGCCCCTTTTGTTGAGCAGATTCAAAAAC
ACTTGCCAAGGACTGATTACAAAGAAACATTGCCCAATGCAGCTAATCTA
GCTCTTTTGGCCTGGGACAAGGAAGCAGATCCTTGCATGATTTTTGTGCC
GAATTACCTCAAACGAGTCGAGGCTGAGGAAAACTGGCTCAAGAACCATA
CCGAGTCTGGCGAGTCTTACATTAAACGCCATGA 4149.3

(SEQ. ID. NO. 264)
ATGATAGAAATCAAGCGAATTCAACAACAGCCTGACCTAGCTCAAGCCAT
CTACGCTGTTATGGCAGCTGTTTACCTAGTCAGTCCTTGGCTCTGGAGC
AAATCCAAGCAGATCTGTCCCAAGACCAGACTTGGTATGCATTGGTTAT
GATGGGGCAGAAGTGATTGGATTTCTAGCTGTGCAGGAGAATCTTTTTGA
AGCAGAAGTCCTGCAAATCGCTGTCAAAGGAGCTTATCAGGGTCAGGGGA
TTGCGTCAgCCTTGTTTGCTCAATTGCCGACAGACAAGGAAATTTTCCTC
GAAGTCAGACAGTCAAATCAACGAGCGCAAGCATTTTACAAGAAAGAAAA

TABLE 1-continued

GATGACAGTTATCGCTGAGCGAAAGGCCTACTACCATGACCCAGTCGAGG
ACGCCATTATCATGAAGAGAGAAATAGATGAAGGATAG 4152.2
(SEQ. ID. NO. 265)
ATGACAAAACAAGTCTTATTAGTGGATGATGAAGAACACATTCTGAAATT
GCTTGACTACCATTTAAGTAAGGAAGGCTTTTCTACTCAATTGGTGACAA
ATGGACGGAAGGCCTTAGCTTGGCAGAAACAGAACCCTTTGATTTTATC
TTGCTTGATATCATGTTACCACAATTAGATGGCATGGAAGTTTGTAAGCG
GCTGAGAGCCAAAGGCGTCAAAACTCCAATTATGATGGTTTCTGCGAAAA
GTGATGAATTTGATAAGGTTTTGGCCTTGGAATTAGGGGCTGATGACTAC
CTGACCAAGCCTTTTAGCCCTAGAGAATTGCTGGCGGCGTGCAAGGCTGT
CCTCAGGCGAACTAAAGGAGAACAAGAAGGAGATGATTCAGATAATATCG
CTGACGATTCTTGGCTATTTGGGACCTTGAAAGTATACCCTGAGCGTCAT
GAAGTCTACAAGGCGAATAAGTTACTGAGTTTGACCCCAAAAGAATTTGA
AAGCGATAAAAATCCGTTTTTTGAAGTTTTCAAAGTTTCGAAAGTAACCG
CCCAATAA 4154.1
(SEQ. ID. NO. 266)
ATGACTACTTTTAAAGATGGATTTTTATGGGGTGGTGCTGTTGCTGCTCA
TCAACTTGAAGGTGGATGGCAAGAAGGTGGCAAGGGAATTAGTGTTGCTG
ATGTTATGACTGCTGGTCGTCATGGAGTAGCTCGTGAAATACTTTGGGAG
TTTTAGAGGGTAAATATTATCCAAATCATGAGGCGATAGATTTTTTATCAC
CGTTATAAAGAAGATATAGCACTTTTTGCTGAAATGGGATTCAAGTGCTT
CCGTACCTCTATTGCATGGACACGTATCTTTCCAAAAGGTGATGAGTTAG
AGCCGAATGAAGAAGGATTACAGTTTTATGATAATCTTTTTGATGAATGC
TTAAAGAATGGTATTGAACCTGTCATCACTCTATCTCATTTTGAAATGCC
TTATCACTTAGTGACCGAATATGGTGGTTGGAAAAATAGGAAATTGATTG
ATTTCTTTGCTCGTTTTGCAGAAGTCGTATTTAAACGTTACAAAGATAAG
GTTAAATATTGGATGACTTTCAATGAAATCAATAATCAAGCGAATTATCA
GGAAGATTTTGCACCATTTACTAACTCAGGTATTGTATATGAGGAAGGTG
ATAATAGAGAAGCAATTATGTATCAAGCAGCACATTACGAATTAGTTGCT
TCTGCACGAGCTGTAAAAATTGGTCATGAGATTAATCCAGATTTTCAAAT
AGGTTGTATGATTGCGATGTGTCCAATTTATCCAGTTACTTGCAATCCTA
AGGATATCTTAATGGCAATGAAAGCTATGCAGAAGCGTTATTATTTTGCT
GATGTGCATGTTTTAGGTAAAATATCCTGAGCATATTTTCAAGTATTGGGA
ACGAAAAGGTATTTCAGTTGATTTTACTGCCCAGGATAAAGAAGATTTAC
TTGGTGGGACTGTAGATTACATTGGTTTCAGTTACTATATGTCCTTTGCT
ATCGACTCTCATCGTGAAAATAATCCTTATTTTGATTATCTTGAAACAGA
AGATTTAGTGAAAAATATATGTTAAGGCTTCTGAATGGGAGTGGCAAA
TTGATCCAGAAGGTTTGCGTTATGCGTTAAATTGGTTTACAGACCACTAT
CACTTACCACTCTTTATTGTTGAAAATGGTTTTGGAGCTATAGATCAAGT
TGCAGCAGATGGTATGGTACATGATGATTATAGAATTGAATATCTAGGTG
CCCATATTCGTGAAATGAAAAAGGCTGTAGTTGAAGATGGTGTTGATTTA
ATGGGTTATACTCCATGGGGATGTATTGATTTGGTTTCAGCTGGTACCGG
TGAAATGCGGAAACGTTATGGCTTTATTTATGTAGATAAAGATGATAATG
GGAAGGGAAGTTATAATCGTTCCCCGAAAAAATCTTTTGGCTGGTATAAG
GAAGTTATTTCATCTAACGGTGAATCAGTAGAATAG 4154.2
(SEQ. ID. NO. 267)
ATGGATCAACAAAACGGGTTGTTTGGTTTTCTTGAAAAACCATGTTATGG
ACCAATGGGCAAACTTGCTCAGTTTAAAGTAGTACGTGCTATCACGGCTG
CAGGTATGGCTGCTGTACCATTTACTATTGTAGGATCAATGTTTTTGGTA
TTCAGTATTTTGCCACAAGCTTTCTCATTTTGGCCAATTGTGGCAGATAT
TTTCTCTGCTTCATTTGATAAATTCACATCACTTTACATGGTTGCAAACT
ATGCGACTATGGGTTCTCTATCTCTTTATTTCGTTCTATCACTTGCATAT
GAATTGACAAAAATTTATGCAGAGGAAGGAAGAACTCAATATGAATCCTCT
TAATGGTGCCTTGCTTGCCTTGATGGCTTTTGTCATGACAGTACCGCAAA
TCATTTTTGATGGTGGAATGATGAAGACTGTGACAAGTCTAAAAGAAGGT
GCAGTAATTGCAGATGGATGGCAATGGGAAATGTCGTCGCACGTTTTGG
GACAACAGGGATTTTTACCGCAATCATTATGGCAATTGTGACTGTTCTTA
TTTATCGTATGTGTGTTAAACATAATTGGTTATTAAATGCCTGAAGCT
GTTCCAGAAGGAGTTTCTCGTGGATTTACCGCTTTGGTTCCGGGATTTGT
TGTTGCATTTGTTGTTATCTTTATCAACGGTCTTCTTGGACGAGAATGGAA
CAGATATTTTAAAGTCATTGTCAATTCCATTTGTTTTTGTATCCAATCTG
ACTAATTCGTGGATTGGTTTAATGATTATTTATCTATTGACTCAACTACT
TTGGATTGTAGGTATCCACGGTGCGAACATTGTTTTGCATTTGTTAGTC
CAATGCTCTTGCTAACATGGCTGAAAATGCTGCTGGCGGGCACTTCGT
GTTGCAGGTGAATTTTCTAATAGTGTTGTAATTGCAGGTGGTTCTGGTGC
AACTTTAGGACTATGTTTATATATTGCTTTTGCCTCTAAATCTGAACAGC
TTAAAGCAATAGGACGAGCATCTGTAGTTCCAGCCTTATTTAATATTAAT
GAACCATTAATTTTTGGATTACCTATTACTGCTACTATTTATTACGTAGCGA
ATTCTCTAAACTTTATTAAGCCAATATCGCACAGGTTCCATGGCCAACT
CCAGTAGGGATTGGAGCTTTCTTAGGGACAGCAGATCTTCGAGCTGTATT
AGTTGCTCTAGTATGTGCATTTGCAGCATTCCTAGTCTATCTTCCATTCA
TCCGTGTATATGATCAAAAATTGGTGAAGAAGAGCAAGGTATCTAA 4155.1
(SEQ. ID. NO. 268)
ATGAAAAAATTTTATGTAAGTCCAATTTTTCCTATTCTAGTAGGATTGAT
TGCGTTTGGAGTCTTATCCACTTTCATTATTTTTGTTAATAATAATCTGT
TGACGGTTTTAATTTTGTTTCTTTTTGTAGGAGGCTATGTTTTTTTATTT
AAGAAACTGAGAGTGCATTATACAAGGAGTGATGTAGAACAGATACAGTA
TGTAAACCACCAAGCGGAAGAAAGTTTGACAGCTCTATTGGAACAGATGC
CTGTAGGTGTTATGAAATTGAATTTATCTTCTGGAGAGGTTGAGTGGTTT
AATCCCTATGCTGAATTGATTTTGACCAAGGAAGATGGTGATTTTGATTT
AGAAGCTGTTCAAACGATTATCAAGGCTTCAGTAGGAAATCCGTCTACTT
ATGCCAAGCTTGGTGAGAAGCGTTATGCTGTTCATATATGGATGCTTCTTCC
GGTGTTTTGTATTTTGTAGATGTATCCAGGGAACAAGCCATAACAGATGA
ATTGGTAACAAGTAGACCAGTGATTGGGATTGTCTCTGTGGATAATTATG
ATGATTTGGAGGATGAAACTTCTGAGTCAGATATTAGTCAAATCAATAGT
TTTGTGCTAATTTTATATCAGAGTTTTCAGAAAAACACATGATGTTTTC
TCGTCGGGTAAGTATGGATCGATTTTATCTATTTACTGACTACACGGTGC
TTGAGGGCTTGATGAATGATAAATTTTCTGTTATTGATGCTTTCAGAGAA
GAGTCGAAACAGAGACAGTTGCCCTTGACCTTAAGTATGGGATTTTCTTA
TGGGCATGGAAATCATGATGAGATAGGGAAAGTTGCTTTGCTCAATTTGA
ACTTGGCTGAAGTACGTGGTGGCGACCAGGTGGTTGTTAAGGAAAACGAC
GAAACGAAAATCCAGTTTATTTTGGTGGTGGGTCTGCTGCTTCAATCAA
GCGTACACGGACTCGTACGCGCGCTATGATGACAGCTATTTCAGATAAGA
TTCGGAGTGTAGATCAGGTTTTTTGTAGTCGGTCACAAAAATTTAGACATG
GATGCTTTGGGCTCTGCTGTAGGTATGCAGTTGTTCGCCAGCAATGTGAT
TGAAATAGCTATGCTCTTTATGATGAAGAACAAATGTCTCCAGATATTG
AACGAGCTGTTTCATTCATAGAAAAAGAAGGAGTTACGAAGTTGTTGTCT
GTTAAGGATGCAATGGGGATGGTGACCAATCGTTCTTTGTTGATTCTTGT
AGACCATTCAAAGACAGCCTTAACATTATCAAAGAAATTTTATGATTAT
TTACCCAAACCATTGTTATTGACCACCATAGAAAGGGATCAGGATTTTCCA
GATAATGCGGTTATTACTTATATCGAAAGTGGTGCAAGTAGTGCCAGTGA
GTTGGTAACGGAATTGATTCAGTTCCAGAATTCTAAGAAAAATCGTTTGA
GTCGTATGCAAGCAAGTGTCTTGATGGCTGGTATGATTGTGGATACTAAA
AATTTCACCTCGCGAGTAACTAGTCGGACATTTGATGTTGCTAGCTATCT
CAGAACGCGCGGAAGTGATAGTATTGCTATCCAGGGAAATCGCTGCGACAG
ATTTTGAAGAATATCGTGAGGTCAATGAACTTATTTTACAGGGGCGTAAA
TTAGGTTCAGATGTACTAATAGCAGAGGCTAAGGACATGAGATCATGA
TACAGTTGTTATTAGTAAGGCAGCAGATGCCATGTTAGCCATGTCAGGTA
TTGAAGCGAGTTTTTGTTCTTGCGAAGAATACACAAGGATTTATCTCTATC
TCAGCTCGAAGTCGTAGTAAACTGAATGTACAACGGATTATGGAAGAGTT
AGGCGGTGGAGGCCACTTTAATTTGGCAGCAGCTCAAATTAAAGATGTAA
CCTTGTCAGAAGCAGGTGAAAAACTGACAGAAATTGTATTAAATGAAATG
AAGGAAAAGGAGAAAGAAGAATGA 4156.1
(SEQ. ID. NO. 269)
ATGAAAGAGAAAAATATGTGGAAAGAATTGTTGAATCGTGCAGGCTGGAT
TTTGGTCTTTTTACTTGCCGTCCTTTTATATCAGGTTCCCCTAGTGGTTA
CCTCTATTTTGACTTTAAAAGAAGTAGCCCTGCTACAGTCAGGGCTGATA
GTTGCTGGCCTTTCAATTGTGGTTCTGGCTCTATTTATTATGGGAGCTCG
TAAAACCAAGTTAGCTAGTTTTAATTTTTCTTTTTTTAGAGCTAAAGATT
TGGCACGTTTGGGCTTGAGTTATCTAGTTATTGTCGGGTCAAATATACTT
GGTTCCATTTTATTGCAACTGTCAAATGAGACGACAACAGCTAACCAGTC
TCAGATTAATATATGGTTCAAAATAGTTCGTTGATTTCCAGTTTTCTTCT
TGCTAGCCTTGCTTGCTCCGATTTGTGAGGAAATCTTGTGTCGTGGGATT
GTTCCTAAAAGATTTTCCGAGGCAAGGAGAACTTGGGATTGTAGTCGG
TACGATTGTGTTTGCTTTATTGCATCAACCAAGTAATTTACCTTCTTTAT
TGATTTATGGAGGTATGTCGACAGTTCTATCTTGGACAGCCATGAGACC
CAACGTTTGGAAATGTCGATCTTGCTTCACATGATTGTTAATGGGATTGC
TTTCTGTTTGTTGGCCTTGTGGTGATTATGAGTCGGACATTAGGAATTT
CTGTTTAAATGAAAGAAAAATATGTGGAAAGAATTGTTGAATCGTGCA
GGCTGGATTTTGGTCTTTTTACTTGCCGTCCTTTTATATCAGGTTCCCCT
AGTGGTTACCTCTATTTTGACTTTAAAAGAAGTAGCCCTGCTACAGTCAG
GGCTGATAGTTGCTGGCCTTTCAATTGTGGTTCTGGCTCTATTTATTATG
GGAGCTCGTAAAACCAAGTTAGCTAGTTTTAATTTTTCTTTTTTTAGAGC
TAAAGATTTGGCACGTTTGGGCTTGAGTTATCTAGTTATTGTCGGGTCAA
ATATACTTGGTTCCATTTTATTGCAACTGTCAAATGAGACGACAACAGCT
AACCAGTCTCAGATTAATATATGGTTCAAAATAGTTCGTTGATTTCCAG
TTTCTTCTTGCTAGCCTTGCTTGCTCCGATTTGTGAGGAAATCTTGTGTC
GTGGGATTGTTCCTAAAAGATTTTCCGAGGCAAGGAGAACTTGGGATTGT
AGTCGGTACGATTGTGTTTGCTTTATTGCATCAACCAAGTAATTTACC
TTCTTTATTGATTTATGGAGGTATGTCGACAGTTCTATCTTGGACAGCCT
ACAAGACCCAACGTTTGGAAATGTCGATCTTGCTTCACATGATTGTTAAT
GGGATTGCTTTCTGTTTGTTGGCTCTTTGTGGTGATTATGAGTCGGACAT
TAGGAATTTCTGTTTAA 4156.4
(SEQ. ID. NO. 270)
ATGGATACACAAAAGATTGAAGCGGCTGTAAAAATGATTATCGAGGCTGT

TABLE 1-continued

```
AGGAGAGGACGCTAATCGCGAGGGCTTGCAGGAAACACCTGCTCGTGTAG
CCCGTATGTATCAAGAGATTTTTTCAGGTCTTGGTCAAACAGCAGAGGAA
CATTTGTCAAAATCCTTTGAAATTATTGACGATAATATGGTGGTAGAAAA
GGATATCTTTTTCCATACCATGTGTGAACACCACTTCTTGCCATTTTATG
GTAGAGCGCACATTGCCTACATTCCAGATGGTCGTGTGGCAGGCTTGTCT
AAGCTAGCCCGTACGGTTGAAGTTTATTCGAAAAAACCACAAATTCAAGA
ACGTTTGAATATCGAAGTGGCCGATGCCTTGATGGACTATCTAGGTGCTA
AAGGAGCCTTTGTTGTCATTGAGGCGGAACATATGTGTATGAGTATGCGT
GGTGTTAGAAAACCAGGCACTGCAACCTTGACGACAGTAGCTCGTGGTCT
ATTTGAAACAGATAAGGATCTCCGTGACCAAGCTTATCGTTTAATGGGGC
TATAA
```

4157.2

(SEQ. ID. NO. 271)
```
ATGAAAGACTTGTTTTTAAAGAGAAAGCAGGCCTTTCGTAAGGAGTGTCT
TGGTTATCTGCGCTATGTGCTCAATGACCACTTTGTCTTGTTCCTGCTTG
TCCTGTTGGGCTTTCTAGCCTACCAGTACAGTCAACTCTTACAACATTTT
CCTGAAAATCATTGGCCTATCCTTTGTTTGTAGGAATTACGTCTGTTTT
ACTTTTACTTTGGGGAGGAACTGCCACCTATATGGAGGCTCCAGACAAGC
TCTTTCTCTTAGTTGGAGAAGAGGAAATTAAGCTCCATCTCAAGCGTCAA
ACTGGCATTTCCCTAGTCTTTTGGCTCTTTGTACAGACCCTTTTCTTGCT
GTTATTTGCGCCTTTATTTTTAGCAATGGGTTATGGCTTGCCAGTTTTTC
TGCTCTATGTGCTTTTATTGGGGGTAGGAAAATATTTCCACTTTTGTCAA
AAGGCCAGCAAATTTTTCACTGAAACTGGACTGGACTGGGACTATGTTAT
TTCTCAAGAAAGCAAGCGTAAGCAAGTCTTGCTTCGTTTCTTTGCCCTCT
TTACGCAGGTCAAGGGAATTTCAAACAGCGTTAAGCGTCGTGCCTATCTG
GACTTTATTTTAAAGGCTGTTCAGAAGGTGCCTGGGAAGATTTGGCAAAA
CTCTCTATCTGCGTTCTTATCTGCGAAATGGCGACCTCTTTGCTCTCAGTC
TTCGTCTTCTTCTTGTTTGCCTTGCTGGCGCAGGTTTTTATCGAGCAAGC
TTGGATTGCGACAGCAGTGGTAGTTCTCTTTAACTACCTCTTGCTCTTCC
AGTTGCTGGCCCTCTATCATGCCTTTGACTACCAGTATTTGACCCAACTC
TTTCCGCTGGACAAGGGGCAAAAGGAAAAAGGCTTACAGGAGGTAGTTCG
AGGATTGACCAGTTTTGTTTTACTTGTGGAACTGGCTTGTTGGGTTGATTA
CCTTCCAAGAAAAACTAGCCCTTCTAGCCTTACTAGGAGCTGGTTTGGTT
TTACTAGTCTTGTATTTGCCTTATCAGGTAAAACGTCAGATGCAGGACTA
A
```

4258.2

(SEQ. ID. NO. 272)
```
ATGAGAAAATCAATAGTATTAGCGGCAGATAATGCCTATCTTATTCCTTT
AGAGACGACTATAAAGTCTGTATTGTATCACAATAGAGATGTTGATTTTT
ATATTCTCAACAGTGATATAGCTCCTGAATGGTTTAAATTATTGGGGAGA
AAAATGGAAGTTGTGAATTCTACAATTCGCAGTGTACACATTGATAAAGA
ACTTTTTGAAAGCTATAAAACAGGACCTCATATAAATTATGCTTCTTACT
TTAGATTTTTTGCGACAGAAGTGGTTGAATCTGATAGGGTATTGTATCTG
GATTCCGATATCATTGTAACTGGGGAACTAGCTACTTTGTTTGAGATAGA
TCTCAAAGGATATTCAATTGGTGCTGTTGATGATGTCTATGCCTATGAAG
GACGAAAATCTGGATTTAATACTGGTATGTTACTAATGGATGTTGCAAAG
TGGAAAGAACATTCTATTGTCAATAGTTTATTGGAATTAGCGGCCGAGCA
GAATCAAGTTGTTCATCTTGGGGATCAGAGTATTTTAAATATTTATTTTG
AGGATAATTGGCTAGCCTTAGATAAACATATAATTATATGGTGGGTATT
GATATTTATCACCTTGCTCAAGAATGTGAACGTCTAGATGACAATCCACC
TACAATTGTTCACTATGCTAGTCATGATAAACCTTGGAATACATATAGTA
TATCTAGACTACGTGAATTGTGGTGGGTTTATAGAGATTTGGATTGGTCA
GAGATTGCTTTTCAACGTTCCGATTTAAATTATTTTGAAAGAAGCAATCA
GTCTAAAAAACAAGTGATGCTTGTGACATGGAGTGCAGATATAAAACATT
TAGAGTATTTAGTACAACGGTTACCTGATTGGCATTTTCATTTGGCTGCA
CCGTGTGATTGTTCTGAGGAGCTGACCTCTCTATCACAGTATACGAATGT
AACAGTATATCAAAATGTATTACATAGTAGAATTGATTGGCTATTGGACG
ATTCTATAGTTTATTTAGATATTAATACAGGTGGAGAGGTTTTAATGTA
GTTACAAGGGCACAAGAAAGTGGCAAGAAAATCTTCGCTTTTGATATCAC
ACGTAAAAGTATGGATGATGGACTCTATGACGGTATTTTTTCTGTGGAGA
GACCAGATGATTTAGTGGATAGAATGAAGAATATAGAGATAGAGTAA
```

4158.2

(SEQ. ID. NO. 273)
```
ATGACTAAGATTTATTCGTCAATAGCAGTAAAAAAAGGACTATTTACCTC
ATTTCTACTGTTTATCTATGTATTGGGAAGTCGTATTATTCTCCCTTTTG
TTGACCTAAATACTAAAGATTTTTTAGGAGGTTCAACAGCCTATCTAGCC
TTCTCAGCCGCCCTAACAGGTGGGAATCTAAGAAGTTTTATCAATTTTTC
TGTTGGATTATCCCCTTGGTGATGTCCGCCATGATTTTATGGCAGATGTTT
CTTTTTTCTAAACGGTTGGGTTAACATCTACGTCTATAGAAATACAAGAT
CGCCGTAAAATGTACCTGACCTTGCTAATTGCTGTGATTCAATCCTTGGC
AGTTAGCTTGAGACTGCCATGCAGTACAATCCTCCTATTCTGCAAATTGGTTG
TTCTAATGAATACAATATTGCTAGATCAGGAACATTTTTTCTTGTTTGG
TTGTCAGATTTAAATGCGATGATATGGGATTGGAGGTTCTATTGTAATCCT
CCTATCCAGTATGGTTTAAATATTCCTCAGGATGTTTTGGAAACATTTC
AGACAGTACACATTCCAACAGGGATTATTGTGTTACTTGCTTTATTACCC
CTTGTCTTTTCTATTTACTTGCCCTTATGTATCGAGCTCGCTATTTGGT
TCCTGTTAATAAAATTGGCTTACACAATCGATTTAAACGCTATTCTTATC
TCGAAATCATGTTGAATCCTGCAGGTGGGATGCCTTATATGTATGTGATG
AGTTTTCTTAGTGTACCAGCTTATTTGTTCATCTTGTTGGGATTATTTT
CCCTAATCATTCAGGGTTAGCGGCTTTATCAAAGGAATTTATGGTTGGAA
AGCCTTTGTGGGTCTATGTTTTATATTTCGGTCTTATTTTTATTTAGTATC
ATTTTTGCTTTTGTTACGATGAATGGAGAAGAGATTGCAGACCGTATGAA
AAAATCTGGAGAATACATTTATGGTATTTATCCAGGTGCGGATACTAGTC
GATTTATTAATCGATTGGTCCTTCGTTTCTCAGTCATAGGTGGTCTCTTT
AATGTGATTATGCAGGTGGTCCCATGCTTTTTGTTTTGTTTGATGAAAA
GTTATTACGATTGGCAATGATTCCAGGCTTATTTATGATGTTCGGGGGCA
TGATTTTTACGATTAGAGACGAGGTCAAGGCTTTAAGGCTAAATGAGACC
TATAGACCTTTGATTTAG
```

4158.3

(SEQ. ID. NO. 274)
```
ATGTCCTCTCTTTCGGATCAAGAATTAGTAGCTAAAACAGTAGAGTTTCG
TCAGCGTCTTTCCGAGGGAGAAAGTCTAGACGATATTTTGGTTGAAGCTT
TTGCTGTGGTGCGTGAAGCAGATAAGCGGATTTTAGGGATGTTTCCTTAT
GATGTTCAAGTCATGGGAGCTATTGTCATGCACTATGGAAATGTTGCTGA
GATGAATACGGGGGAAGGTGGTAAGACCTTGACAGCTACCATGCCTGTATT
TGAACGCTTTTCAGGAGAGGAGTGATGGTTGTGACTCCTAATGAGTAT
TTATCAAAGCGTGATGCCGAGGAAATGGGTCAAGTTTATCGTTTTCTAGG
ATTGACCATTGGTGTACCATTTACGGAAGATCCAAAGAAGGAGATGAAAG
CTGAAGAAAAGAAGCTTATCTATGCTTCGGATATCATCTACACAACCAAT
AGTAATTTAGGTTTTTGATTATCTAAATAGATAACCTAGCCTCGAATGAAGA
AGGTAAGTTTTTACGACCGTTTAACTATGTGATTATTGATGAAATTGATG
ATATCTTGCTTGATAGTGCACAAACTCCTCTGATTATTGCGGGTTCTCCT
CGTGTTCAGTCTAATTACTATGCGATCATTGATACACTTGTAACAACCTT
GGTCGAAGGAGAGGATTATATCTTTAAAGAGGAGAAAGAGGAGGTTTGGC
TCACTACTAAGGGGGCCAAGTCTGCTGAGAATTTCCTAGGGATTGATAAT
TTATACAAGGAAGAGCATGCGTCTTTTGCTCGTCATTTGGTTTATGCGAT
TCGAGCTCATAAGCTCTTTACTAAAGATAAGGACTATATCATTCGTGGAA
ATGAGATGACTGCTTGGTTGATAAGGGAACAGGGCGTCTAATGGAAATGACT
AAACTTCAAGGAGGTCTCCATCAGGCTATTGAAGCCAAGGAACATGTCAA
ATTATCTCCTGAGACGCGGGCTATGGCCTCGATCACCTATCAGAGTCTTT
TTAAGATGTTTAATAAGATATCTGGTATGACAGGGACAGGTAAGGTCGCG
GAAAAAGAGTTTATTGAAACTTACAATATGTCTGTAGTACGCATTATATCC
CAATCGTCCGAGACAACGGATTGACTATCCAGATAATCTCTATATATCACTT
TACCTGAAAAGTGTATGCATCCTTGGAGTACATCAAGCAATACCATGCT
AAGGGAAATCCTTTACTCGTTTTTGTAGGCTCAGTTGAAATGTCTCAACT
CTATTCGTCTCTCTTGTTTCGTGAAGGGATTGCCCATAATGTCCTAAATA
CTAATAATGCGGCGCGTGAGGCTCAGATTATCTCCGAGTCAGGTCAGATG
GGGGCTGTGACAGTGGCTACCTCTATGCAGGACGTGGTACGGATATCAA
GCTTGGTAAAGGAGTCGCAGAGCTTGGGGCTTGATTGTATTGGGACTG
AGCGGATGGGAAAGTCAGCGGATCGACCTACAAATTCGTGGCCGTTCTGGT
CGTCAGGGAGATCCTGCTGTATGAGTGAAATTTTTTGTATCCTTAGAGGATGA
TGTTATCAAGAAATTTGGTCCATCTTGGGTGCATAAAAAGTACAAAGACT
ATCAGGTTCAAGATATGACTCAACCGGAAGTATTGAAAGGTCGTAAATAC
CGGAAACTAGTCTGAAAAGGCTCAGCATGCCAGTGATAGTGCTGAAGTTC
AGCACGTCGTCAGACTCTGGAGTATGCTGAAAGTATGAATATACAACGGG
ATATAGTCTATAAAGAGAGAAATCGTCTAATAGATGGTTCTCGTGACTTA
GAGGATGTTGTTGGATATCATTGAGAGATATACAGAAGAGGTAGCGGC
TGATACTACTATGCTAGTCGTGAATTATTGTTTCACTTATTGTGACCAATA
TTAGTTTTCATGTTAAAGAGGTTTCAGATTATATAGATGTAACTGCAAA
ACTGCAGTTCGTAGCTTTATGAAGCAGGTGATTGATAAAGAACTTTCTGA
AAAGAAAGAATTACGTTAATCAACATGACTTATATGAACAGTTTTTACGA
CTTTCACTGCTTAAAGCCATTGATGACAACTGGGTAGAGCAGGTAGACTA
TCTACAACGACTATCCATGGCTATCGGTGGTCAATCTGCTAGTCAGAAAA
ATCCAATCGTAGAGTACTATCAAGAAGCCTACGCGGGCTTTGAAGCTATG
AAAGAACAGATTCATGCGGATATGGTGCGTAATCTCCTGATGGGCTGGT
TGAGGTCACTCCAAAAGGTGAAATCGTGACTCATTTTCCATAA
```

4158.4

(SEQ. ID. NO. 275)
```
ATGATAGGGACTTTCGCCGCTGCTCTTGTAGCTGTACTAGCAAATTTCAT
CGTCCCTATTGAAATTACCCCAAATAGTGCCAATACTGAAATTGCACCAC
CAGATGGGATTGGGCAGGTTCTCAGCAACCTCTTGCTCAAACTGGTTGAC
AACCCAGTCAACGCCCTGTTACTGCTAACTATATTAGAATCTTATCTTGG
GCAGTCATTTTGGAATCGCTATGAGAGAAGCCAGTAAAAATAGTCAAGA
ATTGCTAAAAACTATCGCTGACGTGCTTCTAAAATTGTCGAATGGATCA
TCAATCTGGCTCCATTTGGAATCCTTGGTCTTGTTTTTAAAACCATTTCT
GACAAGGGAGTCGGAAGCCTTGCCAACTACGTATTTTATTGGTTCTATT
AGTAACGACTATGCTTTTGTTGCCCCTGTGGTCAACCCTTTGATTGCCT
TCTCTTTATGAGACGCAATCTTACCCTCTAGTTTGGAACTGCCTCCGT
GTCAGCGGTGTGACAGCCTTTTTCGCTGTAGTTCTGCGACTAACATTCC
TGTCAACATGAAACTCTGCCATGACCTTGGACTCAACCAGATACCTATT
CTGTTTCTATCCCACTCGGTTCTACTATCAATATGGCTGGAGTAGCGATT
ACCATTAACCTTTTGACCCTTGCTGCAGTTAACACTCTTGGAATTCCTGT
TGACTTTGCCACAGCCTTTGTCCTCAGTGTGGTAGCAGCTATCTCATCCT
```

TABLE 1-continued

GTGATGCTTCAGGTATTGCCGGAGGTTCCCTCCTTCTTATCCCAGTTGCT
TGTAGCCTTTTCGGTATTTCTAACGATATTGCCATACAAATTGTTGGGGT
TGGTTTTGTGATTGGTGTCATCCAAGACTCATGTGAAACAGCCCTTAACT
CTTCTACAGATGTCCTCTTTACCGCCGTTGCCGAATACGCAGCAACCCGT
AAAAAATAA 4158.5

(SEQ. ID. NO. 276)
ATGTCTATTAGCCAACGTACGACCAAGCTCATCTTAGCTACCTGTCTTGC
CTGCCTGCTTGCTTATTTTCTCAATCTTTCGTCAGCAGTTTCGGCTGGAA
TTATCGCTCTCTTGAGCCTATCTGATACGCGTAGAAGTACTTTAAAACTG
GCTCGCAATCGTCTTTTTTCTATGCTTCTAGCTCTGGCTATCGGTGTTCT
AGCTTTTCACTTGAGCGGATTTCATATCTGGAGTCTCGGCCTCTATCTGG
CCTTCTACGTTCCTTTAGCCTACAAGATGGGCTGGGAAATTGGCATCACA
CCAAGCACTGTTTTGGTTAGCCATCTCTTGGTTCAAGAGTCAACCTCTCC
AGACCTTCTAGTCAATGAATTCCTTCTCTTTGCTATTGGTACAGGATTTG
CCTTGCTTGTTAATCTCTATATGCCTTCACGAGAAGAGGAAATCCAGCAC
TACCACACGCTGGTGGAAGAAAAGTTAAAAGATATCCTCCAGCGCTTCAA
ATACTATTTATCCAGAGGAGACGGACGCAACCGAGCACAGCTGGTAGCAG
AATTAGACACGCTTTTGAAAGAAGCCCTCAGACTGGTCTATTTGGACTCA
TCTGACCACCTCTTTCACCAGACAGACTACCCATATCCACTACTTTGAGAT
GAGACAGCGACAAAGTCGTATCCTGAGAAACATGGCCCAACAGATTAACA
CTTGTCACCTTGCCGCCAGTGAAAGCCTGATCTTAGCGCAACTCTTTTCA
AAAATTGCAGGTCAACTGAGCCAGACCAATCCTGCTTCTGATTTGCTAGA
TGAAATTGAACGTTATCTGGAAGTCTTCCGGAACCGCAGTCTGCCCAAGA
CAAGAGAAGAATTTGAAACCCGCGCCACCCTTCTTCAACTCCTACGTGAA
GCCAAAACCTTCATCCAAGTAAAAGTTGATTTTTACCAAAAATATAGACA
GTAA 4158.6

(SEQ. ID. NO. 277)
ATGGAAATCATGTCGCTTGCGATTGCTGTTTTTGCCGTCATCATTGGTTT
AGTCATTGGATATGTCAGCATCTCAAGCTAAGATGAAATCATCTCAGGAAG
CTGCAGAGTTGATGCTTTTAAATGCTGAACAAGAAGCAACTAATTTACGT
GGACAAGCTGAGCGTGAAGCGGATTTACTTGTTAATGAAGCCAAACGTGA
AAGCAAGTCTCTTAAAAAAGAAGCACTATTGGAGGCCAAAGAAGAAGCCA
GAAAATACCGTGAAGAAGTGGACGCTGAATTCAAATCAAGACGTCAAGAA
CTCAAACAAATCGAAAGTCGTTTGACAGAGAGAGCTACTAGCCTTGACCG
TAAGGACGACAATTTGACGAGTAAAGAACAAACACTTGAACAAAAAGAAC
AAAGTATTTCTGATAGAGCGAAAAACCTTGATGCGCGTGAAGAGCAATTA
GAGGAAGTCGAAAGACAAAAAGAAGCAGAACTAGAGCGTATTGGTGCGCT
GTCTCAGGCAGAAGCACGAGATATTATCTTGGCTCAGACAGAGGAAAACT
TGACCAGGGAGATTGCCAGTCGCATTCGCGAAGCTGAGCAAGAGGTCAAG
GAACGTTCTGACAAAATGGCCAAGGACATCTTGGTTCAAGCTATGCAACG
TATCGCTGGTGAATATGTAGCGGAGTCAACAAACTCAACAGTTCATCTGC
CAGACGATACTATGAAGGGACGCATTATTGGTCGTGAAGGTCGTAACATT
CGTACCTTTGAAAGTTTGACAGGGGTCGATGTGATTATCGACGATACACC
AGAAGTGGTGACCTTGTCAGGATTTGATCCGATTCGTCGTGAGATTGCCC
GTATGACTATGGAAATGTTGCTCAAAGATGGTCGTAAATCCAGCTCGT
ATCGAAGAGTTGGTTGAGAAAAACCGTCAAGAGATTGACAATAAGATTCG
TGAATACGGTGAGGCTGCTGCCTATGAAATTGGTGCGCCAAACCTTCATC
CAGACTTGATGAAGATTATGGGACGTTTGCAGTTCCGTACTTCATATGGA
CAAAATGTTTTGCGCCATTCGATTGAGGTTGCTAAGTTGGCTGGTATCAT
GGCGAGCGAACTTGGTGAAAATGCGGCTCTTGCCCGTCGTCGTCGGATTCC
TTCACGATATCGGGAAAGCCATTGACCATGAGGTTGAAGGTAGCCACGTT
GAAATCGGTATGGAATTGGCCCGTAAGTACAAGGAACCCCCAGTTGTGGT
GAATACGATTGCTAGTCACCACGGAGATGTTGAAGCTGAGAGCGTGATAG
CAGTTATCGTCGCTGCAGCAGATGCCCTTGAGCGCGACCCGTCCAGGTCT
CGTAGTGAGTCTCTTGAAAGCTACATCAAGCGTCTCCATGATTTGGAAGA
AATTGCTAACGGCTTGAAGGAGTGCAAACTAGCTTTGCCCTTCAAGCAGG
ACGTGAAATTCGTATCATGGTCAATCCAGGAAAAATCAAGGACGACAAAG
TCACAATCTTGGCTCACAAAGTTCGTAAGAAAATTGAAAACAATCTCGAT
TATCCAGGAAATATCAAGGTAACCGTGATTCGCGAGCTTCGTGCAGTAGA
TTATGCTAAATAA 4158.7

(SEQ. ID. NO. 278)
ATGATGTTAAAACCCTCTATTGATACCTTGCTCGACAAGGTTCCTTCAAA
ATATTCACTCGTAATCTTGGAAGCAAAACGTGCCCACGAATTGGAAGCAG
GTGCCCCAGCAACTCAAGGTTTCAAGTCTGAAAAATCAACTCTTCGCAGT
TTAGAAGAAATCGAATCAGGAACGTTACAATTCACCCAGATCTCAGAAGG
AAAACGTGAAGCAGTCGTCGCCGTATCGAAGAAGAAACGCCGCAAAGA
AGAAGAAGAAAGAAATCAAAGAGCAAATTGCTAAAGAAAAAGAAGATG
GTGAAAAATTTAA 4161.1

(SEQ. ID. NO. 279)
ATGTCAGCATATCAATTACCGACCGTATGGCAGGATGAAGCTAGTAATCA
AGGAGCTTTTACGGGGCTAAACAGACCAACAGCAGGTGCCCGTTTCGAAC

TABLE 1-continued

AAAACTTGCCAAAAGGAGAACAAGCTTTTCAGCTTTATTCACTGGGAACA
CCAAATGGTGTGAAGGTTACTATCTTATTGGAAGAATTACTAGAAGCTGG
TTTTAAGGAAGCGGCTTACGACTTGTATAAGATTGCTATCATGGATGGGG
ATCAATTCGGATCAGACTTTGTGAAGCTCAATCCAAATTCCAAGATTCCA
GCCTTATTGGACCAGTCAGGTACTGAAAACGTAAGAGTCTTTGAGTCTGC
TCATATTCTTCTTTACCTTGCTGAGAAATTTGGAGCCTTTTTACCAAGTA
ATCCTGTGGAAAAGGTAGAAGTTTTGAATTGGCTATTCTGGCAAGCAGGT
GCAGCACCTTTTCTAGGTGGGGGATTTGGACATTTCTTCAATTATGCTCC
TGAAAAATTGGAATATCCTATTAACCGTTTTACGATGGAAGTGAAACGCC
AGTTGGATTTATTGGATAAGGAATTGGCTCAGAAACCTTATATTGCAGGC
AATGACTATACGATTGCAGATATTGCTATCTGGTCTTGGTATGGACAGTT
AGTTCAAGGAAATCTTTACCAAGGTTCTGCAAAATTCTTGGATGCCTCAA
GTTATCAAAATCTAGTAAAATGGGCAGAAAAAATTGCCAATCGTCCAGCT
GTTAAGCGTGGCTTGGAAGTAACTTATACAGAAATTAAATAG 4161.2

(SEQ. ID. NO. 280)
TTGGCAAGCTTGATCACTTCTATCATCATGTTCTATGTCGGTTTCGATGT
TCTAAGAGATACCATTCAAAAGATTCTCAGTCGGGAAGAAACGGTCATTG
ATCCTCTTGGTGCAACTCTAGGAATCATTTCTGCAGCGATTATGTTTGTG
GTCTATCTCTACAATACTCGCCTCAGTAAGAAATCCAACTCCAATGCGCT
GAAGGCAGCTGCTAAGGACAATCTTTCTGACGCTGTTACCTCACTTGGAA
CCGCCATTGCCATCCTAGCTAGTAGTTTCAATTATCCGATTGTGGATAAA
CTGGTTGCTGATCATCACTCACTTTCTTTATCTTGAAGACTGCCTATGATAT
CTTCATCGAGTCTTCCTTTAGTCTTTCAGATGGCTTTGACGACCGCCTGC
TCGAGGACTACCAAAAGGCTATCATGGAAATTCCCAAAATCAGCAAGGTC
AAATCGCAAAGAGGTCGCACCTACGGTAGCAACATCTACCTGGATATTAC
ACTAGAGATGAATCCTGACTTGTCTGTTTTTGAAAGCCATGAAATCGCGG
ATCAGGTCGAGTCTATGCTGGAGGAGCGTTTTGGCGTCTTTGATACCGAT
GTCCATATCGAACCAGCACCTATCCCTGAGGATGAAATTTTAGACAATGT
CTATAAAAAATTGCTTATGCGTGAACAATTGATTGACCAAGGAAACCAAC
TAGAAGAACTCTTGACTGATGATTTTGTCTATATTCGCCAAGATGGAGAG
CAGATGGATAAAGAGCTTTATAAGACCAAAAAAGAGTTAAATTCTGCTAT
CAAGGACATTCAAATTACTTCCATCAGTCAAAAAACCAAACTCATCTGCT
ATGAGTTAGATGGTATCATCCATACCAGTATCTGGCGTCGCCACGAAACC
TGGCAAAATATCTTTCATCAAGAAACCAAAAAAGAATAG 4162.1

(SEQ. ID. NO. 281)
ATGACAATTAAACTAGTAGCAACGGATATGGACGGAACCTTCCTAGATGG
GAATGGACGTCTTGATATGGATCGTCTCAAGTCTCTCTTGGTTTCCTACA
AGGAAAAAGGGATTTACTTTGCGGTAGCTTCGGGTCGGGGATTTCTGTCT
CTAGAAAAATTATTTGCTGGTGTTCGTGATGACATTATTTTCATCGCGGA
AAATGGCAGTTTGGTAGAGTATCAAGGTCAGGACTTGTATGAAGCGACTA
TGTCTCGTGACTTTTATCTGGCAACTTTTGAAAAGCTGAAAACTTCACCT
TATGTAGATATCAATAAACTGCTCTTGACGGGTAAGAAGGGTTCATATGT
TCTAGATACGGTTGATGAGACCTATTTGAAAGTGAGTCAGCACTATAATG
AAAAATATCCAAAAAGTAGCGAGTTTGGAAGATATCACAGATGACATTTTC
AATTTTACAACCAACTTCACAGAAGAAACGCTGGAAGATGGGAGGCTTG
GGTAAACGAAAACGTTCCTGGTGTTAAGGCCATGACAACTGGCTTTGAAT
CCATTGATATTGTTCTGGACTATGTCGATAAGGGAGTGGCCATTGTTGAA
TTAGTTAAAAAACTTGGTATCACAATGGATCAGGTCATGGCTTTTGGAGA
CAATCTTAATGACTTACATATGATGCAGGTTGTGGGACATCCTGTAGCTC
CTGAAAATGCACGACCTGAAATTTAGAATTAGCAAAGACTGTGATTGGTC
ACCATAAGGAACGGTCGGTTATAGCTTATATGGAGGGCTTATAA 4162.2

(SEQ. ID. NO. 282)
ATGGCAGATATAAAATTGATTGCATTGGACTTGGACGGGACCTTGCTGAC
TACTGATAAAAGGCTGACGGATCGTACCAAGGAAACCTTGCAAGCTGCGC
GTGATCGTGGTATCAAGGTCGTATTGACAACTGGTCGTCCCTTAAAAGCC
ATGGATTTCTTTCTCCATGAGTTAGGGATCGACGGTCAGGAAGATGGATA
TACCATTACTTTTAATGGTGGATTAGTTCAGAAAAATACAGGAGAAATCC
TTGATAAAACAGTCTTTTCATATGATGATGTGGCACGTTTGTATGAAGAA
ACAGAGAAATTATCACTGCCTCTTGATGCCATCTCAGAAGGAACAGTTTA
TCAAATCCAATCGGACCAAGAAAGTCTTTATGCCAAATTCAATCCAGCTT
TGACCTTTGTTCCAGTGGACTTTGAAGACTTATCTAGTCAAATGACCTAC
AACAAATGCGTGACTGCCTTTGCTCAAGAACCCTTGGATGCAGCCATTCA
GAAGATTTCTCCAGAATTGTTGACCAATATGAAATCTTTAAATCACGTGA
AATGTTGCTAGAATGGTCACCAAAGAATGTTCATAAAGCAACAGGTTTGG
CAAACTAATCAGCCATCTTGGAATCGACCAAAGTCAAGTGATGGCTTGT
GGTGACGAGGCCAATGACCTCTCTATGATTGAATGGGCAGGTCTTGGTGT
TGCTATGCAAAACGCTGTTCCTGAAGTAAAGGCAGCCGCAAATGTAGTGA
CGCCGATGACCAACGATGAGGAAGCTGTCGCCTGGGCTATCGAAGAATAT
GTGCTAAAGGAGAACTAA 4164.2

(SEQ. ID. NO. 283)
ATGGAAAGTTTACTTATTCTATTATTAATTGCCAATCTAGCTGGTCTCTT

TABLE 1-continued

```
TCTGATTTGGCAAAGGCAGGATAGGCAGGAGAAACACTTAAGTAAGAGCT
TGGAGGATCAGGCAGATCATTTGTCAGACCAGTTGGATTACCGCTTTGAC
CAAGCCAGACAAGCCAGCCAGTTAGACCAAAAAGATTTGGAAGTGGTTGT
CAGCGACCGTTTGCAAGAAGTGCGGATTGAATTGCACCAAGGTCTGACCC
AAGTCCGTCAAGAAATGACAGATAATCTCCTCCAAACTAGAGACAAGACA
GACCAACGTCTCCAAGCCTTGCAGGAATCAAATGAGCAACGTTTGGAACA
AATGCGCCAGACGGTCGAGGAAAAACTAGAAAAGACCTTGCAGACACGCT
TACAGGCTTCCTTTGAGACAGTTTCTAAACAACTGGAGTCTGTCAATCGT
GGCCTTGGAGAAATGCAGACAGTTGCCCGTGATGTCGGAGCTCTTAACAA
GGTTCTCTCTGGAACCAAGACGCGAGGGATTCTGGGAGAATTGCAACTGG
GGCAAATTATTGAAGACATCATGACACCTGCCCAGTACGAACGAGAATAC
GCAACGGTTGAAAACTCTAGTGAACGAGTGGAGTATGCCATCAAGTTACC
CGGACAAGGCGACCAAGAATACGTCTATCTGCCAATTGACTCTAAGTTTC
CACTGGCAGATTATTACCGCTTGGAAGAAGCCTATGAGACAGGTGACAAG
GATGAGATTAACGCTGTCGTAAGTCACTCCTAGCAAGCGTCAAGCGCTT
TGCTAGGGATATTAGGAACAAGTACATAGCACCACCTCGGACGACCAATT
TTGGAGTTTTGTTTGTTCCGACAGAAGGTCTCTACTCAGAAATCGTCCGC
AATCCGGTCTTCTTTGATGATTTGAGACGGGAAGAACAGATTATTGTTGC
AGGACCAAGTACCCTATCAGCCCTTCTTAACTCCCTATCAGTTGGTTTCA
AGACCCTTAATATCCAAAAGAGTGCCGACCATATCAGCAAGACTCTTGCC
AGTGTCAAGACCGAGTTTGGCAAGTTTGGTGGTATTCTGGTCAAGGCACA
AAAACATCTCCAACATGCCTCTGGCAATATTGATGAATTATTAAACCGTC
GTACCATAGCTATCGAGCGGACGATCCGTCACATTGAGTTGTCAGAAGGT
GAGCCTGCGCTTGATCTACTCCATTTTCAAGAAAATGAGGAAGAATATGA
AGATTAG
```

4164.3

(SEQ. ID. NO. 284)
```
ATGAAGATTAGTCACATGAAAAAGATGAGTTATTTGAAGGCTTTTACCT
AATCAAATCAGCTGACCTGAGGCAAACTCGAGCTGGGAAAAACTACCTAG
CCTTTACCTTCCAAGATGATAGTGGCGAGATTGATGGGAAGCTCTGGGAT
GCCCAACCTCATAACATTGAGGCCTTTACCGCAGGTAAGGTTGTCCACAT
GAAAGGACGCGCGAGAAGTTTATAACAATACCCCTCAAGTCAATCAAATTA
CTCTCCGCCTGCCTCAAGCTGGTGAACCCAATGACCCAGCTGATTTCAAG
GTCAAGTCACCAGTTGATGTCAAGGAAATTCGTGACTACATGTCGCAAAT
GATTTTCAAAATTGAAAATCCTGTCTGGCAACGGATTGTCCGAAATCTCT
ACACCAAGTATGATAAGGAATTCTACTCCTATCCAGCTGCCAAGACCAAC
CACCATGCCTTTGAAACGGGCTTGGCCTATCATACGGCGACCATGGTGCG
TTTGGCAGACGCTATTAGCGAAGTTTATCCTCAGCTCAATAAGAGCCTGC
TCTATGCGGGGATTATGTTGCATGACTTAGCTAAGGTCATCGAGTTGACG
GGGCCAGACCAGACAGGATACACAGTGCGAGGTAATCTTCTTGGACATAT
CGCTCTCATTGATAGCGAAATTACCAAGACAGTTATGGAACTCGGCATCG
ATGATACCAAGGAAGAAGTCGTTTTGCTTCGTCATGTCATCCTCAGTCAC
CACGGCTTGCTTGAGTATGGAAGCCCAGTCCGTCCACGCATTATGGAAGC
AGAGATTATCCATATGATTGACAATCTGGATGCAAGCATGATGATGATGT
CAACAGCTCTTGCTTTGGATAAAGGAGAGATGACCAATAAAATCTTC
GCTATGGATAATCGTTCCTTCTATAAACCAGATTTAGATTAA
```

4166.2

(SEQ. ID. NO. 285)
```
ATGAGTGAAAAAGCTAAAAAAGGGTTTAAGATGCCTTCATCTTACACCGT
ATTATTGATAATCATTGCTATTATGGCAGTGCTAACTTGGTTTATCCCTG
CGGGGGCCTTTATAGAAGGTATTTACGAGACTCAGCCTCAAAATCCACAA
GGGATTTGGGATGTCCTGATGGCACCGATTCGGGCTATGCTAGGTACTCA
TCCAGAGGAAGGTTCGCTCATTAAAGAACGAGCGCAGCGATTGATGTAG
CCTTCTTCATCCTTATGGTTGGTGGTTTCCTTGGCATTGTCAACAAAACT
GGTGCTCTTGACGTAGGGATTGCCTCTATCGTGAAGAAGTATAAGGGCCG
CGAAAAAATGTTAATTTTGGTACTGATGCCTTTGTTTGCCCTCGGTGGTA
CAACTTATGGTATGGGTGAAGAAACAATGGCCTTCTATCCACTCCTTGTG
CCAGTTATGATGGCCGTTGGTTTTGATAGCCTGACTGGTGTTGCAATTAT
TTTGCTCGGTTCTCAAATCGGCTGTTTGGCATCTACTCTGAATCCATTTG
CGACAGGTATTGCTTCAGCGACTGCGGGAGTTGGTACAGGAGCGGTATC
GTACTTCGTCTGATCTTCTGGGTTACCTTGACTGCTCTTAGTACTTGGTT
TGTTTACCGTTATGCGGATAAGATTCAAAAAGATCCGACTAAGTCACTGG
TTTATAGTACTCGCAAAGAAGATTTGAAACACTTTAACGTAGAAGAATCT
TCATCTGTAGAATCTACACTTAGCAGCAACAAAAATCAGTTCTCTTCTT
ATTTGTGTTGACATTCATCTTGATGGTATTGAGCTTCATTCCATGGACAG
ACCTTGGCGTTACCATTTTTGATGACTTTAATACTTGGTTGGACTGGTCTT
CCAGTTATTGGTAATATTGTCGGTTCATCTACTTCTGCACTAGGTACTTG
GTACTTCCCAGAAGGCGAATGCTCTTTGCCTTTGATTTATGGGTATCCTGATTG
GTGTTATTTATGGTCTTAAAGAAGATAAGATTATCTCTTCCTTCATGAAT
GGTGCTGCTGACTTGCTCAGTGTTGCCTTGATCGTAGCGATTGCTCGTGG
TATTCAAGTTATCATGAACGACGGTATGATTACCGATACAATCCTCAACT
GGGGTAAGAAAGGCTTGAGCGGTCTATCTTCACAAGTCTTTATCGTTGTA
ACTTATATCTTCTATCTACCTATGTCATTCTTGATCCCATCTTCATCTGG
TCTTGCCAGCGCAACTATGGGTATCATGGCTCCACTTGGAGAATTTGTAA
ATGTCCGTCCTAGCTTGATTATCACTGCTTACCAATCTGCTTCAGGTGTC
TTGAACTTGATTGCACCAACATCTGGTATTGTGATGGGAGCTCTTGCACT
TGGACGTATCAACATTGGTACTTGGTGGAAATTCATGGGCAAACTCGTAG
```

4166.3

(SEQ. ID. NO. 286)
```
ATGAAAATAGATATAACAAATCAAGTTAAAGATGAATTTCTTATATCATT
AAAAACCTTGATTTCCTATCCTTCAGTACTCAATGAAGGAGAAAATGGAA
CACCTTTTGGACAAGCAATCCAAGATGTCCTAGAAAAAACTTTAGAGATT
TGTCGAGACATAGGTTTCACTACCTATCTTGACCCTAAAGGTTATTACGG
ATATGCAGAAATCGGTCAGGGAGCAGAGCTTCTGGCCATTCTCTGTCATT
TGGATGTTGTTCCATCAGGTGATGAAGCAGATTGGCAGACACCGCCATTT
GAAGCAACTATCAAAGACGGCTGGGTATTCGGACGTGGTGTCCAAGATGA
TAAAGGCCCTTCGCTCGCAGCTCTCTATGCAGTAAAAAGCTTGCTGGACC
AAGGTATTCAGTTCAAAAAGCGCGTACGCTTTATCTTTGGTACCGATGAG
GAAACCCTCTGGCGCTGCATGGCACGCTACAATACCATCGAAGAACAGGC
CAGTATGGGCTTTGCACCTGACTCATCTTTTCCTCTGACCTATGCTGAAA
AAGGGCTTCTACAGGTCAAACTTCATGGCCCTGGATCGGGATCAACTAGAG
CTTGAAGTAGGAGGCGCCTTTAACGTTGTACCAGACAAGGCCAACTACCA
AGGTCTCCTCTATGAACAGGTTTGTAACGGTCTCAAAGAAGCTGGTTATG
ATTACAAACCACTGAACAAACCGTAACGGTTCTCGGAGTGCCAAAGCAT
GCTAAGGATGCTAGTCAAGGTATCAATGCTGTCATCCGACTAGCTACCAT
TCTTGCTCCTCTCCAAGAACACCCTGCTCTCAGTTTTCTTGCAACACAAG
CAGGTCAAGACGGCACAGGAAGACAAATCTTTGGTGATATAGCAGATGAA
CCTTTCTGGTCACCTATCCTTTAATGTCGCAGGTCTCATGATCAATCATG
AACGTTCTGAAATCCGTATTGACATTCGGACTCCTGTCTTAGCTGACAAG
GAAGAACTAGTAGAGTTGCTTACAAGATGTGCACAAAACTACCAACTCCG
CTACGAAGAGTTTGACTATCTAGCGCCTCTATCGTCGCAGAAGACAGTA
AACTCGTTAGCACACTGATGCAAATCTACCAAGAAAAGACTGGCGATAAC
AGTCCTGCTATTTCATCCGGTGGTGCCACTTTTGCTCGCACATGCCAAA
TTGTGTAGCCTTCGGCGCCTTATTCCCAGGAGCGAAGCAGCAGACAACATC
AGGCAAATGAATGCCGTTCTAGAAGATTTGTACCGTGCTATGGATATT
TATGCCGAAGCCGTCTATCGACTTGCAACTTAA
```

4169.1

(SEQ. ID. NO. 287)
```
ATGTCTAATTCATTTGTCAAGTTGTTAGTCTCTCAATTATTTGCAAATTT
AGCAGATATTTCTTTAGGATAACAATCATTGCTAACATATACATTATTT
CAAATCAGTAATTGCCACATCACTAGTTCCTATCTTAATAGGAATATCC
TCTTTTGTTGCGAGTCTTTTAGTTCCGTTGGTTACTAAAAGGTTAGCGCT
AAATAGGGTTTTATCTTTATCTCAATTTGGAAAGACTATATTATTGGCGA
TACTGGTAGGAATGTTTACCGTAATGCAATCCGTAGCGCCTTTGGTGACC
TATCTATTTGTTGTTGCAATTTCCATACTAGATGGTTTGCAGCACCCGT
TTCCTATGCTATTGTGCCACGCTATGCGACCGATTTGGGTAAGGCTAATT
CAGCCTTATCAATGACTGGTAAGCTGTTCAATTGATAGGTTGGGGATTA
GGTGGACTCTTGTTTGCAACAATTGGTCTGTTACCTACCACGTGTATAA
TTTAGTCTTGTATATCATTTCTAGCTTTCTGATGTTATTCTTCCTAACG
CTGAAGTGGAGGTGTTAGAGTCAGAAACTAATCTTGAAATTTTGCTCAAA
GGTTGGAAGTTAGTTGCTAGAAATCCTAGATTAAGACTTTTTGTATCAGC
AAATTTATTGGAAATTTTTTCAAATACGATTTGGGTTTCTTCCATTATAC
TTGTTTTTGTAACGGAGTTATTAAATAAAACGGAAAGTTACTGGGGATAT
TCTAATACAGCATACTCTATTGGTATTATAATTAGTGGCTTAATTGCTTT
TAGGCTATCTGAAAAGTTCCTTGCTGCTAAATGGGAAGGGGAATTATTCA
CCCCAAATCTAAAAACCATCCAGAATCCTGCCTTAGCTTAGATCCTGGAT
GGTTTCTTTTTCACCCAATGGGTGTTTTTTTACTAGACAAAGAAGAGTTT
CCCCTTTATGGTAAGTGTAGAAAAAACACAAAAGAAAGGAAACTCA
CATGAACAGTTTACCAAATCATCACTTCCAAAACAAGTCTTTTACCAAC
TATCTTTCGATGGAGGTCATTTAACCCAGTATGGTGGTCTTATCTTTTTT
CAGGACTTTTTTCCCAGTTGAAATAAAGAGCGGATTTCTAAGTATTT
AGTAACGAATGACCAAGCCGCTACTGTCGTTATTCGGATTCAGATATCC
TTGTCCAGTTCCTCTTTCAACTGTTAACAGGTTATGGAACGGACTATGCT
TGTAAAGAATTGTCAGCTGATGCCTACTTTCCAAAATTGTTGGAAGGAGG
GCAGCTTGCTTCACAGCCAACCTTATCCCGTTTCTTTCCCAGAACTGACG
AGGAAACAGTCCATAGTTTGCGATGCCTCAACCTTGAATTGGTCGAATTC
TTTTTACAGTTTCACCAGCTAAACCAACTCATTGTAGATATCGATTCTAC
CCATTTCACAACTTATGGCAAGCAAGAAGGTGTTGCTTATAACGCCCACT
ATCGTGCTCATGGCTATCATCCTCTTTATGCTTTCGAGGGGAAGACAGGT
TATTGTTTCAATGCCCAGCTTCGTCCTGGTAATGTTATTGTTCTGAAGA
GGCAGACAGCTTTATCACACCTGTTTTAGAACGGTTTAATCAACTTCTC
TTTCGAATGGATAGTGGCTTTGCGACCCCAAAATTATACGATTTAATTGA
AAAAACAGGGCAATACTACCTCATAAAACTCAAAGAAAATACTGTTCTGA
GCCGTCTTGGGAGACCTTTCCCTCCCCTTGCCCACAGGATGAGGACTTAACC
ATCTTGCCCCACTCCGCCTACTCAGAAACTCTCTATCAAGCAGGATCTTG
GTCGCACAAGCGTCGTGTCTGCCAGTTCTCTGAACGAAAAGAAGGAAACT
TGTTCTACGATGTATTTCTCTCGTTACAAATATGACGAGTGGAACAAGC
CAAGACCAGTTTGCTTTATCGTGGACGTGGTCAAGCCGAGAATTCAT
CAAGGAGATGAAGGAGGGATTTTTGGCGATAAAACGGATAGTTCAACCT
TAATCAAAAACGAAGTTCGTATGATGATGAGCTGTATCGCCTACAATCTC
TATCTTTTTCTCAAACATCTAGCTGGAGGTGACTTCCAAACTTTAACAAT
CAAACGCTTCCGCCATCTTTTTCTTCACGTGGTGGGAAAATGTGTTCGAA
```

TABLE 1-continued

CAGGACGCAAGCAGCTCCTCAAATTGTCTAGTCTCTATGCCTATTCCGAA
TTGTTTTCAGCACTTTATTCTAGGATTAGAAAAGTCAACCTGAATCTTCC
TGTTCCTTATGAACCACCTAGAAGAAAAGCGTCGTTAATGATGCATTAA 4169.3

(SEQ. ID. NO. 288)
ATGATGGAGTTTTTTCAACAGCTTCCTCATTTAGAGCCATATGGCAATCC
TCAGTATTTTGTTTATGTGATTGCTGCAACCTTGCCCATCTTTATAGGTC
TCTTTTTCAAGAAACGCTTTGCCTGGTATGAAGTGTTGGTAAGTCTCTTC
TTTATTGTCACCATGTTGGTGGGTGGAAAGACCAATCAACTAGCTGCCTT
GGGTATTTACCTTTGCTGGGAAATATTGCTCCTGCTTTTCTACAAGCATT
ATCGAAAAAGCAAGGATGGCAAGTGGGTCTTCTACTTAGTTAGTTTTCTG
TCCCTACTTCCGATTATCTTTGTCAAGGTGCAACCAGCTATCAATGGAAC
GCAGTCTTTGCTTGGGTCTTGGGAATTTCTTACCTGACCTTTCGTTCGG
TTGGAATTGTCATCGAGCTGAGAGATGGAGTGATTAAGGATTTTACCCTC
TGGGAATTCCTCCGTTTCCTTCTCTTCATGCCAACTTTCTCGAGTGGTC
AATCGATCGCTTTAAGCGATTTAATGAAAATTATCAGGCTATTCCTGAGC
GAGATGAGTTGATGGATATGCTGGATGAATCTGTCCGCTATATCATGTGG
GGCTTTTTGTATAAGTTTATCCTAGCTCATGTTTAGGAGAGACCTTACT
ACCTCCTCTGAAGAATTTAGCCTTGCAGTCAGGTGGCTTCTTTAATCTCT
ATGCCTTGGCAGTTATGTATACTTTTGGTCTGGAACTCTTCTTTGACTTT
GCAGGTTATTCTATGTTTGCTTTGGCCATCTCAAACTTGATGGGAATCCG
TAGCCCTATCAACTTTAACAAGCCCTTTTTATCAAGGGATTTAAAGGAGT
TTTGGAATCGCTGGCATATGAGTCTGTCCTTCTGGTTCCGTGACTTTGTC
TTTATGCGAATGGTGATGGTGTTAACCAGAAAGAAAGTCTTTAAAAATCG
TAATGTAACCTCAAGCATGGCCTACATTGTAAATATGCTGATTATGGGAT
TTTGGCATGGTGTGACCTGGTACTATATCGCCTATGGACTCTTTCATGGA
CTAGGCTTGGTCATCAATGATGCCTGGGTTCGCAAGAAAAACGCTCAA
TAAGGACGCAGAAAACGCAGGGAAGGCTGCCCTACCTGAGATCGCTGGA
TTCAGTTGCTTGGCATGGTTGTCACTTTCCATGTTGTCATGTTGTCATTC
TTAATCTTTTCTGGATTCTTGAATAATCTATGGTTTAAAAAATAA 4169.4

(SEQ. ID. NO. 289)
ATGCTTAAACGCTTATGGATGATCTTCGGACCGGTCTTGATCGCTGGTTT
GTTGGTTTTTCTGCTCATTTTCTTTTATCCTACTGAGATGCATCATAATC
TAGGAGCTGAAAAGCGTTCAGCAGTGGCTACTACTATCGATAGTTTTAAG
GAGCGAAGTCAAAAAGTCAGAGCACTATCTGATCCAAATGTGCGTTTTGT
TCCCTTCTTTGGCTCTAGTGAATGGCTTCGTTTTGACGGTGCTCATCCTG
CGGTATTAGCTGAGAAATACAATCGTTCCTACCGTCCTTATCTTTTAGGA
CAGGGGGGAGCTGCATCGCTTAACCAATATTTTGGAATGCAACAGATGTT
ACCACAGCTGGAGAATAAACAAGTTGTGTATGTTATCTCACCTCAGTGGT
TCAGTAAAAATGGCTATGATCCAGCAGCCTTCCAGCAGTATTTTAATGGA
GACCAGTTGACTAGTTTTCTGAAACATCAATCTGGGGATCAGGCTAGTCA
ATATGCAGCGACTCGCTTACTGCCAACAGTTCCCCAAACGTAGCTATGAAGG
ACCTGGTTCAGAAGTTGGCAAGTAAAGAAGAATTGTCGACAGCAGACAAT
GAAATGATTGAATTATTGGCTCGTTTTAATGAACGCCAAGCTTCCTTTTT
TGGTCAGTTTTCGGTTAGAGGCTATGTTAACTACGATAAGCATGTAGCTA
AGTATTTAAAAATCTTGCCAGACCAGTTTTCTTATCAGGCAATAGAAGAT
GTTGTCAAAGCAGATGCTGAAAAAATACTTCCAATAATGAGATGGGAAT
GGAAAATTATTTCTATAATGAGCAGATCAAGAAGGATTTGAAGAAATTAA
AGGATTCTCAGAAAAGCTTTACCTATCTCAAGTCGCCAGAGTATAATGAC
TTGCAGTTGGTTTTAACACAGTTTTCTAAATCTAAGGTAAACCCGATTTT
TATCATTCCACCTGTTAATAAAAAATGGATGAACTATGCTGGTCTACGAG
AGGATATGTACCAACAAACGGTGCAGAAGATTCGCTACTTAGAAAGT
CAAGGTTTTACCAATATAGCGATTTTTCTAAGGACGGCGGGGAGCCTTT
CTTTATGAAGGACACCATTCACCTTGGTTGGTTGGGTTGGTTGGCTTTTG
ACAAGGCAGTTGATCCTTTCCTATCCAATCCCACACCAGCTCCGACTTAC
CATCTGAATGAGCGCTTTTTCAGCAAAGATTGGGCGACTTATGATGGAGA
TGTCAAAGAATTTCAATAG 4169.6

(SEQ. ID. NO. 290)
ATGGAGAAAAACCTCAAGGCTTTGAAACAAACAACAGACCAAGAAGGCCC
AGCAATTGAACCTGAAAAGGCAGAGGATACCAAGACAGTCCAAAATGGTT
ACTTCGAGGATGCAGCTGTCAAGGACCGCACCTTGAGTGACTATGCAGGT
AACTGGCAATCAGTTTATCCTTCCTTGAAGACGGCACGTTTGACCAAGT
CTTTGACTACAAGGCTAAGTTGACTGGTAAGATGACCCAGGCTGAGTACA
AGGCTTACTATACAAAAGGCTATCATACAGATGTGACTAAGATTAACATT
ACTGATAATACTACTTGGAATTTGTTCAAGGTGGACAAAGCAAGAATACAC
TTACAAGTATGTCGGTAAGAAAATTTTGACTTACAAGAAAGGCAATCGTG
GCGTGCGTTTCCTCTTTGAAGCCACAGATGCTGACGCTGGACAATTCAAG
TATGTTCAGTTTAGTGACCACAATGTTGCCCCAGTTAAGGCAGAACATTT
CCTATATCTTCTTTGGAGGCACAAGCCAAGAAGCCCTCTTTGAAGAAATGG
ACAACTGGCCAACCTACTACCCAGATAACCTATCTGGCCAAGAAATCGCC
CAAGAAATGTTGGCGCATTGA

TABLE 1-continued 4170.3

(SEQ. ID. NO. 291)
ATGAAAGATGGTCATTTGCTAGCCCATCATATTCGTTTGTTGAATGGGCG
GATTTTTCAAAAGTTACTGAGTCAAGATCCTGAGGCTCTTTATAGGGGTG
AACAGGGCAAGATTTTAGCGGTTTTATGGAATAGTGAAACTGGCTGCGCA
ACTGCGACAGATATCGCGCTTGCGACTGGACTTGCGAATAATACGCTGAC
GACTATGATAAAAAGCTAGAGGAACAAAAGCTTGTAATTGTTAGTCCGT
GTGGAAAAGACAAGCGTAAGAAGTATTTAGTTTTAACGGAGTTAGGCAAG
TCCCAGAAAGAAGTGGGGCATCGTGTCAGTCAGAAATTGGATACATCTT
TTACAAAGGATTTTCAGAGGAAGAAATTCACCAATTTGAAGGTTTTCAAG
AAAGAATTTTGGCGAATCTGAAAGAGAAGGGAAATGAGGTTTAG 4170.4

(SEQ. ID. NO. 292)
ATGACTAATTTAATTGCAACTTTTCAGGATCGTTTTAGTGATTGGTTGAC
AGCTCTATCTCAACATTTGCAGTTGTCGCTTTTGACCTTGTTACTAGCTA
TTTTGCTTGCGATTCCCTTGGCTGTTTTTCTTCGCTATCATGAGAAGCTG
GCCGACTGGGTCTTGCAGATTGCAGGTATTTTCCAGACCATCCCGTCTCT
GGCCTTGTTGGGGCTCTTTATCCCTTTGATGGGAATTGGGACCTTGCCGG
CTTTGACAGCTCTAGTGATTTATGCGATTTTCCCTATTTTGCAAAATACT
ATCACTGGGCTGAAGGGAATTGATCCGAACCTGCAAGAGGCTGGGATTGC
CTTTGGGATGACCAGATGGGAACGTCTCAAGAAATTTGAAATTCCACTCG
CCATGCCTTGTACATGTCTGGGATTCGGACGGCAGCTGTTTTGATTATC
GGTACGGCAACCTTGGCGGCCTTGATTGGTGCAGGGGACTAGGTTCCTT
TATTCTTTTGGGAATTGACCGTAATAATGCCAGTTTGATTTTGATTGGGG
CACTTTCTTCTGCAGTGCTAGCCATTGCCTTTAACTTCCTACTAAAAGTG
ATGGAAAAAGCAAAATTACGGACGATTTTCTCAGGTTTTGCCTTGGTGGC
TTTATTACTGGGTCGTCTTATAGTCCAGCTCTTTTGGTTCAAAAAGAGA
AGGAAAACTTGGTTATTGCTGGGAAAATAGGTCCAGAACCAGAATTTTG
GCCAATATGTATAAGTGCTGATTGAGAAAATACCAGCATGACTGCGAC
TGTTAAACCGAATTTTGGGAAGACAAGCTTCCTTTATGAAGCTCTGAAAA
AAGGCGATATTGACATCTATCCTGAATTTACTGGTACGGTGACTGAAAGT
TTGCTTCAACCATCACCCAAGGTGAGTCATGAACCAGACAGGTTTATCA
GGTGGCGCGTGATGGCATTGCTAAGCAGGATCATCTAGCCTATCTCAAAC
CCATGTCTTATCAAAACACCTATGCTGTAGCTGTTCCGAAAAAGATTGCT
CAAGAATATGGCTTGAAGACCATTTCAGACTTGAAAAAAGTGGAAGGGCA
GTTGAAGGCAGGTTTTACACTCGAGTTTAACGACCGTGAAGATGGAAATA
AGGGCTTGCAATCAATGTATGGTCTCAATCTCAATGTAGCGACCATTGAG
CCAGCCCTTCGCTATCAGGCTATTCAGTCAGGGGATATTCAAATACGGA
TGCCTATTCGACTGATGCGGAATTGGAGCGTTATGATTTACGGCTTGG
AAGATGACAAGCAACTCTTCCCACCTTATCAAGGGGCTCCACTCATGAAA
GAAGCTCTTCTCAAGAAACACCCAGAGTTGGAAAGAGTTCTTAATACATT
GGCTGGTAAGATTACAGAAAGCCAGATGAGCCAGCTCAACTACCAAGTCG
GTGTTGAAGGCAAGTCAGCAAAGCAAGTAGCCAAGGAGTTTCTCCAAGAA
CAAGGTTTGTTGAAGAAATGA 4170.5

(SEQ. ID. NO. 293)
ATGATGCATACTTATTTGCAAAAGAAAATTGAAAATATCAAAACAACCCT
AGGTGAAATGTCAGGTGGTTACCGTCGTATGGTTGCGGCTATGGCTGATT
TAGGATTTTCAGGAACTATGAAGGCTATCTGGGATGACCTCTTTGCCCAT
CGTAGTTTTGCCCAGTGGATTTATTTGCTGGTTTTAGGAAGTTTTCCTCT
CTGGCTGGAGTTGGTTTACGAACATCGTATTGTTGACTGGATTGGGATGA
TTTGTAGCTTGACAGGGATTATCTGTGTAATCTTTGTATCGGAAGGTCGA
GCAAGTAATTATCTTTTTGGCTTGATTAACTCTGTTATTTACCTTATTTT
GGCCCTACAGAAAGGCTTTTATGGTGAGGTGCTGACGACACTTTACTTCA
CAGTCATGCAGCCAATTGGACTTCTAGTTTGGATTTATCAGGCACAGTTT
AAGAAGGAAAAGCAGGAGTTTGTCGCGCGTAAACTGGACGGCAAGGGCTG
GACAAAGTATCTTTCCATTAGTGTGCTTTGGTGGTTGGCCTTTGGCTTCA
TTTATCAGTCTATTGGTGCAATCGTCCCTATCGTGATTCAATCACAGAT
GCAACCAATGGGGTAGGGCAAATCCTCATGACAGCTGTTTACCGTGACA
GTGGATATTCTGGGCGGCTACCAATGTCTTTTCAATCTATCTCTGGTGGG
GAGAAAGCCTGCAAATTCAGGGAAATCTAATTTATCTCATTAACAGT
CTAGTTGGTTGGTATCAATGGAGCAAGGCAGCTAAGCAGAATACTGATTT
ACTTAACTAG 4170.6

(SEQ. ID. NO. 294)
ATGAGAAATATGAAGGCAAAATATGCTGTTTGGGTGGCTTTTTTCTTAAA
TTTGACTTATGCCATTGTTGAGTTTATGCAGGTGGAGTATTTGGTTCTAG
CGCTCGTTCTTGCTGACTCTGTGCATGACTTGGGAGATGCGATTGCAATTG
GAATATCAGCTTTTCTAGAAACAATCTCCAATCGTGAAGAAGACAATCAG
TACACCTTGGGCTATAAGCGGTTAGCCTGCTAGGAGCCTTGGTAACAGC
TGTGATTCTCGTAACGGGCTCTGTTCTGTCATTTTGGAAAATGTCACGA
AGATTTCATCCGCAACCAGTCAATGATGAGGGGATTCTCGGTTAGGAA
TTATTGCGATTACTATCAATCTGTTAGCGAGTCTGGTGGTTGGTAAGGGA
AAGACAAAGAATGAGTCTATTCTGAGTCTGCATTTTCTGGAAGATACGCT
AGGGTGGGTAGCTGTTATCCTGATGGCGATTGTTCTTCGATTTACGGACT

TABLE 1-continued

GGTATATCCTAGATCCTCTTTTGTCCCTTGTCATTTCTTTCTTTATTCTT
TCAAAAGCCCTTCCACGTTTTGGTCTACACTCAAGATTTTCTTGGATGC
TGTGCCAGAAGGTCTTGATATCAAGCAAGTAAAGAGTGGCCTGGAGCGAT
TGGACAATGTGGCCAGCCTTAATCAGCTTAATCTCTGGACTATGGATGCT
TTGGAAAAAAATGCCATTGTCCATGTTTGTCTAAAAGAAATGGAACATAT
GGAAACTTGTAAAGAGTCTATTCGAATTTTCCTAAAAGATTGTGGTTTTC
AAAATATTACCATTGAAATTGATGCTGACCTAGAAACTCACCAAACCCAT
AAGCGAAAGGTGTGTGACTTGGAACGGAGTTATGAGCATCAACATTAG 4170.8
(SEQ. ID. NO. 295)
ATGATTGAATACAAAAATGTAGCACTGCGCTACACAGAAAAGGATGTCTT
GAGAGATGTCAACTTACAGATTGAGGATGGGGAATTTATGGTTTTAGTAG
GGCCTTCTGGGTCAGGTAAGACGACCATGCTCAAGATGATTAACCGTCTT
TTGGAACCAACTGATGGAAATATTTATATGGATGGGAAGCGCATCAAAGA
CTATGATGAGCGTGAACTTCGTCTTTCTACTGGTTATGTTTTACAGGCTA
TTGCTCTTTTTCCAAATCTAACAGTTGCGGAAATATTTGCTCTCATTCC
TGAAATGAAGGGTGGAGCAAGGAAGAAATTACGAAGAAAACAGAAGAGC
TTTTGGCTAAGGTTGGTTTACCAGTAGCCGAGTATGGGCATCGCTTACCT
AGTGAATTATCTGGTGGAGAACAGCAACGGGTCGGTATTGTCCGAGCTAT
GATTGGTCAGCCCAAGATTTTCCTCATGGATGAACCCTTTTCGGCCTTGG
ATGCTATTTCGAGAAAACAGTTGCAGGTTCTGACAAAAGAATTGCATAAA
GAGTTTGGGATGACAACGATTTTTGTAACCCATGATACGGATGAAGCCTT
GAAGTTGGCGGACCGTATTGCTGTCTTGCAGGATGGAGAAATTCGCCAGG
TAGCGAATCCCGAGACAATTTTAAAAGCGCCTGCAACAGACTTTGTAGCA
GACTTGTTTGGAGGTAGTGTTCATGACTAA 4171.1
(SEQ. ID. NO. 296)
ATGTCAGCAGTTGCTATTTCAGCTATGACCAAGGTTATGCAAGAAACCCA
CGGAAATCCTTCTAGTATTCATGGTCATGGTCGTCAAGCTGGCAAACTCT
TGCGAGAAGCCCGTCAGGAACTAGCCCAGTTACTAAGGACAAAACCTCAA
CATATCTTTTTCACTTCTGGTGGGACTGAAGGCAATAATACTACCATAT
TGGCTACTGTCTTCGTCACCAAGACAAGGAAAACATATCATCACAACTG
CCATCGAGCACCATGCTGTCCTTGAAACAATTGATTACTTGGTTCAACAC
TTTGGGTTTGAAGCAACCATTATCCAGCCAGAAAATCAAGAAATCACAGC
CCAGCAAATTCAAAAGGCTTTACGTGACGATACGATTTTGGTTTCTACCA
TGTTTGTCAATAATGAGACAGGAAACCTACTGCCCATCGCTGAAATTGGC
CAAATACTCAAGCAACACCCTGCTGCCTATCATGTTGATGCAGTTCAGGC
TATTGGTAAAATCCCAATTCATTCAGAAGAATTGGGCATTGATTTTCTCA
CTGCTTCTGCCCACAAATTCCATGCTCCTAAGGGAATCGGTTTTTCTCAC
GCATCTAGCATGGACTTTGATTCTATCTACATGGCGGAGACCAGGAACA
GAAAAAACGTGCAGGAACTGAAAATCTGCCTGCCATTGTAGGCATGGTTG
CAGCCCTAAAAGAAGACCTAGAAAACAAGAAGAACATTTTCAACATGTA
CAAAATCTAGAAACTGCCTTTCTGACAGAGCTGGAGGCATTCAGTATTA
CCTGAATAGAGGAAAACATCATCTCCCTTTATGTTCTCAATATTGGATTTC
CTGGTCAGAAAAATGACCTCTTACTCCTTCGGCTAGATTTAGCTGGAATT
TCAATCTCTACTGGCTCAGCCTGTACTGCAGGCGTTGTCCAATCCAGCCA
TGTTCTTGAAGCCATGTATGGCGCAAATTCAGAACGCTTGAAGGAATCCC
TTCGCATCAGTTTGTCGCCACAAAATACCGTTGAAGACCTACAAACCCTC
GCAAAAACCTTAAAAGAAATTATCGGAGGTTAG 4172.1
(SEQ. ID. NO. 297)
ATGTTATTCAAATTATCTAAGGAAAAAATAGAGCTAGGCTTATCTCGTTT
ATCGCCAGCCCGTCGTATTTTTTGAGTTTTGCCTTGGTCATTTTACTAG
GCTCTCTTCTTTTGAGCTTGCCCTTTGTCCAAGTTGAAAGCTCACGAGCG
ACTTATTTTGATCATCTTTTCACTGCTGTCTCTGCAGTCTGTGTGACGGG
TCTCTCAACCCTTCCAGTAGCTCACACCTATAATATCTGGGGTCAAATAA
TCTGTTTGCTCTTGATTCAGATCGGTGGTCTAGGGCTCATGACCTTTATT
GGGGTTTTCTATATCCAGAGCAAGCAAAGCTTAGTCTTCGTAGCCGTGC
AACTATTCAGGATAGTTTTAGTTATGGAGAAATCTGATCTTTGAGAAAGT
TTGTCTATTCTATTTTTCTCACGACCTTTTGGTTGAGAGCTTGGGAGCT
ATTTTGCTTAGTTTTCGCCTTATTCCTCAACTTGGCTGGGACGTGGTCT
TTTTAGTTCCATTTTTCTAGCGATCTCAGCCTTCTGTAATGCCGGTTTTG
ATAATTTAGGGAGCACCAGTTTATTTGCTTTTCAGACCGATTTTACTGGTG
AATCTGGTGATTGCAGGCTTGATTATTACAGGCGGCCTTGGTTTTATGGT
CTGGTTTGATTTGGCTGGTCATGTAGGAAGAAAGAAAAAAGGACGTCTGC
ACTTTCATACGAAGCTTGTACTATTATTGACTATAGGTTTGTTGTTATTT
GGAACAGCAACTACTCATTCTTTGAGTGGAACAATGCTGGAACGATTGG
CAATCTCCCTGTTGCCGATAAGGTTTTAGTTAGCTTTTTTCAAACAGTGA
CGATGCGAACAGCTGGCTTTTCTACGATAGATTATACTCAGGCTCATCCT
GTGACTCTTTTGATTTATATCTTACAGATGTTTCTAGGTGGGGCACCTGG
AGGAACAGCTGGGGGACTCAAGATTACGACATTTTTTGTCCTCTTGGTC
TTGCACGAAGTGAGCTTCTAGGCTTGCCTCATCGCGGTTCTGCGAGACGA
ACGATCGCCGCGAACGGTTCAAAAATCCTTTAGTGTCTTTATTATCTT
TTTGATGAGCTTCTTGATAGGATTGATTCTGCTAGGGATAACAGCCAAAG
GCAATCCTCCCTTTATCCACCTCGTATTTGAAACCATTTCAGCTCTTAGT
ACAGTTGGTGTAACGGCAAATCTGACTCCTGACCTTGGGAAATTGGCTCT 4172.2
(SEQ. ID. NO. 298)
ATGTCAGATCGTACGATTGGAATTTTGGGCTTGGGAATTTTTGGGAGCAG
TGTCCTAGCTGCCCTAGCCAAGCAGGATATGAATATTATCGCTATTGATG
ACCACGCAGAGCGCATCAATCAGTTTGAGCCAGTTTTGGCGCGTGGAGTG
ATTGGTGACATCACAGATGAAGAATTATTGAGATCAGCAGGGATTGATAC
CTGCGATACCGTTGTAGTCGCGACAGGTGAAAATCTGGAGTCGAGTGTGC
TTGCGGTTATGCACTGTAAGAGTTTGGGGGTACCGACTGTTATTGCTAAG
GTCAAAAGTCAGACCGCTAAGAAAAGTGCTAGAAAAGATTGGAGCTGACT
CGGTTATCTCGCCAGAGTATGAAATGGGGCAGTCTCTAGCACAGACCATT
CTTTTCCATAATAGTGTTGATGTCTTTCAGTTGGATAAAAATGTGTCTAT
CGTGAGATGAAATTCCTCAGTCTTGGCAGGTCAAAGTCTGAGTAAAT
TAGACCTCCGTGGCAAATACAATCTGAATATTTTGGGTTTCCGAGAGCAG
GAAAATTCCCCATTGGATGTTGAATTTGGACCAGATGACCTCTTGAAAGC
AGATACCTATATTTTGGCAGTCATCAACAACCAGTATTTGGATACCCTAG
TAGCATTGAATTCGTAA 4172.3
(SEQ. ID. NO. 299)
ATGAAGTTATTGTCTATCGCAATTTCTAGCTATAATGCAGCAGCCTATCT
TCATTACTGTGTGGAGTCGCTAGTGATTGGTGGTGAGCAAGTTGGGATTT
TGATTATCAATGACGGGTCTCAGGATCAGACTCAGGAAATCGCTGAGTGT
TTAGCTAGCAAGTATCCTAATATCGTTAGAGCCATCTATCAGGAAAATAA
ATGCCATGGCGGTGCGGTCAATCGTGGCTTGGTAGAGGCTTCTGGGCGCT
ATTTTAAGTAGTTGACAGTGATGACTGGGTGGATCCTCGTCGCTACTTG
AAAATTCTTGAAACCTTGCAGGATTGAGAGCAAAGGTCAAGAGGTGGA
TGTCTTTGTGACCAATTTTGTCTATGAAAAGGAAGGGCAGTCTCGTAAGA
AGAGTATGAGTTACGATTCAGTCTTGCCTGTTCGGCAGATTTTGGCTGG
GACCAGGTCGGAAATTTCTCCAAAGGCCAGTATACCATGATGCACTCGCT
GATTTATCGGACAGATTTGTTGCGTGCTAGCCAGTTCTAA 4172.4
(SEQ. ID. NO. 300)
ATGAAATTCAATCCAAATCAAAGATATACTCGTTGGTCTATTCGCCGTCT
CAGTGTCGGTGTTGCCTCAGTTGTTGTGGCTAGTGGCTTCTTTGTCCTAG
TTGGTCAGCCAAGTTCTGTACGTGCCGATGGGCTCAATCCAACCCCAGGT
CAAGTCTTACCTGAAGAGACATCTCAGCAACGAAAGAGGGTGACTTATCGA
AAAACCAGGAGACACCGTTCTCACTCAAGCGAAACCTGAGGGCGTTACTG
GAAATACGAATTCACTTCCGACACCTACAGAAAGAACTGAAGTGAGCGAG
GAAACAAGCCCTTCTAGTCTGGATACACTTTTTGAAAAGATGAAGAAGC
TCAAAAATCCAGAGCTAACAGATGTCTTAAAAGAAACTGTAGATACAG
CTGATGTGGATGGGACACAAGCAAGTCCAGCAGAAACTACTCCTGAACAG
GTAAAAGGTGGAGTGAAAGAAAATACAAAAGACAGCATCGATGTTCCTGC
TGCTTATCTTGAAAAAGCTGAAGGGAAAGGTCCTTTCACTGCCGGTGTAA
ACCAAGTAATTCCTTATGAACTATTCGCTGGTGATGGTATGTTAACTCGT
CTATTACTAAAAGCTTCGGATAATGCTCCTTGGTCTGACAATGGTACTGC
TAAAAATCCTGCTTTACCTCCTCTTGAAGGATAACAAAAGGGAAATACTT
CTATGAAGTAGACTTAAATGGCAATACTGTTGGTAAACAAGGTCAAGCTT
TAATTGATCAACTTCGCGCTAATGGTACTCAAACTTATAAAGCTACTGTT
AAAGTTTACGGAAATAAAGACGGTAAAGCTGACTTGACTAATCTAGTTGC
TACTAAAAATGTAGACATCAACATCAATGGATTAGTTGCTAAAGAAACAG
TTCAAAAGCCGTTGCAGACAACGTTAAAGACAGTATCGATGTTCCAGCA
GCCTACCTAGAAAAAAGCCAAGGGTGAAGGTCCATTCACAGCAGGTGTCAA
CCATGTGATTCCATACGAACTTCGCAGGTGATGGTATGTTGACTCGTC
TCTTGCTCAAGACTGACAAGGCACCATGGTCAGATAACGGTGACGACGCT
AAAAACCCAGCCCTATCTCCACTAGGCGAAAACGTGAAGACCAAAGGTCA
ATACTTCTATCAAGTAGCCTTGGACGAAATGTAGCTGGCAAAGAAAAAC
AAGCGCTCATTGACCAGTTCCGAGCAAATGGTACTCAAACTTACAGCGCT
ACAGTCAATGTCTATGGTAACAAAGACGGTAAACCAGACTTGGACAACAT
CGTAGCAACTAAAAAAGTCACTATTAACATAAACGGTTTAATTTCTAAAG
AAACAGTTCAAAAAGCCGTTGCAGACAACGTTAAAGACAGTATCGATGTT
CCAGCAGCCTACCTAGAAAAAGCCAAGGGTGAAGGTCCATTCACAGCAG
TGTCAACCATGTGATTCCATACGAACTCTTCGCAGGTGATGGTATGTTGA
CTCGTCTCTTGCTCAAGGCATCTGACAAGGCACCATGGTCAGATAACGGT
GACGCTAAAAACCCAGCCCTATCTCCACTAGGTGAAAACGTGAAGACCAA
AGGTCAATACTTCTATCAAGTAGCCTTGGACGGAAATGTAGCTGGCAAAG
AAAAACAAGCGCTCATTGACCAGTTCCGAGCAAACGGTACTCAAACTTAC
AGCGCTACAGTCAATGTCTATGGTAACAAAGACGGTAAACCAGACTTGGA
CAACATCGTAGCAACTAAAAAAGTCACTATTAACATAAACGGTTTAATTT
CTAAAGAAACAGTTCAAAAAGCCGTTGCAGACAACGTTAAGACAGTATCG
ATGTTCCAGCAGCCTACCTAG 4172.5
(SEQ. ID. NO. 301)
ATGAAACTAAAAAGTTATATTTTGGTTGGATATATTATTTCAACCCTCTT

TABLE 1-continued

AACCATTTTGGTTGTTTTTTGGGCTGTTCAAAAAATGCTGATTGCGAAAG
GCGAGATTTACTTTTTGCTTGGGATGACCATCGTTGCCAGCCTTGTCGGT
GCTGGGATTAGTCTCTTCTCCTATTGCCAGTCTTTACGTCGTTGGGCAA
ACTCAAGGAGCATGCCAAGCGGGTAGCGGCCAAGGATTTTCCTTCAAATT
TGGAGGTTCAAGGTCCTGTAGAATTTCAGCAATTAGGGCAAACTTTTAAT
GAGATGTCCCATGATTTGCAGGTAAGCTTTGATTCCTTGGAAGAAAGCGA
ACGAGAAAAGGGCTTGATGATTGCCCAGTTGTCGCATGATATTAAGACTC
CTATCACTTCGATCCAAGCGACGGTAGAAGGGATTTTGGATGGGATTATC
AAGGAGTCGGAGCAAGCTCATTATCTAGCAACCATTGGACGCCAGACGGA
GAGGCTCAATAAACTGGTTGAGGAGTTGAATTTTTTGACCCTAAACACAG
CTAGAAATCAGGTGGAAACTACCAGTAAAGACAGTATTTTTCTGGACAAG
CTCTTAATTGAGTGCATGAGTGAATTTCAGTTTTTGATTGAGCAGGAGAG
AAGAGATGTCCACTTGCAGGTAATCCCAGAGTCTGCCCGGATTGAGGGAG
ATTATGCTAAGCTTTCTCGTATCTTGGTGAATCTGGTCGATAACGCTTTT
AAATATTCTGCTCCAGGAACCAAGCTGGAAGTGGTGGCTAAGCTGGAAA
GGACCAGCTTTCAATCAGTGTGACCGATGAAGGGCAGGGTATTGCCCCAG
AGGATTTGGAAAATATTTTCAAACGCCTTTATCGTGTCGAAACTTCGCGT
AACATGAAGACAGGTGGTCATGGATTAGGACTTGCGATTGCGCGTGAATT
GGCCCATCAATTGGGTGGGGAAATCACAGTCAGCAGCCAGTACGGTCTAG
GAAGTACCTTTACCCTCGTTCTCAACCTCTCTGGTAGTGAAAATAAAGCC
TAA 4172.6
(SEQ. ID. NO. 302)
ATGTTTGGTCAAACGGCTCAACATGGTCTTACGAATAGCCTGAAAGACTT
CTGGATTTTTCTGCTGAATATAGGTCCACAATTGGCGTTTTTTTGCCAGA
TGCTCCGCTGTTCCAGATCGGTTGAGCAGGGTACTGGAAATCACCGTCGT
GAGTTCAATATGATTCAGCAGATATTCTCGCATTTTGGGATGACTCACTT
GGGACAAATCAAGTTGGTCTATCAAGAGTCGATTGACCTTGAGTTGCTGG
TCAATGCACTTAATCATCACTTGCTCATTGACAGACTGGTCCTCACGCCC
AATCAAATAACGATAGAAATCGACAGGCAGATAGTACATGGTCTTGACCT
GCTGAAGGGGCGTAAAGACAAAGAGATTATCGACATAAAAAGTATGTTCA
GGCAGTTAGAACTGGCTAGCACGCAACAAATCTGTCCGATAAATCAGCGA
GTGCATCATGGTATACTGGCCTTGGAGAAATTTCCGACCTGGTCCCAGCC
AAAAATCTGCCGAACAGGCAAGACTGA 4174.1
(SEQ. ID. NO. 303)
ATGGAACATTTAGCAACTTATTTTTCAACCTATGGAGGAGCTTTCTTCGC
TGCATTGGGAATTGTATTGGCGGTTGGATTAAGCGGTATGGGGTCTGCTT
ATGGAGTTGGTAAGGCTGGGCAATCTGCCGCAGCTTTACTGAAAGAACAG
CCTGAAAAGTTTGCCTCAGCTTTGATATTGCAATTATTGCCCGGAACACA
AGGATTATATGGTTTTGTTATTGGAATTTTAATTTGGTTGCAATTAACTC
CAGAACTTCCTTTAGAAAAGGCGTTGCTTATTTCTTTGTAGCTCTTCCA
ATTGCTATTGTAGGATACTTTTCAGCTAAGCATCAAGGAAATGTAGCAGT
AGCGGGAATGCAAATCTTGGCTAAAAGACCAAAAGAATTCATGAAGGGAG
CAATTTTAGCTGCCATGGTAGAAACCTATGCAATTCTTGCTTTTGTCGTA
TCATTCATTTTTGACCCTTCGTGTATTA 4175.2
(SEQ. ID. NO. 304)
ATGTTAAAATCAGAAAAACAATCACGTTATCAAATGTTAAATGAAGAATT
GTCCTTCCTATTGGAAGGCGAAACCAATGTTTTGGCTAATCTTTCCAACG
CCAGTGCTCTCATAAAATCACGTTTTCCTAATACCGTATTTGCAGGCTTT
TATTTGTTCGATGGAAAGGACATTGGTTTTAGGCCCCTTCCAAGGAGGTGT
TTCCTGCATCCGTATTGCACTAGGCAAGGGTGTTTGTGGTGAGGCAGCTC
ACTTTCAGGAAACTGTTATTGTTGGAGATGTGACGACCTATCTCAACTAT
ATTTCTTGTGATAGTCTAGCTAAAAGTGAAATTGTGGTGCCGATGATGAA
GAATGGTCAGTTACTTGGAGTTCTGGATCTGGATTCTTCAGAGATTGAGG
ATTACGATGCTATGGATCGAGATTATTTGGAACAATTTGTCGCTATTTTG
CTTGAAAAGACAGCATGGGACTTTACGATGTTTGAGGAAAAATCTTAA 4175.3
(SEQ. ID. NO. 305)
ATGTCAGTATTAGAGATCAAAGATCTTCACGTTGAGATTGAAGGAAAAGA
AATTTTAAAAGGGGTTAACCTGACCCTGAAAACAGGAGAAATTGCCGCTA
TCATGGGACCAAATGGTACAGGTAAATCGACTCTTTCTGCCGCTATCATG
GGAAATCCAAACTATGAAGTAACTAAAGGTGAAGTTTTCGTTGATGGCGT
AAACATCCTTGAGTTGGAAGTGGATGAGCGTGCGCGTATGGGACTTTTCC
TTGCTATGCAATACCCATCAGAAATCCCTGGAATTACCAATGCTGAGTTT
CTTCGTGCCGCTATGAATGCGGGTAAAGAAGATGATGAGAAGATTCAGT
TCGTGAGTTTATTACTAAGCTAGATAGATAAAAATGGAATTGCTCAACATGA
AAGAAGAAATGGCAGAGCGTTACCTCAACGAAGGCTTCTCTGGTGGTGAG
AAAAAACGCAATGAATTCTTCAACTTTTGATGTTGGAGCCAACATTTGC
TCTTTTGGACGAGATTGACTCAGGTCTTGATATTGACGCTCTTAAAGTTG
TGTCTAAAGGTGTCAATGCCATGCGTGGTGAAGGTTTTGGTGCTATGATC
ATCACTCACTACCAACGTCTTTTGAACTATATCACACCTGATGTGGTACA
CGTGATGATGGAAGGTCGTGTTGTCCTTTCTGGTGGTCCAGAATTGGCTG

CGCGTTTGGAACGTGAAGGATACGCAAAATTAGCTGAAGAACTTGGCTAC
GACTACAAGGAAGAATTGTAA 4174.4
(SEQ. ID. NO. 306)
ATGCCCTACAAAAGACAAAGGAGTTTTTCAATGGCACTTTCTAAACTAGA
TAGCCTTTATATGGCAGTGGTAGCAGACCATTCGAAAAATCCACATCACC
AAGGGAAGTTAGAAGATGCTGAGCAAATCAGTCTCAACAATCCGACTTGT
GGGGATGTCATCAACCTCTCTGTCAAGTTTGATGCAGAGGACCGTTTGGA
AGATATTGCTTTTCTAAATTCAGGATGCACGATTTCAACTGCTTCTGCTA
GTATGATGACAGATGCCGTTTTAGGAAAAACCAAACAAGAAATTTTAGAA
CTGGCGACTATTTTTTCTGAAATGGTTCAAGGGCAAAAAGATGAGCGTCA
AGACCAACTTGGAGACGCGGCATTCTTGTCAGGTGTTGCCAAATTCCCTC
AAAGAATCAAGTGTGCAACCCTAGCTTGGAATGCCCTTAAGAAAACAATT
GAAAATCAAGAAAAACAGTAA 4175.5
(SEQ. ID. NO. 307)
ATGAAAATTCAAGACCTATTGAGAAAAGATGTCATGTTGCTAGATTTGCA
GGCAACTGAAAAACAGCTGTCATCGACGAGATGATTAAAAATTTGACAG
ACCACGGTTATGTAACAGATTTTGAAACATTTAAAGAAGGAATTTTGGCG
CGTGAAGCTTTGACTTCTACTGGTTTGGGTGATGGAATCGCAATGCCTCA
CAGCAAAAACGCTGCTGTCAAAGAAGCGACAGTTCTATTTGCTAAGTCAA
ATAAGGGTGTTGACTACGGACTTGGATGGACAAGCAACTGACCTCTTC
TTCATGATTGCAGCTCCAGAAGGTGCCAATGATACTCACTTGGCAGCCTT
GGCAGAATTGTCTCAATACTTGATGAAAGACGGTTTTGCAGACAAACTTC
GTCAAGCAACATCTGCAGACCAAGTTATCGAACTTTTTGACCAAGCTTCA
GAAAAAACTGAGGAACTTGTTCAAGCACCTGCTAATGACTCTGGTGACTT
TATCGTAGCTGTTACAGCTTGTAACAGGTATTGCCCACACTTACATGG
CCCAAGAAGCCCTTCAAAAAGTAGCTGCTGAAATGGGGGTTGGTATCAAG
GTCGAAACCAACGGTGCTAGCGGTGTTGGAAATCAACTAACTGCAGAAGA
TATCCGTAAGGCTAAAGCTATTATCATTGCAGCAGACAAGGCCGTTGAAA
TGGATCGATTTGATTGGAAAACCATTGATCCATCGTCCAGTTGCTGACGGT
ATCCGTAAGACAGAAGAGCTAATTCATTTGGCTCTTTCAGGAGATACTGA
AGTCTACCGTGCCGCTAATGGTGCCAAAGCTGCAACAGCCTCTAACGAAA
ACAAAGCCTTGGTGGTGCCTTGTACAAACACTTGATGAGTGGTGTATCT
CAAATGTTACATCTTCGTTATCGGTGGTGGTGTATCATGATTGCCCTTGCTT
CTTGATTGACGGTGCTTTGGGTGTTCCAAATGAAAACCTTGGCAATCTTG
GTTCTTACCATGAGTTAGCTTCTATGTTCATGAAATTGGTGGAGCTGCC
TTTGGTTTGATGCTTCCAGTCTTTGCGGGTTATGTTGCCTACTCTATTGC
TGAAAAACCGGGTTTGGATGCAGGTTTCGTGGCTGGTTGCTATTGCCAAG
AAGGTTTTGCCTTTGTAAAATTCCTTATGCCGCAGGTGGTGAAGCAACT
TCAACTCTTGCAGGTGTCTCATCTGGTTTCCTAGGTGCCCTTGTTGGTGG
ATTTATCGCAGGTGCCTTGGTTCTTGCCATCAGAAATACGTTAAAGTTCC
TCGTTCACCTCGAAGGTTGCTAAATCAATCCTTCTATTTCCACTTCTTGGAA
CAATCTTGACAGGATTTGTTATGCTAGCTGTGAATATCCCAATGAGTGCA
ATCAACACTGCTATGAATGACTTCCTAGGCGGTCTTGGAGGAGGTTCAGC
TGTCCTCTTGGTATCGTCCTTGGTGGAATGATGGCTGTTGACATGGGTG
GACCAGTTAATAAAGCAGCTTATGCTCTTTGGTACAGGTACGCTTGCAGCA
ACTGTTTCTTCAGGTGGTCTGTAGCCATGGCAGCAGTTATGGCTGGAGG
AATGGTGCCACCACTTGCAATCTTTGTCGCAACTCTTCTTTTCAAAGATA
AATTTACTAAGGAAGAACGTAACTCTGGTTTGACAAACATCATCATGGGC
TTGTCATTTATCACTGAGGGAGCGATTCCATTTGGTGCCGCTGACCCAGC
TCGTGCGATTCCAAGCTTCATCCTTGGTTCAGCAGTAGCAGGTGGACTCG
TTGGCTTACTGGTATCAAACTCATGGCGCCACACGGGAATCTTCGTT
ATCGCCCTTACTTCAAATGCTCTCCTTTACCTCGTTTTCTGTCTTGGTAGG
AGCAATCGTAAGTGGTGTGGTTTATGGTTACCTACGCAAACCACAAGCAT
AA 4175.6
(SEQ. ID. NO. 308)
ATGGCAAACAAGAATACAAGTACAACAAGACGGAGACCGTCTAAAGCAGA
ACTGGAAAGAAAAGAAGCGATTCAACGAATGTTGATTTCGTTAGGAATTG
CGATTTTATTGATTTTCGCAGCCTTCAAATTAGGGCTGCAGGTATAACC
CTTTATAATTTAATTCGCTTGCTAGTGGGTAGCCTAGCTTATCTGGCGAT
ATTCGGCCTATTAATCTATCTCTTCTTTTTTCAAGTGGATACGAAAACAG
AAGGACTCTTATCTGGCTTTTTCACCCATATTTGCTGGCTTACTCTTGATT
TTTGAGGCCTACTTGGTTTGGAAATATGTTTGGACAAGTCCGTTCTAAA
AGGGACCATGGCTCAGGTTGTGACAGATCTGACTGGTTTCGAACGACTA
GCTTTGCTCGGAGGGGCTTGATCGGGGTCGCTCTTTATATTCCACAGCCT
TTCTCTTTTCAAATATCGGAACTTACTTATTGGTTCTATCTGATTTTAG
TGGGTTCTCTCCTAGTCAGCCCTTGGTCTGTTTACGATATTGCTGAATTT
TTCAGTAGAGGCTTTGCCAAATGGTGGAAGGGCACGAGCGTCGAAAAGA
GGAACGCTTTGTCAACAAGAAGAAAAGCTCGCCAAAAGGCTGAGAAAG
AGGCTAGATTAGAACAAGAAGAGACTGAAAAAGCCTTACTCGATTTGCCT
CCTGTTGATATGGAAACGGGTGAAATTCTGACGAGGAAGCTGTTCAAAA
TCTTCCACCTATTCCAGAAGAAAGTGGGTGGAACCAGAAATCATCCTGC
CTCAAGCTGAACTTAAATTCCCTGAACAGGAAGATGACTCAGATGACGAA
GATGTTCAGGTCGATTTTTCAGCCAAAGAAGCCCTTGAATACAAACTTCC

TABLE 1-continued

AAGCTTACAACTCTTTGCACCAGATAAACCAAAAGATCAGTCTAAAGAGA
AGAAAATTGTCAGAGAAAATATCAAAATCTTAGAAGCAACCTTTGCTAGC
TTTGGTATTAAGGTAACAGTTGAACGGGCCGAAATTGGGCCATCAGTGAC
CAAGTATGAAGTCAAGCCGGCTGTTGGTGTAAGGGTCAACCGCATTTCCA
ATCTATCAGATGACCTCGCTCTAGCCTTGGCTGCCAAAGATGTCCGGATT
GAAGCACCAATCCCTGGGAAATCCCTAATCGGAATTGAAGTGCCCAACTC
CGATATTGCCACTGTATCTTTCCGAGAACTATGGGAACAATCGCAAACGA
AAGCAGAAAATTCTTGGAAATTCCTTTAGGGAAGGCTGTTAATGGAACC
GCAAGAGCTTTTGACCTTTCTAAAATGCCCCACTTGCTAGTTGCAGGTTC
AACGGGTTCAGGGAAGTCAGTAGCAGTTAACGGCATTATTGCTAGCATTC
TCATGAAGGCGAGACCAGATCAAGTTAAATTTATGATGGTCGATCCCAAG
ATGGTTGAGTTATCTGTTTACAATGATATTCCCCACCTCTTGATTCCAGT
CGTGACCAATCCACGCAAAGCCAGCAAGGCTCTGCAAAAGGTTGTGGATG
AAATGGAAAACCGTTATGAACTCTTTGCCAAGGTGGGAGTTCGGAATATT
GCAGGTTTTAATGCCAAGGTAGAAGAGTTCAATTCCCAGTCTGAGTACAA
GCAAATTCCGCTACCATTCATTGTCGTGATTGTGGATGAGTTGGCTGACC
TCATGATGGTGGCCAGCAAGGAAGTGGAAGATGCTATCATCCGTCTTGGG
CAGAAGGCGCGTGCTGCAGGTATCCACATGATTCTTGCAACTCAGCGTCC
ATCTGTTGATGTCATCTCTGGTTTGATTAAGGCCAATGTTCCATCTCGTG
TAGCATTTGCGGTTTCATCAGGAACAGACTCCCGTACAGTTTTGGATGAA
AATGGAGCAGAAAAACTTCTTGGTCGAGGAGACATGCTCTTTAAACCGAT
TGATGAAAATCATCCAGTTCGTCTCCAAGGCTCCTTTATCTCGGATGACG
ATGTTGAGCGCATTGTGAACTTCATCAAGACTCAGGCAGATGCAGACTAC
GATGAGAGTTTTGATCCACGGTGAGGTTTCTGAAAATGAAGGAGAATTTC
GGATGGAGATGCTGGTGGTGATCCGCTTTTTGAAGAAGCTAAGTCTTTGG
TTATCGAAACACAGAAAGCCAGTGCGTCTATGATTCAGCGTCGTTTATCA
GTTGGATTTAACCGTGCGACCCGTCTCATGGAAGAACTGGAGATAGCAGG
TGTCATCGGTCCAGCTGAAGGTACCAAACCTCGAAAGTGTTACAACAAT
AA 4176.1
(SEQ. ID. NO. 309)
ATGAGTTATTTTAAAAAATATAAATTCGATAAATCCCAGTTCAAACTTGG
TATGCGAACCTTTAAAACAGGTATTGCTGTTTTTCTAGTTCTCTTGATTT
TTGGCTTTTTTGGCTGGAAAGGTCTTCAAATTGGTGCTTTGACAGCCGTT
TTTAGCCTGAGGGAGAGTTTTGATGAGAGTGTTCATTTTGGGACTTCGCG
TATTCTAGGAAATAGTATCGGTGGACTCTATGCCTTGGTCTTCTTCTTAT
TAAATACCTTTTTCCACGAAGCCTTTGGGTGACCTTGGTAGTTGTTCCA
ATCTGCACCATGTTAACCATTATGACAAATGTAGCCATGAATAACAAAGC
AGGGGTTATTGGTGGTGTAGCAGCTATGTTAATCATTACCCTATCAATTC
CAAGTGGTGAGACAATTTTGTACGTGTTTGTGCGTGTATTAGAAACGTTT
ATGGGAGTTTTTGTCGCAATTTATCGTAAATTACGATATTGATCGTATTC
GTCTCTTTTTAGAGAAAAAAGAAAAATAA 4178.2
(SEQ. ID. NO. 310)
ATGAATAAATCAGAACACCGCCACCAACTTATACGCGCTCTTATCACAAA
AAACAAGATTCATACACAGGCTGAGTTGCAAGCCCTTCTTGCTGAGAACG
ACATTCAAGTAACCCAGGCAACCCTCTCACGCGACATCAAAAATATGAAC
CTATCAAAAGTCCGCGAAGAAGATAGCGCTTATTATGTTCTTAACAATGG
TTCCATCTCAAAATGGGAAAACGTCTCGAACTCTACATGGAAGACGCCC
TTGTCTGGATGCGCCCAGTTCAACACCAAGTCCTACTAAAAACCCTTCCT
GGACTGGCTCAATCCTTTGGTTCTATCATTGATACTTTGAGCTTCCCTGA
CGCTATCGCTACCCTTTGTGGTAATGATGTCTGTCTTATCATCTGTGAAG
ATGCAGATACTGCTCAAAAGTGCTTTGAAGAACTGAAAAAATTCGCCCCA
CCATTTTTCTTTGAAGAATAA 4179.1
(SEQ. ID. NO. 311)
ATGAAAGTATAAAATTAAATGCTCTATCTTACATGGGAATTCGTGTCTT
GAATATTATTTTCCCATCCTAACTGGAACCTATGTCGCGCGTGTCTTGG
ACCGAACTGACTATGGTTACTTCAACTCAGTCGACATATTTTGTCATTT
TTCTTGCCCTTTGCAACTTATGGTGTCTATAACTACGGTTTAAGGGCTAT
CAGTAATGTCAAGGATAACAAAAAGATCTTAACAGAACCTTTTCTAGTC
TTTTTTATTTGTGCATCGCTTGTACGATTTTGACCACTGCTGTCTATATC
CTAGCCTATCCTCTTCTACTGATAATCAATCGTCAAAAAGGTCTAA
TTGTTATGGGGATTCAACTCATTGCCCAGATTTTTCAATCGAATGGGTC
AATGAAGCTCTGGAAAATTACAGTTTTCTCTTTTACAAAACTGCCTTCAT
CCGTATCCTGATGCTGGTCTCTATTTTCTTATTGTTAAAAATGAACACG
ATATTGTTGTCTATACATCTGTATGGATGTTTATCGACGCTGATTAACTAC
CTGATTAGTTATTTTTGGATTAAAAGAGACATCAAACTTGTTAAAATTCA
CCTAAGTGATTTTAAACCACTCTTTCTCCCTCTGACAGCCATGTTAGTCT
TGCCAATGCCAATATGCTCTTCACTTTTTAGATCGCCTCTTCCTCGTT
AAACAGGATTGATGTCAACGTTAGTTACTATACATAGCTCAGCGAAT
TGTGACCGTTATAGCTGGGGTTGTAACAGGTGCAATTGGAGTGAGTGTGC
CTCGTCTCAGTTACTATCTGGGAAAGGAGACAAAGAAGCCATGTTTCT
CTGGTTAATAGAGGTAGTCGAATCTTTAACTTCTTTATCATTCCACTGAG
TTTTGGACTCATGGTTTTAGGACCAAATGCCATCCTACTTTACGGTAGTG
AAAAATATATCGGAGGCGGCATCTTGACCCTCTCTCTTCGCTTTTTCGTACG

ATTATCCTGGCCTTAGATACCATTCTTGGTTCCCAAATTCTCTTTACCAA
TGGCTATGAAAAACGTATCACAGTCTATACAGTCTTTGCTGGGCTACTCA
ATTTGGGCTTGAATAGTCTCCTTTTTTTCAACCATATCGTGGCTCCTGAA
TACTACTTACTGACAACTATGCTATCAGAGACTTCTCTACTTGTTTTCTA
TATCATTTTCATCCATAGAACAACCTCATCCACTTGGGACATATCTTTA
GCTATACTGTTCGATACTCTCTCTTTTCACTTTCCTTTGTAGCAATTTAT
TTCCTGATTAATTTCGTGTATCCTGTAGATATGGTCATTAATTTGCCATT
TTTGATTAATACTGGTTTGATTGTCTTGCTATCAGCTACTCTTATATTA
GTCTACTTGTCTTCACAAAAGATAGCATTTTCTATGAATTTTTAAACCAT
GTCCTAGCCTTAAAAAATAAATTTAAAAAATCATAG 4179.2
(SEQ. ID. NO. 312)
ATGAAACAACTAACCGTTGAAGATGCCAAACAAATTGAATTAGAAATTTT
GGATTATATTGATACTCTCTGTAAAAAGCACAATATCAACTATATTATTA
ACTACGTACTCTGATTGGGGCGGTTCGACATGAGGGCTTTATCCCTTGG
GACGACGATATTGATCTGTCCATGCCTAGAGAAGACTACCAACGATTTAT
TAACATTTTTCAAAAGGAAAAAGCAAGTATAAGCTCCTATCCTTAGAAA
CTGATAAGAACTACTTTAACAACTTTATCAAGATAACCGACAGTACGACT
AAAATTATTGATACTCGAAATACAAAAACCTATGAGTCTGGTATCTTAT
CGATATTTTCCCTATAGATCGCTTTGATGATCCTAAGGTCATTGATACTT
GTTATAAACTGGAAAGCTTCAAACTGCTGTCTTTCAGTAAACATAAAAAT
ATTGTCTATAAGGATAGCCTTTTAAAAGATTGGATACGAACAGCCTTCTG
GTTACTCCTTCGACCGGTTTCTCCTCGTTATTTTGCAAATAAAATCGAGA
AAGAAATTCAAAAATATAGTCGTGAAAATGGGCAATATATGGCTTTTATC
CCTTCAAAATTTAAGGAAAGGAAGTCTTCCCAAGTGGTACCTTTGATAA
AACAATCGATTTACCCTTTGAGAATTTAAGCCTTCCTGCACCTGAAAAAT
TTGATACTATTTTGACACAATTTTATGGAGATTATATGACCCTACCACCA
GAAGAAAAACGCTTCTACAGTCATGAATTTCACGCTTATAAATTGGAGGA
TTAG 4179.3
(SEQ. ID. NO. 313)
ATGATAAAAATCAATCATCTAACCATCACACAAAACAAAGATTTACGAGA
TCTTGTATCTGACCTAACCATGACCATCCAAGACGGGGAAAAGGTTGCTA
TTATTGGTGAAGAAGGGAAATGGCAAATCAACCTTACTTAAAATTTTAATG
GGGGAAGCTTTGTCTGATTTCTACATCTACAAGGGAAACATCCAATCTGACTA
TCAGTCACTGGCCTACATTCCTCAAAAAGTCCCTGAGGACCTAAAAAGA
AAACTTTACACGACTACTTCTTTTTAGATTCTATTGATTTAGACTACAGT
ATCCTCTATCGTTTGGCGGAGGAATTGCATTTTGATAGCAATCGTTTCGC
AAGTGACCAAGAGATTGGCAATCTATCAGGGGGCGAAGCTTTGAAAATTC
AGCTTATCCATGAGTTAGCCAAACCCTTTGAGATTCTATTTTTAGATGAA
CCTTCAAATGACCTAGACCTTGAGACAGTTGATTGGCTAAAAGGCCAGAT
TCAAAAGACCAGGCAAACCGTTATTTTCATTTCCCATGATGAAGACTTTC
TTTCTGAAACGGCAGACACTATTGTTCACTTGCGACTGGTCAAACACCGT
AAAGAAGCGGAAACGCTAGTAGAGCATTTAGACTATGATAGCTATAGTGA
GCAGAGAAAGGCTAATTTTGGCAAACAAAGTCAGCAAGCTGCTAACAACC
AAAAGAGCCTACGATAAAACCATGGAAAAACATCGGAGAGTTAAGCAAAAT
GTAGAAACTGCGCTTCGAGCTACCAAAGATAGTACTGCCGGTCGCCTATT
GGCTAAAAGATGAAAACTGTCCTCTCACAAGAAAAACGCTACGAAAAGG
CAGCTCAGTCCATGACTCAAAAGCCACTTGAAGAGGAACAAATCCAACTT
TTCTTTTCAGACATCCAACCATTACCAGCTTCTAAAGTCTTAGTCCAACT
GGAAAAAGAAAATTTGTCCATTGACGACCGAGTTTTGGTTCAAAAACTAC
AACTAACTGTCCGTGGCCAAGAAAAACATCGGTATTATCGGGCCAAATGT
GTTGGGAAATCAACTCTGTTAGCCAAGTTACAGAGACTTCTGAATGATAA
AAGAGAGATTTCACTTGGTTTTATGCCAAGATTACCACAAAAACTGC
AATTGGATTTATCCCCAATAGCCTATCTCAGTAAAACTGGGGAAAAGAG
GAACTACAGAAAATCAATCTCACCTAGCTAGTCTCAATTTCAGTTATCC
AGAAATGCAGCATCAAATTCGCTCCTTATCTGGCGGACAACAGGGAAAAC
TCCTGCTTTTGGATTTAGTCCTGCGCAAACAAACTTTCTCCTGCTGGAT
GAACCCACACGAAACTTTTCTCCCACTTCTCAACCCAAATCAGAAAACT
CTTTGCTACCTATCCAGGCGGTCTCATCACTGTTTCGCATGACCGTCGTT
TCTTAAAAGAAGTCTGCTCGATCATCTATCGCATGACAGAACACGGTTTG
AAGCTAGTTAATTTAGAAGATTATAA 4179.4
(SEQ. ID. NO. 314)
ATGAAACCAAAACATTTTACAACTTGCTTGCCGAGCAGAATCTTCCACT
TTCGGACCAGCAAAAAGAACAATTTGAACGTTATTTTGAGCTCTTGGTCG
AGTGAGATGAGAAGATTAATTTGACGGCGATTACGGACAAGGAAGAAGTT
TATCTCAAACATTTTTACGATTCGATTGCACCCATTCTTCAAGGTTTGAT
TCCCAATGAAACTATCAAACTTCTTGATATCGGGGCTGGGGCAGGATTTC
CTAGTCTACCAATGAAAATTCTCTATCCGGAGTTAGATGTGACCATTATT
GATTCACTCAATAAGCGCATCAACTTCCTACAACCTCTTGGCTCAAGAACT
GGATTTGAACGGAGTTCATTTCTACCACGGACGTGCCGAAGATTTTGCCC
AAGCAAGAACTTCCGTGCTCAATATGATTTTGTAACAGCTCGTGCGGTT
GCCCGTATGCAGGTCCTATCTGAATTGACTATTCCCTACCTTAAGGTTGG
TGGCAAACTATTAGCACTCAAGGCTAGCAATGCGCCTGAGGAATTATTAG
AAGCTAAGAATGCCCTCAATCTCCTTTTTAGTAAGGTCGAAGACAATCTC

TABLE 1-continued 4179.6
(SEQ. ID. NO. 315)
AGctACGCCCTACCGAATAGAGATCCGCGCTATATCACAGTGGTAGAAAA
GAAAAAAGAAACACCCAAATAAATATCCACGTAAGGCTGGTATGCCAAATA
AACGCCCACTTTAA 4179.6
(SEQ. ID. NO. 315)
ATGAGTATTAAACTAATTGCCGTTGATATCGACGGAACCCTTGTCAACAG
CCAAAAGGAAATCACTCCTGAAGTTTTTTCTGCCATCCAAGATGCCAAAG
AAGCTGGTGTCAAAGTCGTGATTGCAACTGGCGCCCTATCGCAGGCGTT
GCCAAACTTCTAGACGACTTGCAGTTGAGAGACGAGGGGGACTATGTGGT
AACCTTCAACGGTGCCCTTGTCCAAGAAACTGCTACAGGACATGAGATTA
TCAGCGAATCCTTGACTTATGAGGATTATCTAGATATGGAATTCCTCAGT
CGCAAGCTCGGTGTCCACATGCATGCCATTACCAAGGACGGTATCTATAC
TGCAAATCGCAATATCGGAAATACACTGTACACGAATCAACCCTCGTCA
GCATGCCTATCTTCTACCGTACCCCTGAAGAAATGGCTGGCAAAGAAATT
GTTAAATGTATGTTTATCGATGAACCAGAAATTCTCGATGCTGCGATTGA
AAAAATTCCAGCAGAATTTTACGAGCGCTACTCCATCAACAAATCTGCTC
CTTTCTACCTCGAACTCCTTAAAAAGAATGTAGACAAGGGTTCAGCCATT
ACTCACTTGGCTGAAAAACTCGGATTGACCAAAGATGAAACCATGGCAAT
CGGTGATGAAGAAAATGACCGTGCCATGCTGGAAGTCGTTGGAAACCCCG
TTGTCATGGAAAATGGAAATCCAGAAATCAAAAAAATCGCCAAATACATC
ACCAAAACAAATGACGAATCCGGCGTTGCCCATGCCATCCGAACATGGGT
ACTGTAA 4179.7
(SEQ. ID. NO. 316)
ATGACTTGGATTATTCTTGGAGTTATCGCTCTTATTGTTATTTTTGTGAT
TGTTAGCTATAACGGTTTGGTTAAAAATCGTATGCAAACCAAGGAGGCTT
GGAGTCAGATTGATGTTCAGTTGAAAGTCGCAATGACCTCTGCCAAAC
TTGATTGAGACTGTAAAAGGTTATGCCAAATATGAAGGTTCTACCCTTGA
AAAGGTGGCAGAACTACGTAACCAAGTGGCGGCAGCGACTTCACCAGCAG
AAGCTATGAAAGCCAGTGATGCCCTCACTCGTCAGGTTTCAGGTATTTTT
GCAGTTGCAGAAAGCTATCCAGATTTGAAAGCTAGTGCTAACTTTGTTAA
ATTGCAAGAGGAGTTGAAAACACAGAAAATAAATTTCTTACTCTCGTC
AACTCTATAACAGTGTTTGTCAGCAACTACAATGTAAATTAGAAACTTT
CCCGAGCAATATATCGCTGGAATGTTTGGATTTAAAGCGGCAGATTTCC
TTCAAACACCTGAAGAGGAAAAGTCGGTTCCTAAAGTTGATTTTAGCGGT
TTAGGTGACTAA 4179.8
(SEQ. ID. NO. 317)
ATGTTGTTTGATCAAATTGCAAGCAATAAACGAAAAACCTGGATTTTGTT
GCTGGTATTTTTCCTACTCTTAGCTCTTGTTGGTTATGCGGTTGGTTATC
TCTTTATAAGATCTGGACTTGGTGGTTTGGTTATTGCACTGATTATCGGC
TTTATCTACGCTTTGTCTAAACTTGTCAATCGACAGAGTTTACTTGGTCC
CATGAATGGAGCGCGTGAGGTGGATGAGCAAACGGCACCAGACCTCTACC
ATGTAGTGGAAGATATGGCTCTGGTCGCTCAGATTCCTATGCCCCGTGTT
TTCATCATTGATGATCCAGCCTTAAATGCCTTTGCGACAGGTTCTAATCC
TCAAAATGCGGCTGTTGCTGACTTCAGGTCTACTAGCTATCATGAATG
GTGAAGAACTAGAAGCTGTTATGGGACATGAAGTCAGTCATATTCGTAAT
TATGATATCCGTATTTCGACTATTGCAGTTGCCCTTGCTAGTGCTATCAC
CATGCTTTCTAGTATGGCAGGTCGTATGATGTGGTGGGGTGGAGCAGGTC
GCAGACGAAGTGATGATGACCGAGATGGAAATGGTCTTGAAATCATTATG
CTAGTGGTTTCCCTACTAGCTATTGTACTGGCACCTCTCGCTGCAACCTT
GGTTCAGCTCGCTATTTCTCGTCAGAGGGAATTTCTGGCAGATGCATCTA
GTGTCGAGCTGACTCGCAATCCCCAGGGAATGATTAATGCCCTAGATAAG
TTGGACAATAGCAAACCTATGAGTCGCCACGTCGATGATGCTAGCAGTGC
CCTTTATATCAATGATCCTAAGAAAGGTGGGGGTTCCAAAAACTCTTTT
ATACCCACCCACCTATCTCAGAACGGATTGAACGTTTAAAACAGATGTAA 4179.9
(SEQ. ID. NO. 318)
ATGAAATTAAATATTCAAGAAATTCGTAAGCAGTCTGAAGGTTTGAACTT
TGAACAAACGTTAGATTAGTTGATGACCTGCGTGCACGTAATCAAGAAA
TTTTAGATGTAAAAGATATCCTTGCAGTTGGGAAAGTACAATATGAAGAC
CGTATGTATTTCTTAGATTATCAACTATCTTATACCATTGTTCTTGCTTC
GAGTCGCAGTATGGAGCCAGTTGAGTTAGTTGAATCTTATCCAGTCACGG
AAGTTTTCATGGAAGGCGCAACTAACCAGCTAGATCAAGAAGTTTTAGAT
GATGACTTGGTCTTGCCCATCGAAAATGGGGAGCTTGACCTTGCTGAGAG
TGTATCAGACAATATCCTGCTAAACATTCCTATCAAGGTCTTGACGGCTG
AAGAAGAAGCTGGTCAAGGATTTATCTCAGGAAATGACTGGCAAATCATG
ACAGAGGAAGAATACCAAGCTCAAAAAGCAGTAAAGAAAGAAGAAAACAG
TCCTTTTGCTGGCTTACAAGGACTATTTGACGGAGATGAATAA 4179.12
(SEQ. ID. NO. 319)
ATGGAGTTATTTATGAAAATCACAAACTATGAAATCTATAAGTTAAAAAA
ATCAGGTTTGACCAATCAACAGATTTTGAAAGTGCTAGAATACGGTGAAA
ATGTTGATCAGGAGCTTTTGTGGGTGATATTGCAGATATCTCAGGTTGCC TABLE 1-continued GTAATCCAGCCGTTTTTATGGAACGTTATTTTCAGATAGACGATGCGCAT
TTGTCGAAAGAGTTTCAAAAATTTCCATCTTTCTCTATTTTAGATGACTG
TTATCCTTGGGATTTGAGTGAAATATATGATGCGCCTGTACTTTTATTTT
ACAAGGGAAATCTTGACCTCCTGAAATTCCCGAAGGTAGCGTCGTGGGC
AGTCGTGCTTGTAGCAAACAGGGAGCTAAGTCAGTTGAAAAAGTCATTCA
AGGCTTGGAAAATGAACTGGTTATTGTCAGTGGTCTGGCCAAGGGCATTG
ACACAGCAGCTCATATGGCAGCTCTTCAGAATGCGGAAAAACCATTGCA
GTGATTGGAACAGGACTGGATGTGTTTATCCTAAAGCCAATAAACGCTT
GCAAGACTACATCGGCAATGACCATCTGGTTCTAAGTGAATATGGACCTG
GTGAACAACCTCTGAAATTTCATTTTCCTGCCCGTAATCGCATCATTGCT
GGACTTTGTCGTGGTGTGATTGTAGCAGAGGCTAAGATGCGTTCAGGTAG
TCTCATTACGTGTGAGCGAGCAATGGAACAGGACGTGCGATGTCTTTGCTA
TTCCTGGTAGCATTTTAGATGGACTATCAGACGGTTGCCATCATTTGATT
CAAGAAGGAGCAAAATTGGTCACCAGTGGGCAAGATGTTCTTGCGGAATT
TGAATTTTAA 4181.1
(SEQ. ID. NO. 320)
ATGAAACGTCAATTAGCCTTGGTCGTCTTTAGTGGTGGTCAAGATTCAAC
AACCTGCCTTTTCTGGGTCATGCAACACTATGAAACAGTCGAAGCTGTCA
CCTTTGCCTACGGCCAACGTCATCACCTCGAAATTCAAATTACTAGAGAA
ATCGCTAAGGAACAGGGCATTCGTCACCATATCCTCGATATGTCTCTGCT
GGGACAAATCACTGCTCAGCCAGACTTTGCGACGATTCATATTTCCTACA
TTCCTGACAAGCTCTGTGTCGAGTCAAAATCCCTCAAACTATATCTATTT
AGCTACCGAAACCACGGAGATTTCCACGAAAACTGTATCAACACCATCGG
GAAAGACTTGGTCAACTTGCTAGACCCTCGCTATTTAGAAGTCTGGGGAA
AATTCACTCCGCGCGGTGGCATTTCAATGACCCCTACTACAACTACGGT
AAGCAAGGAACTAAGTATGAGGGCTTGGCAGAACAACGCCTCTTCCAACA
CGACCTTTATCCAGAGAAAATTGACAACCGCTAA 4181.2
(SEQ. ID. NO. 321)
ATGACCGAAACGGTAGAAGATAAAGTAAGTCATTCAATTACTGGGTTGA
TATCCTCAAGGGGATAGTTGCTGCGGGAGCTGTCATAAGTGGAACCGTTG
CAACTCAAACGAAGGTATTTACAAATGAGTCAGCAGTACTTGAAAAAACT
GTAGAGAAAACGGATGCTTTGGCAACAAATGATACAGTAGTTCTAGGTAC
GATATCTACAAGTAATTCAGCGAGTTCAACTAGTTTGTCAGCTTCAGAT
CGGCAAGTACATCTCATCTGAGTCAGCCTCAACCAGCGCTTCGACCTCA
GCAAGTACAAGTGCATCAGAATCAGCAAGTACATCGGCTTCGACAAGTAT
TTCTGCATCATCTACTGTGGTAGGTTCACAAACAGCTGCCGCTACAGAAG
CAACTGCTAAGAAGGTCGAAGAAGATCGTAAGAAACCAGCTAGTGATTAT
GTAGCATCAGTTACAAATGTCAATCTCCAATCTTATGCTAAGCGACGCAA
GCGTTCAGTGGATTCCATCGAGCAATTGCTGGCTTCATAAAAAATGCTG
CTGTTTTTTCTGGCAATACGATTGTAAATGGCGCCCTGCAATTAATGCA
AGTCTAAACATTGCTAAAGTGACAATGTTTTATACAGGTGAAGGTGT
AGATTCGGTATATCGTGTTCCAATTTACTATAAAATTGAAAGTGACAAATG
ATGGTTCAAAATTGACCTTTACCTATACGGTTACGTATGTGAATCCTAAA
ACAAATGATCTTGGTAATATATCAAGTATGCGTCCTGGATATTCTATCTA
TAATTCAGGTACTTCAACACAAATAATCAATGTTAACCCTTGGCAGTGATCTTG
GTAAACCTTCAGGTGTAAAGAACTACATTACTGACAAAAATGGTAGACAG
GTTCTATCCTATAATACATCTACAATGACGACGCAGGGTAGTGGGTATAC
TTGGGAAATGGTGCCCAAATGAATGGTTTCTTTGCTAAGAAAGGATATG
GATTAACATCATCTTGGACTGTACCAATTACTGGAACGGATACATCCTTT
ACATTTACCCCTTACGCTGCTAGAACAGATAGAATTGGAATTAACTACTT
CAATGGTGGAGGAAAGGTAGTTGAATCTAGCACGAGCAGTCAGTCACTTT
CACAGTCTAAGTCACTCTCAGTAAGTGCTAGTCAAAGCGCCTCAGCTTCA
GCATCAACAAGTGCGTCGGCTTCAGCATCAACCAGTGCCTCGGCTTCAGC
GTCAGCATGCGTCAGCTTCAGCAAGTGCCAGTGCTTCAGTCAGTCAGC
CAACAAGTGCTTCAGCCTCAGCATCGACAAGTGCCTCGGCTTCAGCAAGC
ACATCAGCATCTGAATCAGCGTCAACCAGTGCTTCGGCTTCAGCAAGTAC
CAGTGCTTCAGCTTCAGCATCAACCAGCGCCTCGGCCTCAGCAAGCACCT
CAGCTTCTGAATCGGCTCCAACCAGCGCCTCGGCCTCAGCATCAACGAGTGC
TTCGGCTTCAGCAAGCACAAGCGCCTCGGGTTCAGCATCAACGAGTACGT
CAGCTTCAGCGTCAACCAGTGCTTCAGCCTCAGCATCAACAAGTGCGTCA
GCCTCAAGTATCTCAGCGTCTGAATCAACAAGTGCCTCGGCTTCAGC
GTCAGCATCAACGAGTACGTCAGCTCAGCAAGCACCTCAGCTTCTGAAT
CGGCCTCAACCAGTGCGTCAGCCTCAGCATCGACAAGCGCCTCAGCTTCA
GCAAGTACCAGTGCTTCAGCCTCAGCGTCGACAAGTGCGTCGGCCTCAAC
CAGTGCATCTGAATCAACAACCAGTGCGTCGGCTTCAGCGTCAACCAGT
GCGTCAGCTTCAGCAAGTACCAGTGCTTCAGTCTCAGCATCAACAAGTGC
TTCAGCCTCAGCATCGACAAGTGCCTCGGCTTCAGCAAGCACATCAGCAT
CTGAATCAGCGTCAACCAGCGCCTCAGCTTCAGCAAGCACCTCAGCTTCTGA
ATCGGCCTCAACCAGCGCCTCGGCCTCAGCAAGCACCTCAGCTTCTGAAT
CGGCCTCAACCAGCGCCTCAGCCTCAGCATCAACGAGTGCTTCGGCTTCA
GCAAGCACAAGCGCCTCGGGTTCAGCATCAACGAGTACGTCAGCTTCAGC
GTCAACCAGTGCTTCAGCCTCAGCATCAACAAGTGCGTCAGCCTCAGCAA TABLE 1-continued GTATCTCAGCGTCTGAATCGGCATCAACGAGTGCGTCTGAGTCAGCATCA
ACGAGTACGTCAGCCTCAGCAAGCACCTCAGCTTCTGAATCGGCCTCAAC
CAGTGCGTCAGCCTCAGCATCGACAAGCGCCTCAGCTTCAGCAAGTACCA
GTGCTTCAGCCTCAGCTCGACAAGTGCGTCGGCCTCAACCAGTGCATCTG
AATCGGCATCAACCAGTGCGTCAGCCTCAGCAAGTACTAGTGCATCAGCT
TCAGCATCAACGAGTGCATCGGCTTCAGCATCAACCAGTGCCTCGGCTTC
AGCGTCAACCAGTGCGTCAGCTTCAGCAAGTACCAGTGCTTCAGTCTCAG
CATCAACAAGTGCTTCAGCCTCAGCATCGACAAGTGCcTCGGCTTCAGCA
AGCACATCAGCATCTGAATCAGCGTCGACAAGCGCcTCAGCTTCAGCAAG
TACCAGTGCGTCAGCCTCAGCGTCGACAAGTGCGTCAGCCTCAGCAAGTA
CTAGTGCATCAGCTTCAGCATCAACGAGTGCATCGGCTTCGGCGTCAACC
AGTGCATCAGAGTCAGCAAGTACCAGTGCGTCAGCTTCCGCATCAACAAG
TGCCTCGGCTTCAGCAAGCACCAGTGCGTCGGCTTCAGCAAGTACTAGCG
CCTCAGCCTCAGCCTCAACCAGTGCGTCAGCCTCAGCAAGTATCTCAGCG
TCTGAATCGGCATCAACGAGTGCGTCCGCTTCAGCAAGTACTAGCGCCTC
AGCCTCAGCGTCAACAAGTGCATCGGCTTCAGCAAGTACTAGCGCGTCTG
AATCGGCATCAACGAGTGCGTCCGCTTCAAGCAAGTACTAGCGCCTCAGCC
TCAGCGTCAACAAGTGCATCGGCTTCAGCATCAACGAGTGCGTCCGCTTC
AGCAAGTACTAGCGCCTCAGCCTCAGCGTCAACAAGTGCATCGGCTTCAG
CGTCAACGAGTGCGTCTGAGTCAGCATCAACGAGTGCGTCAGCCTCAGCA
AGCACATCAGCTTCTGAATCTGCATCAACCAGTGCGTCAGCCTCAGCATC
GACAAGCGCCTCAGCTTCAGCAAGTACCAGTGCGTCAGCCTCAGCGTCGA
CAAGTGCGTCGGCTTCAGCAAGTACCAGTGCGTCAGCCTCAGCAAGTACC
AGTGCCTCAGCCTCAGCGTCGACAAGTGCGTCGGCCTCAACCAGTGCATC
TGAATCGGCATCAACCAGTGCGTCAGCCTCAGCAAGTACTAGTGCATCAG
CTTCAGCATCAACGAGTGCATCGGCTTCAGCATCAACCAGTGCATCAGAG
TCAGCAAGTACCAGTGCGTCAGTTCCGCATCAACAAGTGCCTCGGCTTCA
GCAAGTACTAG 4183.1
(SEQ. ID. NO. 322)
ATGGGGGTCGAAACTTGGTTTTATTCTAGCATCTGCTGGCTGGCCATCGG
GCTTGGTTCCGTTTGGAAGTTTCCCTACATGACTGCTGCTAATGGCGGTG
GAGGCTTTTTACTAATCTTTCTCATTTCCACTATTTTAATCGGTTTCCCT
CTCCTGCTGGCTGAGTTTGCCCTTGGCCGTAGTGCTGGCGTTTCCGCTAT
CAAAACCTTTGGAAAACTGGGCAAGAATAACAAGTACAACTTTATCGGTT
GGATTGGCGCCTTTGCCCTCTTTATCCTCTTATCTTTTTACAGTGTTATC
GGAGGATGGATTCTAGTCTATCTAGGTATTGAGTTTGGGAAATTGTTCCA
ACTTGGTGGAACGGGTGATTATGCTCAGTTATTTACTTCAATCATTTCAA
ATCCAGCCATTGCCCTAGGAGCTCAAGCGGCCTTTATCCTATTGAATATC
TTCATTGTATCACGTGGGGTTCAAAAAGGAGTTGAAGAGCTTCAAAAGT
CATGATGCCCCTGCTCTTTATCGTCTTTGTTTTTATCATCGGTCGCTCTC
TCAGTTTGCCAAATGCCATGGAAGGGGTTCTTTACTTCCTCAAACCAGAC
TTTTCAAAACTGACTAGCACTGGTCTCCTCTATGCTCTGGGACAATCTTT
CTTTGCCCTCTCACTAGGGGTTACAGTCATGTTGACCTATGCTTCTTACT
TAGACAAGAAAACCAATCTAGTCCAGTCAGGAATCCCATCGTAGCCATG
AATATCTCGATATCCATCATGGCAGGTCTAGCCATTTTCCAAGCTCGATC
CCCCTTCAATATCCAGTCTGAAGGGGGACCCAGCCTGCTCTTTATCGTCT
TGCCTCAACTCTTTGACAAGATGCCTTTGGAACCATTTTCTACGTCCTC
TTCCTCTTGCTCTTCCTTTTTGCGACAGTCACTTTTTCTGTCGTGATGCT
GGAAATCAATGTAGACAATATCACCAACCAGGATAACAGCAAACGTGCCA
AATGGAGTGTTATTTAGGAATTTTGACCTTTGTCTTTGGCATTCCTTCA
GCCCTATCTTACGGTGTCATGGCGGATGTTCACATTTTTGGTAAGACCTT
CTTTGACGCTATGGACTTCTTGGTTTCCAATCTCCTCATGCCATTTGGAG
CTCTCTACCTTCACTTTTTACAGGCTATATCTTTAAAAGGCTCTTGCAA
TGGAGGAACTCCATCTCGATGAAAGAGCATGAAACAAGGACTGTTCCAA
GTCTGGCTCTTCCTTCTTGTTTCTTCGTTTCGTCATTCCAATCATCATC
ATTGTGGTCTTCATTGCCCAATTTATGTAATCAAAAAGGACTTGAGTAG 4183.5
(SEQ. ID. NO. 323)
ATGTTGAAAAAATGGCAGTTAAAAGATGTTATCTTGCTTGCTTTCTTGTC
TATCTTTTTTGGTGGGGTTTTCGTTGGTTCAGGATATGTGTATAATATTC
TCAGTCTACTCTTAACACCTCTTGGTTTGCAGGCCTTTGCCAATGAAATC
CTCTTCGGTCTCTGGTGTATGGCTGCGCCCATTGCTGCCATCTTTGTTCC
GAGAGTCGGAAGTGCAACGATTGGAGAAGTGCTAGCTGCGTTGCTGAAG
TCCTTTATGGTAGCCAATTTGGTCTAGGAGCTCTTTTGTCTGGCTTTGTT
CAAGGTTTGGGAAGTGAATTTGGTTTTATCGTAACTAAGAATCGCTATGA
AAGTTGGCTCTCTCTAACTGCTAATAGTATTGGGATTACGCTTGTTAGCT
TTGTCTATGAATACATTAAGTTAGGTTACTACGCTTTTCCCTTCCGTTT
GTCCTTTCCTTGCTTGTGTAGTTTTATTTCTGTTTATTTCTTCTGTAC
CATCTTGGTTCGTGCCATTGTCAAACCTATCATCAGTTTGCAACTGGAG
GAAAAGCATAG 4183.6
(SEQ. ID. NO. 324)
ATGGTCAAAGTAGCAACCCAGACACCGATTATCAGTCTCTTCTTGCTGAT
TTTATCCTTGGGAAACATCTTTCATTCCTTCGATTGCTCTGACTCTTTCGG
TAGTCGCATTTTGTATTCTCTTTATGCTCTATTACCGTCGATTTAAAATG TTAGCTTGGATGATCATACTTGCCATTTTACCATCTTTTGCCAACTACTG
GGCAGTTCAGTTCACGGAGATGCTTCACAGGCAGTCATGCTTGGAACGA
GGGCCTTTGTGACAGTTTGTATCGGCCTTGTCTTTGTTTCCTCTGTTTCA
CTAAAAGAGCTTCTCTTTGTACTTGGCTCAAAAGGGGCTATCACGCTCTTG
GTCCTATGCCTTGATTGTGGTATTCAATTCTTTTCCTCTCATTCAGCAAG
AAATCAAGTCCCTCAAAGAAGCTTGCCTATTACGTGGTCAAGAACTACAT
TTTTGGTCGCCCTTGATTTACAGTAAGGTTCTGATGACAGTCTTTAGGTG
GCGCCATCTTTACCTGAGAGCTCTATCTGCTCACGGATATGACGAACATG
CACAGTTGAAGAATAGCTATCGGACTTTTATATTCCTAAAAAAACAAAA
TTAATCTACCTGCTTTTCTTTTTATTGCTTCAAACCAGTCTATTTTTATA
A 4183.7
(SEQ. ID. NO. 325)
ATGAGAAAGCACCAATTACAAGTTCACAAATTAACCATTTTATCTATGAT
GATTGCCCTTGATGTAGTCCTTACACCTATCTTTCGAATTGAGGGAATGG
CACCGATGTCCAGTGTAGTCAATATTCTAGCAGGAATCATGATGGGACCT
GTTTATGCCTTGGCTATGGCTACAGTCACAGCCTTTATCCGTATGACGAC
TCAAGGGATTCCGCCTTTAGCTCTCACAGGAGCGACTTTTGGAGCCCTTC
TAGCAGGTCTCTTTTATAAGTACGGTCGAAAATTTCACTATTCTGCTTTA
GGAGAGATTTTGGGAACAGGTATTATTGGTTCCATTGTTTCCTATCCTGT
TATGGTACTCTTTACAGGATCAGCTGCTAAGCTTAGCTGGTTTATCTACA
CGCCTCGATTTTTCGGAGCAACCTTGATTGGTACAGCGATTTCCTTTATT
GCCTTTCGATTTTTAATCAAGCAGGAATTCTTTAAAAAAGTGCAGGGATA
TTTCTTTAGTGAAAGGATAGACTGA 4183.8
(SEQ. ID. NO. 326)
ATGCAGGAATTTACAAATCCCTTTCCTATAGGCTCTAGTTCCCTCATTCA
CTGCATTACCAATGAGATTCTTGTGAGATGCTGGCAAATGGGATTTTGG
CTCTGGGATGCAAACCTGTCATGGCAGATGATTCCCGTGAAGTTCTTGAT
TTTACTAAGCAAAGTCAGGCTCTCTTCATCAATTTGGGGCATTTGTCAGC
TGAGAAGGAAAACAATCCGCATGGCAGCTTCGTATGCAACAAACCAATCTT
CTCTCCCGATGGTAGTAGATGCGGTTGGCGTAACGACTTCATCCATCGT
AAGAGCTTAGTTAAAGACCTTTTAGACTATAGACCTACGGTCCTTAAAGG
AAACATGTCAGAAATTCGAAGTCTTGTTGGATTAAAGCACCACGGCGTTG
GGGTCGATGCGAGTGCTAAAGATCAAGAAACGGAGGATTTGCTTCAAGTC
TTGAAAGACTGGTGTCAGACCTATCCTGGTATGTCTTTCTTAGTCACAGG
TCCCAAGGACCTCGTCGTTTCGAAAAATCAGGTCGCTGTACTGGGAAATG
GCTGTACTGAATTAGACTGGATAACAGGGACAGGAGACTTGGTTGGAGCC
TTAACAGCTGTTTTTCTCAGCCAAGGAAAGACTGGTTTTGAAGCTTCTTG
CTTAGCAGTCTCTTATCTCAATATCGCTGCTGAGAAAATAGTTGTTCAAG
GAATGGGATTGGAAGAATTTCGTTACCAAGTACTCAATCAGCTTTCGCTC
CTAAGAAGAGATGAAAATTGGCTAGATACCATCAAAGGAGAGGTTTATGA
ATAG 4185.3
(SEQ. ID. NO. 327)
ATGAACCATAAAATCGCAATTTTATCAGATGTTCATGGCAATGCGACGGC
GCTAGAAGCAGTGATTGCAGATGCTAAAAATCAAGGGGCCAGTGAATATT
GGCTTCTGGGAGATATTTTCTTCCTGGTCCAGGCGCAAATGACTTAGTC
GCCCTGCTAAAGGACCTTCCTATCACAGCAAGTGTTCGAGGCAATTGGGA
TGATGCTGTCCTTGAGGCTTTAGATGGGCAATATGGCTTAGAAGACCCAC
AGGAAGTTCAGCTCTTGCGTATGACACAGTATTTGATGGAGCGAATGAT
CCTGCAACGATTGCTGGCTACGAAGCTTGCCTTTGCTGGAAAAGAAGA
AATTGACGGATTGCGCTTTTCTATCTCTCATAATTTACCTGACAAAAACT
ATGGTGGTGACTTGCTAGTTGAGAATGATACAGAGAAATTTGACCAACTG
CTAGATGCGGAAACGGACGTGGCAGTTTATGGTCATGTTCACAAGCAGTT
GCTTCGTTATGGAAGTCAAGGGCAACAAATCATCAATCCAGGGTCGATTG
GCATGCCCTATTTAATTGGGAGCGTTAAAAAATCACCGTTCCCAGTAT
GCCGTGATAGAAGTTGAAGATGGGGAATTACTCAATATCCAATTTCGTAA
AGTTGCTTATGATTACGAAGCTGAGTTAGAATTGGCCAAGTCCAAGGGGC
TTCCCTTTATGAAATGTATGAAGAACTGCGTCGTGACGATAACTATCAG
GGGCACAATCTGGAATTATTAGCCAGCTAATAGAAAAGCATGGGTATGT
AGAGGATGTGAAGAATTTTTTTGATTTTTTGTAA 4186.1
(SEQ. ID. NO. 328)
ATGAATGTAAATCAGATTGTACGGATTATTCCTACTTTAAAAGCTAATAA
TAGAAAATTAAATGAAACATTTTATATTGAAACCCTTGGAATGAAGGCCT
TGTTAGAAGAATCGGCCTTTCTGTCACTAGGTGACGCAAACGGGTCTTGAA
AAGCTGGTTTTAGAAGAAGCTCCCAGTATGCGTACTCGTAAGGTAGAGGG
AAGAAAAAACTAGCTAGATTGATTGTCAAGGTGGAAAATCCCTTAGAAA
TTGAAGGAATCTTATCTAAAACAGATTCGATTCATCGATTATATAAAGGT
CAAATGGCTACGCTTTTGAAATTTCTCACCAGAAGATGATTTGATTTT
GATTCATGCGGAAGATGACATAGCAAGTCTAGTAGAAGTAGGAGAAAAGC
CTGAATTTCAAACAGATTTGGCATCAATTTCTTTAAGTAAATTTGAGATT
TCTATGGAATTACATCTCCCAACTGATATCGAAAGTTTCTTGGAATCATC
TGAAATTGGGGCATCCCCTTGATTTATTCCAGCTCAGGGGCAGGATTGA TABLE 1-continued CTGTGGACAATACGGTTACCTGGGACTTATCTATGCTCAAGTTCTTGGTC
AATGAATTAGACATAGCAAGTCTTCGCCAGAAGTTTGAGTCTACTGAATA
TTTTTATTCCTAAGTCTGAAAAATTCTTCCTGGTAAAGATAGAAATAATGT
TGAATTGTGGTTTGAAGAAGTATGA 4186.2

(SEQ. ID. NO. 329)
ATGAAGTGGACCAAGATTATTAAAAAAATAGAAGAACAAATCGAGGCAGG
GATTTATCCCGGAGCCTCTTTTGCGTATTTTAAGGACAATCAATGGACAG
AGTTCTATTTAGGCCAGAGTGACCCAGAGCATGGCTTGCAGACTGAGGCA
GGACTAGTTTATGACCTAGCTAGTGTCAGCAAGGTTGTTGGGGTTGGCAC
AGTTTGTACCTTCTTGTGGGAAATAGGTCAATTAGATATTGATAGACTGG
TAATAGATTTTTTACCTGAGAGTGATTATCCAGACATCACTATTCGCCAG
CTCTTGACTCATGCAACAGACCTTGATCCTTTTATTCCTAATCGTGATCT
TTTAACAGCCCCTGAATTAAAGGAAGCGATGTTTCATCTCAACAGACGAA
GTCAGCCAGCCTTTCTTTATTCGGATGTCCATTTTTTGCTGTTGGGCTTT
ATTTTGGAAAGAATTTTTAATCAAGATTTGGATGTGATTTTAAAGGATCA
AGTCTGGAAACCTTGGGGAATGACGGAAACTAAGTTTGGGCCAGTTGAGC
TTGCTGTTCCAACAGTTAGAGGTGTAGAGGCAGGCATAGTGCATGATCCC
AAGGCTCGTCTCCTGGGTAGACATGCTGGGAGTGCTGGTTTTATTTTGAC
TATAAAGGATTTACAAATCTTTTTAGAACACTATTTAGCAGATGATTTTG
CAAGAGACTTAAATCAAAATTTTTCTCCTTTGGATGACAAGGAACGTTCT
TTAGCATGGAATTTGGAAGGAGATTGGCTAGACCATACGGGCTATACAGG
TACCTTTATCATGTGGAATCGTCAGAAGCAAGAAGCCACTATTTTCCTAT
CGAATCGTACCTATGAAAAGGACGAGAGAGCTCAATGGATATTAGACCGC
AATCAAGTGATGAACTTGATTCGCAAAGAAGAGTAA 4187.2

(SEQ. ID. NO. 330)
ATGATGAAGAAGACTTATAATCATATTTTGGTCTGGGGAGTCATTTTCTA
TAGCATTTGCATTGTCTGTTTTTGCTTTACTCCTCAAGAACAATCTACCG
TGGGAGTGGGAACTCCAGGTATTCAGCATCTTGGACGCCTGGTTTTTCTT
TTGACTCCTTTCAATTCTCTCTGGAAACTGGGCGAAGTGAGTGACATTGG
ACAATTATGTTGGATTTTTTACAAAATATCCTCAATGTCTTCTTGTTTT
TTCCTCTGATTTTCCAACTCCTTTATCTATTTCCAAATTTGCGGAAAACA
AAAAGGTCCTTCTTTTTAGTTTTCTTGTGAGTCTTGGAATCGAGTGTAC
GCAATTAATCTTGGACTTTTTCTTTGATTTCAATCGCGTCTTTGAGATTG
ATGATTTGTGGACCAACACTTTGGGTGGCTATCTGGCTTGGCTCCTTTAT
AAACGATTACATAAAAACAAGGTAAGGAATTAA 4188.1

(SEQ. ID. NO. 331)
ATGAAGATTCCTCTCTTAACTTTTGCAAGGCATAAATTTGTTTATGTCTT
GCTTACTTTGCTTTTTCTTGCTTTGGTTTATCGTGATGTTTTGATGACTT
ATTTCTTTTTTGATATTCATGCGCCGATCTAGCTAATTCGATGGACAA
GCAATTAAAAATGACTTATTAAATCAGCATTAGATTTTCGTATTCTCCA
GTTCAATCTAGGTTTTTATCAATCATTTATTATTCCAATCATCCATTGTTT
TGCTAGGTTTTCAATATATTGAGCTGAAAAATAAAGTTTTACGATTGAGT
ATTGGAAGAGAAAGTGAGTTATCAAGGGTTAAAAAGAAAGTTGACTTTGCA
AGTTGCAAGTATCCCTTGTTTGATATATTTAGTGACTGTGCTGATAATTG
CAATTATAACCTATTCTTTGGGACTTTTTCTCCTCTTGGATGAATTCT
CTATTTTCTGATGGAAGTGGTTTACAAAGACTCCTAGATGGAGAGATAAA
AAGCTATTTGTTCTTTACTTGTGTCCTACTAATCGGTATTTTCATCAATG
CAATCTATTTTTTACAAATAGTTGATTATGTGGGGAATGTGACTCGTTCG
GCAATCACCTATTTGATGTTTCTTTTGGCTTGGTTCTATGCTGCTTTATA
GTGCCTTGCCTTACTATATGGTTCCTATGACGAGTTTGATGCAAGCTAGC
TATGGGATGTAAGTTTGATGAAACTCTTTACTCCTTATATCCTTTATAT
TGTCCCTTACATGGTGCTTGAAAAATATGAAGATAATGTTTAA 4188.2

(SEQ. ID. NO. 332)
ATGAAGATAATGTTTAAGAATTTTAACAATATTTGCTAAATAGAAAGAT
TGTTTTACTACTTCGTATAGTTCTGATGATGATTTTGATAAAACCATCTAT
TGTCAACAGCGGTTCAAAGCAGGATGCTGTTATCTTTTTCAAGAGAGAAT
TGATTTCAATTTTTTCCTATAATGACTATTCTGAAGCGAATTTAGAAATC
CCCAAACTATTGTTAAACCTTTGCTTTCATGGTAGGATGGCTCTCTGTA
CATTTTACTTGAAAGTGATTTGGCAGACATTACCATCACTTGATTCGCT
ATCAATCAAGCTCCTTTTTCGATTATACAAGGAAACGATTGGTTGTCATT
TCTAAATTTTTTACTCAAGATTTGTTTGTCTGGTTTCTTGGTTTACTTCC
TCTAGGAATTCATTTCAAAACAGTCATCGCACTTTCTTTTTACTTGCTCAGT
TAATGATGTTGTACTTACTACTGTCTTATCTGATAGCACTGATTAGTGCG
GGCGCTGGTTTTTCCTTTTTTCTCTATTTTTTAGCATTTGTGGGACAAGA
ATGGATGATGGATCATATTGTAACAGTGTATTTAGTACTCTTAAGTTTAT
TAGTTATGTTGATTGTTAGTCGCTTGGAAGAGAAATTTAAGAAAGGATAA 4188.5

(SEQ. ID. NO. 333)
ATGGGCAAAGGAGAGATGGGCAAGGAGTTATTGGCTTGGAGTTCGACTC
AGAAGTATTGGTCAACAAGGCTCCAACCCTTCAATTGGCAAATGGTAAAA

CAGCGACTTTCCTAACCCAGTATGATAGCAAGACCTTGTTGTTTGCAGTA
GATAAGGAAGATATCGGACAGGAAATTATTGGTATAGCTAAAGGAAGCAT
CGAAAGTATGCATAATCTTCCTGTAAATCTAGCAGGTGCCAGAGTTCCTG
GCGGAGTAAATGGTAGCAAAGCAGCGGTGCATGAAGTTCCAGAATTTACA
GGGGGAGTTAATGGTACAGAGCCAGCTGTTCATGAAATCGCAGAGTATAA
GGGATCTGATCGCTTGTAACTCTTACTACAAAAAAAGATTATACTTACAA
AGCTCCTCTTGCTCAGCAGGCACTTCCTGAAACAGGAAACAAGGAGAGTG
ACCTCCTAGCTTCACTAGGACTAACAGCTTTCTTCCTTGGTCTGTTTACG
CTAGGGAAAAAGAGAGAACAATAA 4188.10

(SEQ. ID. NO. 334)
ATGTTTAAAGTTTTACAAAAAGTTGGAAAAGCTTTTATGTTACCTATAGC
TATACTTCCTGCAGCAGGTCTACTTTTGGGGATTGGTGGTGCACTTTCAA
ACCCAACCACGATAGCAACTTATCCAATACTAGACAATAGTATTTTTCAA
TCAATATTCCAAGTAATGAGCTCTGCAGGAGGAGGTTGTATTCAGTAATTT
GTCACTACTTCTCTGTGTGGGATTATGTATTGGCTTAGCGAAACAGATA
AAGGAACCGCTGCGTTAGCAGGAGTAACTGGTTACTTAGTTATGACTGCA
ACGATCAAAGCTTTGGTAAAACTTTTTATGGCAGAAGGATCTGCAATTGA
TACTGGGATTATTGGAGCATTAGTTGTCGGAATAGTTGCCGTAATTTGC
ACAACCGATATAACAATATTCAATTACCTTCCGCTTTAGGATTCTTTGGA
GGTTCACGCTTCGTTCCTATTGTTACATCGTTCTTCTATCTTGATTGG
CTTTGTCTTCTTTGTTATTTGGCCACCTTTCCAACAACTTCTTGTTTCTA
CAGGTGGATATATTTCTCAGGCGGGTCCAATTGGAACTTTTCTATATGGA
TTTTTAATGAGACTTTCTGGAGCGAGTAGGCTTTACATCATATAATTTACCC
TATGTTTTGGTATACTGAACTTGGTGGTGTTGAAACTGTTGCAGGACAAA
CAGTGGTTGGAGCTCAAAAATATTTTTTGCTCAATTAGCCGATTTGGCC
CATTCTGGATTATTTACAGAAGGAACAAGGTTTTTTGCAGGTCGTTTCTC
AACAATGATTCGGTTTACCGGCTGCCTGTTTAGCGATGTACCATAGTG
TTCCTAAAAATCGTCGTAAAAAATACGCGGGTTTGTTTTTTGGAGTTGCT
TTAACATCTTTTATTACCGGTATTACAGAACCAATTGAATTTATGTTTCT
ATTCGTCAGTCCGGTTCTATATGTTGTTCACGCATTCCTTGATGGTGTTA
GCTTCTTTATTGCAGACGTCTTAAATATTTCAATAGGAAACACATTTTCA
GGAGGTGTAATCGATTTCACTTTTATTTGGAATTTTGCAGGGGAACGCTAA
GACGAATTGGGTTCTTCAGATTCCATTTGGACTTATTTGGAGTGTTTTGT
ATTATATTATTTTTAGATGGTTCATTACTCAATTCAACGTTCTAACGCCA
GGGCGAGGAGAAGAAGTAGATTCTAAAGAAATTTCTGAATCCGCAGATTC
AACTTCAAATACTGCAGATTATTTAAAACAGGATAGCCTACAAATTATCA
GAGCCTTGGGTGGATCAAATAATATAGAAGATGTAGATGCTTGTGTGACA
CGTTTACGTGTAGCTGTAAAAGAAGTTAATCAAGTTGATAAAGCACTTTT
AAAACAAATTGGTCAGTTGATGTCTTAGAAGTGAAGGGTGGCATTCAAG
CAATCTATGGAGCAAAAGCAATCTTATATAAAAATAGTATTAATGAAATT
TTAGGTGTAGATGATTAA 4188.11

(SEQ. ID. NO. 335)
ATGAAATTTAGAAAATTAGCTTGTACAGTACTTGCGGGTGCTGCGGTTCT
TGGTCTTGCTGCTTGTGGCAATTCTGGCGGAAGTAAAGATGCTGCCAAAT
CAGGTGGTGACGGTGCCAAAACAGAAATCACTTGGTGGGCATTCCCAGTA
TTTACCCAAGAAAAAACTGGTGACGGTGTTGGAACTTATGAAAAATCAAT
CATCGAAGCGTTTGAAAAAGCAAACCCAGATATAAAAGTGAAATTGGAAA
CCATCGACTTCAAGTCAGGTCCTGAAAAAATCACAACAGCCATCGAAGCA
GGAACAGCTCCAGACGTACTCTTTGATGCACCAGGACGTATCATCCAATA
CGGTAAAAACGGTAAATTGGCTGAGTTGAATGACCTCTTCACAGATGAAT
TTGTTAAAGATGTCAACAATGAAAACATCGTACAAGCAAGTAAAGCTGGA
GACAAGGCTTATATGTATCCGATTAGTTCTGCCCCATTCTACATGGCAAT
GAACAAGAAAATGTTAGAAGATGCTGGAGTAGCAAACCTTGTAAAAGAAG
GTTGGACAACTGATGATTTTGAAAAAGTATTGAAAGCACTTAAAGACAAG
GGTTACACACCAGGTTCATTGTTCAGTTCTGGTCAAGGGGGAGACCAAGG
AACACGTGCCTTTATCTCTAACCTTTATAGCGGTTCTGTAACAGATGAAA
AAGTTAGCAAATATAACAACTGATGATCCTAAATTCGTCAAAGGTCTTGAA
AAAGCAACTAGCTGGTATTAAAGACAATTTGATCAATAATGGTTCACAATT
TGACGGTGGGCAGATATCCAAAACTTTGCCAACGGTCAAACATCTTACA
CAATCCTTTGGGCACCAGCTCAAAATGGTATCCAAGCTAAACTTTTAGAA
GCAAGTAAGGTAGAAGTGGTAGAAGTACCATTCCCATCAGACGAAGGTAA
GCCAGCTCTTGAGTACCTTGTAAACGGGTTTGCAGTATTCAACAATAAGA
ACGAAGAAAGTCGCTGCATCTAAGAAATTCATCCAGTTTATCGCAGAT
GACAAGGAGTGGGGACCTAAAGACGTAGTTCGTACCAGGTGCTTTCCCAGT
CCGTACTTCATTTGGAAACTTTATGAAGACAAACGCATGGAAACAATCA
GCGGCTGACTCAATACTACTCACCATACTACAACACTATTGATGGATTT
GCTGAAATGAGAACCTTTGTTCCCAATGTTGCAATCTGTATCAAATGG
TGACGAAAACCAGCAGATTGCTTTGAAGCCTTCACTGAAAAGCGAACG
AAACAATCAAAAAGCTATGAACAATAG 4188.12

(SEQ. ID. NO. 336)
ATGCAATCTACAGAAAAAAAACCATTAACAGCCTTTACTGTTATTTCAAC
AATCATTTTGCTCTTGTTGACTGTGCTGTTCATCTTTCCATTCTACTGGA
TTTTGACAGGGGCATTCAAATCACAACCTGATACAATTGTTATTCCTCCT

TABLE 1-continued

CAGTGGTTCCCTAAAATGCCAACCATGGAAAACTTCCAACAACTCATGGT
GCAGAACCCTGCCTTGCAATGGATGTGGAACTCAGTATTTATCTCATTGG
TAACCATGTTCTTAGTTTGTGCAACCTCATCTCTAGCAGGTTATGTATTG
GCTAAAAAACGTTTCTATGGTCAACGCATTCTATTTGCTATCTTTATCGC
TGCTATGGCGCTTCCAAAACAAGTTGTCCTTGTACCATTGGTACGTATCG
TCAACTTCATGGGAATCCATGATACTCTCTGGGCAGTTATCTTGCCTTTG
ATTGGATGGCCATTCGGTGTCTTCCTCATGAAACAGTTCAGTGAAAATAT
CCCTACAGAGTTGCTTGAATCAGCTAAAATCGACGGTTGTGGTGAGATTC
GTACCTTCTGGAGTGTAGCCTTCCCGATTGTGAAACAGGGTTTGCAGCC
CTTGCAATCTTTACCTTCATCAATACTTGGAATGACTACTTCATGCAATT
GGTAATGTTGACTTCACGTAACAATTTGACCATCTCACTTGGGGTTGCGA
CCATGCAGGCTGAAATGGCAACCAACTATGGTTTGATTATGGCAGGAGCT
GCCCTTGCTGCTGTTCAATCGTCACAGTCTTCCTAGTCTTCCAAAAATC
CTTCACACAGGGTATTACTATGGGAGCGGTCAAAGGATAA 4191.1
(SEQ. ID. NO. 337)
ATGAAAAAAACTTTTTTCTTACTGGTGTTAGGCTTGTTTTGCCTTCTTCC
ACTCTCTGTTTTTGCCATTGATTTCAAGATAAACTCTTATCAAGGGGATT
TGTATATTCATGCAGACAATACGGCAGAGTTTAGACAGAAGATAGTTTAC
CAGTTTGAGGAGGACTTTAAGGGCCAAATCGTGGGACTTGGACGTGCTGG
TAAGATGCCTAGCGGGTTTGACATTGACCCTCATCCAAAGATTCAGGCCG
CGAAAAACGGTGCAGAACTAGCAGATGTGACTAGCGAAGTAACAGAAGAA
GCGGATGGTTATACTGTGAGAGTCTATAATCCAGGTCAGGAGGGCGACAT
AGTTGAAGTTGACCTCGTCTGGAACTTAAAAATTTACTTTTCCTTTATG
ATGATATCGCTGAATTAAATTGGCAACCTCTGACAGATAGTTCAGAGTCT
ATTGAAAAGTTTGAATTTCATGTAAGGGGAGACAAGGGGGCTGAAAAACT
CTTTTTCCATACAGGGAAACTTTTTAGAGAGGGAACGATTGAAAAGAGTA
ACCTTGATTATACTATCCGTTTAGACAATCTTCCGGCTAAGCGTGGAGTT
GAGTTGCATGCCTATTGGCCTCGGACCGATTTTGCTAGCGCTAGGGATCA
GGGATTGAAAGGGAATCGTTTAGAAGAGTTTAATAAGATAGAAGACTCGA
TTGTTAGAGAAAAGATCAGAGTAAACAACTCGTTACTTGGGTCCTCCCT
TCGATCCTTTCCATCTCCTTGTATTGAGTGTCTGCTTCTATTTATTTAT
AGAAGAAAGACCCACTCCTTCAGTCAAATATGCCAAAAATCATCGTCTCTA
TGAACCACCAATGGAATTAGAGCCTATGGTTTATCAGAAGCAGTTCTACT
CGACCTCCTTGGAGGAAGTGAGTCCCTTGGTCAAGGGAGCTGGAAAATTC
ACCTTTGATCAACTTATTCAAGCTACCTTGCTAGATGTAGAGACCGTGG
GAATGTCTCTATCATTTCAGAAGGAGATGCAGTTGGTTTGAGGCTAGTAA
AAGAAGATGGTTTGTCAAGCTTTGAGAAAGACTGCCTAAATCTAGCTTTT
TCAGGTAAAAAGAAGAAACTCTTTCCAATTGTTTGCGGATTACAAGGTA
TCTGATAGTCTTTATCGTAGAGCCAAAGTTTCTGATGAAAAAGCGGATTCA
AGCAAGAGGGCTTTCAACTCAAATCTTCTTTTGAAGAGGTATTGAACCAG
ATGCAAGAAGGAGTGAGAAAACGAGTTCCTTCTGGGGGCTCCCAGATTA
TTATCGTCCTTTAACTGGTGGGGAAAAGGCCTTGCAAGTGGGTATGGGTG
CCTTGACTATCCTGCCCCTATTTATCGGATTTGGTTTGTCTTGTACAGT
TTAGACGTTCATGGCTATCTTTACCTCCCTTTTGCCAATACTTGGTTTTCT
AGGGTTAGTTTTGTCTGTTTTCTATTATTGGAAGCTTCGACTAGATAATC
GTGATGGTGTTCTAAATGAAGCGGGAGCTGAGGTCTACTATCTCTGGACC
AGTTTTGAAAATATGTTGCGTGAGATTGCACGATTGGATCAGGCTGAACT
GGAAAGTATTGTGGTCTGGAATCGCCTCTTGGTCTATGCGACCTTATTTG
GCTATGCGGACAAGGTTAGTCATTTGATGAAGGTTCATCAGATTCAAGTG
GAAAATCCAGATATCAATCTCTATGTAGCTTATGGCTGGCACAGTACGTT
TTATCATTCAACAGCACAAATGAGCCATTATGCTAGTGTCGCAAATACAG
CAAGCACCTACTCTGTATCTTCTGGAAGTGGAAGTTCTGGTGGTGGCTTC
TCTGGAGGCGGAGGTGGCGGCAGTATCGGTGCCTTTTAA 4191.2
(SEQ. ID. NO. 338)
ATGAAAAAAGTAAGAAAGATATTTCAGAAGGCAGTTGCAGGACTGTGCTG
TATATCTCAGTTGACAGCTTTTTCTTCGTAGATTGCTTTAGCAGAAACGC
CTGAAACCAGTCCAGCGATAGGAAAAGTAGTGATTAAGGAGACAGGCGAA
GGAGGAGCGCTTCTAGGAGATGCCGTCTTTGAGTTGAAAAACAATACGGA
TGGCACAACTGTTTCGCAAGGACAGAGGCGCAAACAGGAGAAGCGATAT
TTTCAAACATAAAACCTGGGACATACACCTTGACAGAAGCCCAACCTCCA
GTTGGTTATAAACCCTCTACTAAACAATGGACTGTTGAAGTTGAGAAGAA
TGGTCGGACGACTGTCCAAGGTGAACAGGTAGAAAATCGAGAGAGGCTC
TATCTGACCAGTATCCAAACAGGGCATTTTATCCAGATGTTCAAACACCT
TATCAGATTATTAAGGTAGATGGTTCGGAAAAAAACGGACAGCACAAGGC
GTTGAATCCGAATCCATATGAACGTGTGATTCCAGAAGGTACACTTTCAA
AGAGAATTTATCAAGTGAATAATTTGGATGATAACCATATGAACTTTGAA
TTGACGGTTAGTGGGAAAACAGTGTATGAACAAAAAGATAAGTCTGTGCC
GCTGGATGTCGTTATCTTGCTCGATAACTCAAATAGTATGAGTAACATTC
GAAACAAGAATGCTCGACGTGCGGAAAGAGCTGGTGAGGCGACACGTTCT
CTTATTGATAAATTAACTCTGATTCAGAAAATAGGGTAGCGCTTGAGGCA
TTATGCTTCCACTATCTTTGATGGGACGGAGTTTACAGTAGAAAAGGGG
TAGCAGATAAAAACGGAAAGCGATTGAATGATTCTCTTTTTTGGAATTAT
GATCAGACGAGTTTTACAACCAATACCAAAGATTATAGTTATTTAAAGCT
GACTAATGATAAGAATGACATTGTAGAATTAAAAAATAAGGTACCTACCG
AGGCAGAAGACCATGATGGAAATAGATTGATGTACCAATTCGGTGCCACT

TTTACTCAGAAAGCTTTGATGAAGGCAGATGAGATTTTGACACAACAAGC
GAGACAAAATAGTCAAAAAGTCATTTTCCATATTACGGATGGTGTCCCAA
CTATGTCGTATCCGATTAATTTTAATCATGCTACGTTTGCTCCATCATAT
CAAAATCAACTAAATGCATTTTTTAGTAAATCTCCTAATAAAGATGAGAT
ACTATTAAGTGATTTTATTACGCAAGCAACTAGTGGAGAACATACAATTG
TACGCGGAGATGGGCAAAGTTACCAGATGTTTACAGATAAGACAGTTTAT
GAAAAAGGTGCTCCTGCAGCTTTCCCAGTTAAACCTGAAAAATATTCTGA
AATGAAGGCGGCTGGTTATGCAGTTATAGGCGATCCAATTAATGGTGGAT
ATATTTGGCTTAATTGGAGAGAGAGTATTCTGGCTTATCCGTTTAATTCT
AATACTGCTAAATTACCAATCATGGTGACCCTACAAGATGGTACTATAA
CGGGAATATTGCTCCTGATGGGTATGATGTCTTTACGGTAGGTATTGTA
TTAACGGAGATCCTGGTACGGATGAAGCAACGGCTACTAGTTTTATGCAA
AGTATTTCTAGTAAACCTGAAAACTATACCAATGTTACTGACACGACAAA
AATATTGGAACAGTTGAATCGTTATTTCCACACCATCGTAACTGAAAAGA
AATCAATTGAGAATGGTACGATTACAGATCCGATGGGTGAGTTAATTGAT
TTGCAATTGGGCACAGATGGAAGATTTGATCCAGCAGATTACACTTTAAC
TGCAAACGATGGTAGTCGCTTGGAGAATGGACAAGCTGTAGGTGGTCCAC
AAAATGATGGTGGTTTGTTAAAAAATGCAAAAGTGCTCTATGATACGACT
GAGAAAAGGATTCGTGTAACAGGTCTGTACCTTGGAACGGATGAAAAAGT
TACGTTGACCTACAATGTTCGTTTGAATGATGAGTTTGTAAGCAATAAAT
TTTATGATACCAATGGTCGAACAACCTTACATCCTAAGGAAGTAGAACAG
AACACAGTGCGCGACTTCCCGATTCCTAAGATTCGTGATGTGCGGAAGTA
TCCAGAAATCACAATTTCAAAAGAGAAAAAACTTGGTGACATTGAGTTTA
TAAGGTCAATAAAATGATAAAAAACCACTGAGAGGTGCAGTCTTTAGT
CTTCAAAAACAACATCCGGATTATCCAGATATTTATGGAGCTATTGATCA
AAATGGCACTTATCAAAATGTGAGAACAGGTGAAGATGGTAAGTTGACCT
TTAAAAATCTGTCAGATGGGAAATATCGATTATTTGAAAATTCTGAACCA
GCTGGTTATAAACCCGTTCAAAATAAGCCTATCGTTGCCTTCCAAATAGT
AAATGGAGAAGTCAGAGATGCAGCTTCAATCGTTCCACAAGATATACCAG
CGGGTTACGAGTTTACGAATGATAAGCACTATATTACCAATGAACCTATT
CCTCCAAAGAGAGAATATCCTCGAACTGGTGGTATCGGAATGTTGCCATT
CTATCTGATAGGTTGCATGATGATGGGAGGAGTTCTATTATACACACGGA
AACATCCGTAA 4191.3
(SEQ. ID. NO. 339)
ATGAAATCAATCAACAAATTTTTAACAATGCTTGCTGCCTTATTACTGAC
AGCGAGTAGCCTGTTTTCAGCTGCAACAGTTTTTGCGGCTGGGACGACAA
CAACATCTGTTACCGTTCATAAACTATTGGCAACAGATGGGGATATGGAT
AAAATTGCAAATGAGTTTAGAAACAGGTAACTATGCTGGTAATAAAGTGGG
TGTTCTACCTGCAAATGCAAAAGAAATTGCCGGTGTTATGTTCGTTTGGA
CAAATACTAATAATGAAATTATTGATGAAATGGCCAAACTCTAGGAGTG
AATATTGATCCACAAACATTTAAACTCTCAGGGGCAATGCCGGCAACTGC
AATGAAAAAATTAACAGAAGCTGAAGGAGCTAAATTTAACACGGCAAATT
TACCAGCTGCTAAGTATAAAATTTATGAAATTCACAGTTTATCAACTTAT
GTCGGTGAAGATGGAGCAACCTTAACAGGTTCTAAAGCAGTTCCAATTGA
AATTGAATTACCATTGAACGATGTTGTGGATGCGCATGTGTATCCAAAAA
ATACAGAAGCAAAGCCAAAAATTGATAAAGATTTCAAAGGTAAAGCAAAT
CCAGATACAACCACGTGTAGATAAAGATACACCTGTGAACCACCAAGTTGG
AGATGTTGTAGAGTACGAAATTGTTACAAAAATTCCAGCACTTGCTAATT
ATGCAACAGCAAACTGGAGCGATAGAATGACTGAAGGTTTGGCATTCAAC
AAAGGTACAGTGAAAGTAACTGTTGATGATGTTGCACTTGAAGCAGGTGA
TTATGCTCTAACAGAAGTAGCAACTGGTTTTGATTTGAAAATTAACAGATG
CTGGTTTAGCTAAAGTGAATGACCAAAACGCTGAAAAAACTGTGAAAATC
ACTTATTCGGCAACATTCAATGACAAAGCAATTGTAGAAGTACCAGAATC
TAATGATGTAACATTTAACTATGGTAATAATCCAGATCACGGGAATACTC
CAAAGCCGAATAAGCCAAATGAAAACGGCGATTTGACATTGACCAAGACA
TGGGTTGATGCTACAGGTGCACCAATTCCGGCTGGAGCTGAAGCAACGTT
CGATTTGGTTAATGCTCAGACTGGTAAAGTTGTACAAACTGTAACTTTGA
CAACAGACAAAATACAGTTACTGATTGGATTGGATAAAATACAGAA
TATAAATTCGTTGAACGTAGTATAAAAGGGTATTCAGCAGATTATCAAGA
AATCACTACAGCTGGAGAAATTGCTGTCAAGAACTGGAAAGACGAAAATC
CAAAACCACTTGATCCAACAGAGCCAAAAGTTGTTACATATGGTAAAAAG
TTTGTCAAAGTTAATGATAAAGATAATCGTTTAGCTGGGCAGAATTTGT
AATTGCAAATGCTGATAATGCTGGTCAATATTTAGCACGTAAAGCAGATA
AAGTGAGTCAAGAGAGAAGCAGTTGGTTGTTACAACAAAGGATGCTTTA
GATAGAGCAGTTGCTGCTTATAACGCTCTTACTGCACAACAACAAACTCA
GCAAGAAAAGAGAAAGTTGACAAAGCTCAAGCTGCTTATAATGCTGCTG
TGATTGCTGCCAACAATGCATTTGAATGGGTGGCAGATAAGGACAATGAA
AATGTTGTGAAATTAGTTTCTGATGCACAAAGGTGCTTTGAAATTACAGG
CCTTCTTGCAGGTCATATATTACTTGAAAGAACAAAACAGCCTGCTGGTT
ATGCATTACTAACTAGCCGTCAGAAATTTGAAGTCACTGCAACTTCTTAT
TCAGCGACTGGACAAGGCATTGAGTATACTGCTGGTTCAGGTAAAGATGA
CGCTACAAAAGTAGTCAACAAAAAAATCACTATCCCACAAACGGGTGGTA
TTGGTACAATTATCTTTGCGTAGCGGGGCTGCGATTATGGGTATTGCA
GTGTACGCATATGTTAAAAACAACAAAGATGAGGATCAACTTGCTTAA

TABLE 1-continued 4191.4

(SEQ. ID. NO. 340)
ATGACAATGCAGAAAATGCAGAAAATGATTAGTCGTATCTTCTTTGTTAT
GGCTCTGTGTTTTTCTCTTGTATGGGGTGCACATGCAGTCCAAGCGCAAG
AAGATCACACGTTGGTCTTGCAATTGGAGAACTATCAGGAGGTGGTTAGT
CAATTGCCATCTCGTGATGGTCATCGGTTGCAAGTATGGAAGTTGGATGA
TTCGTATTCCTATGATGATCGGGTGCAAATTGTAAGAGACTTGCATTCGT
GGGATGAGAATAAACTTTCTTCTTTCAAAAAGACTTCGTTTGAGATGACC
TTCCTTGAGAATCAGATTGAAGTATCTCATATTCCAAATGGTCTTTACTA
TGTTCGCTCTATTATCCAGACGGATGCGGTTTCTTATCCAGCTGAATTTC
TTTTTGAAATGACAGATCAAACGGTAGAGCCTTTGGTCATTGTAGCGAAA
AAAACAGATACAATGACAACAAAGGTGAAGCTGATAAAGGTGGATCAAGA
CCACAATCGCTTGGAGGGTGTCGGCTTTAAATTGGTATCAGTAGCAAGAG
ATGTTTCTGAAAAAGAGGTTCCCTTGATTGGAGAATACCGTTACAGTTCT
TCTGGTCAAGTAGGGAGAACTCTCTATACTGATAAAAATGGAGAGATTTT
TGTGACAAATCTTCCTCTTGGGAACTATCGTTTCAAGGAGGTGGAGCCAC
TGGCAGGCTATGCTGTTACGACGCTGGATACGGATGTCCAGCTGGTAGAT
CATCAGCTGGTGACGATTACGGTTGTCAATCAGAAATTACCACGTGGCAA
TGTTGACTTTATGAAGGTGGATGGTCGGACCAATACCTCTCTTCAAGGGG
CAATGTTCAAAGTCATGAAGAAGAAAGCGGACACTATACTCCTGTTCTT
CAAAATGGTAAGGAAGTAGTTGTAACATCAGGGAAAGATGGTCGTTTCCG
AGTGGAAGGTCTAGAGTATGGGACATACTATTTATGGGAGCTCCAAGCTC
CAACTGGTTATGTTCAATTAACATCGCCTGTTTCCTTTACAATCGGGAAA
GATACTCGTAAGGAACTGGTAACAGTGGTTAAAAATAACAAGCGACCACG
GATTGATGTGCCAGATACAGGGGAAGAAACCCTTGTATATCTTGATGCTT
GTTGCCATTTTGTTGTTTGGTAG 4191.5

(SEQ. ID. NO. 341)
ATGAGCCACATATACTTATCTATTTTCACAAGTCTCTTGCTGATGCTAGG
ACTTGTCAATGTTGCTCAAGCCGATGAATATTTACGCATCGGTATGGAAG
CAGCATATGCTCCCTTTAACTGGACCCAGGATGATAGCAACGGAGCT
GTCAAAATCGATGGGACCAATCAGTAGGCCAACGGATACGATGTTCAAAT
CGCCAAGAAAATCGCTAAGGACTTAGGTAAAGAACCTTTGGTTGTTAAAA
CCAAGTGGGAAGGTCTAGTCCCTGCCCTTACTTCTGGTAAGATTGACATG
ATTATCGCAGGTATGAGTCCAACTGCAGAACGCAAACAAGAAATTGCCAT
TTCGAGCAGTTACTATACTAGCGAACCAGTTTTGCTTGTCAAAAAAGATT
CTGCCTACGCAAGTGCTAAATCTTTGGATGACTTTAACGGTGCAAAAATC
ACTTCTCAACAAGGGGTCTACCTTTATAACTTGATTGCACAAATCCCAGG
TGCTAAAAAAGAAACAGCCATGGGAGCTTCACTCAAATGCGACAAGCTC
TTGAGGCTGGTGTCATTGATGCTTATGTTTCTGAACGTCCAGAAGCACTG
ACTGCTGAAGCTGCGAACTCTAAGTTCAAGATGATTCAAGTAGAACCTGG
TTTCAAAACTGGGGAAGAAGATACAGCTATCGCTATCGGGCTTCGTAAAA
ATGACATCGTATTAGCCAAATCAATGCCAGCATTGAAACATTTCAAAA
GATGACCAAGTTGCCTTGATGGATCGTATGATCAAGGAACAACCTGCCGA
AGCTACAACAACTGAAGAGACTAGCAGTAGTTTCTTTAGCCAAGTTGCTA
AAATTCTTTCTGAAAACTGGCAACAACTCTTGCGTGGTGCTGGTATCACT
CTTTTAATCTCTATCGTCGGAACATCATAGGTCTCATTATTGGACTTGC
CATTGGTGTCTTCCGTACTGCTCCTCTCTCTGAAAACAAAGTCATTTACG
GCCTACAAAACTAGTCGGCTGGGTTCTCAATGTCTACATTGAAATTTTC
CGTGGTACGCCAATGATTGTTCAATCGATGGTTATCTACTATGGAACTGC
CCAAGCTTTCGGGATCAACCTTGACCGTACACTGGCTGCTATCTTCATCG
TTTCAATCAATACCGGTGCCTACATGACTGAAATCGTCCGTGGTGGTATC
CTAGCAGTTGACAAGGGACAATTTGAAGCTGCGACTGCTCTTGGTATGAC
CCATAACCAGACCATGCGTAAGATTGTCCTACCTCAGGTAGTCCGTAACA
TCCTACCTGCAACTGGTAATGAATTTGTCATCAATATCAAAGATACATCT
GTATTGAACGTTATCTCTGTGCAACTTTATTTCTCAGGAAATATCTCG
GCAACACAAACCTATCAATACTTCCAGACATTTACAATCATCGCCGTGAT
TTACTTTGTCCTCACCTTCACCGTAACACGTATCCTACGCTTTATCGAGC
GCAGAATGGACATGGATACCTACACTACAGGTGCTAACCAAATGCAAACG
GAGGATTTGAAATAA 4191.6

(SEQ. ID. NO. 342)
ATGACACAAGCAATCCTTGAAATTAAACACCTCAAAAAATCCTATGGACA
AAACGAAGTGCTAAAAGACATTTCACTCACTGTCCACAAGGGAGAAGGTCA
TCTCTATCATCGGAAGCTCTGGAAGCGGAAAATCGACCTTCCTACGCTCC
ATTAACCTACTTGAAACACCAACTGATGGACAAATCCTTTATCATGGACA
AAACGTCCTCGAAAAAGGCTATGACCTCACGCAATACCGTGAAAAGTTGG
GGATGGTTTTCCAATCCTTTAACCTCTTTGAAAATCTCAATGTTCTTGAA
AACACAATCGTCGCTCAGACAACTGTCCTAAAACGCGAACGCACAGAAGC
TGAAAAGATTGCCAAAGAAAACCTGGAAAAGGTCGGCATGGGAGAACGCT
ACTGGCAAGCCAAACCAAAACAACTCTCAGGTGGTCAAAAACAACGTGTG
GCCATCGCTCGTGCCCTCTCCATGAATCCGGACGTATTCTCTTTGATGA
ACCAACATCAGCTCTCGATCCAGAAATGGTTGGAGAAGTCCTCAAAATCA
TGCAGGACCTGGCTCAGGAAGGCTTGACCATGATTGTCGTAACCCATGAA
ATGGAATTTGCCCGTGATGTCTCTCACCGTGTTATCTTTATGGATAAGGG
CGTGATCGCTGAAGAAGGTAAACCAGAAGACCTCTTCACCAATCCTAAAG
AAGACCGAACAAAAGAGTTCCTTCAACGCTATCTCAAATAA 4192.3

(SEQ. ID. NO. 343)
ATGAAAAAGTATCAACTTCTATTCAAAATAAGTGCAGTCTTCTCTTACTT
ATTTTTTCGTATTTAGTCTTTCTCAGCTGACGCTTATCGTCCAAAACTATT
GGCAATTTTCTTCTCAGATAGGCAATTTATTCTGGATTCAAAATATCTTG
AGTTTACTTTTTATTGGAGTCATGATTGTGGTTCTTGTTAAGACAGGCCA
TGGTTATCTCTTCCGCATTCCAAGAAAAAATGGCTTTGGTATTCGATTT
TGACAGTATTAGTGCTAGTGTTCCAGATCTCTTTTAACGTTCAGACAGCT
AACGTTGCTCAACTGCGGAAGGTTGGGCTGTATTGATTGGTTATAG
TGGGACTAACTTTGCAGAGTAGGTATTTATATAGCCCTGTTCTTTCTGG
TTCCACTGATGGAAGAATTGATTATAGAGGATTACTGCAACATGCTTTC
TTTAAGCATTCGCGATTTGGTCTTGATTTGCTTCTTCCTTCTATTTTATT
TGCTCTCCCTCATTTTTCAAGCCTGCCTAGTCTGTTAGATATCTTCGTCT
TTGCAACAGTTGGAATCATCTTTTGCTGGTTTGACCCGCTATACCAAGAG
CATTTATCCATCCTATGCGGTGCATGTGATCAATAATATTGTAGCGACCT
TCCCGTTTTTGCTCACTTTTCTACATAGGGTCTTGGGGTAA 4193.1

(SEQ. ID. NO. 344)
ATGAACAAGAAACAATGGCTAGGTCTTGGCCTAGTTGCAGTGGCAGCAGT
TGGCTTGCTGCATGTGGTGTAACCGCTCTTCTCGTAACGCAGCTTCATCTT
CTGATGTGAAGACAAAAGCAGCAATCGTCACTGATACTGGTGGTTGAA
GACAAATCATTCAACCAATCAGCTTGGGAAGGTTTGCAGGCTTGGGGTAA
AGAACACAATCTTTCAAAAGATAACGGTTTCACTTACTTCCAATCAACAA
GTGAAGCTGACTACGCTAACAACTTGCAACAAGCGGCTGGAAGTTACAAC
CTAATCTTCGGTGTTGGTTTGCCCTTAATAATGCAGTTAAAGATGCAGC
AAAAGAACACACTGACTTGAACTATGTCTTGATTGATGATGTGATTAAAG
ACCAAAAGAATGTTGCGAGCGTAACTTTCGCTGATAATGAGTCAGGTTAC
cTTGCAGGTGTGGCTGCAGCAAAACAACTAAGACAAACAAGTTGGTTT
TGTAGGTGGTTCAGATCTGAAGTTATCTCTCGTTTTGAAGCAGGATTCA
AGGCTGGTGTTGCGTCAGTAGACCCCATCTATCAAAGTCCAAGTTGACTAC
GCTGGTTCATTTGGTGATGCGGCTAAAGGTAAAACAATTGCAGCCGCACA
ATACGCAGCCGGTGCAGATATTGTTTACCAAGTAGCTGGTGGTACAGGTG
CAGGTGTCTTTGCAGAGGCAAATCTCTCAACGAAGCCGTCCTGAAAAT
GAAAAAGTTTGGGTTATCGGTCGTGATCGTGACCAAGAAGCAGAAGGTAA
ATACACTTCTAAAGATGGCAAAGAATCAAACTTTGTTCTTGTATCTACTT
TGAAACAAGTTGGTACAACTGTAAAAGATATTTCTAACAAGGCAGAAAGA
GGAGAATTCCCTGGCGGTCAAGTGATCGTTTACTCATTGAAGGATAAGG
GGTTGACTTGGCAGTAACAAACCTTTCAGAAGAAGGGTAAAAAGCTGTCG
AAGATGCAAAAGCTAAATCCTTGATGGAAGCGTAAAAGTTCCTGAAAAA
TAA 4193.3

(SEQ. ID. NO. 345)
ATGTCTAAAAAATTACAACAAATTTCGGTTCCCTTGATTCTGTATTCCT
AGGAATTTTACTCGGAGCCCATTTGTCATGTGGATCTTCGGTTATGATGCT
ATTTGGGGCTACGAAGAATTGTTCTATACAGCCTTTGGCAGTCTGCGTGG
GATTGGAGAAATCTTCCGTGCTATGGGTCCTCTGGTCTTGATTGGTCTTG
GTTTTGCCGTTGCCAGTCGAGCTGGTTTCTTTAACGTCGGACTTCCTGGT
CAGGCTTTGGCAGGTTGGATTCTCAGTGGTTGGTTTGCCCTGTCGCATCC
AGATATGCCCCGTCCCTTGATGATTCTAGCAACCATCGTGATTGCCTTGA
TTGCTGGTGGATTGTCGGAGCGATTCCAGGTATGCTTAGGGCCTATCTA
GGGACGTCAGAGGTTATTGTAACCATCATGATGAACTACATTGTCTTGTA
TGTAGGGAATGCCTTTATCCATGCTTTCCCTAAAGACTTCATGCAAAGTA
CAGATTCGACCATTCGTGTTGGGGCTAATGCAACCTATACGACTCCTTGA
TTGGCTGAGTTGACTGGTAACTCACGGATGAATATTGGTATTCTTTGC
CATCATTGCCGTTGCAGTTATTGGTTCATGCTCAAGAAAACAACTCTTG
GTTTTGAAATCCGTGCAGTTGGTCTTAATCCACATGCTTCAGAATATGCT
GGTATTTCTGCCAAGCGACATTATCCTATCTATGATTATTTCAGCTGC
CTTGGCAGGTCTTGGTGGAGCTGTTGAAGGTTTGGGAACCTTCCAGAACG
TCTATGTTCAAGGTTCGTCATTAGCTATCGGATTTAACGGAATGGCGGTT
AGTTTGCTTGCGGCCAACTCACCAATTGGTATACTCTTTGCAGCCTTCCT
ATTTGGCTTCTCCAAGTTGGGGCTCCTGGTATGAATGCGGCGCAGGTAC
CATCTGAGCTTGTCAGCATTGTAACAGCGTCTATTATCTCTTTGTCAGT
GTTCATTACCTTATCGAACGCTTTGTCAAACCGAAAAACAAGTTAAAGG
AGGTAAGTAA 4194.1

(SEQ. ID. NO. 346)
ATGGGAGTGAAAAAGAAACTAAAGTTGACTAGTTTGCTAGGACTGTCTCT
GTTAATCATGACACGCCTGTGCAGACTAATGGGGTAACTAGCGATATTACA
CCGAATCGGCTGATTTTTGGAGTAAATTGGTTTACTTCTTTGCGGAAATC
ATTCGCTTTTTATCGTTTGATATTAGTATCGGAGTGGGGATTATTCTCTT
TACGGTCTTGATTCGTACAGTCCTCTTGCCAGTCTTTCAGGTGCAAATGG
TGGCTTCTAGGAAAATGCAGGAAGCTCAGCCACGCATTAAGGCGCTTCGA
GAACAATATCCAGGTCGAGATATGGAAAGCAGAACCAAACTAGAGCAGGA

TABLE 1-continued

AATGCGTAAAGTATTTAAAGAAATGGGTGTCAGACAGTCAGACTCTCTTT
GGCCGATTTTGATTCAGATGCCGGTTATTTTGGCCCTGTTCCAAGCCCTA
TCAAGAGTTGACTTTTTAAAGACAGGTCATTTCTTATGGATTAACCTTGG
TAGTGTGGATACAACCCTTGTTCTTCCGATTTTAGCAGCAGTATTCACCT
TTTTAAGTACTTGGTTGTCCAACAAAGCTTTGTCTGAGCGAAATGGCGCT
ACGACTGCGATGATGTATGGGATTCCAGTCTTGATTTTTATCTTTGCAGT
TTATGCGCCAGGTGGAGTCGCCCTATACTGGACAGTGTCTAATGCTTATC
AAGTCTTGCAAACCTATTTCTTGAATAATCCATTCAAGATTATCGCAGAG
CGCGAGGCCGTAGTACAGGCACAAAAAGATTTGGAAAATAGAAAAGAAA
AGCCAAGAAAAAGGCTCAGAAAACGAAATAA 4194.4

(SEQ. ID. NO. 347)
ATGGTTATCGATCCATTTGCTATCAACGAACTAGACTATTACTTAGTTTC
ACACTTCCACAGTGATCATATCGACCCATACACAGCTGCAGCAATTCTCA
ATAATCCTAAGTTAGAGCATGTTAAGTTTATCGGTCCTTACCACTGTGGA
CGAATCTGGGAAGGATGGGGTGTTCCAAAAGAACGTATCATCGTTGTTAA
ACCAGGTGACACTATCGAATTAAAAGATATGAAGATTCATGCAGTAGAAT
CATTTGACCGTACTTGCTTGGTAACTCTCCCAGTGAACGGTGCTGATGAG
ACAGGCGGTGAACTTGCTGGCTGTTACAGATGAAGAAATGGCCTACA
AAAGGCTGTTAACTATATCTTTGAAACACCAGGTGGAACCATCTATCATG
GTGCAGATTCTCACTTCTCAAACTATTTTGCAAACATGGTAAAGACTTT
AAAATTGATGTTGCTTTGAATAACTATGGTGAAAATCCGGTAGGTATCCA
AGACAAAATGACATCTATCGACCTTCTTCGTATGGCAGAAATCTGCGTA
CCAAAGTCATTATCCCAGTTCACTATGATATCTGGTCTAACTTCATGGCT
TCTACTAATGAGATTCTAGAACTTTGGAAAATGCGAAAAGATCGCTTGCA
ATACGATTTCCATCCATTTATCTGGGAAGTTGGCGGTAAGTACACTTATC
CTCAAGATCAACACTTAGTAGAATACCATCATCCACGTGGTTTTGATGAT
TGTTTTGAACAAGACTCTAACATTCAATTTAAAGCTTTGCTATAA 4196.2

(SEQ. ID. NO. 348)
ATGTTCCTTTCAGGCTGGTTGTCTAGTTTTGCTAATACTTATATCCATGA
TTTACTGGGGGTTCTTTTCCCAGATAGTCCATTTTTAAATGCCTTTGAAA
GTGCTATTGCGGCTCCTTTGGTAGAAGAACCCTTGAATTATTGTCACTT
GTTTTTGTTTTGGCTTTGATTCCTGTGCGAAAATTAAAATCTTTGTTTTT
ACTTGGAATTGCTTCCGGTTTGGGATTCCAAATGATTAAGGATATTGGTT
ATATTCGTACGGATTTGCCAGAGGGCTTTGACTTTACTATTTCGCGAATT
TTAGAGCGTATCATCTCAGGAATTGCCTCTCACTGGACTTTTTCAGGTCT
AGCTGTAGTAGGTGTTTACTTGCTTTACAGAGCCTATAAAGGACAGAAGG
TTGGCAAGAAACAGGGCCTTATTTTTCTAGGTTTAGCCTTGGGAACTCAC
TTCTTGTTTAACTCTCCTTTTGTGGAGTTGGAAACAGAGTTGCCTTTAGC
GATTCCAGTGGTTACGGCTATTGCTCTCTATGGTTTTTATCATGCTTATT
GCTTTGTTGAGAAACACAATGAGTTGATGACCTAG 4197.1

(SEQ. ID. NO. 349)
ATGAAGGTGGAACCACGTTGCGACGTCCTTTCGAGGATGTCGCATTTTTT
TATTAGGATACTAATTATGGAGTTGCAAGAATTAGTGGAGCGCAGTTGGG
CAATCCGACAAGCTTATCACGAACTGGAAGTTAAGCATCATGATTCCAAG
TGGACGGTAGAAGAAGACCTCTTGGCTTTATCTAATGATATTGGAAATTT
CCAACGACTGGTGATGACAAAGCAAGGACGCTACTATGATGAAACACCCT
ACACACTGGAACAAAAACTTTCAGAAAATATCTGGTGGCTATTAGAACTT
TCTCAACGTTTGGATATAGACATTCTGACGGAAATGGAAAACTTCCTCTC
TGATAAAGAAAAGCAATTGAACGTTAGGACTTGGAAGTAG 4197.4

(SEQ. ID. NO. 350)
ATGCTTGATTGGAAACAATTTTTTCTAGCCTATCTGCGCTCCCGTAGTCG
TCTTTTTTATCTATCTGCTTTCTTTGGCATTTCTTGTCTTACTCTTTCAGT
TTTTTATTTGCCAGTCTAGGAATTTACTTCCTCTACTTTTTCTTCTTGTG
TTGCTTTGTAACCATATTATTTTTCACTTGGGACATATTGGTGGAAACC
AGGTCTATCGCCAGGAAGTTCTCTATGGAGAGGGAAGCCAAGTCTCCT
TTGGAAATAGCTTTAGCAGAAAAATTAGAAGCGCGTGAGATGGAACTCTA
TCAGCAGAGGTCAAAAGCAGAAAGAAAACTGACGGATTTGCTGGATTACT
ATACCTTGTGGGTCCATCAGATCAGATAGAGACCCCCATTGCAGCCATCCT
TTAGTTGCAGAAGTGGTCGACCGCCAACTGAAGCAGCAGCTAGAACAGGA
AATTTTCAAAATCGACTCCTATACCAACCTAGTTTTACAGTACCTGCGTT
TAGAAAGTTTCCATGATGATTTGGTCTTAAAGCAGGTTCAAATTGAGGAC
TTGGTCAAGGAAATAATTCGTAAATATGCTCTTTTCTTTTATTCAAAAGG
CTTAAATGTCAATCTACATGACCTTGATAAAGAAATCGTGACGGATAAAA
AGTGGCTGCTAGTGGTTATTGAGCAAATCATCTCAAACAGTCTCAAGTAC
ACCAAGGAAGGTGGTCTGGAGATTTATATGGATGACCAAGAGCTTTGTAT
CAAAGACTGGAAATCGGGAATAAAACAACAGTGATGTCCTCCGAGTATTTG
AACGTGGCTTTTCAGGATACAATGGCCGTTTGACCCGAGTCCTCTGGA
CTTGGCCTTTATCTATCTAAGAAAATTTCTGAAGAACTGGGGCACCAGAT
TCGTATCGAGTCTGAGGTCGGAAAAGGAACGACAGTGCGGATTCAGTTTG
CTCAAGTGAACTTAGTCCTTGAGTAA 4211.2

(SEQ. ID. NO. 351)
ATGGAACTTAATACACACAATGCTGAAATCTTGCTCAGTGCAGCTAATAA
GTCCCACTATCCGCAGGATGAACTGCCAGAGATTGCCCTAGCAGGGCGTT
CAAATGTTGGTAAATCCAGCTTTATCAACACTATGTTGAACCGTAAGAAT
CTCGCCCGTACATCAGGAAAACCTGGTAAAACCCAGCTCCTGAACTTTTT
TAACATTGATGACAAGATGCGCTTTGTGGATGTGCCTGGTTATGGCTATG
CTCGTGTTTCTAAAAAGGAACGTGAAAAGTGGGGGTGCATGATTGAGGAG
TACTTAACGACTCGGGAAAATCTCCGTGCGGTTGTCAGTCTAGTTGACCT
TCGTCATGACCCGTCAGCAGATGATGTGCAGATGTACGAATTTCTCAAGT
ATTATGAGATTCCAGTCATCATTGTGGCGACCAAGGCGGACAAGATTCCT
CGTGGTAAATGGAACAAGCATGAATCAGCAATCAAAAAGAAATTAAACTT
TGACCCGAGTGACGATTTCATCCTCTTTTCATCTGTCAGTAAGGCAGGGA
TGGATGAGGCTTGGGATGCAATCTTAGAAAAATTGTGA 4211.3

(SEQ. ID. NO. 352)
ATGACAAAGAAACAACTTCACTTGGTGATTGTGACAGGGATGAGTGGCGC
AGGGGAAAACTGTAGCCATTCAGTCCTTCGAGGATCTAGGTTATTTCACCA
TTGATAATGCCGCCAGCTCTCTTGCCTAAGTTTTTGCAGCTGGTTGAA
ATTAAGGAAGACAATCCTAAGTTGGCCTTGGTAGTGGATATGCGTAGCCG
TTCTTTCTTTTCAGAGATTCAAGCTGTTTTGGATGAGTTGGAAAATCAAG
ATGGGTTTGGATTTCAAAATCCTCTTTTTGGATGCGGCTGATAAGGAATTC
CTCGCTCGTTACAAGGAAACCAGACGGAGTCACCCACTAGCAGCAGACGG
TCGTATTTTAGATGGAATCAAGTTGGAACGTGAACTCTTGGCACCTTTGA
AAAATATGAGCCAAATGTGGTGGATACGACTGAACTCACTCCACGTGAG
cTGCGCAAAACCCTTGCAGAGCAGTTTTCAGACCAAGAACAAGCCCAGTC
TTTCCGTATCGAAGTCATGTCTTTCGGATTTAAGTATGGAATCCCGATTG
ATGCGGACTTGGTCTTTGATGTCCGTTTCTTGCCAAATCCCTATTATTTA
CCAGAATCTGAGAACCAAACGGGTGTGGATGAACCTGTTTATGATTATGT
CATGAACCATCCTGAGTCAGAAGACTTTTATCAACATTTATTGGCCTTGA
TTGAGCCGATTCTGCCAAGTTACCAAAAGGAAGGTAAGTCCGTTTTGACC
ATTGCCATGGGATGTACGGGTGGACAACCACCGTAGTGTGGCATTTGCTAA
ACGCTTGGCGCAGGACTTATCCAAGAATTGGTCTGTTAATGAAGGGCATC
GCGACAAAGACCGCAGAAAGGAAACGGTAAACCGTTCATGA 4211.4

(SEQ. ID. NO. 353)
ATGAGAAAACCAAAGATAACGGTGATTGGTGGAGGGACTGGAAGTCCCGT
CATTCTAAAAAGTCTGCGGGAAAAAGATGTGGAAATCGCAGCTATCGTGA
CGGTGGCAGATGATGGTGTTCTTCAGGTGAACTCCGAAAAAATATGCA
CAGTTGACACCGCCAGGTGATCTTCGTAATGTCCTTGTGGCCATGTCGGA
TATGCCTAAGTTTTATGAGAAGGTCTTTCAGTATCGGTTCTCTGAGGATG
CCGGAGCCTTTGCTGGCCATCCATTGGGAAATCTCATCATTGCTGGCTTG
TCAGAAATGCAGGGTCAACCTATAATGCCATGCAGTTATTGAGCAAATTT
TTCCATACAACAGGGAAAATTTATCCTTCCAGTGACCATCCTTTGACCCT
TCATGCAGTCTTTCAGGATGGGACAGAAGTGGCTGGAGAGAGTCATATTG
TAGACCATCGAGGCATAATTGACAATGTCTATGTGACCAATGCCCTAAAC
GATGATACGCCTCTGGCCAGCCGTCGAGTAGTGCAGACCATCCTTGAAAG
TGACATGATTGTCCTAGGGCCAGGTTCCCTCTTTTACCTCTATTTTGCCCA
ATATCGTGATTAAGGAAATTGGGCGGCTCTTTTGGAAACCAAGGCAGAA
ATTGCCTATGTCTGCAATATCATGACCCAACGTGGGGAGACGGAACACTT
TACAGATAGCGACCACGTGGAAGTCTTGCATCGTCACCTTGGTCGCCCTT
TTATCGACACTGTCTTGGTGAATATTGAAAAAGTGCCTCAGGAATACATG
AATTCCAACGTTTTGATGAATACTTAGTGCAAGTGGAACACGATTTTGT
AGGTCTTTGTAAGCAAGTTTCGCGCGTGATTTCATCTAACTTCCTTCGTC
TGGAAAATGGCGGTGCCTTCCACGATGGAGATTTGATTGTGGACGAGTTG
ATGCGCATTATACAGGTGAAAAAATGA 4213.1

(SEQ. ID. NO. 354)
ATGAAAAATTTGATAAAGTTGCTAATAATTAGATTGATTGTTAACTTAGC
AGACAGTGTATTTATATAGTAGCATTGTGGCACGTTAGCAATAATTATT
CTTCGAGCATGTTCTTAGGAATATTTATTGCAGTAAATTATCTACCGGAT
TTGTTACTAATCTTTTTTGGACCAGTTATTGACAGAGTAAATCCGCAAAA
AATTCTTATAATTCAATTTTGGTTCAATTAGCAGTGGCTGTAATATTTT
TATTATTATTAAACAAATATCATTTTGGGTGATAATGAGTCTAGTGTTT
ATTTCAGTAATGGCTAGCTCCATAAGTTACGTGATAGAAGATGTGTTGAT
TCCTCAAGTGGTAGAATATGATAAGATTGTATTTGCAAATTCTCTTTTTA
GTATTTCTAAAAGTATTAGATTCTATTTTTAATTCATTCGCATCATTT
TTACAGGTGGCAGTAGGATTTATTTTATTGGTTAAGATAGATATAGGCAT
ATTTTTACTTGCTCTATTTATATTGTTGTTAAAATTTAGAACTAGCA
ATGCGAATATAGAAACTTCTCTTTCAAATATTACAAGAGAAGTGTTG
CAAGGTACAAGTTTATTTTAAATAATAATTATTTAAAACGTAT
TTCTTTAACGCTTATAAACTTTTTTATTCATTTCAGACAGTAGTTGTACC
GATTTTTCTATTCGATATTTTGATGGTCCGATTTTTTATGGTATTTTT
TAACTATTGCTGGTTTGGGTGGTATATTGGGAAATATGCTAGCGCAATC
GTAATAAAAATATTTAAAATCGAATCAAATTGTTGGTGTATTTCTTTTTTT
GAACGGCTCAAGTTGGTTAGTAGCAATTCTTATAAAAGACTATACTTTAT

TABLE 1-continued

CACTTATTTTATTTTTCGTTTGTTTTATGTCTAAAGGAGTCTTCAATATT
ATTTTTAATTCGTTGTACCAACAAATACCTCCACATCAACTTCTTGGTAG
GGTAAATACTACCATTGATTCTATTATTTCTTTTGGAATGCCAATTGGTA
GTTTAGTTTGCAGGAACGCTTATTGATTTGAATATTGAATTAGTGTTAAT
TGCTATTAGCATACCTTATTTTTTGTTTTCTTATATTTTTTATACGGATA
ATGGATTGAAAGAATTTAGTATATATTAG 4213.2
(SEQ. ID. NO. 355)
ATGATGTCTAACAAAAATAAGGAAATTCTGATTTTTGCGATTCTCTATAC
AGTCCTCTTTATGTTTGATGGCGTTAAATTGCTGGCTTCTTTAATGCCAT
CTGCCATTGCAAATTATCTTGTTTATGTAGTTTTAGCTCTATATGGCTCC
TTCTTGTTCAAGGATAGATTGATCCAACAATGGAAGGAGATTAGAAAGAC
TAAAAGAAAATTCTCTTTGGAGTCTTAACAGGATGGCTCTTTCTCATTC
TGATGACTGTTGTCTTTGAATTTGTATCAGAGATGTTGAAGCAGTTTGTG
GGACTAGATGGACAAGGTCTAAATCAGTCTAATATTCAAAGTACCTTTCA
AGAACAACCACTACTGATAGCTGTTTTTGCTTGTGTCATTGGACCTCTGG
TAGAAGAATTATTTTTCCGTCAGGTCTTATTGCATTACTTGCAGGAACGG
TTGTCAGGTTTACTAAGCATTATTCTGGTAGGACTTGTTTTTGCTCTGAC
TCATATGCACAGTTTGGCTCTATCAGAGTGGATTGGTGCAGTTGTTACT
TAGGTGGAGGCCTTGCCTTTTCTATTATTTATGTGAAAGAAAAAGAGAAT
ATCTACTATCCCTACTTGTTCACATGTTAAGCAACAGCCTCTCCTTAAT
CATTTTAGCTATCAGTATAGTAAAATGA 4224.1
(SEQ. ID. NO. 356)
TTGAAAAAGCCAATTATCGAATTCAAAAACGTCTCTAAAGTTTTTGAAGA
CAGCAACACCAAGGTTCTCAAAGACATCAACTTTGAGTTGGAAGAAGGGA
AATTCTACACCCTTCTAGGTGCATCTGGTTCGGGGAAATCAACTATCCTA
AACATTATTGCAGGTTTACTGGATGCGACGACAGGAGATATCATGCTAGA
CGGTGTTCGTATCAATGATATTCCAACCAACAAGCGCGACGTACATACCG
TCTTCCAATCCTATGCCTTGTTCCCACATATGAATGTGTTTGAAAATGTT
GCCTTTCCACTTCGCTTGCGTAAAATTGATAAGAAAGAAATCGAGCAGCG
TGTAGCGGAAGTTCTCAAGATGGTTCAGTTGGAAGGTTATGAAAAGCGTT
CCATCCGCAAACTTTCTGGAGGACAACGTCAGCGTGTGGCCATCGCCCGT
GCTATCATCAACCAACCCCGTGTGGTCTTGTTGGACGAGCCTTTATCAGC
GCTGGACTTGAAATTGAGAACAGACATGCAGTAAGACGAATTGCGTGAATTAC
AACAACGATTGGGCATTACCTTTGTCTTTGTCACTCACGATCAGGAAGAA
GCTCTTGCCATGAGTGACTGGATTTTCGTTATGAATGATGGCGAGATTGT
CCAGTCTGGAACCCCTGTGGACATCTACGATGAGCCAATCAACCACTTTG
TTGCCACCTTTATCGGGAGTCAAACATCTTGCCAGGTACCATGATTGAG
GACTACTTGGTCGAATTAACGGCAAACGCTTTGAAGCGGTTGATGGTGG
GATGAAGCCAAATGAACCTGTTGAGGTCGTTATTCGTCCAGAGGACTTGC
GCATTACCCTTCCTGAAGAGGCAAGCTCCAAGTTAAGGTCGATACCCAG
CTTTTCCGTGGAGTTCATTATGAAATTATCGCTATGACGAACTTGGAAA
TGAATGGATGATCCACTCAACCCGTAAGGCTATCGTGGGTGAGGAAATCG
GTCTGGACTTTGAACCAGAAGACATCCACATCATGCGTCTCAATGAAACC
GAAGAAGAGTTCGATGCTCGTATTGAGGAGTACGTAGAAATCGAAGAGCA
AGAAGCAGGTTTGATCAATGCAATCGAGGAGGAAAGAGATGAAGAAAACA
AGCTCTAA 4252.1
(SEQ. ID. NO. 357)
ATGAAATCAATGAGAATCTTATTTTTGTTAGCTTTAATTCAAATCAGTTT
GAGTAGCTGTTTCCTATGGAAGGAATGCATCTTGTCCTTTAAACAAAGTA
CAGCTTTTTTCATCGGAAGCATGGTTTTCGTTTCAGGAATCTGTGCTGGA
GTAAATTATCTTTATACCCGTAAGCAAGAAGTCCATAGTGTCCTAGCCAG
TAAGAAGTCGGTGAAGCTTTTTTACAGTATGTTACTCTTAACTTAATTTGT
TAGGAGCTGTTCTTGTTTTGTCAGATAACTTGTTCATCAAAAATACGCTG
CAGCAAGAATTAGTTGACTTTTTATTGCCATCCTTCTTTTTCCTATTTGG
GCTAGATTTGCTGATTTTTTACCCTTGAAAAATACGTGCGCGATTTTC
TTGCTATGCTGGACAGAAAAAGACAGTGTTGGTGACTATTTTAGCACAA
CTTCTTTTCTTAAGAAATCCAATGACCATTGTCTCACTTCTGATTTATAT
TGGACTGGGCTTGTTTTTGCAGCCTATCTTGTCCCAAATTCGGTTAAGA
AGGAAGTTTCCTTTTTATGGTCATATTTTCCGAGATCTTGTATTGGTCAT
TGTTACGCTCATTTTCTTTTAG 4252.2
(SEQ. ID. NO. 358)
ATGGTTAAAAAAATTATTGGAATGGTGCTAGCTTTATTTTTCTGTAACTGT
AGTAGGAGTAGGTGTTTTTGCTTATACTATTTATCAACAAGGGACAGAAA
CCTTAGCTAAAACCTATAAAAAAATCGGTGAAGAAACCAAGGTTATTGAA
GCGACTGAACCTCTAACCATTCTGTTAATGGGAGTGGACACCGGAAATGT
CAGTAGAATCCTAAAACGAAAAAAACAACAATGATGAGTTTAGACGGGAT
ATTCGACGCGCATTGAATCAGGGAATGGTCAGGCTCATGAAGCGAAACTG
AACTCAGCATATGCAGATGGTGGAGCAGAGCTTGCTATAGAAACCATTCA
AAAAATGATGAATATCCATATTGATCGCTATGTGATGGTCAATATGGAG
GATTGCAAAAACTAGTGGATGCAGTAGGAGGTATTACAGTCAATAATATC 4256.2
(SEQ. ID. NO. 359)
ATGAAAAAACAAGCCTATGTCATTATTGCTCTCACCTCCTTCCTATTTGT
CTTTTTTTTCTCCCACAGCTTGCTGGAAATACTTGATTTTGACTGGTCTA
TCTTTTTGCACGATGTCGAAAAAACAGAAAAATTTGTCTTTTTATTGTTG
GTTTTCAGCATGTCCATGACCTGTCTCTTAGCCCTGTTTTGGCGAGGGAT
CGAAGAGCTTTCTCTAAGAAAAATGCAGGCTAATCTCAAGCGTTTATTAG
CAGGGCAAGAGGTGGTTCAGGTTGCAGATCCAGATTTGGATGCCAGTTTC
AAGTCCTTATCAGGTAAACTTAACCTTTTGACAGAGGTCTTCAAAAAGC
TGAAAATCAGAGCCTTGCTCAGGAAGAGGAAATCATCGAGAAGGAACGGA
AGCGAATTGCTCGGGATTTGCACGATACAGTCAGTCAGGAGTTGTTTGCG
GCCCACATGATTTTATCGGGTATCAGTCAGCAGGCTTTGAAATTGATAGA
GAAAAGATGCAGACCCAGTTGCAGAGTGTCACAGCTATTTTAGAAACAGC
CCAGAAGGATTTGCGGGTTTTGCTCTTGCATTTGCGACCAGTTGAACTGG
AGCAGAAGAGCTTGATAGAAGGGATTCAAATTCTTTTAAAAGAGCTTGAG
GACAAGAGTGATCTTAGGGTTAGTCTCAAGCAGAATATGACGAAATTGCC
TAAGAAATCTGAGGAGCATATCTTCCGTATCCTGCAAGAGTTGATTAGCA
ATACCCTCCGCCATGCCCAGGCATCCTTGCCTAGATGTCTACCTCTATCAG
ACAGATGTTGAATTGCAACTGAAGGTGGTGGACAATGGGATTGGTTTCCA
GTTAGGGAGCTTAGACGACTTGAGTTATGGACTGCAAATATCAAGGAGC
GGGTTGAAGATATGGCTGGAACAGTTCAACTCTTGACAGCTCCCAAGCAA
GGGCTGGCGGTTGATATCCGTATTCCCCTGTTAGATAAGGAATGA 4263.1
(SEQ. ID. NO. 360)
ATGATTGTTTCCATTATTTCTCAAGGATTTGTCTGGGCTATTCTAGGTCT
GGGAATCTTTATGACATTTAGGATTTTAAACTTTCCAGATATGACGACAG
AAGGTTCCTTCCCTCTTGGGGGAGCTGTTGCTGTCACTTTGATAACCAAA
GGCGTGAACCCATTTTTAGCGACACTTGTTGCTGTAGGAGCAGGTTGTTT
GGCTGGAATGCGAGCAGGCCTTCTTTATACAAAAGGGAAGATCCCAACCT
TGCTCTCAGGGATTTTGGTGATGACTTCTTGTCACTCAATCATGCTCTTG
ATTATGGGACGTGCGAATTTAGGCCTGCTGGAACCAAGCAAATTCAGGAT
GTTTGCTTTTGATTCGGATTTGAATCAACTCTTGACAGGTCTCATCTTT
GTGAGTATTGTTATTGCTCTCATGCTCTTTTTCTTGGACACTAAACTCGG
ACAAGCCTATATTGCTACAGGGGATAATCCTGATATGGCTAGAAGTTTCG
GGATTCATACTGGACGCATGGAGCTCATGGGCTTGGTCTTATCAAATGGT
GTGATTGCCCTTGCAGGTGCCCTCATTGCTCAGCAAGAAGGGTTATGCCGAA
TGTGTCTCGAGGGATCGGGGTTATCGTTGTGGGGCTTGCAAGTTTGATTA
TTGGAGAAGTTATTTTCAAGAGTTTGAGCTTGGCAGAGCGTTTGGTTACT
ATCGTTGTAGGTTCTATCGCTTATCAATTTTTAGTGTGGGCAGTTATCGC
ACTTGGCTTTAATACAAGTTACCTTCGTTTATACAGTGCCTTGATTTTAG
CAGTCTGCCTCATGATTCCAACATTTAAGCAAACAATCTTGAAAGGAGCC
AAGTTAAGCAAATGA 4346.1
(SEQ. ID. NO. 361)
ATGAAAAAAATGAAAGTTTGGTCTACTGTACTTGCAACGGGAGTTGCTCT
TACTACACTTGCTGCTTGCTCTGGAGGTTCAAATTCTACGACTGCTTCTT
CATCTGAAGAAAAGCTGATAAAAGTCAAGAATTAGTTATCTATTCGAAC
TCAGTCTCAAATGGCTGTGATGATTGGTTAACTGCTAAAGCAAAAGAAGG
TGGTTTTAATATAAAAATGGTTGATATCGCTGGCGCTCAATTAGCAGACC
GTGTTATTGCTGAGAAGAATAATGCAGTTGCAGATATGTATTTGGAATT
GGTGCTGTTGATTCAAATAAAAATTAGAGATCAAAAATTACTAGTACAGTA
CAAGCCTAAATGGTTAGATAAAAATTGATCAATCTTTATCAGATAAAGATA
ATTATTATAATCCTGTGATTGTTCAACCATTAGTTTTAATTGGGGCGCCT
GATGTAAAAGAAATGCCTAAAGATTGGACTGAATTAGGTAGTAAGTATAA
AGGTAAATATTCAATTTCTGGTCTTCAAGGAGGTACAGGACGGGCAATTC
TAGCAAGTATCTTAGTTCGATACCTTGATGATAAAGGTGAATTAGGTGTT
TCCGAAAAAGGTTGGGAAGTAGCAAAAGAATATTTGAAAAATGCATACAC
TCTTCAAAAGGGAGAAAGTTCAATTGTTAAGATGTTAGACAAAGAAGATC
CAATACAATATGGAATGATGTGGGGTTCTGGTCATTAGTTGGACAAAAA
GAACAAAATGTTGTTTTCAAAGTTATGACTCCTGAGATTGGTGTACCATT
TGTAACTGAACAAACTATGGTTTTAAGCACTAGTAAAAACAAGCGTTAG
CTAAAGAATTTATTGATTGGTTTGGTCAATCAGAAATTCAAGTAGAATAT
AGTAAGAACTTTGGATCTATTCCTGCAAATAAAGATGCCCTCAAAGATCT
ACCTGAAGATACGAAGAAATTTGTTGATCAAGTGAAACCACAAAATATTG

TABLE 1-continued

```
ACTGGGAAGCTGTTGGAAAGCATTTGGATGAATGGGTAGAAAAAGCTGAA
TTAGAATACGTACAATAA 4346.2
                                       (SEQ. ID. NO. 362)
ATGATTAAATTTGATAATATTCAAATTAAATATGGTGATTTTGTTGCAAT
TGATAATCTGAATTTAGATATACATGAAGGGGAATTTTTTACATTTCTTG
GGCCTTCAGGATGTGGTAAATCAACTACTTTGAGAGCATTGGTAGGTTTT
CTAGATCCATCATCAGGAAGTATTGAAGTTAATGAACAGATGTCACTCA
TTTGGAACCTGAAAAGCGTGGAATTGGTATTGTATTTCAATCTTATGCGC
TATTTCCAACTATGACTGTTTTTGATAATATTGCATTTGGTTTAAAGTTA
AGAAGGTAGCTCCAGATGTTATTAAAGCTAAAGTATCAGCAGTGGCAGCA
AAAATTAAGATCTCTGATCAACAGTTACAGCGTAATGTATCAGAATTATC
TGGGGGTCAACAACAAAGGGTAGCATTGGCTCGTGCTCTGGTTCTTGAAC
CTAAAATTCTTTGTCTAGATGAACCATTGTCAAACCTTGACGCAAAATTA
CGTGTAGATTTGAGAAAAGAGTTGAAAAGACTTCAAAAAGAGTTAGGTAT
TACTACTTTATATGTTACTCATGATCAAGAGGAAGCCTTGACTTTATCTG
ATAGAATTGCAGTCTTTAACAATGGATACATCGAACAGGTCGGTACACCA
GTAGAGATTTATCATAATTCTCAAACTGAATTTGTATGTGATTTTATTGG
AGATATTAATGTTTTGACCGATGAACAGTCCACGAAGTATTATTGAGA
ATACAAGCGTTTTCTTGAGGATAAAAAGGATACATTCGATTAGAGAAA
GTTCGATTCAATCGTGAAACTGAACAAGATTTTATTCTAAAAGGGACAAT
TATTGATGTTGAGTTTTCTGGAGTTACAATTCACTATACAATAAAAGTTT
CTGAAAGTCAGATTCTTAATGTAACAAGTATTGATAGTCAGGCTGCTATT
AGATCTGTCGGAGAAAGTGTGGAATTATTTATCACACCATCAGACGTTCT
GCAATTTTAA 4346.3
                                       (SEQ. ID. NO. 363)
ATGCGTCATAAAATTAAATTTAAAAGATTGGCTTATTCGTTTAGGGTTAAT
CTGGTTCTTAGTAACATTTATTATTTATCCAAACTTTGATCTAGTAGTGA
ATGTATTTGTAAAAGGAGGAGAATTTTCCCTTGATGCTGTACATCGTGTT
CTAAAATCTCAGAGGGCACTTCAGATGTATTATGAACAGTTTTAAGTTAGC
ATTTTCACTCATTATTACAGTTAATGTCGTAGGTATTCTTTGTGTTCTAT
TTACAGAGTACTTTGATATTAAAGGTGCTAAAATTTTAAAATTAGGTTAT
TGTCTATGGTCCTTATGGATTGATTACAAAATTTTTACAAAATGTTATCC
CTTCTTTAGACCCTAACTGGTTTATTGGGTATGGTGCAGTCTTATTCATT
ATGACATTTTCAGGAACTGCTAATACACATTGTTTTTAACAAATACAAT
TCGAAGCGTTGACTATCACACTATTGAGGCTGCTCGAAATATGGGAGCAA
AACCATTTCAGTTTTTTCCAAAAGTAGTGTTACCAACCTTAATTCCAACT
CTATTTGCACTTACATATATGGTTTTTTCTTAGTGGTTTATCTGCAGTAGC
AGCACCCATGATTGTTGGTGGTAAAGAATTTCAAACTATAAATCCAATGA
TTATTACATTTGCAGGGATGGGGAATTCTCGTGATTTAGCTGCCCTACTT
GCAATATTTAGGTATTGCAACTACAATTTTGCTTACTATCATGAATAA
GATAGAAAAGGTGGAATTATATTTCTATCTAAGACTAAAGCGCCTC
TTAAAAAACAAAAATTGCGTCTAAGCCTTGGAATACATTGCTCACATT
GTAGCATATGGATTGTTCACAGTTTTCATGCTTCCACTAATTTTTATAGT
ATTATACTCATTTACAGATCCAGTTGCAATTGAACAGGTAACTTAACAT
TATCAAACTTTACTTTAGAAAATTATCGCTCTTATTCTTTAGTAATAGTGCG
GCATTCTCTCCATTCTTGGTCAGCTTTATTATTCTTATTATTGCTGCGAC
AACAGCAACAATTCTCGCAGTTGTATTTGCTCGTGTTGTCAGAAAACATA
AATCTCGTTTTGATTCTTATTTGAATATGGTGCTCTACTTCCTTGGTTA
CTACCAAGTACACTTTGACTGCAGTAAGTTTATTATTTACTTTTAATCAGCC
ACAATTTCTTGCTTGAATCAGATTTTGGTAGGTAGTTTGGTAATTCTAC
TTATTGCATATATAGTTGTAAAAATCCCATTTCTTATAGAATGGTACGT
GCTATTTTATTTAGTGTTGATGATGAGATGGAAGATGCAGCAAGAAGTAT
GGGTGCTTCACCTTTTTATACTATGATGAAGGTTATCATTCCATTTATTT
TACCGGTTGTTCTCTCGTTATTGCTTTAAACTTTAACTCTTTATTAACT
GACTTCGACTTATCTCATTCCTTTACCATCCCCTAGCTCAACCATTAGG
TATTACGATTCGATCTGCAGGTGATGAAACAGCAACATCTAATGCACAAG
CTCTGGTATTGTTTATACAATTGTTCTGATGATTATTTCTGGAACGGTA
TTATACTTCACACAAAGACCGGGCGTAAAGTAAGGAAATAA
```

TABLE 2

```
                                       (SEQ ID. NO. 1)
MEELVTLDCLFIDRTKIEANANKYSFVWKKTTEKFSAKLQEQIQVYFQEE
ITPLLIKYAMFDKKQKRGYKESAKNLANWHYNDKEDSYTHPDGWYYRFHH
TKYQKTQTDFQQEIKVYYADEPESAPQKGLYMNERYQNLKAKECQALLSP
QGRQIFAQRKIDVEPVFGQIKASLGYKRCNLRGKRQVRIDMGLVLMANNL
LKYSKMKZ (SEQ ID. NO. 2)
MGKGHWNRKRVYSIRKFAVGACSVMIGTCAVLLGGNIAGESVVYADETLI
THTAEKPKEEKMIVEEKADKALETKNIVERTEQSEPSSTEAIASEKKEDS
```

TABLE 2-continued

```
AVTPKEEKVSAKPEEKAPRIESQASNQEKPLKEDAKAVTNEEVNQMIEDR
KVDFNQNWYFKLNANSKEAKPDADVSTWKKLDLPYDWSIFNDFDHESPAQ
NEGGQLNGGEAWYRKTFKLDEICDLKKNVRLTFDGVYMDSQVYVNGGQLVG
HYPNGYNQPFSYDITKYLQKDGRENVIAVHAVNKQPSSRWYSGSGIYRDVT
LQVTDKVHVEKNGTTILTPKLEEQQHGKVETHVTSKIVNTDDKDHELVAE
YQIVERGGHAVTGLVRTASRTLKAHESTSLDAILEVERPKLWTVLNDKPA
LYELITRVYRDGQLVDAKKDLFGYRYYHWTPNEGFSLNGERIKFHGVSLH
HDHGALGAEENYKAEYRRLKQMKEMGVNSIRTTHNPASEQTLQIAAELGL
LVQEEAFDTWYGGKKPYDYGRFFEKDATHPEARKGEKWSDFDLRTMVERG
KNNPAIFMWSIGNEIGEANGDAHSLATVKRLVKVIKDVDKTRYVTMGADK
FRFGNGSGGHEKIADELDAVGFNYSEDNYKALRAKHPKWLIYGSETSSAT
RTRGSYYRPERELKHSNGPERNYEQSDYGNDRVGWGKTATASWTFDRDNA
GYAGQRWTGTDYIGEPTPWHNQNQTPVKSSYFGIVDTAGIPKHDFYLYQS
QWVSVKKKPMVHLLPHWNWENKELASKVADSEGKIPVRAYSNASSVELFL
NGKSLGLKTFNKKQTSDORTYQEGANANELYLEWKVAYQPGTLEAIARDE
SGKEIARDKITTAGKPAAVRLIKEDHAIAADGKDLTYIYYEIVDSQGNVV
PTANNLVRPQLHGQGQLVQVDNGEQASRERYKAQADGSWIRKAFNGKGVA
IVKSTEQAGKFTLTAHSDLLKSNQVTVFTGKKEGQEKTVLGTEVPKVQTI
IGEAPEMPTTVPFVYSDGSRAERPVTWSSVDVSKPGIVTVKGMADGREVE
ARVEVIALKSELPVVKRIAPNTDLNSVDKSVSYVLIDGSVEEYEVDKWEI
AEEDKAKLAIPGSRIQATGYLEGQPIHATLVVEEGNPAAPAVPTVTVGGE
AVTGLTSQKPMQYPXLAYGAKLPEVTASAKNAAVTVLQASAANGMRASII
IQPKDGGPLQTYAIQFLEEAPKIAHLSLQVEKADSLKEDQTVKLSVRAHY
QDGTQAVLPADKVTFSTSGEGEVAIRKGMLELHKPGAVTLNAEYEGAKDQ
VELTIQANTEKKIAQSIRPVNVVTDLHQEPSLPATVTVEYDKGFPKTHKV
TWQAIPKEKLDSYQTFEVLGKVEGIDLEARAKVSVEGIVSVEEVSVTTPI
AEAPQLPESVRTYDSNGHVSSAKVAWDAIRPEQYAKEGVVVNGRLEGTQL
TTKLHVRVSAQTEQGANISDQWTGSELPLAFASDSNPSDPVSNVNDKLIS
YNNQPANRWTNWNRTNPEASVGVLFGDSGILSKRSVDNLSVGFHEDHGVG
VPKSYVIEYYVGKTVPTAPKNPSFVGNEDHVFNDSANWKPVTNLKAPAQL
KAGEMNHFSPDKVETYAVRIRMVKADNKRGTSITEVQIFAKQVAAAKQGQ
TRIQVDGKDLANFNPDLTDYYLESVDGKVPAVTASVSNNGLATVVPSVRE
GEPVRVLAKAENGDILGEYRLHFTKDKSLLSHKPVAAVKQARLLQVGQAL
ELPTKVPVYFTGKDGYETKDLTVEWEEVPAENLTKAGQFTVRGRVLGSNN
VAEITRVTDKLGETLSDNPYDENSNQAFASATNDIDKNSHDRVDYLND
GDHSENRRWTNWSPTPSSNPEVSAGVIFRENGKIVERTVTQGKVQFFADS
GTDAPSKLVLERYVGPEFEVPTYYSNYQAYDADHPFNNPENWEAVPYRAD
KDIAAGDEINVTFKAIKAKAMRWRMERKADKSGVAMIEMTFLAPSELPQE
STQSKILVDGKELADFAENRQDYQITYKGQRPKVSVEENNQVASTVVOSG
EDSFPVLVRLVSESGKQVKEYRIHLTKEKPVSEKTVAAVQEDLPKIEFVE
KDLAYKTVEKKDSTLYLGETRVEQEGKVGKERIEFAINPDGSKEEKLREV
VEVPTDRIVLVGTKPVAQEAKKPQVSEKADTKPIDSSEASQTNKAQLPST
GSAASQAAVAAGLTLLGLSAGLVVTKGKKEDZ (SEQ. ID. NO. 3)
MKIMKXKYWTLAILFFCLFNNSVTAQEIPKNLDGNITHTQTSESFSESDE
KQVDYSNKNQEEVDQNKFRIQIDKTELPVTTDKHLEKNCCKLELEPQINN
DIVNSESNNLLGEDNLDNKIKENVSHLDNRGGNIEHDKDNLESSIVRXYE
WDIDKVTGGGESYKLYSKSNSKVSIAILDSGVDLQNTGLLKNLSNMSKNV
VPNKGYLGKEEGEEGIISDIQDRLGHGTAVVAQIVGDDNINGVNPHVNIN
VYRIFGKSSASPDWIVKAWDAVDDGNDHNLSTGQYLMIDGEYEDGTNDFE
TFLKYKKAIDYANQKGVIIVAALGNDSLNVSNQSDLLKISSRIZKVRKP
GLVVDVPSYFSSTISVGGIDRIGNLSDFSNKGDSDAIYAPAGSTLSLSEL
GLNNFINAEKYKEDWIFSATLGGYTYLYGNSFAAPKVSGAIAMIIDKYKL
KDQPYNYMFVKKFWKKHYQZ (SEQ. ID. NO. 4)
MKKTWKVFLTLVTALVAVVLVACGQGTASKDNKEAELKXVDFILDWTPNT
NHTGLYVAKEKGYFKEAGVDVDLKLPPEESSSDLVINGKAPFAVYFQDYM
AKKLEKGAGITAVAAIVEHNTSGILSRKSDNVSSPKDLVGKKYGTWNDPT
ELAMLKTLVESQGGDFEKVEKVPNNDSNSITPIANGVFDTAWIYYGWDGI
LAKSQGVDKFMYLKDYVKEFDYYSPVIIANNDYLKDNKEEARKVIQAIK
KGYQYAMEHPEEAADILIKNAPELKEKRDFVIESQKYLSKEYASDKEKWG
QFDAARWNAFYKWDKENGILKEDLTDKGFTNEFVKZ (SEQ. ID. NO. 5)
MKRTWRNSFVTNLNTPFMIGNIEJPNRTVLAPMAOVTNSAFRTIAKELGA
GLVVMEMVSDKGIQYNNEKTLHMLHIDEGENPVSIQLFGSDEDSLARAAE
FIQENTKTDIVDINMGCPVNKIVKNEAGAMWLKDPDKIYSIINIVQSVLD
IPLTVKIMRTGWADPSLAVENALAAEAAGVSALAMHGRTREQMYTGHADL
ETLYKVAQALTICIPFIANGDIRTVQEAKQRIEEVGADAVMIGRAAMGNP
YLFNQINHYFETGEILPDLTFEDKMKIAYEHLKRLINLKGENVAVRERGL
APHYLRGTSGTSGAAKLRGAISQASTLAEIETLLQLEKAZ (SEQ. ID. NO. 6)
MIKNPKLLTKSFLRSFAILGGVGLVIHIAIYLTPPFYYIQLEGEKFNESA
RVFTEYLKTKTSDEIPSLLQSYSKSLTISAHLKRDIVDKRLPLVHDLDIK
DGKLSNYIVMLDMSVSTADGKQVTVQFVHGVDVYKEAKNILLLYLPYTFL
VTIAPSFVFSYFYTKRLLNPLFYISEVTSKMQDLDDNIRFDERJCDEVGE
```

TABLE 2-continued

VGKQINGMYEELLKVIYELESRNEQIVKLQNQKVSFVRGASHELKTPLAS
LRMLENMQHNIGDYKDHPKYIAKSINKIDQMSHLLEEvLESSKFQEWTEC
RETTVKPVLVDILSRYQELAHSIGVTIENQLTDATRVVMSLRALDKVLTN
LISNAIKYSDKNGRVHSEQDGYLSIKNTCAPLSDQELEHLFDFYHSQIVT
DKDESSGLGLY1VNNILESYQMDYSFLPYEHGMEFKISLZ (SEQ. ID. NO. 7)
MYLGDLMEKAECGQFSILLQESQTTVKAVMEETGFSKATLTKYVTLLNDK
ALDSGLELAIHSEDENLRLSIGAATKGRDIRSLFLESAVKYQILVYLLYH
QQFLAHQLAQELVISEATLGRHLAGLNQILSEFDLSIQNGRWRGPEHQIH
YFYFCLFKVWSSQEWEGHMQKPERKQEIANLEEICGASLSAGQKLDVLLW
AHISQQRLRVNACQFQVIEEKMRCYPDNIFYLRLLRKVPSFFAGQHIPLG
VEDGEMMIFFSFLLSHRILPLHTMEYILGFGGQLADLLTQLIQEMKKEEL
LGDYTEDHVTYELSQLCAQVYLYKGYILQDRYKYQLENRHPYLLMEHDFK
ETAEEIFHALPAFQQGTDLDKKILWEWLQLIEYMAEGGQHMRIGLDLTSG
FLVFSRMAAILKRYLEYNRFITTIEAYDPSRHYDLLVTNNPIHKKEQTPV
YYLKNDLDMEDLVAIRQLLFTZ (SEQ. ID. NO. 8)
MEFSKKTRELSIKKMQERTLDLLHGGGITGAGVALQAAASGLETGLIEMQ
DFAEGTSSRSTKLVHGGLRYLKQFDVEVVSDTVSERAVVQQIAPHIPKSD
PMLLPVYDEDGATFSLFRLKVAMDLYDLLAGVSNTPAANKVLSKDQVLER
QPNLKKEGLVGGGVYLDFRNNDARLVIENIKRANQDGALANHKAEGFLFD
ESGKITGVVARDLLTDQVFEIKARLVINTTGPWSDKVRNLSNKGTQPSQM
RKGVHLVVDSSKIKVSQPVYFDTGLGDGRMVFVLPRENKTYEGTTDTDYT
GDLEHPKVTQEDVDYLLGIVNNRFPESNITIDDIESSWAGLRPLIAGNSA
SDYNGGNNGTISDESFDNLIATVESYLSKEKTREDVESAVSKLESSTSEK
HLDPSAVSRGSSLDRDDNGLLTLAGGKITDYRKMAEGAMERVVDIICAEF
DRSFKLINSKTYPVSGGELNPANVDSEIEAFAQLGVSRGLDSKEAHYLAN
LYGSNAPKVFALAHSLEQAPLSLADTLSHYAMRNELLTLSPVDFLLRRTN
HMLFMRDSLDSIVEPILDEMGRFYDWTEEEKATYRADVEAALANNDLAEL
KNZ (SEQ. ID. NO. 9)
MMNELFGEFLGTLIILLGNGVVAGVVLPKTKSNSSGWIVITMGWGIAVAV
AVFVSGKLSPAYLNPAVTIGVALKGGLPWASVLPYILAQFAGAMLGQILV
WLQFKPHYEAEENAGNILATFSTGPAIKDTVSNLISEILGTFVLVLTIPA
LGLYDFQAGIGTFAVGTLIVGIGLSLGGTTGYALNPARDLGPRIMHSILP
IPNKGDGDWSYAWIPVVGPVIGAALAVLVFSLFZ (SEQ. ID. NO. 10)
MTKKKERISVIHREKILWLKWYFMRDKEQPKYSVLERKMFDAAKNQDMLA
YQKYATIKQTSEADIRVQTSEADILEAVKEVYVYNHMNVIGACQRILFIS
QSPAYDKLNKWPNIYSDLYFSVVPLPKMGVYHEMVGIZ (SEQ. ID. NO. 11)
MKNSNEAEMKLLYTDIRTSLTEILTREAEELVAAGKRVFYIAPNSLSFEK
ERAVLEYLSQQASFSITVTRFAQMARYLVLNDLPAKTTLDDIGLGLAFYK
CLAELFDPKDLRVYGAIKQDPQLIQQLIELYHEMTKSQMSFLDLENLTDED
KRADLLLIFEKVTAYLNQGGQLAQESQLSHLIEAIENDKVSSDFNQIALVI
DGFTRFSAEEERVVDLLHGKGVEWIGAYASKKAYTSPFSEGNLYQAVKFL
HHLASKYQTPAQDCSQTHEKMDSFDKASRLLESSYDFSELALDVDEKDRE
NLQIWSCLTQKEELELVARSIRQKLHENSDLSYKHFRJLLGDVASYQLSL
KTIFDQYQIPFYLGRSEAMAHHPLTQFVESILALKRYRPRQEDLINLLRT
DLYTDLSQSDIDAFEQYIRYLGINGLPAFQQTFTKSHHGKFNLERLNVLR
LRILAPLETLFASRKQKAEKLLQKWSVFLKEGAVTKQLQDLTITLEAVEQ
ERQAEVWKAFCNVLEQFATVFAGSQVSLEDFLALLHSGMSLSQYRTIPAT
VDTVLVQSYDLIAPLTADFVIAIGLTQDNLPKISQNTSLLTDEERQNLNQ
ATEEGVQLLIASSENLKKNRYTMLSLVNSARKQLFLSAPSLFNESESKES
AYLQELIHFGFRRREKRMNHKGLSKEDMGSYHSLLSSLVAYHQQGEMSDT
EQDLTFVKVLSRVIGKKLDQQGLENPAIPTSPSSKTLAKDTLQALYPAKQ
EFYLSTSGLTFYRNEYSYFLRYVLGLQEELRLHPDARSHLHRPEAIQHRE
QLPNEDSFDQRLEQAIQETSQERBFSAIYQESLEAQITKEVLLDVARTTG
HILRRHNPAIETIKEEANFGGKDQAFIQLDNGRSVFVRGKVDRIDRLKANG
AIGVVDYKSSLTQFQFPHFFNGLNSQLPTYLAALKREGEQNFFGAMYLEM
AEPVQSLMAVKSLAGAVVEASKSMKYQGLFLEKESSYLEGEFYNKNKANQL
TDEEFQLLLDYNAYLYKKAAEKILAGRFAINPYTENGRSIAPYVQQHQAI
TGFEANYHLGQARFLEKLDLADGKRLVGEKLKQAWLEKIREELNRZ (SEQ. ID. NO. 12)
MKLIPFLSEEEIQKLQEAEANSSKEQKKTAEQIEAIYTSAQNILVSASAG
SGKTFVMAERLDQLARGVEISQLFISTFTVKAATELKERLEKJCISKKIQ
ETDDVDLKQHLGRQLADLPNAAIGTMDSFTQKFLGKHGYLLDIAPNFRIL
QNQSEQULENEVFHEVFHGYGKQKETFSHLLKNFAGRGKDRGLRQQV
YKIYDFLQSTSNPQKWLSESFLKGFEKADFTSEKEKLTEQIKQALWDLES
FFRYHLDNDAKEIAAYLENVQLILWDEEGSLNQESDSQAYQAVLARVV
AISKEKNGRALTNASRKADLKPLADAYNEERKTQFAKLGQISDQIAILDY
QERYHGDTWKLAKTFQSFMSDFVEAYRQRKRQENAPEFADISHYTIEILE
NFPQVRESYQERFHEVMVDEYQDTNHIQERMLELLSNGHNRFMVGDIKQS (SEQ. ID. NO. 13)
IYRFRQADPQCFNEKFQRYAQNPQEGRLIILKENFRSSSEVLSATNDVFE
RLMDQEVGEINYDNKHQLVFANTKLTPNPDNKAAFLLYDKDDTGEEESQ
RETKLTGEMRLVIKEILKLHQEKGVAFKRIALLTSSRSRNOQILLALSEY
GEPVKTLDGQNNYLQSLEVQVMLDTLRVIHNPLQDYALVALMKSPMFGFD
EDELARLSLQKAEDGVHENLYEKLVNAQKMASSQKGLIHTALAEKLKQFM
DILASWRLYAKTHSLYDLIWKIYNDRFYYDYVGALPNGPARQANLYALAL
RADQFEKSNFEKGLSRFIRMIDQVLEAQHDLASVAVAPPKDAVELMTIHK
SKGLEFPYVFILNMDQDINKQDSMSEVILSRQNGLGVKYIAKMETGAVED
HYPKTIKLSIPSLTYRQNEEELQLASYSEQMRLLYVAMTRAEKKLYLVGK
GSREKLESKEYPAAKNGKLNSNTRLQARNFQDWLWAISKVFTKDKLNFSY
RFIGEDQLTREAIGELETKSPLQDSSQADNRQSDTIKEALEMLKEVEVYN
TLHRAAIELPSVQTPSQUCKPYEPVMDMEGVEIAGQGQSVGKKISFDLPD
FSTKEKVTGAEIGSATHELMQRIDLSQQLTLASLTETLKQVQTSQAVRDK
INLDKILAFFDTVLGQEILANTDHLYREQPFSMLKRDQKSQEDFVVRGIL
DGYLLYENKIVLFDYKTDRYDEPSQLVDRYRGQLALYEEALSRAYSIENI
EKYLILLGKDEVQVVKVZ (SEQ. ID. NO. 14)
MYKTKCLREKLVLFLKIFFPIUYQFANYSASFVDTAMTGQYNTMDLAGVS
MATSTWNPPFTPLTGIVSALVPIIGHHLGRGKKEEVASDFYQFIYLALGL
SVVLLGMVLPLAPIILNHIGLEAAVAAVAVRYLWFLSIGIIPLLLFSVIR
SLLDSLGLTKLSMYLMLLLLPLNSGFNYLLIYGAFGVPELGGAGAGLGTS
LAYWVLLGISVLVLFKQEKLKALHLEKRIPLNMDKIKEGVRLGLPIGGTV
FAEVAIFSVVGLIMAKFSPLIIASHQSAMNFSSLMYAFPMSISSSAMAIVV
SYEVGAKRFDDAKTYIGLRWTALIFAAFTLTFYIFRGNVASLYGNDPK
FIDLTVRFLTYSLFFQLADTFAAPLQGILRGYKDTVIPPFYLGLLGYWGVA
IPVYAIZ (SEQ. ID. NO. 15)
MSTLAKIEALLFVAGEDGIRVRQLAELLSLPPTGIQQSLGKLAQKYEKDP
DSSLALIETSGAYRLVTKPQFAEILKEYSKAPINQSLSRALETLIIAYKQ
PITRIEIDAIRGVNSSGALAKLQAFDLIKEDGKKEVLGRPNLYWITDYFL
DYMGINHLEELPVIDELEIQAQESQLFGERIEEDENQZ (SEQ. ID. NO. 16)
MDTMISRFFRHLPEALKSLKRNGWMTVAAVSSVMITLTLVAIFASVIFNT
AKLATDIENNVRVVVYIRKDVEDNSQTIEKEGQTVTNNDYHKVYDSLKNM
STVKSVTFSSKEEQYEKLTEIMGDNKIFEGDANPLYDAYIVEANTPNDV
KTIAEDAKKIEGVSEVQDGGANTERLFKLASFIRVWGLGIAALLIFIAVF
LISNTIRITIISRSREIQIMRLVGAKNSYIRGPPLLEGAFIGLLGAIAPS
VLVFIVYQIVYQSVNKSLVGQNLSMISPDLFSPLMIALLFVIGVFIGSLG
SQGISMRRFLKIZ (SEQ. ID. NO. 17)
MKKVRFIFLALLFFLASPEGAMASDGTWQGGQYLKEDGSQAANEWVFDTH
YQSWFYIKADANYEAENEWLKQGDDYFYLKSGGYMAKSEWEVEDKGAFYYLD
QDGKMKRNAWVGTSYVGATGAKVIEDWVYDSQYOAWFYIKADGQHAEKEW
LQIKGKDYYFKSGGYLLTSQWINQAYVNASGAKVQQGWLFDKQYQSWFYI
KBNGNYADKEWIFENGFHYYYLKSGGYMAANEWEWDKESWFYLKFDGKMA
EKEWVYDSHSQAWYYFKSGGYMTANEWIWDKESWFYLKSDGKIAEKEWVY
TDSHSQAWYYFKSGGYMAKNEWSWFYLKSDGKIABEKEWVYDSHSQA
WYYFKSGGYMAKNETVDGYQLGSDGKWLGGKTTNENAAYYQVVPVTANVY
DSDGEKLSYISQGSVVWLDKDRKSDDKRLAITISGLSGYMKTEDLQALDA
SKDFIPYYESDGHRFYHYVAQNASIPVASHLSDMEVGKKYYSADGLHFDG
FKLENPFLFICDLTEATNYSAEELDKVFSLLNINNSLLENKGATFKWGA
HYHINALYLLAHSALESNWGRSKIAKDKNNFFGITAYDITPYLSAKTFDD
VDKGILGATKWIKENYIDRGRTFLGNKASGMNVEYASDPYWGEKIASVMM
KINEKLGGKDZ (SEQ. ID. NO. 18)
MKKVLQKYWAWAFVVIPLLLQAIPFYVPMFQGAFYSFTNWTGLTYNYKFV
GLNNFKLLFMDPKFMNAIGFTAIIAIAMVVEIALCIARVLNSKIKGQTFF
RAWFFPAVLSGLTVALIFKQVFNYGLPAIGNALHIEFFQTSLLGTKWGA
IFAAVFVLLWQOVVAMPEIIFLAGLGSIPTEITEAARIDGATSKQVFWNIE
LPYLLPSVSMVFELALKGGLTAFDQVFAMTGGGPNNAITSLGLLVYNYAF
KNNQFGYANAIAVILFFLIVVISHQLRVSKKFEIZ (SEQ. ID. NO. 19)
MMKQDERKALIGKYILLILGSVLILVPLLATLFSSFKPTKDIVDNFFGFF
TNFTWDNFSRLLADGIGGYYWNSVVITVLSLLAVMIFIPMAAYSIARNMS
KRKAFTIMYTLLILGIIFVPFQVIMIPITVMMSKLGLANTPGLILLYLTY
AIPQTLFLYVGYIKISIPESLDEAAEIDGANQFTTYFRIIFPMMKPMHAT

TABLE 2-continued

TMIINALWFWNDFMLPLLVLNRDSKMWTLPLFQYNYAGQYFNDYGPSFAS
YVVGIISITIVYLFFQRHIHSGMSNGAVKZ (SEQ. ID. NO. 20)
MKSILQKMGEHPMLLLFLSYSTVISILAQNWMGLVASVGMFLFTIFFLHY
QSILSHKFFRLILQFVLFGSVLSAAFASLEHPQIVKKPNYAPLSPNMQVW
HQNRAEVTFFNPNYYGIICCFCIMIAPYLFTTTKLNWLKVFCVIAGPVNL
FGLNFTQNRTAPPAIIAGAIIYLFTTTKNWKAFWLSIGVFAIGLSPLFSS
DLGVRMGTLDSSMEERISIWDAGMALFKQNPFWGEGPLTYMNSYPRIHAP
YHEHAHSLYIDTILSYGIVGTILLVLSSVAPVRLMMDMSQESGKRPIIGL
YLSFLTVVAVHGIFDLALFWIQSGFIFLLVMCSIPLEHRMLVSDMTDZ (SEQ. ID. NO. 21)
MSKMDVQKIIAPMMKFVNMRGIIALIKDGMLAILPLTVVGSLFLIMGQLP
FEGLNKSIASVFGANWTEPPMQVYSGTFAIMGLISCFSIAYSYAKNSGVE
ALPAGVLSVSAPFILLRSSYIPKQGEAIGDAISKVWFGGQGHAHIGLVV
GSIYTFFIKRKIVIKMPEQVPQAIAKQFEAMIPAVIFLSSMIVYILAKSL
TNGGTFIEMIYSAIQVPLQGLTGSLYGAIGIAFFISFLWWFGVHGQSVVN
GVTALLLSNLDANKAMLASANLSLENGAHIVTQQFLDSFLTLSGSGITFG
LVVAMLFAAKSKQYQALGKVAAFPAIFNVNEPVVFGPPEVMNPVMFVPFI
LVPVLAAVIVYGAIATGFMQPFSGVTLPWSTPAILSGFLVGGWQGVETQL
VILAMSTLVYFPPFFKVQDRLAYQNEIKQSZ (SEQ. ID. NO. 22)
MKKKDLVDQLVSEIETGKVRTLGIYGHGASGKSTFAQELYQALDSTTVNL
LETDPYITSGRHLVVPKDAPNQKVTASLPVAHELESLQRDILACRRVWMS
Z (SEQ. ID. NO. 23)
MKKRYLVLTALLALSLAACSQEKTKNEDGETKTEQTAKADGTVGSKSQGA
AQKKAEVVNKGDYYSIQGKYDEIIVANKHYPLSKDYNPGENPTAKAELVK
LIKAMQEAGPPISDHYSGFRSYETQTKLYQDYVNQDGKAAADRYSARPGY
SEHQTGLAFDVIGTDGDLVTEEKAAQWLLDHAADYGFVVRYLKGKEKETG
YMAEEEWHLRYVGKEAIKEIAASGLSLEEYYGFEGGGDYVDZ (SEQ. ID. NO. 24)
MREPDFLNHFLKKGYFKKHAKAVLALSGGLDSMFLFKVLSTYQKELEEEL
ILAHVNHKQRIESDWEEKELRKLAAEAELPIYISNFSGEFSEARARNFRY
DFFQEVMKKTGATALVTAHHADDQVETIFMRLIRGTRLRYLSGIKEKQVV
GEIEIIRPFLHFQKKDFPSIFHFEDTSNQENHYFRNRIRNSYLPELEKEN
PRFRDAILGIGNEILDYDLAIAELSNNINVEDLQQLPSYSESTQRVLLQT
YLNRFPDLNLTKAQFAEVQQILKSKSQYRHPIKNGYELEKEYQQFQICKI
SPQADEKBDELVLHYQNQVAYQGYLFSFGLPLEGELIQQIPVSRETSIHI
RHRRKTGDVLIKNGHRKKLRRLFIDLKIPMEKRNSALIIEQFGEIVSILGI
ATNNLSKKTKNDIMNTVLYIEKIDRZ (SEQ. ID. NO. 25)
MRKPLIILLLPSFLTISKVVSTEKEVVYTSKEIYYLSQSDFGIYFRBKLS
SPMVYGEVPVYANEDLVVESGKLTPKTSFQITEWRLNKQGIPVPKLSNHQ
FIAADKRFLYDQSEVTPTIICKVWLESDFKLYNSPYDLKEVKSSLSAYSQ
VSIDKTMFVEGREFLHIDQAGWVAKESTSEEDNRMSKVQEMLSEKYQKDS
FSIYVKQLTTGKSAGINQDEKMYAASVLKLSYLYYTQEKINEGLYQDTT
VKYVSAVNDFPGSYKPEGSGSLPKKEDNKEYSLKDUTKVSKESDNVAHNL
LGYYISNQSDATFKSKMSAIMGDDWDPKEKLISSKMAGKFMEAIYNQNGF
VLESLTKTDFDSQRIAKGVSVKVAHKIGDADEFKHDTGVVYADSPFILSI
FTKNSDYDTISKIAKDVYEVLKZ (SEQ. ID. NO. 26)
MKKQNNGLIKNPFLWLLFIFFLVTGFQYFYSGNNSGGSQQINYTELVQEI
TDGNVKELTYQPNGSVIEWSGVYKNPKSTKEETGIQFFTPSVTKVEKFTS
TILPADITVSELQKLATDHKAEVTVKHBSSSGIWINLLVSWPFGILFFFL
FSNIMGNMGGGNGRNPMSFGRSKAXANKBDIKVRFSDVAGAEEEKQELVE
VVEFLKDPKRFKLGARIPAGVLLEGPPGTGKLLLAKAVAGEAGVPPFSDS
GSDLVEMFVGVGASRVRSLFEDAKKAAPAIIFIDEIDAVGRQRGVGLGGG
NFRTRQTLNQLLIEMDGFEGNEGIIVIAATNSDVLDPALLRPGRFDRKVL
VGRPDVKGEAILKVHAKNKPLAEDVDLKLVAQQTPGPGFVGADLENVLNE
AALVAARRNSIIDASDIDEAEDRVIAGPSKKKDKTVSQKERELVAYHEAG
HIVGLVLSNARVVHKVTIVPRGRAGGYMIALPKEDQMLEDMKEQLAGLMG
GRVAEEIIFNVQITGASNDFEQATQMARMVIVTEYGMSEKLGPVQYEGNH
AMLGAQSPQSEQTAYEIDEEVRSLLNEARINKAAEHQSNRETHKLLEALL
KYETLDSTQIKALYETGKMPEAVEEESHALSYDEVKSKMNDEKZ (SEQ. ID. NO. 27)
MKRSSLLVRMVISIFLVFLILLALVGTFYYQSSSSAIEATIEGNSQSQTS
HFIQSYIKKLETTSTGLTQQPTDVLAYAENPSQDKVEGIRDLFLTILK SDK
DLKTVVLVTKSGQVISTDDSVQMKTSSDMMAEDWYQKAIHQGAMPVLTPA
RKSDSQWVISVTQELVDAKGANLGVLRLDISYETLEAYLNQLQLGQQGFAF
IINENHEFVYHPQHTVYSSSSKMEAMKPYIDTGQGYTPGHKSYVSQEKIAG
TDWTVLGVSSLEKLDQVRSQLLWTLLGASVTSLLVCLCLVWFSLKRWIAP

LKDLRETMLEIASGAQNLRAKEVGAYELREVTRQFNAMLDQIDQLMVAIR
SQEETTRQYQLQALSSQINPHFLYNTLDTIIWMAEFHDSQRVVQVTKSLA
TYFRLALNQGKDLICLSDEINHVRQYLFIQKQRYGDKLEYEINENVAFDN
LVLPKLVLQPLVENALYHGIKEKEGQGHIKLSVQKQDSGLVIREDDGVGF
QDAGDSSQSQLKRGGVGLQNVDQRLKLHPGANYHMKIDSRPQKGTKVEIY
INRIETSZ (SEQ. ID. NO. 28)
MKRSSLLVRMVISIFLVFLILLALVGTIYYQSSSSAIEATIEGNSQTTIS
QTSHFIQSYIKKLETTSTGLTQQTDVLAYAENPSQDKVEGIRDLFLTILK
SDKDLKTVVLVTKSGQVISTDDSVQMKTSSDMMAEDWYQKAIHQGAMPVL
TPARKSDSQWVISVTQELVDAKGANLGVLRLDISYETLEAYLNQLQLGQQ
GFAFIIINENHEFVYHPQHTVYSSSSKMEAMKPYIDTGQGYTPGHKSYVSQ
EKIAGTDWTVLGVSSLEKLDQVRSQLLWTLLGASVTSLLVCLCLVWFSLK
RWIAPLKDLRETMLEIASGAQNLRKEVGAYELREVTRQFNAMLDQIDQLM
VAIRSQEETTRQYQLQALSSQINPHFLYNTLDTUWMAEFHDSQRVVQVTK
SLATYFRLALNQGKDLICLSDENHVRQYLPIQKQRYGDKLEYEINENVAF
DNLVLPKLVLQPLVENALYHGIKEKEGQGHIKLSVQKQDSGLVIRIEDDG
VGFQDAGDSSQSQLKRGGVGLQNVDQRLKLHFGANYHMKIDSRPQKGTKV
EIYINRIETSZ (SEQ. ID. NO. 29)
MFFKLLREALKVKQVRSKILETIFWLVFRIGTSITVPGVNANSLNALSGL
SFLNMLSLVSGNALKNFSIFALGVSPYITASIVVQLLQMDILPKFVEWGK
QGEVGRRKLNQATRYIALVLAFVQSIGITAGFNTLAGAQLIKTALTPQVF
LTIGIILTAGSMIVTWLGEQETDKGYGNGVSMHFAGWSSIPEMIQGIYVD
YFVNVPSSRITSSIIFVHLIITVLLIIYFTTYVQQAEYKIPIQYTKVAQG
APSSSYLPLKVNPAGVIPVIFASSITAAPAAILQFLSATGHDWAWVRVAQ
EMLATTSPTGIAMYALLIILFTFFYTFVQINPEKAAERYKRVVPISMEFV
LVKVQKNICLNFFVVLQLLVPSSLVZ (SEQ. ID. NO. 30)
MDIRQVTETIAMIIEEQNFDIRTITMGISLLDCIDPDENRAAEKIYQKIT
TKAANLVAVGDEIAAELGIPIVNKRVSVTPISLIGAATDATDYVVLAKAL
DKAAKE1GVDFIGGFSALVQKGYQICGDEIILNSIPRALAETDKVCSSV
NIGSTKSGINMTAVADMGRIIKETANLSDMGVAKLVVFANAVEDNPFMAG
AFHGVEADVIINVGVSGPGVVKRALEKVRGQSPDVVAETVKKTAFKITR
IGQLVGQMASERLGVEFGIVDLSLAPTPAVGDSVARVLEEMGLETVGTHG
TTAALALLNDQVKKGGVMACNQVGGLSGAFIPVSEDEGMEAAVQNGSLNL
EKLEAMTAICSVGLDMIAIPEDTPAETIAAMIADEAAIGVINMKTTAVRI
IPKGKEGDMIEIGGLLGTAPVMKVNGASSVDFISRGGQIPAPIHSFKNZ (SEQ. ID. NO. 31)
MTQIIDGKALAAKLQGQLAEKTAKLKEETGLVPGLVVILVGDNPASQVYV
RNKERSALAAGFRSEVVRVPETITQEELLDLIAKYNQDPAWHGILVQLPL
PKHIDEEAVLLAIDPEKDVDGFHPLNMGRLWSGHPVMIPSTPAGIMEMFH
EYGIDLEGKNAVVIGRSNIVGKPMAQLLLAKNATVTLTHSRTHNLSKVAA
XADILVVAIGRAKFVTADFVKPGAVVIDVGMNRDENGKLCGDVDYEAVAP
LASHITPVPGGVGPMTITMLMEQTYQAALRTLDRKZ (SEQ. ID. NO. 32)
MSKFNRIHLVVLDSVGIGAAPDANNFVNAGVPDGASDTLGHISKTVGLNV
PNMAKIGLGNIPRETPLKTVAAESNPTGYATKLEEVSLGKDTTGHWEIMG
LNITEPFDTFWNGFPEE1LTKIEEFSGRKVIREANKPYSGTAVIYDFGPR
QMSTGELHYTSADPVLQIAAHEDIIPLDELYRICEYARSITLERPALLGR
IIARPYVGEPGNFTRTANRRDLAVSPFFPTVLDKLNEAGIDTYAVGKIND
IFNGAGINHDMGHNKSNSHGIDTLLKTMGLAEFEKGFSFTNLVDFDALYG
HRRNAHGYRDCLHEPDERLPEHAAMRENDLLLITADHGNDPTYAGTDHTR
EYIPLLAYSPAFKGNGLIPVGHFADISATVADNFGVETAMIGESFLDKLV
Z (SEQ. ID. NO. 33)
MFISISAGLVTFLLTLVEPAFIQFYRKAQITGQQMNEDVKQHQAKAGTPT
MGGLVPLITSVLVAFFFALFSSQFSNNVGMIILFILVLYGLVGFLDDFLK
VFRKINEGLNPKQKLALQLLGGVIFYLFYERGGDILSVPGYPVHLGFFYI
PFALFWLVGFSNAVNLTDGVDGLASISVVISLSAYGVIAYVQGQMDLLLV
ILAMIGGLLGFFIPNHKPAKVFMGDVGSLALGGMLAAISMALHQEWTLLU
GIVYVFEFTSVMMQVSYFKLTGGKPIFRMTPVHHHFELGGLSGKGNPWSE
WKVDFFFWGVGLLASLLTLAILYLMZ (SEQ. ID. NO. 34)
LFKKNKDELNIALPAMGENFLQMLMGMVDSYLVAHLGLIAISGVSVAGNI
MYQAIRALGAAISSVLSKSIGQKDQSKLAYNVTEALKITLLLSILLGFLS
IFAGKSMIGLLGTERDVAESGGLYLSLVGGSIVLLGMTSLGALIRATHN
PRLPLYVSFLSNALNILFSSLAIFVLDMGIAGVAWGTIVSRLVGLVILWS
QLKLPYGKPTFGLDKELLTLALPAAGERLMMRAGDVVHALVVSFGTEAVA
GNAIGEVLTQFNYMPAFGVATATVMLLARAVGEDDWKRVASLSKQTLFLS
LFMLPLSFSIYVLGVPLTHLYTDSLAVEASVLVTLFSLLGTPMTTGTVIY

TABLE 2-continued

TAVWQGLGNARLPFYATSIGMWCIRGTGYLMGIVLGWGLPGIWAGSLLD
NGFRWLFLRYRYQRYMSLKGZ (SEQ. ID. NO. 35)
MQTQEKRSQAAVLGLQHLAMYSGSILVPIMIATALGYSAEQLTYLISTDI
FMCGVATFLQLQLNKYFGIGLPVVLGVAFQSVAPLIMIGQSHGSGAMFGA
LIASGIYVVLVSGIFSKVANLFPSIVTGSVITTIGLTLIPVAIGNMGNNV
PEPTGQSLLAAITVLIILNIFTKGFIKSISILIGLVVGTAIAATMGLVDF
SPVAVAPLVHPTPLYFG, PTFEISSIVMMCIIATVSMVESTGVYLALSDI
TKDPIDSTRLRNGYREGLAVLLGGIFNTFPYTGFSQNVGLVKLSGIKKRL
PIYYAAGFLVLLGLLPKFGALAQIIPSSVLGGAMLVMFGFVSIQGMQILA
RVDFANNEHNFLIAAVSIAGVGLNNSNLFVSMPTAFQMFFSNGIVVASLL
AIVLNAVLNHKKKZ (SEQ. ID. NO. 36)
MKDRKEYLQDKGKVTVNDLAQALGKDSSKDFRELIKTLLMERKHQIRFEE
DGSLTLEIKKKHEITLKGIFHAHKNGFGFVSLEGEEDDLFVGKNDVNYAI
DGDTVEVVHCKVADRNKGTAAEAKIIDILEHSLTTVVGQIVLDQEKPKYA
GYISKNQK1SQPIYVKKPALKLEGTEVLKVPEDKYPSKKHDFFVASVLDV
VGHSTDVGIDVLEVLESMDIVSVEFPEAVVKEAESVPDAPSQKDMEGRLDL
RDEDGADAKDLDOAVHIKALKNGNLEPGVHADVSYYEGSALDKEALNRTS
VYVTDRVVPMLPERSNGICSLNPQVDRLTQSAIMEIDKHGRVVNTQTVIK
TSFRMTYSDVNDILAGDEEKEYHKIVSSIELMAKLHETLENMRVKRGALN
FDTNEAKILVDKGQKPVDIVLRQRGIAERMIESFMLMANETVAEHFSKLD
LPRYIHEBPKAEKVQKFIDYASSFGLRIYGTASELSQEALQDIMRAVEGB
PYADVLSMMLRSMQQARYSEHNHGHYGLAADYYTHFTSPIRRYPDLLVHR
MIRDYGRSKEIAEHFEQVIPEIATQSSNRERRAIEAEREVEAMKKAEYME
EYVGEEYDAVVSSIVKFGLFVELPNTVEGLINTNLPEFYHFNERDLTLRG
EKSGITFRVGQQIRIRVERADKMTGEIDFSFVPSEDFDVIEKGLKQSSRS
GRGRDSNRRSDKKEDKRKSGRSNDKRKHSQKDKKKKGKKPFYKEVAKKGA
KHGKGRGKGRRTKZ (SEQ. ID. NO. 37)
MGTTGFTIIDLIILIVYLLAVLVAGIYFSKKEMKGKEFFKGDGSVPWYVT
SVSIFATMLSPISFLGLAGSSYAGSWLWFAQLGMVVAIPLTHIILPIFAR
DIDTAYDYLDKRFNSKALRISALLFIIYQLGRMSUMYLPSAGLSVLTGID
INILILMGVVAIVYSYTGGLKSVLWTDFIQGVILJSGVVLALFVLIANI
KGGFGAVAETLANGKFLAANENKLFDPNLLSNSIFLIVMGSGPTILSSYAS
SQDLVQRFTTTQNIKKLNKMLFTNGVLSLATAVFYLIGTGLYVFYQVQNA
DSAASNIPQDQIFMYFIAYQLPVGITGLILAAIYAASQSTISTGLNSVAT
SWTLDIQDVISKNMSDNRRTKIAQFVLSLAVGLPSIGVSIVMAHSDIKSAY
EWFNSFMGLVLGLLGGVRLGVSKKANKQGAYAALPIVMVFICYFLPPTAV
SYWAYSLISISVSVVSGYIVSVLTGNKVSAPKYTTIEDITEIKADSSWEV
RMZ (SEQ. ID. NO. 38)
MKFSKKYAGSAVIVSLSLCAYALNQHRSQENKDNNRVSYVDGSQSSQKSE
NLTPDQVSQKEGIQAEQAEQIVIKITDQGYVTSHGDHYHYYNGKVPYDAL
FSEELLNBDPNYQLKDADIVNEVKGGYUKVDGKYYVLKDAAHADNVRTK
DEINRQKQEHVKDNEKVNSNVAVARSQGRYTNDGYVPNPADIIEDTGNAY
IVPHGGHYHYIPKSDLSASELAAAKAHLGKNMQPSQLSYSSTASDNNTQS
VAKGSTSKPANKSENLQSLLKELYDSPSAQRYSESDGLVIDPAKIISRTP
NGVAIPHGDHYHPIPYSKLSALEEKTARVPISGTGSTVSTNAKPNEVVSS
LGSLSNPSSLTTSKELSSASDGYIFNPKDIVEETATAYWRHGDHFHYIPK
SNQIGQPTLPNNSLATPSPSLPINPGTSHEKHEEDGYGFDANRIIAEDES
GFVMSHGDHNHYFFKKDLTEEQIKVRKNIZ (SEQ. ID. NO. 39)
MKKRAIVAVIVLLLIGLDQLVKSYIVQQIPLGEVRSWIPNFVSLTYLQNR
GAAPSILQDQQLLFAVITLVVVIGAIWYLHKHMEDSFWMVLGLTLUAGGL
GNFIDRVSQGPVVDMFHLDFINFAIFNVADSYLTVGVIILLIAMLKEEIN
GNZ (SEQ. ID. NO. 40)
MNTNLASFIVGLHDENDRFYFVQKDGQTYALAKEEGQHTVGDTVKGFAYT
DMKQKLRLTTLEVTATQDQFGWGRVTEVRKDLGVFVDTGLPDKEIVVSLD
ILPELKELWPKXGDQLYIRLEVDKKDRIWGLLAYQEDFQRLARPAYNNMQ
NQNWPAIVYRKLSGTFVYLPENNNMLGFIHPSERYAEPRLGQVLDARVIG
FREVDRTLNLSLKPRSFEMLENDAQMILTYLSSNGGFMTLNDKSSPDDIK
ATFGISKGQFKKALGGLMKAGKIKQDQFGTELIZ (SEQ. ID. NO. 41)
MKDVSLFLLKKVFKSRLNWIVLALFVSVLGVTFYLNSQTANSHSLESRLE
SR1AANERAINENEEKLSQMSDTSSEEYQFAXNNLDVQKNLLTRKTEILT
LLKEGRWKEAYYLQWQDEBKNYEFVSNDPTASPGLKMGVDRERKIYQALY
PLNIKAHTLEFPTHGIDQIVWILEVIIPSLFVVAIIFMLTQLFAERYQNH
LDTAHLYPVSKVTFAISSLGVGVGYVTLVLFIGICGFSPLVGSLISGFGQL
DYPYNYSLVNQEVTIGKIQDVLFPGLLLAFLAFIVIVEVVYLIAYPFKQK (SEQ. ID. NO. 42)
MPVLFLSLIGIVGLLFGIQTIQPLQRIAHLIPFTYLRSVEILSGRLPKQI
DNVDLNWSMGMVLLPCLIIFLLLGILFISRWGSSQKICEFFNRFZ (SEQ. ID. NO. 43)
MMKFILDIVSTPAILVALIAILGLVLQKKKLPDIIKGGIKTFVGFLVVSG
GAGIVQNSLNPFGTMPEHAPHLSOVVPNNEAIVAVAUITYGSATAMIMFA
GMVFNILIARFTRFKYIFLTGHHTLYMACMIAVILSVAGFTSLPLILLGG
LALGUMSISPAFVQKYMVQLTGNDKVALGHFSSLGYWLSGFTGSLIGDKS
KSTEDIICPPKSLAPLRDSTVSITLSMAVIYUVAIFAGSEYIEKEISSGT
SGLVYALQLAGQFAAGVFVLAGVRLILGEIVPAPKGISERLVPNSKPALD
CPIVYTYAPNAVLIGFTSSFVGGLVSMVIMIASGTVVILPGVVPHFFCGA
TAGVGTGNASGGVRGATIGAPLQGILISFLPVFLMPVLGGLFQGSTFSDA
DFGLSGIILGMLNQPFGSQAGIVIGLVLILAVMFGVSPIKKPSATEEZ (SEQ. ID. NO. 44)
MIKTFLSALSVILFSIPIITYSFPPSSNLNZWLSTQPILAQIYAFPLATA
TMAAILSLFLFFFLSFYKKNKQIRFYSGILLLLSLILLLFGTDKTLSSASN
KTKTLKLVTWNVANQIEAQHIERIFSKFDADMAIFPELATNIRGEQENQR
IKLLFHQVGLSMANYDIFTSPPTNSGIAPVTVIVKXSYGFYTEAKTFHTT
RFGTIVLHSRKQNIPDIIALHTAPPLPGLMEIWKQDLNIIHNQLASKYPK
AIIAGDFNATMRHGALAKISSHRDALNALPPFERGTWNSQSPKLFNATID
HILLPKNHYYVKDLDIVSFQNSDHRCIFTEITFZ (SEQ. ID. NO. 45)
MLHNAFAYVTRKFFKSIVTFLIILLMASLSLVGLSIKGATAKASQETFKN
ITNSFSMQINRRVNQGTFPGAGNEKGEDIKKITENKAIESYVKRINAIGD
LTGYDLIETPETKKNLTADRAKRFGSSLMITGVNDSSKEDKFVSGSYKLV
EGEHLTNDDKDKILLHKDLAAKHGWKVGDKVKLDSNIYDADNEKGAKETV
EVTIKGLFDGHNKSAVTYSQELYENTAITDIHTAAKLYGYTEDTAIYGDA
TFFVTDKNLDDVMKELNGISGINWKSYTLVKSSSNYPALEQSISGMYXM
ANLLFWGSLSPSVLLLALLLSLWINARRKEVGILLSIGLKQASILGQFIT
ESILIAIPALVSAYFLANYTARAIGNTVLANVTSGVAKQASKAAQASNLG
GGAEVDGFSKTLSSLD1SIQTSDFIIIFVLALVLVVLVMALASSNLLRKQ
PKELLLDGEZ (SEQ. ID. NO. 46)
MSQDKQMKAVSPLLQRVINISSIVGGVGSLIFCIWAYQAGILQSKETLSA
FIQQAGIWGPPLFIFLQILQTVVPIIPGALTSVAGVFIYGHIIGTIYNYI
GIVIGCAIIFYLVRLYGAAFVQSVVSKRTYDKYIDWLDKGNRFDRFFIFM
MIWPISPADFLCMLAALTKMSFKRYMTIIILTKPFTLVVVYTYGLTYIIDF
EWQMLZ (SEQ. ID. NO. 47)
MRNMWVIKETYLRHVESWSFFFMVISPPFLFLGISVGIGHLQGSSMAKNNK
VAVVTTVPSVAEGLKNVNGVNFDYKDEASAKEAIKEEKLKGYLTIDQEDS
VLKAVYHGETSLENGIKFEVTGTLNELQNQLNRSTASLSQEQEKRLAQTI
QFTEKIDEAKENXKFIQTIAAGALGFFLYMILITYAGVTAQEVASEKGTK
IMEVVFSSIRASHYFYARMMALFLVILTHIGIYVVGGLAAVLLFKDLPFL
AQSGILDHLGDAISLNTLLFILISLFMYVVLAAFLGSMVSRPEDSGKALS
PLMILIMGGFFGVTALGAAGDNLLLKIGSYIPFISTFFMPFRTINDYAGG
AEAWISLALTVWAVVATGFIGRMYASLVLQTDDLGIWKTFKRALSYKZ (SEQ. ID. NO. 48)
MTETIKLMIKAHTSVRRFKEQEIPQVDLNEILTAAQMASSWKNFQSYSVI
VVRSQEKKDALYELVPQEAIRQSAVFLLFVGDLNRAEKGARLHTDTFPQY
GVEGLLISSVDAALAGQNALLAAESLGYGGVHGLVRYKSEEVAELFNLPD
YYTYSVFGMALGVPNQHHDMKPRLPLENVVFEEEYQEQSTEAIQAYDRVQ
ADYAGARATTSWSQRLAEQFGQAEPSSTRKNLEQKKLLZMLKLIAIVGTN
SKRSTNLQLQYMQKHFTDKAEIELVEIKAIPVFNKPADKQVPAEILEIA
AKIEEADGVHGTPEYDHSIPAVLMSALAWLSYGIYPLLNKPIMITGASYG
TLGSSRAQLQLRQILNAPEIKANVLPDEFLLSHSLQAFNPSGDLVDLDVI
KKLDAIFDDPRIFVKITEKLRNAQELLRKDAEDFDWENLZ (SEQ. ID. NO. 49)
MNTYQLNNGVEIPVLGFGTFICAKDGEEAYRAVLEALKAGYRHIDTAAIY
QNEESVGQAIKDSGVPREEMFVTTKLWNSQQTYSQTRQALEKSIEKLGLD
YLDLYLIHWPNPKPLRENDAWFTRNAEVVWRAMEDLYQEGKIRAIGVSNFL
PHHLDALLETATIVPAVNQVRLAPGVYQDQVVAYCREKGILLEAWGPPGQ

TABLE 2-continued

GELFDSKQVQEIAANHGKSVAQLALAWSLAEGFLPLPKSVTTSRIQANLD
CFGIELSHEERETLKTIAVQSGAPRVDDVDFZ (SEQ. ID. NO. 50)
MRCKMLDPIAIQLGPLAIRWYALCIVTGLILAVYLTMKEAPRKKIIPDDL
DPILVAPPLAILGARLYYVIFRFDYYSQNLGEIFAIWNGGLAIYGGLITG
ALVLYIFADRKLINTWDFLDIAAPSVMIAQSLGRWGNFFNQEAYGATVDN
LDYLPGRRDQMYIEGSYRQPTFLYESLWNLLGFALILIERRKWKSLRRGH
ITAFYLIWYGFGRMVIEGMRTDSLMFFGFRVSQWLSVVLIGLGIMIVIYQ
NRKKAPYYITEEENZ (SEQ. ID. NO. 51)
MGKLSSILLGTVSGAALALFLTSDKGKQVCSQAQDPLDDLREDPEYAKEQ
VCEKLTEVKEQATDFVLKTKEQVESGEITVDSILAQTKSYAFQATEASKN
QLNNLKEQWQEKAEALDDSEEIVIDITEEZ (SEQ. ID. NO. 52)
MKTKLIFWGSMLFLLSLSILLTIYLAWIFYPMEIQWLNLTNRVYLKPETI
QYNFHILMNYLTNPFSQVLQMPDFRSSAAGLNHFAVVKNLFHLVQLVALV
TLPSFYVFVNRIVKKDFLSLYRKSLLALVVLPVMIGLGGVLIGFDQFFTL
FHQILFVGDDTWLFDPAKDPVIMILPETFFLHAFLLFFALYENFFGYLYL
KSRRKZ (SEQ. ID. NO. 53)
MTYHFTEEYDHVIGAGHAGVEASLAASRMGCKVLLATINIEMLAFMPCNP
SIGGSAKGIVVREVDALGGEMAKTIDKTYIQMKMLNTGKGPAVRALRAQA
DKELYSKEMRKTVENQENLTLRQTMIDEILVEDGKVVGVRTATHQEYAAK
AVNTTGTALRGEIIIGDLKYSSGPNHSLASINLADNLKELGLEIGRFKTG
TPPRVKASSINYDVTEIQPGDEVTHPFSYTSRDEDYVKDQVPCWLTYTNG
TSHEUQNNLHRAPMFTGVVKGVGPRYCPSIEDKIVRFADKERHQLFLEPE
GRNTEEVYVQGLSTSLPEDVQRDLVHSIKGLENAEMMRTGYAIEYDMVLP
HQLRATLETKKISGLFTAGQTNGTSGYEEAAGQGUAGINAALKIQGKPEL
ILKRSDGYIGVMIDDLVTKGTIEPYRLLTSRAEYRLILRHDNADMRLTEM
GREIGLVDDERWARFEIKICNQFDNEMKRLDSIKLKPVKETNAKVEEMGF
KPLTDAVTAKEFLRRPEVSYQDVVAFIGPAAEDLDDKIIELIETEIKYEG
YISKAMDQVAKMKRMEEKRIPANIDWDDIDSIATEARQKFKUNPETIGQA
SRISGVNPADISILMVYLEGKNRSISKTLQKSKZ (SEQ. ID. NO. 54)
MTKQVLLVDDEEHILKLLDYHLSKEGFSTQLVTNGRKALALAETEPFDFI
LLDIMLPQLDGMEVCKRLRAKGVKTPIMMVSAKSDEFDKVLALELGADDY
LTKPFSPRELLARVKAVLRRTKGEQEGDDSDNIADDSWLFGTLKVYPERH
EVYKANKLLSLTPKEFESDKNPFFEVFKVSKVTAQZ (SEQ. ID. NO. 55)
MTTFKDGFLWGGAVAAHQLEGGWQEGGKGISVADVMTAGRHGVAREITLG
VLEGKYYPNHEAIDFYHRYKEDIALFAEMGFKCPRTSIAWTRFPKGDELE
PNEEGLQFYDNLPDECLKNGIEPVITLSHFEMPYHLVTEYGGWKNRKLID
FPAREAEVVFKRYKDKVKYWMTFNEINNQANYQEDFAPFTNSGIVYEEGD
NREAIMYQAAHYELVASARAVKIGHEINPDFQIYYMSFAIDSHRENNPYD
YLETEDLVKNNYVKASEWEWQIDPEGLRYALNWFTDHYHLPLFNENGFGM
DQVAADGMVHDDYREYLGAHIREMKKAVVEDGVDLMGYTPWGCIDLVSAG
TGEMRKRYGFIYVDKDDNGKGSYNRSPKKFGWYKEVISSNGESVEZ (SEQ. ID. NO. 56)
MDQQNGLFGFLENHVMGPMGKLAQPKVVLTAAGMAAVPFWGSMFLVFSIL
PQAPSPPWADIFSASFDKFTSLYMVANYATMGSLSLYFVLSLAYELTKIY
AEEEELNMNPLNGALLALMAFVMTVPQUFDGGMMKTSLKEGAVIADGWAM
GNVVARFGTTGIFTAHMAIVTVLIYRMCVKHNWVIKMPEAVPEGVSRGPT
ALVPGFVVAFVVIFINGLLVAMGTDIKVLMPFGFVSNLTNSWIGLMUYLL
TQLLWWGIHGANIVFAFVSPIALANMAANAAGPHEINAAGGPIHEINAMRREAQIISESGQMQAVT
GSGATLGLCLYIAFASKSEQLKIGRSVVPALFNINEPLILGLPIIYNPAL
AIPFILAPMVTATIYYVANSLNFIKPIIAQVPWPTPVGIGAFLGTADLRA
VLVALVCAFAAPLVYLPFTRVYDQKLVKEEQGIZ (SEQ. ID. NO. 57)
MKKFYVSPIPFILVGLIAFGVLSTFIIFVNNNLLTVLILPLFVGGYVFLF
KKLRVHYTRSDVEQIQYVNHQAEESLTALLEQMPVGVMKLNLSSGEVEWF
NPYAELILTKEGDFDLEAVQTIIKASVGNPSTYAKLGEKRYAVHMDASSG
VLYFVDVSREQAITDELVTSRPVIGVSVDNYDDLEDETSESDISQENSFV
ANFISEFSEKHMMFSRRVSMDRFYLFTDYTVLEGLMNDKFSVIDAFREES
KQRQLPLTLSMGFSYGDGNHDEIGKVALLNLNLAEVRGGDQVVVKENDST
KNPVYFGGGSAASTIKRTRTRTRAMMTASDKIRSVDQVFVVGHKNLDMDA
LGSAVGMQLFASNVIENSYALYDEEQMSPDIERAVSFIEKEGVTKLLSVK
DAMGMVTNRSLLILVDHSKTALTLSKEFYDLFTQTIVIDHHRRPQDFPDN
AVITYIESGASSASELVTELIQPQNSKKNRLSRMQASVLMAOMMLDTKNF
TSRVTSRTFDVASYLRTRGSDSIAIQEIAATDFEEYREVNEULQGRKLGS

DVLIAEAKDMKCYDTVVISKAADAMLAMSGIEASFVLAKNTQOFISLSAR
SRSKLNVQR1MEELGGGGHFNLAAAQIKDVTLSEAGEKLTEIVLNEMKEK
EKEEZ (SEQ. ID. NO. 58)
MKEKNMWKELLNRAGWILVFLLAVLLYQVPLVVTSILTLKEVALLQSGLI
VAGLSIVVLALFIMGARKTKLASFNFSFFRAKDLARLGLSYLVIVGSNIL
GSILLQLSNETTTANQSQINDMVQNSSIISSFFLLALLAPICEEILCRGI
VPKKIFRGKENLGFVVGTIVFALLHQPSNLPSLLIYGGMSTVLSVIAYKT
QRLEMSILLHMIVNGIAFCLLALVVIMSRTLGISVZ (SEQ. ID. NO. 59)
MKEKNMWKELLNRAGWILVFLLAVLLYQVPLVVTSILTLKEVALLQSGLI
VAGLSIVVLALFIMGARKTKLASFNFSFFRAKDLARLGLSYLVIVGSNLG
SILLQLSNETITANQSQINDMVQNSSLISSPFLLALLAPICEEILCRGIV
PKKIPRGKENILGFVVGTWFALLHQPSNLPSLLIYGGMSTVLSWAYKTQR
LEMSILLHMIVNGIAFCLLALVVIMSRTLGISVZ (SEQ. ID. NO. 60)
MDTQKIEAAVKMUEAVGEDANREGLQETPARVARMYQEIFSGLGQTAEHH
LSKSFEIIDDNMVVEKDIFFHTMCEHHFLPFYGRAHIAYIPDGRVAGLSK
LARTVEVYSKKPQIQERLNIEVADALMDYLGAKGAFVVIEAEHMCMSMRG
VRKPGTATUTVARGLFETDKDLRDQAYRLMGLZMKDLFLKRKQAFRKECL
GYLRYVLHPVFLLVLLGFLAYQYSQLLQHFPENHWPILLFVGITSVL
LLLWGGTATYMEAPDKLFLLVGEEEIKLHLKRQTGISLVFWLFVQTLFLL
LFAPLFLAMGYGLPVFLLYVLLLGVGKYFHFCQKASKFFTETGLDWDYVI
SQESKRKQVLLRFFALFTQVKGISNSVKRRAYLDFILKAVQKVPGKIWQN
LYLRSYLRNGDLFALSLRLLLLSLLAQVFIEQAWIATAVVVLFNYLLLPQ
LLALYHAFDYQYLTQLFPLDKGQKEKGLQEVVRGLTSFVLLVELVVGLIT
FQEKLALLALLGAGLVLLVYLPYQVKRQMQDZ (SEQ. ID. NO. 61)
MRKSIVLAADNAYLIPLETTIKSVLYHNRDVDFYILNSDIAPEWFKLLGR
KMEVVNSTIRSVHIDKELFESYKTGPHINYASYFRFFATEVVESDRVLYL
DSDIIVTGELATLFEIDLKGYSIGAVDDVYAYEGRKSGFNTGMLLMDVAK
WKEHSIVNSLLELAAEQNQVVNLGDQSILNIYFEDNWLALDKTYNYMVGI
DEYHLAQECERLDDNPPTIVHYASHDKPWNTYSISRLRELWWVYRLDLWS
EIAFQRSDLNYFERSNQSKKQVMLVTWSADIKHLEYLVQRLPDWHPHLAA
PCDCSEELTSLSQYTNVTVYQNVLHSRIDWLLDDSEVYLDINTGGEVFNV
VTRAQESGKICIFAFDITRKSMDDGLYDGIFSVERPDDLVDRMKNIEIEZ (SEQ. ID. NO. 62)
MTKIYSSIAVKKGLFTSFLLFIYVLGSRIILPFVDLNTKDFLGGSTAYLA
FSAALTOGNLRSLSIFSVGLSPWMSAMILWQMFSFSKRLGLTSTSIEIQD
RkKMYLTLLIAVIQSLAVSLRLPVQSSYSAILVVLMNTILLIAGTFFLVW
LSDLNASMGIGGSIVILLSSMVLNIPODVLETFQTVHIPTGHVLLALLTL
VFSYLLALMYRARYLVPVNKIGLHNRFKRYSYLEIMLNPAGGMPYMYVMS
FLSVPAYLFILLGFIFPNHSGLAALSKEIMVGKPLWVYVYISVLFLFSII
FAFVTMNGEEIADRMKKSGEYIYGIYPGADTSRFINRLVLRFSVIGGLFN
VIMAGGPMLFVLFDEKLLRLAMIPGLFMMFGGMIFTIRDEVKALRLNETY
RPLIZ (SEQ. ID. NO. 63)
MSSLSDQELVAKTVEFRQRLSEGESLDDILVEAFAVVREADKRILGMFPY
DVQVMGAIVMHYGNVAEMNTGEGKTLATMPVYLNAPSGEGVMVVTPNEY
LSKRDAEEMGQVYRFLGLTXGVPPFTEDPKKEMKASEKKLIYASDWTTINS
NLGPDYLNDNLASNEEGKFLRPFNYVUDEIDDILLDSAQTPLIIAGSPRV
QSNYYAIIDTLVTTLVEGWYIPKEEKEEVWLTTKGAKSAENELGIDNLYK
EEHASFARHLVYAIRAHKLFTKDKDYHRGNEMVLVDKGTGRLMEMTKLQG
GLHQAIEAKEHVKLSPETRAMASITYQSLPKMFNKISGMTGTGKVAEKEF
IETEYNMSVVRIPTNRPRQRIDYPDNLYITLPEKVYASLEYIKQYHAKGNP
LLVFVGSVNEMSQLYSSLLFREGIAHNVLNANNAAREAQIISESGQMQAVT
VATSMAGRGTDCKLGKGVAELGGUVIGTERMESQRIDLQIRGRSGRQGDP
GMSKFFVSLEDDVIKKFGPSWHHKKYKDYQVQDMTQPEVLKGRKYRKLVE
KAQHASDSAGRSARRQTLEYAESMNIQRDIVYKERNRLIDGSRDLEDVVV
DIIERYTEEVAADHYASRELLFWPIVTNISFHVKEVPDYIDVTDKTAVRS
FMKQVIDKELSEKKELLNQHDLYEQPLRLSLLKAIDDNWVEQVDYLQQLS
MAIGGQSASQKNPEVEYYQEAYAGFEAMKEQIHADMVRNLLMGLVEVTPK
GEIVTHFPZ (SEQ. ID. NO. 64)
MIGTFAAALVAVLANRVPIEITPNSANTEIAPPDGIGQVLSNLLLKLVDN
PVNALLTANYIRILSWAVIFGIAMREASKNSQELLKTIADVTSKIVEWII
NLAPFGILGLVFKISDKGVGSLANYGILLVLLVTTMLPVAPVVNPLIAPF
FMRRNPYPLVWNCLRVSGVTAPFTRSSATNTPVNMKLCMDLGLNPDTYSV
SIPLOSTINMAGVAITINLLTLAAVNTLGTPVDFATAFVLSVVAAISSCD
ASGIAGGSLLUPVACSLFGISNDIAIQIVGVGPVIGVQDSCETALNSSTD
VLFTAVAEYAATRKKZ

TABLE 2-continued (SEQ. ID. NO. 65)
MSISQRTTKLILATCLACLLAYFLNLSSAVSAGIIALLSLSDTRRSTLKL
ARNRLFSMLLALAIGVLAFHLSGFHIWSLGLYLAVPLAYKMGWEIGITPS
TVLVSHLLVQESTSPDLLVNEFLLFAIGTGFALLVNLYMPSREEEIQHYH
TLVEEKDILQRFKYYLSRGDGRNRAQLVAELDTLLKEALRLVYLDHSDHL
FHQTDYHIHYFEMRQRQSRILRNMAQQINTCHLAASESLILAQLFSKAGQ
LSQTNPASDLLDEIERYLEVFRNRSLPKTREEPETRATLLQLLREAKTFI
QVKVDFYQKYRQZ (SEQ. ID. NO. 66)
MEIMSLAIAVFAVIIGLVIGYVSISAKMISSQEAAELMLLNAEQEATNLR
GQAEREADLLVNEAKRESKSLKKEALLEAKEEARKYREEVDAEFKSERQE
LKQIESRLTERATSLDRXDDNLTSKEQTLEQKEQSISDRAKNLDAREEQL
EEVERQKEAELERIGALSQAEARDIILAQTSENLTREIASRIREAEQEVK
ERSDKMAKDILVQAMQRIAGEYVAESTNSTVHLPDDTMKGRIIGRGRNIR
TFESLTGVDVIIDDTPEVVTLSGFDPIRREIARMTMEMLLKDGRIHPARI
EELVEKNRQEIDNKIREYGEAAAYEIGAPNLHPDLMKIMGRLQPRTSYGQ
NVLRHSIEVAKLAGIMASELGENAALARRAGPLHDIGKAIDHEVEGSHVE
IGMELARKYKEPPVVVNTIASHHGDVEAESVIAVIVAAADALSAARPGAR
SESLESYIKRLHDLEEIANGFEGVQTSFALQAGREIRIRIMVNPGKIKDDKV
TILAHKVRKKIENNLDYPGNIKVTVIRELRAVDYAKZ (SEQ. ID. NO. 67)
MMLKPSIDTLLDKVPSKYSLVILBAKRAHELEAGAPATQGFKSEKSTLRA
LEEIESGNVTIHPDPEGKREAVRRRIEEEKRRKEEEEKKIKEQIAKEKED
GEKIZ (SEQ. ID. NO. 68)
MSAYQLPTVWQDEASNQGAFTGLNRPTAGARFEQNLPKGEQAFQLYSLGT
PNGVKVTILLEELLEAGFKEAAYDLYKIAIMDGDQFGSDPFKLNPNSKIP
ALLDQSGTENVRVFESAHILLYLAEKFGAFLPSNPVEKVEVLNWLFWQAG
AAPFLGGGFGHFFNYAPEKLEYPINRFTMEVKRQLDLLDKELAQKPYIAG
NDYTIADIAIWSWYGQLVQGNLYQGSAKFLDASSYQNLVKWAEKANRPAV
KRGLEVTYTEIKZ (SEQ. ID. NO. 69)
LASLITSIIMFYVGFDVLRDTIQKILSREETVIDPLGATLGIISAAIMFV
VYLYNTRLSKKSNSNALKAAAKDNLSDAVTSLGTAIAILASSFNYPIVDK
LVAIIITFFILKTAYDIFIESSFSLSDGFDDRLLEDYQKAIMEIPKISKV
KSQRGRTYGSNIYLDITLEMNPDLSVFESHEIADQVESMLEERPGVFDTD
VHIEPAPIPEDEILDNVYKKLLMREQLIDQGNQLEELLTDDFVYIRQDGE
QMDKEAYKTKKELNSAIKDIQITSISQKTKLICYELDGIIHTSIWRRMET
WQNIFHQETKKEZ (SEQ. ID. NO. 70)
MTIKLVATDMDGTFLDGNGRFDMDRLKSLLVSYKEKGIYFAVASGRGFLS
LEKLFAGVRDDIIFIAENGSLVEYQGQDLYEATMSRDFYLATFEKLKTSP
YVDINKLLLTGKKGSYVLDTVDETYLKVSQHYNENIQKVASLEDITDDIF
KFTTNFTEETLEDGEAWVNENVPGVKAMTTGFESIDIVLDYVDKGVAIVE
LVKKLGITMDQVMAFGDNLNDLHMMQVVGHPVAPENARPEILELAKTVIG
HHKERSVIAYMHGLZ (SEQ. ID. NO. 71)
MADIKLIALDLDGTLLITTDKRLTDRTKETLQAARDRGIKVVLTTGRPLK
AMDFFLHELGTDGQEDEYTITFNGGLVQKNTGEILDKTVFSYDDVARLYE
ETEKLSLPLDAISEGTVYQIQSDQELYAKFNPALTFVPVDFEDLSSQMTY
NKCVTAFAQEPLDAAEQKISPELFDQYEIFKSREMLLEWSPKNVHKATGL
AKLISHLGIDQSQVMACGDEANDLSMIEWAGLGVAMQNAVPEVKAAANVV
TPMTNDEEAVAWAIEEYVLKENZ (SEQ. ID. NO. 72)
MESLLILLLIANLAGLFLIWQRDQREKHLSKSLEDQADHLSDQLDYRFD
QARQASQLDQKDLEVVVSDRLQEVRKELHQGLTQVRQEMTDNLLQTRDKT
DQRLQALQESNEQRLEQMRQTVEEKLEKTLQTRLQASFETVSKQLESVNR
GLDEMQTVARDVGALNKVLSGTKTRGALGELQLGQHEDIMTPAQYEREYA
TVENSSERVEYAIKLPGQGDQEYVYLPIDSKFPLQDYLPEYLEEAYETGDKD
EIERCRKSLLASVKRFARDIRNKYIAPPRTTNFGVLFVPTEGLYSEIVRN
PVFFDDLRREEQIWAGPSTLSALLNSLSVGPKTLNIQKSADHISKTLASV
KTEFGKFGGILVKAQKHLQHASGNIDELLNRRTIAIERTLRHIELSEGEP
ALDLLHFQENEEEYEDZ (SEQ. ID. NO. 73)
MKISHMKKDELFEGFYLIKSADLRQTRAGKNYLAFTFQDDSGEIDGKLWD
AQPHNIEAFTAGKVVHMKGRREVYNNTPQVNQITLRLPQAGEPNDPADFK
VKSPVDVIKEIRDYMSQMIFKINPVWQRIVRNLYTKYDKEFYSYPAAIC
TNHHAFETGLAYHTATMVRLADALSEVYQLNKSLLYAGIMLHDLAKVIEL
TGPDQTEYTVRGNLLGHIALIDSEITKTVMELGIDDTKEEVVLLRHVILS
HHGLLEYGSPVRPRIMEAEIIHMIDNLDASMMMMSTALALVDKGEMTNKI
FAMDNRSFYKPDLDZ (SEQ. ID. NO. 74)
MSEKAKKGFKMPSSKTVLLIIIAIMAVLTFIPAGAPIEGIYETQPQNPQG
IWDVLMAPIRAMLGTHPEEGSLIKBTSAAIDVAPRLMVGGFLGIVNKTGA
LDVGIASIVKKYKGREKMLILVLMPLFALGGTTYGMGEETMAFYPLLVPV
MMAVGFDSLTGVAIILLGSQIGCLASTLNPFATGIASATAGVGTGDGVLR
LIFWVTLTALSTWFVYRYADKIQKDPTKSLVYSTRKEDLKHFNVEESSSV
ESTLSSKQKSVLFLPVLTFILMVLSRPWTDLGVTIPDDFNTWLTGLPVIG
NIVGSSTSALGTWYFPEGAMLFAFMGILIGVIYGLKEDKUSSFMNGAADL
LSVALIVAIARGIQVIMNDGMITDTILNWGKEGLSGISSQVFIVVTYIFY
LPMSFLIPSSSGLASATMGIMAPLGEFVNVRPSLIITAYQSASGVLNLIA
PTSGIVMGALALGRINIGTWWKFMGKLVVAIIVVTIALLLLGTPLPFLZ (SEQ. ID. NO. 75)
MSNSFVKLLVSQLFANLADIFFRVTIIANIYUSKSVIATSLVPILIGISS
FVASLLVPLVTKRLALNRVLSLSQFQLFTILLAILVGMPTVMQSVAPLVTY
LFVVAISILDGFAAPVSYAIVPRYATDLGKANSALSMTGEAVQLIGWGLG
GLLFATIGLLPTTCINLVLYIISSFLMLFLPNAEVEVLESETNLEILLKG
WKLVARNPRLRLIWSANLLEFSNTIWVSSHLVFVTELLNKTESYWGYSNT
AYSIGIIISGLLRISEKFLAAKWEPQLFTPNLIVFIQNPCLSLDPGWFLF
SPNGCFLLDKKEFPLYGISVEKNTKRKETHMNSLPNHHIQNKSFYQLSFD
GGHLTQYGGLIFFQELFSQLKLKERISKYLVTNDQRRYCRYSDSDILVQP
LPQLLTGYGTDYACKELSADAYFPKLLEGGQLASQPRFSRTDEETVHSLR
CLNLELVEFFLQPHQLNQLIVDEDSTHFTTYGKQEGVAYNAHYRAHGYHP
LYAFEGKTGYCFNAQLRPGNRYCSEEADSFTTPVLERFNQLLFRMDSGFA
TPKLYDLIEKTGQYYUKLKKNTVLSRLGDLSLPCQDEDLTILPHSAYSET
LYQAGSWSHKRRVCQFSERKEONLPYDVISLVTNMTSGTSQDQFQLYRGR
GQAENFIKEMKBGFFGDKTDSSTLIKNEVRMMMSCIAYNLYLFLKHLAGG
DFQTLTIKRFRMLHVVGKCVRTGRKQLLKLSSLYAYSELFSALYSRIRKV
NLNLPVPYEPPRRKASLMMHZ (SEQ. ID. NO. 76)
MMEFFQQLPHLEPYGNPQYFVYVIAATLPIFIGLFFKKRFAWYEVLVSLF
FIVTMLVGGKTNQLAALGIYLCWEILLLLFYKHYRKDGKWVFYLVSFLSL
LPIIFVKVQPAINGTQSLLGFLGISYLTPRSVGIVIELRDGVIKDPTLWE
FLRFLLFMPTFSSGPIDRFKRFNENYQAIPERDELMDMLDESVRYIMWGF
LYKFILAHVLGETLLPPLKNLALQSGGFFNLYALAVMYTFGLELFFDFAG
YSMPALAISNLMGINGIRSPINFNKPFLSRDLKEFWNRWHMSLSFWFRDFVPM
RMVMVLTRKKVFKNRNVTSSMAYIVNMLMGFWHGVTWYYIAYGLFHGLGL
VINDAWVRKKKTLNKERKKAGKAALPENRWIQLLGMVVTFHVVMLSFLIF
SGFLNNLWFKKZ (SEQ. ID. NO. 77)
MLKRLWMIFGPVLIAGLLVFLLIFFYPTEMHHNLGAEKRSAVATTIDSFK
ERSQKVRALSDPNVRFVPPFGSSEWLRFDGAHPAVLAEKYNRSYRYLLGQ
GGAASLNQYFGMQQMLPQLENKQVVYVISPQWFSKNGYDPAAPQQYPNGD
QLTSFLKHQSGDQASQYAATRLLQQPPNVAMKDLVQKLASKEELSTADNE
MIELLARFNERQASFFGQPFSVRGYVNYDKHVAKYLKILPDQPSYQAIEDV
VKADAEKTSNNEMGMENYPYNEQIKKDLKKLKDSQKSPTYLKSPEYNDLQ
LVLTQFSKSKVNPIFIIPPVNKKWMNYAGLREDMYQQTVQKIRYQLESQG
FTNIADFSKDGGEPPFFMKDTIHLGWLGWLAFDKAVDPFLSNPTPAPTYHL
NERFFSKDWATYDGDVKEFQZ (SEQ. ID. NO. 78)
MEKNLKALKQTTDQEGPAIEPEKAEDTKTVQNGYFEDAAVKDRTLSDYAG
NWQSVYPFLEDGTFDQVFDYKAKLTGKMTQAEYKAYYTKGYHTDVTKINI
TDNTMEFVQGGQSKKYTYKYVGKKILTYKKGNRGVRFLFEATDADAGQFK
YVQFSDHNVAPVKAEHFHIFFGGTSQEALFEEMDNWPTYYPDNLSGQEIA
QEMLAHZ (SEQ. ID. NO. 79)
MKDGHLLAHHIRLLNGRIFQKLLSQDPEALYRGEQGKILAVLWNSETGCA
TATDIALATGLANNTLTTMIKKLEEQKLVIVSPCGKDKRKKYLVLTELGK
SQKEVGHRVSQKLDTIFYKGFSEEEIHQFEGFQERILANLKEKGNEVZ (SEQ. ID. NO. 80)
MTNLIATFQDRFSDWLTALSQHLQLSLLTLLLAILLAIPLAVFLRYHEKL
ADWVLQIAGIFQTIPSLALLGLFIPLMGIGTLPALTALVLYAIFPILQNT
GLKGIDPNLQEAGIAFGMTRWERLKIFEIPLAMPVIMSGIRTAAVLIGTA
TLAALIGAGGLGSPILLGIDRNNASLILIGALSSAVLAIAFNFLLKVMEK
KLRTSGFALVALLLGLSYSPALLVQKEKENLVIAGKIGPEPEILANMYKL
LIEENTSMTATVKPNPGKTSFLYEALKKGDIDIYPEETGTVTESLLQPSP
KVSHEPEQVYQVARDGIAKQDHLAYLICPMSYQNTYAVAVPKKIAQEYGL
KTISDLKKVEGQLKAGFTLEFNDREDGNKGLQSMYGLNLNVATIEPALRY
QAIQSGDIQITDAYSTDAELERYDLQVLEDDKQLFPPYQGAPLMKEALLK
KHPELERVLNTLAGKITESQMSQLNYQVGVEGKSAKQVAKEFLQEQGLLK
KZ TABLE 2-continued (SEQ. ID. NO. 81)
MMHTYLQKKIENIKTTLGEMSGGYRRMVAAMADLGFSGTMKAIWDDLPAH
RSFAQWIYLLVLGSFPLWLELVYEHRIVDWIGMICSLTGICVIFVSEGR
SNYLFGLINSVIYLILALQKGFYGEVLTTLYFTVMQPIGLLVIYQAQFKK
EKQEFVARKLDGKGWTKYLSISVLWWLAFGFIYQSIGANRPYRDSITDAT
NGVGQILMTAVYREQWIFWAATNVFSIYLWWGESLQIQGKYLIYLINSLV
GWYQWSKAAKQNTDLLNZ (SEQ. ID. NO. 82)
MRNMKAKYAVWVAPFLNLTYAIVEFIAGGVFGSSAVLADSVHDLGDAIAI
GISAFLETISNREEDNQYTLGYKRFSLLGALVTAVILVTGSVLVILENVT
KILHPQPVNDEGILWLGILTINLLSLVVGKGKTKNESILSLHFLEDTLGW
VAVILMAIVLRFTDWYILDPLLSLVISFFILSKALPRFWSTLKIFLDAVP
EGLDIKQVKSGLERDNVASLNQLNLWTMDALEKNAIVHVCLKEMEHMETC
KESIRIFLKDCGFQNITIEIDADLETHQTHKRKVCDLERSYEHQHZ (SEQ. ID. NO. 83)
MIEYKNVALRYTEKDVLRDVNLQIEDGEFMVLVGPSGSGKTTMLKMINPL
LEPTDGNIYMDGKRIKDYDERELRLSTGYVLQAIALIPNLTVAENIALIP
EMKGWSKEEITKKTEELLAKVGLPVAEYGHRLPSELSGGEQQRVGIVLRA
MIGQPICIFLMDEPFSALDAISRKQLQVLTKELIEFGMTTIFVTHDTDEA
LKLADRJAVLQDGEIRQVANPETILKAPATDFVADLPGGSVHDZ (SEQ. ID. NO. 84)
MSAVAISAMTKVMQETHGNPSSIHGHGRQAGKLLREARQELAQLLRTKPQ
HIFFTSGGTEGNNTTIIGYCLRHQEQGKHIITTAIEHHAVLETIDYLVQH
FGFEATIIQPENQEITAQQIQKALRDDTILVSTMFVNNETGNLLPIAEIG
QILKQHPAAYHVDAVQAIGKIPHSEELGIDFLTASAHKFHGPKGIGFLYA
SSMDFDSYLHGGDQEQKRAGTENLPAIVGMVAALKEDLEKQEEHFQHVQN
LETAFLAELEGIQYYLNRGKHHLPYVLNIGFPGQKNDLLLLRLDLAGIST
GSACTAGVVQSSHVLEAMYGANSERLKESLRISLSPQNTVEDLQTLAKTL
KEUGGZ (SEQ. ID. NO. 85)
MLFKLSKEKIELGLSRLSPARRIFLSFALVILLGSLLLSLOFVQVESSRA
TYFDHLFTAVSAVCVTGLSTLPVAHTYNIWGQIICLLLIGLGLMTFI
GVFYIQSKQKLSLRATIQDSFSYGSLRFVYSIFLTTFLVESLGAILLSFR
LIPQLGWGRGLFSSIFLAISAFCNAGPDNLGSTSLFAFQTDLLVNLVIAG
LIITGGLGPMVWFDLAGHVGRKKKGRLHFHTKLVLLLTIGLLLFGTATTL
FLEWNNAGTIGNLPVADKVLVSFFQTVTMRTAGFSTIDYTQAHPVTLLIY
ILQMFLGGAPGGTAGGLKITTFFVLLVFARSELLGLPHANVARRTIAPRT
VQKSFSFIIFLMSFLIGILLGITAKGNPPFIHLVFETISALSTVGVTANL
TPDLGKLALSVIMPLMFMGRIGPLTLFVSLADYXPEKKDMIHYMKADISI
GZ (SEQ. ID. NO. 86)
MSDRTIGILGLGIFGSSVLAALAKQDMNIIAIDDHAERINQFEPVLARGV
IGDITDEELLRSAGIDTCDTVVVATGENLESSVLAVMHCKSLGVPTVAK
VKSQTAKKVLEKIGADSVSPEYEMGQSLAQTILFHNSVDVFQLDKNVSI
VEMKIPQSWAGQSLSKLDLRGKYNLNILGFREQENSPLDVEFGPDDLLKA
DTYILAVINNQYLDTLVALNSZ (SEQ. ID. NO. 87)
MKLLSIAISSYNAAAYLHYCVESLVIGGEQVGILIINDGSQDQTQEIAEC
LASKYPNIVRAIYQENKCHGGAVNRGLVEASGRYFKVVDSDDWVDPRAYL
KILETLQELESKGQEVDVFVTNFVYEKEGQSRKKSMSYDSVLPVRQIFGW
DQVGNFSKGQYTMMHSLIYRTDLLRASQFZ (SEQ. ID. NO. 88)
MKFNPNQRYTRWSRRLSVGVASVVVASGFFVLVGQPSSVRADGLNPTPGQ
VLPEETSGTKEGDLSEKPGDTVLTQAKPEGVTGTNTNSLPTPTERTEVSE
TSPSSLDTLPBKDEEAQKNPELTDVLXETVDTADvDGTQASPAERRPEQV
KGGVKENTKDSIDVPAAYLEKAEGKGPFTAGVNQVIPYELFAGDGMLTRL
LLKASDNAPWSDNGTAKNPALPPLEGLTICGKYFYEVDLNGNTVGKQGQA
UDQLRANGTQTYKATVKVYGNKDGKADLTNLVATKKVTLNNGLSKETAKETV
QKAVADNVKDSIIDVPAAYLEKGEGPTAGVNHVIPYELFAGDGMLTRLLL
LSDKAPWSDNGDAKNPALSPLGENVKTKGQYFYQVALDGNVAGKEKQALI
DQFRANGTQTYSATVNVYGNKDGKPDLDNIVATKKVTLNNGLSKETVQKA
VADNVKDSIDVPAAYLEKAKGEGPFTAGVNHVIPYELFAGDGMLTRLLLK
ASDKAPWSDNGDAKNPALSPLGENVKTKGQYFYQLALDGNVAGKEKQALI
DQFRANGTQTYSATVNVYGNKDGKPDLDNIVATKXVTININGLISKETVQ
KAVADNVKTVSMFQQPTZ (SEQ. ID. NO. 89)
MKLKSYILVGYIISTLLTILVVFWAVQKMLIAKGEIYFLLGMTIVASLVG
AGISLFLLLPVFTSLGKLKEHAKRVAAKDFPSNLEVQGPVEFQQLGQTFN
EMSHDLQVSFDSLEESEREGLMIAQLSHDIKTPITSIQATVEGILDGIIK
ESEQAHYLATIGRQTERLNKLVEELNFLTLNTARNQVETTSKDSIFLDKL TABLE 2-continued

LIECMSEFQFLIEQERRDVHLQVIPESARIEGDYAKLSRJLVNEITVSSQ
YGLGSTETLVLNLSGSENKAZ (SEQ. ID. NO. 90)
MFGQTAQHGLTNSLKDFWIFLLNIGPQLAFFCQMLRCSRSVEQGTGNHRR
EFNMIQQIFSHFGMTHLGQIKLVYQESIDLELLVNALNHHLLIDRLVLTP
NQITIEIDRQIVHGLDLLKGRXDKEIIDIKSMFRQLELASTQQICPNQRV
HHGILAFGEISDLVPAKNLPNRQDZ (SEQ. ID. NO. 91)
MEHLATYPSTYGGAPAALGWLAVGLSGMGSAYGVGKAGQSAAALLKEQPE
KFASALILQLLPGTQOLYGFVIGLIWLQLTPSLPLEKGVAYFVALPIA1V
GYFSAKHQGNVAVAGMQILAKRPKEFMKGAILAAMVETYAILAIWVSFIL
TLRVZ (SEQ. ID. NO. 92)
MLKSEKQSRYQMLNEELSFLLEGETNVLANLSNASALIKSRFPNTVFAGF
YLFDGKELVLGPFQGGVSCIIRIALGKGVCGEAAGHFQETVIVGDVTTYL
NYISCDSLAKSEIVVPMMKNGQLLGVLDLDSSEIEDYDAMDRDYLEQFVA
ILLEKTAWDFTMFEEKSZ (SEQ. ID. NO. 93)
MSVLEKDLHVEIEGKEILKGVNLTLTGEAAIMGPNGTGKSAAIMGNPNYE
VTKGEVLFDGVNILELEVDERARMGLFLAMQYPSEIPGITNAEFLRAAMN
AGKEDDEKISVREFITKLDEKMELLNMKEEMAERYLNEGFSGGEKKRNEI
LQLLMLEPTFALLDEIDSGLDIDALKVVSKGVNAMRGEGFGAMIITTHYQ
RLLNYITPDVVHVMMEGRVVLSGGPELAARLEREGYAKLAEELGYDYKEE
LZ (SEQ. ID. NO. 94)
MPYKRQRSFSMALSKLDSLYMAVVADHSKNPHHQGKLEDAEQISLNNPTC
GDVINLSVKFDAEDRLEDIAFLNGCTISTASASMMTDAVLGKKQEILELA
T1FSEMVQGQKDERQDQLGDAAGVAKFPQPJKCATWNALKIENQEKQZ (SEQ. ID. NO. 95)
MKIQDLLRKDVMLLDLQATEKTAVIDEMIKNLTDHGYVTDEFETFKEGIL
AREALTSTGLGIAMPHSKNAAVKEATVLFAKSNKGVDYESLDGQATDLFF
MIAAPEGANDTHLAALAELSQYLMKDGFADKLRQATSADQVIELFDQASE
KTEELVQAPANDSGDFIVAVTACTTGIAHTYMAQEALQKVAAEMGVGIKV
ETNGASGVGNQLTAEDIRKAKAIIIAADKAVEMDRFDGKPLINRPVADGI
RKTEELINLALSGDTEVYRANGAJ (AATASNEKQSLGGALYLMSGVSQML
PFVIGGGIMIALAFLIDGALGVPNENLGNLGSYHELASMFMKIGGAAFGL
MLPVFAGYVAYSIAEKPGLVAGFVAGALAKEGFAFGKIPNDFLGGLGGGS
AVLLGIVLGGMMAVDMGGPVNKAAYVFGTGTLAATVSSGGSVAMAAVMAG
GMVPPLAIFVATLLFVLVGAIVSGVVYGYLRKPQAZ (SEQ. ID. NO. 96)
MANKNTSTTRRRPSKAELERKEAIQRMLISLGIAILLIFAAFKLGAAGIT
LYNLIRLLVGSLAYLAIFGLLIYLFFFKWIRKQEGLLSGGFFTIFAGLLLI
FEAYLVWKYGLDKSVLKGTMAQVVTDLTGFRTTSFAGGGLIGVALYPTAF
LFSNIGTYFIGSLILVGSLLVSPWSVYDIAEFSRGFAKWWEGHERRXEER
FVKQEEKARQKAEKEARLEQEETEKALLDLPPVDMETGEILTEEAVQNLP
PIPEEKWVEPEI1LPQAELKFPEQEDDSDDEDVQVDFSAKEALEYKLPSL
QLFAPDKPKDQSKEKKWRENIKILEATFASFGIKVTVERAEIGPSVTKYE
VKPAVGVRVNRISNLSDDLALALAAKDVRIEAPIPGKSUGTEVPNSDIAT
VSFELWEQSQTKAENFLEIPLGKAVNGTARAFDLSKMPHLLVAGSTGSGK
SVAVNGIIASILMKARPDQVKFMMVDPKMVELSVYNDIPILLJPVVTNPR
KASKALQKVVDEMENRYELFAKVGVRNIAGFNAKVEEFNSQSEYKQIPLP
FIVVIVDELADLMMVASKBVEDAIIRLGQKARAAGIHMILATQRPSVDVI
SGUKANVPSRVAFAVSSGTDSRTLDNGAEKLLGRGDMLFKPIDENHPVRL
QGSFISDDDVERIVNPIKTQADADYDESFDPGEVSENEGEFSDGDAGGDP
LFEEAXSLVIETQKASASMIQRRLSVGFNRATRLMEELEIAGVIGPAEGT
KPPJCVLQQZ (SEQ. ID. NO. 97)
MSYFKKYKFDKSQFKLGMRTKTGIAVFLVLLIFGFGWKGLQIGALTASVN
LRESFDESVHFGTSRILGNSIGGLYALVFLLNTFFWEAWVTLVVVPICTM
LTIMTNVAMNNCAGVIGGVAAMLHTLSPSGETILYVFVRVLETPMGVFVA
UVNYDIDRIRLFLEKKEKZ (SEQ. ID. NO. 98)
MNKSEHRHQLIRAUTKNKIHTQAELQALLAENDIQVTQATLSRDIKNMNL
SKVREEDSAYYVLNNGSISKWEKRLELYMEDALVWMRPVQHQVLLKTLPG
LAQSFGSHDTLSFPDAATLCGNDVCLIICEDADTAQKCFEELKKFAPPFF
FEEZ (SEQ. ID. NO. 99)
MCSIKLNALSYMGRVLNIFPItTGTYVARVLDRTDYGYFNSVDTILSFFL
PFATYGVYNYGLRAISNVKDNKKDLNRTFSSLFYLCIACTILTRAVYILA

TABLE 2-continued

```
YPLFFTDNPIVKKVYLVMGIQLIAQFSIEWVNBALENYSILFYKTAFRIL
MLVSIFLPVKNEHDEVVYTLVMSLTLINYLSYFWKRDIKLVKIHLSDFKP
LFLPLTAMLVANANMLVFTTLDRLFLVICTGIDVNVSYAQRJVTVIAGVV
TGAIGVSVPRLSYYLGKGDKEAYVSLVNRCSRIFNPPHPLSPGLMVLGNA
ILLYGSEKYIGGGILTSLFAFRTULALDTILGSQILFTNGYHKRTVYTVF
AGLLNLGLNSLLFFNHVAPEYYLLTRMLSETSLLVFYIIFEHRKQLIHLG
HIFSYTVRYSLFSLSWAIYFUNFVYPVDMVINLPFLINTGLIVVLLSAISY
ISLLVFRKDStFYEFLNHVLALKNKFKKSZ (SEQ. ID. NO. 100)
MELFMKITNYEIYXLKKSGLTNQQILICVLEYGENVDQELLLGDIADISG
CRNPAVFMERYPQIDDAHLSKEFQKFPSPSILDDCYPWDLSEIYDAPVLL
FYKGNLDLLKFPKVAVVGSRACSKQGAKSVEKVIQGLENELVIVSGLAXG
DTAAHMAALQNGGKTAVIGTGLDVFPKANKRLQDYIGNDHLVLSEYGPGE
QPLKHFPARNRIAGLCRGVIVAEAKMRSGSLTCERAMEEGRDVFAIPGSI
LDGLSDGCIIMLIQEGAKLVTSGQDVLAEFEPZ (SEQ. ID. NO. 101)
MKQLTVEDAKQIELEILDYIDTLCKKIININYIINYGTLIGAVRHEGFIP
WDDDIDLSMPRBDYQRFINIFQKKSKYKLLSLERDKNYNNFIKTDSTRK
IIDTRNTKTYESGIIDIFPDRFDDPKVIDTCYKESKLLSFSKHKNWYKDS
LLKDWIRTAFWLLLRPVSPRYFANKIEKEIQKYSRENGQYMAFIPSKFKE
KEVFPSGTFDKTIDLPPENLSLPAPEKPDTILTQFYGDYMTLPPEEKRFY
SHEFHAYKLEDZ (SEQ. ID. NO. 102)
MIKINHLTITQNKDLRDLVSDLTMTIQDGEKVAIIGEEGNGKSTLLKLMG
EALSDFTIKGNIQSDYQSLAYPQKVPEDLKKKTLHDYFFLDSIDLDYSIL
YRLAEELHFDSNRFASDQEIGNLSGGEALKIQLIHELAICPFEILFLDEP
SNDLDLETVDWLKGQIQKTRQTVTFISHDEDPLSETADTIVLRLVKHRKE
AETHVEHLDYDSYSEQRKANFAKQSQQAANNQRAYDKTMEKIRRVKQNVE
TALRATKDSTAGRLLAKKMKTVLSQEKRYEKAAQSMTQKPLEEEQIQLFF
SDIQPLPASKVLVQLEKENLSIDDRVLVQKLQLTVRGQEKIGIIGPNVQ
KSTLLAKLQRLLNDKREISLGIMPQDYHXJCLQLDLSPIAYLSKTGEKEE
LQKQSHLASLNFSYPMQHQRSLSGGQQGKLLLLDLVLRKPNFLLLDEPTR
NPSPTSQPQIRKLFATYPGGLITVSHDRRFLKEVCSIIYRMTEHGLKLVN
LEDLZ (SEQ. ID. NO. 103)
MKPKTFYNLLAEQNLPLSDQQKEQFERYFELLVEWNEKINLTAITDKEEV
YLKNFYDSIAPILQGLIPNETIKLLDIGAGAGFPSLPMKILYPELDVTII
DSLNKRINFLQLLAQELDLNGVHFYHGRAEDFAQDKNFRAQYDFVTARAV
ARMQVLSELTIPYLKVGGKLLALKASNAPEELLEAKNALNLLFSKVEDNL
SYALPNRDPRYITVVEKKKETPNKYPRKAGMPNKRPLZ (SEQ. ID. NO. 104)
MSIKUAVDIDGTLVNSQKEITPEVFSAIQDAKEAGVKVVIATGRPIAGVA
ICLLDDLQLRDEGDYVVTFNGALVQETATGHEIISSLTYEDYLDMEFLSR
KLGVHMHAITKDGIYTANRNIGKYTVHESTLVSMPYRTPEEMAGKJVKCM
FIDEPEIPEIKKIAKYITKTNDESGVAHAIRTWVLZ (SEQ. ID. NO. 105)
MTWIILGVIALIVIIVSYNGLVKNRMQTKEAWSQIDVQLKRRNDLLPNLI
ETVKGYAYEGLEKVAELRNQVTSPAEAMKASDALTRQVSGIFAVAESYPD
LKASANPVICLQEELTNTENKSYSRQLYNSVVSNYNVKLETFSNIIAGMF
GFKAADFLQTPEEEKSVPKVDPSGLGDZ (SEQ. ID. NO. 106)
MLFDQIASNKRKTWILLLVFFLLLALVGYAVGYLIRSGLGGLVIALIIGF
IYALSMIFQSTEVMSMNGAREVDEQTAPDLYHVVEDMALVAQIPMPRVFI
IDDPALNAFATGSNPQNAAVAATSGLLAIMNREELEAVMGHEVSHIRNYD
IRISTIAVALASAITMLSSMAGRMMWMGGAGRRRSDDDRDGNGLEIIMLV
VSLLAIVLAPLAATLVQLAISRQREFLADASSVELTRNPQGMINALDKLD
NSKPMSRHVDDASSALYINDPKKGGGFQKLFYTHPPtSERIERLKQMZ (SEQ. ID. NO. 107)
MKLNIQEIRKQSEGLNFEQTLDLVDDLRARNQEILDVKDILAVGKVQYED
RMYFLDYQLSYTIVLASSRSMEPVELVESYPVTEVFMEGATNQLDQEVLD
DDLVLPIENGELDLAESVSDNLLNIPIKVLTAEEBAGQCPISGNDWQIMT
EEEYQAQKAVKKEENSPFAGLQGLFDGDEZ (SEQ. ID. NO. 108)
MKRQLALVVPSGGQDSRTCLWVMQHYETVEAVTFAYGQRMHLEQRRREIA
KEQGRHHILDMSLLGQITAQPDFATIHSYIPDKLCVESKSLKLYLFSYRN
HGDFHENCNTIGKDLVNLLDPRYLEVWGKFTPRGGISDPYYNYGKQGTKY
EGLAEQRLFQHDLYPEKIDNRZ (SEQ. ID. NO. 109)
MTETVEDKVSHSn*GLDILKGIVAAGAVISGTVATQTKVFTNESAVLEKT
```

```
VEKTDALATNDTVVLGTISTSNSASSTSLSASESASTSASESASTSASTS
ASTSASESASTSASTSISASSTVVGSQTAAATEATAKKVEEDRKKPASDY
VASVTNVNLQSYAgRRKRSVDSIEQLLASIKNAAVSGNTVNGAPAINASL
NLAKSETKVYTGEGVDSVYRVPIYYKLKVTNDGSKLTFTYTVTYVNPKTN
DLGNISSMRPGYSYNSGTSTQTMLTLGSDLGKPSGVKNYITDKNGRQVLS
YNTSTMTRQGSGYTWGNGAQMNGFFAKKXGYGLTSSWTVPITGTDTSFTFT
PYAARTDRIGINYFNGGGKVVESSITSQSLSQSKSLSVSASQSASASAST
SASASTSASASASTSASASASTSASVSASTSASASASTSASASASTSASA
SESASTSASASASTSASASASTSASASASTSASESASTSASASASTSASE
SASTSASASASTSASTSASASTSASGSASTSTSASASTSASASASTSASA
SISASESASTSASESASTSTSASASTSASESASTSASASASTSASASASA
SASASASTSASASASTSASESASTSASASASTSASASTSASASASTSASA
SASTSASVSASTSASASASTSASASASTSASESASTSASASASTSASASA
STSASASASTSASASASTSASASASTSASESASTSASASASTSASASAST
SASGSASTSTSASASTSASASASTSASASASISASESASTSASESASTST
SASASTSASASTSASASASTSASASASTSASASARQVRRPQPVHLNRM
QPVRQPQQVLVHQLQHQRVHRLQHQPVPRLQRQPVRQLQQVPVLQSQHQQ
VLQPQHRQVPRLQQAHQHLNQRRQAPQLQQVPVRQPQRRQVRQPQQVLVH
QLQHQRVHRLRRQPVHQSQQVPVRQLPHQQVPRLQQAPVRRLQQVLAPQP
QPQPVRQPQQVSQRLNRIIQRVRTQRLLQQVLAPQPQRQQVHRLQRQRVR
LNRHQRVRPLQQVLAPQPQRQQVHRLQHQRVPLQQVLAPQPQRQQVHRLQRQ
RVRLSQHQRVRQPQQAHQLLNLHQPVRQPQHRQAPQLQQVPVRQPQRRQV
RRLQQVPVRQPQQVPVRQPQRRQVRRPQPVHLNRNQPVRQPQQVLVHQLQ
MQRVHRLQHQPVHQSQQVPVRQPRINKCLGFSKYZ (SEQ. ID. NO. 110)
MGVETWFYSSICWLALGLGSVWKFPYMTAANGGGGFLLIFLLSTILIGPL
LLAEALGRSAGVSAIKTFGKLGKNNKYNIGWIGAFALFLLSFYSVIGGWT
LVYLGIEFGKLFQLGGTGDYAQLFTSfLSNPAIALGAQAAPILLNIFIVS
RGVQKGIERASKVMMPLLFIVFVFIIGRSLSLPNAMEGVLYPDSKLTSTG
LLYALGGQSFALSLGVTVMLTYASYLDKXTNLVQSGISIVAMNISISIMAG
LAFQARSPFNQSEGGPSLLVLPQLIDKMPFGTUYVLFLLLFLFATVTFSV
VMLEINVDNITNQDNSKRAXWSVILGLTFVFGTPSALSYGVMADVHIFGK
TFFDAMDFLVSNLLMPFGALYLSLTGYTFKKALAMEELHLDERAWKQGLF
QVWLFLLRFFVSSFQSSSLWSSLPNLCNQKGLEZ (SEQ. ID. NO. 111)
MLKKWQLKDVILLAFLSIFFC3GVFVGSGYVYNELSLLLTPLGLQAFANE
ILFGLWCMAAPIAAIFVPRVGSATIGEVLAALAEVLYGSQFGLGALLSGF
VQGLGSEFGFIVTKNRYESWLSLTANSIGITLVSFVYEYIKLGYYAFSLP
FVLSLLVVRFISVYFFCTILVRAIVKLYHQFATGGKAZ (SEQ. ID. NO. 112)
MVKVATQTPHSLLLILSLETSFIPSIALTLSVVAPCILFMLYYRRFKMLA
WMLLLAILPSFANYWAVQLHGDASQAVMLGTRAFVTVCIGLVFVSSVSLK
ELLLYLAQKGLSRSWSYALIVVFNSFPLQQEIKSLKEACLLRGQEHFWS
PLIYSKVLMTVFRWRHLYLRALSAHGYDEHAQLKNSYRTFYPKKTKLIYL
LFFLLLQTSLLZ (SEQ. ID. NO. 113)
MRKHQLQVHKLTLSMMALDVVLTPRIEGMAPMSSVVNLAGIMMGPVYALA
MATVRAFXRNfFRQGIPPLALTGATFGALLAGLFYKYGRKFHYSALGEIL
GTGUGSIVSYPVMVLFTGSAAKLSWFEYTPREFGATLIGTALSFIAFRFL
KQEFFKKVQGYFFSERIDZ (SEQ. ID. NO. 114)
MQETNPFPIGSSSLIHCFLNEISCEMLANGILALGCKPVMADDSREVLDF
IKQSQALNLGHLSAEKEKJJRMAASYANQSSLPMVVDAVGVRSSIRKSLV
KDLLDYRPRVLKGNMSEIRSLVGLKHHGVGVDASAJCDQETEDLLQVLKD
WCQTYPGMSFLVTGPKDLVVSKNQVAVLGNGCTELDWITGTGDLVGALTA
VFLSQGKTGPEASCLAVSYLNIAAEKIVVQOMGLEEFRYQVLNQLSLLRR
DENWLDTIKGEVYEZ (SEQ. ID. NO. 115)
MNHKAILSDVMGNATALEAVL&DAXNQGASEYWLLGDIFLPGPGANDLVA
LLKDLPPASVRGNWDDRVLEALDGOYGLEDPQEVQLLRMTQYLMERMDPA
TIVWLRSLPLLEKKEIDGLRFSISHNLPDKNYGGDLLVENDTEKFDQLLD
AETDVAVYGHVHKQLLRYGSQGQQIINPGSIGMPYFNWEALKNHRSQYAV
IEVEDGELLNIQFRKVAYDYEAELELAKSKGLPFIEMYEELRRDDNYQGH
NLELLASLIEKHGYVEDVKNFFDFLZ (SEQ. ID. NO. 116)
MNVQIVRIIPTLKANNRKLNETFYIETLGMKALLEESAFLSLGDQTGLEK
LVLEEAPSMRTRKVEGRKKLARLIVKVENPLEIEGTTDSIHRLYKGQNGY
AFEIPSPEDDLILIHAEDDIASLVEVGEKPEQTDLASKEISMELHLDIFL
ESSEIGASLDFIPAQGQDLTVDNTVTWDLSMLKFLVNEDLSLRQKFEST
EYFIPKSEKGKDNVELWEVZ
```

TABLE 2-continued (SEQ. ID. NO. 117)
MKWTKHIIKKIEEQIEAGIYPGASFAYFKDNQWTEFYLGQSDPEHGLQTE
AGLVYDLASVSKVVGVGTVCTFLWEIGQLDIDRLVIDFLPESDYPDTIRQ
LLTRATDLDPPIPNRDLLTAPELKEAMFHLNRSQPAFLYSDVHPLLLGFL
EFNQDLDVILKDQVWKPWGMTETKFGPVELAVPTVRGVEAGIVHDPKARL
LGREAGSAGLFSTIKDLQIFLEHYLADDFALNQNFSPLDDKERSLAWNLE
GDWLDHTGYTGTFIMWNRQKQEATFLSNRTYEKDERAQWILDRINQVMNL
IEEZ (SEQ. ID. NO. 118)
MMKKTYNHILVWGVIFYSICIVCFCFTPQEQSTVGVGTPGIQHLGRLVFL
LTPFNSLWKLGEVSDIGQLCWIFLQNILNVFLFFPLIFQLLYLFPNLRKT
KKVLLFSFLVSLGIECTQLILDFFFDFNRVFEIDDLWTNTLGGYLAWLLY
KRLHKVRNZ (SEQ. ID. NO. 119)
MKIPLLTFLARHKFVYVLLTLLFLALVYRDVLMYFFDIHAPDLAKFDGQA
IKNDLLKSALDFRILQNLGQSFIIPIIIVLLGFQYIELKNXVLRLSRBVS
YQGLKRKLTLQVASIPCLIYLVTVLUAHTYFFGTFSPLGWNSLSDGSGLQ
RLLDGEIKSYLFFTCVLLIGIFINAIYFLQIVDYVGNVTRSAITYLMFLW
LGSMLLYSALPYYMVPMTSLMQASYGDVSLMKLPYILYIVPYMVLEICYE
DNVZ (SEQ. ID. NO. 120)
MFKVLQKVGKAFMLPIAILPAAGLLLGLGGALSNPRTIATYPILDNSIFQ
SIFQVMSSAGEVVFSNLSLLLCVGLCIGLAKRDKGTAALAGVTGYLVMTA
TUALVKLFMAEGSAIDTGVIGALVVGIVAVYLHNRYNNIQLPSALGGGSP
PISFSSILIGFVFFVWPPFQQLLVSTGGYSQAGPIGTLYGFLMRLSGAVG
LHHIIYPMTYTELGGVETVAGQTVGAQKIPAQLADLAHSGLFREGTREAG
RFSTMMFGLPAACLAMYHSVPKNRRKKYAGLFGVALTSFITGITEPIEFM
FLPVSPVLYVHAFLDGVSPFIADVLNISIGNTFSGGVIDFRLFGILQGNA
KTNWVLQIPGLIWSVLYYIIFRWFTQNVLTRGEEVDSKEISESADSTSNT
ADYLKQDSLQIIRALGGSNNIEDVDACVTRLRVAVEVNQVDKALLKQIGA
VDVIEVKGGIQAIYGAKAILYKNSINEILGVDDZ (SEQ. ID. NO. 121)
MKFRKLACVLAGAAVLGLAACGNSGGSKDAAKSGGDGAKTEITWWAFPVF
TQEKTGDGVGTYEKSUEAFEKANPDIKVKLETDFKSGPEKNTAIEAGTAP
DVLFDAPGRIIQYGKNGKLAELNDLFTDEFVKDVNNENRVQASKAGDKAY
MYPISSAPFYMAMNKKMLEDAGVANLVKEGWITDDFEKVLKALKDKGYTP
GSLFSSGQGGDQGTRAFISNLYSGSVTDEKVSKYTRDDPKFVKGLEKATS
WIKDNLINNGSQFDGGADIQNFANGQTSYTILWAPAQNGIQAKLLEASKV
EVVEVPPFPSDEGKPALEYLVNGFAVNNKDDKKVAASKKIQFIADDKEWGP
KDVVRTGAFPVRTSFGKLYEDKRMETSGWTQSPYYNTIDGFAEMRTLWPM
LQSVSNGDEKPADALKAFTEKANETIKKAMKQZ (SEQ. ID. NO. 122)
MQSTEKKPLTAFTVISTIILLLLTVLFIPPFYWILTGAFKSQPDTIVIPP
QWFPKMPTMENFQQLMVQNPALQWMWNSVFISLVTMFLVCATSSLAGYVL
AKKRFYGQRILFAIFIAAMALPKQVVLVPLVRIVNFMGHDTLWAVILPLI
GWPFGVFLMKQFSENIPTELLESAKIDGCGEIRTFWSVAPPVKPGFAALA
IPTFINTWNDYFMQLVMLTSRNNLTISLGVATMQAEMATNYGLMAGAALA
AVPIVTVFLVFQKSTQGITMGAVKGZ (SEQ. ID. NO. 123)
MKIMFKNFNNILLNRCIVLLLRIVLMMILINHLLSTAVQKQDAVIFFKRE
LSFSYNDYSEANLEIPICLLNLSIFMVGWLSVILLESDLADHYHHLIRY
QSSSFFDYTRKRLVVISKFFTQDLFVWFLGLLPLGIHFKTVALFFLLAQL
MMLYLLLSYUALISAGAGFSFFLYPLAFVGGQEWMMDHIVTVYLVLLSLLV
MLVSRLESKFKKGZ (SEQ. ID. NO. 124)
MGKGEMGKGVIGLEFDSEVLVNKAPTLQLANGKTATFLTQYDSICTLLPA
VDKEDIGQEIIFIAKGSIESMHNLPVNLAGARVPGVNGSKAAVHEVPEFT
GGVNGTEPAVHEIAEYKGSDSLVTLTTGKDYTYKAPLAQQALPETGNKES
DLLASLGLTAFLGLFTLGKXREQZ (SEQ. ID. NO. 125)
MKKTFFLLVLGLFCLLPLSVIAIDFKINSYQGDLYIHADNTAEFRQKIVY
QFEEDFKGQIVGLGRAGKMPSGFDIDPHPKIQAAKNGAELADVTSEVTEA
DGYTVRVYNPGQEGDIVEVDLWNL,KNLLPLYDDIAELNWQPLTDSSES
IEKFEFHVRGDKGAEKLFFTGKLBGTIEKSNLDYTIRLDNLPAKRGVELH
AYWPRTDFASARDQGLKNRLEENKIEDSIVREKDQSKQLVTWVLPSILS
ISLLLSVCYFIYRRKTRPSVKYAKNHRLYEPPMELEPMVLSEAVY5TSLE
EVSPLVKGAGKFTFDQLIQATLLDVIDRGNVSIISEGDAVGLRLVKEDGL
SSFEKDCLNLAFSGKICEETLSNLFADYKVSDSLYRRAKVSDEKRIQARG
LQLKSSPEEVLNQMQEGVRKRVSFWGLPDYYRPLTGGEKALQVGMGALTL
PLFIGFGLFLYSLDVNGYLYLPLPILGFLGLVLSVFYYWKLRLDNRDGVL (SEQ. ID. NO. 126)
NBAGAEVYYLWTSFENMLRIARLDQAELESVVWNRLLVYATLFGYADKVS
HLMKVNQIQVENPDINLYVAYGWHSTYHSTAQMSHYASVANTASTYSVSS
GSGSSGGGFSGGGGGGSIGAFZ (SEQ. ID. NO. 126)
MKKVRKIFQKAVAGLCCISQLTASSIVALAETPETSPAIGKVVIKBTOEG
GALLGDAVFELKNNTDGTTVSQRTEAQTGEAIFSNIKPGTYTLTEAQPPV
GYKPSTKQWTVEVEKNGRTTVQGEQVENREEALSDQYPQTGTYPDVQTPY
QUCVDGSEKNGQHKALNPNPYERVPEGTLSKRIYQVNNLDDNQYGIELTV
SGKTVYEQKDKSVPLDVVILLDNSNSMSNIRNKNARRAERAGEATRSLID
KTSDSENRVALVTYASTIFDGTEFTVBKGVADKNGKRLNDSLFwNYDQTS
VITNTKDYSYLKLTNDKNDIVELKNKVPTEAEDHDGNRLMYQFGATFTQK
ALMKADEILTQQARQNSQKVIFHITDGVPTMSYPINFNHATFAPSYQNQL
NAFFSKSPNKDGLLSDRTQATSGEITIVRGDGQSYQMFTDKTVYEKGAPA
AFPVKPEKYSEMKAAGYAVGDPNGGYWLNWRESILAYPFNSNTAKITNHG
DPTRWYYNGNIAPDGYDVFTVGIGINGDPGTDEATATSFMQSISSKPENY
TNVTDTRKILEQLNRYFHTIVTEKKSENGTITDPMGELIDLQLGTDGRFD
PADYTLTANDGSRLENGQAVGGPQNDGGLLKNAKVLYDRREKRIRVTGLY
LGTDEKVTLTYNVRLNDEFVSNKFYDTNGIfLRLHPKEVEQNTVRDFPIP
KIRDVRKYPEITSKEKKLGDLFBIKVNKNDKKPLRGAVFSLQKQHPDYPD
IYGAIDQNGTYQNVRTGEDGLTFKNLSDGKYRLFENSEPAGYKPVQNKPI
VAFQIVNGEVRDVTSVPQDIPAGYEFTNDKHYRRNEPIPPKREYPRTGGI
GMLPFYLIGCMMMGGVLLYRRKHPZ (SEQ. ID. NO. 127)
MKSINKFLTMLAALLLTASSLFSAATVFAAGTTTSVTVHKLLATDGDMD
KIANELETGNYAGNKVGVLPANAKEIAGTLTGSKAVPIEIELPLNDVVDA
HVYPKNTEAKPKIDKDFKGKANPDTPRVDKDTPVNHQVGDVVEYEIVTKI
PALANYATANWSDRMTEGLAFNKGTVVTVDDVALEAGDYALTEVATGFDL
KLTDAGLAKVNDQNAEKTVKITYSATLNDKAIVEVPESNDVTINYGNNPD
HGNTPKPNKPNENGDLTLTKTWVDATGAPIPAGAEATFDLVNAQTGKVVQ
TVTLDKNTVTVNGLDKNTEYKFVERSIKGYSADYQEITTAGEIAVKNWKD
ENPKPLDTEPKVVTYGKKFVCNKDKDNRIAGAEFEWVADKDNENVVKLVS
DAQGRFEITGLLAGTYYLEETKQPAGYALLTSRQKFEVTATSYSATGQGI
EYTAGSGKDDATKVVNKKITIPQTGGIGTIIFAVAGAAIMGIAVYAYVKN
NKDEDQLAZ (SEQ. ID. NO. 128)
MTMQKMQKMSRJFFVMALCPSLVWGAHAVQAQEDHTLVLQLENYQEVVSQ
LPSRDGHRLQVWKLDDSYSYDDRVQIVRDLHSWDENKLSSFKKTSFEMTF
LENQIEVSHIPNGLYYVRSUQTDAVSYPAEPLFEMTDQTVEPLVIVAKJC
TDTMVKLIKVDQDHNRLEGVGFKLVSVARDVSEKEVPLIGEYRYSSSGQV
GRTLYTDKGEIPVRNLPLGNYRYKEVELAGYAVTTLDTDVQLVDHQLVTI
TVVNQKLPRGNVDFMKVDORTNTSLQGAMFKVMKEESGHYTPVLQNGKEV
VVTSGKDGRFRVEGLEYGTYYLWELQAPTGYVQLTSPVSFTIGKDTRKEL
VTVVKNNKRRJDVPDTGEETLVYLDACCHVVWZ (SEQ. ID. NO. 129)
MSHIYLSIFTSLLLMLGLVNVAQADEYLRIGMEAAYAPFNWTQDDDSNA
VKIDGTNQYANGYDVQIAKKAKDLGKEPLVVKTKWEGLVPALTSGKIDMI
IAGMSAERICQEIAPSSSYYTSEPVLLVKKDSAYAS&YLDDPNGAKITSQ
QGVYLYNLL4QIPGAKICITAMGDFAQMRQALEAGVDAYVSERPEALTAE
AANSKFKMIQVEPGFKGEEDTAIAIGLRKNDNRISQINASIETSKDDQVA
LMDRMIKEGQPAEATITEETSSSFFSQVAKILSENWQQLLRGAGITLLISV
GTIIGLIIGLAIGVFRTAPLSENKVIYGLQKLVGWVLNVYIEIRGTPMVQ
SMVIYYGTAQAFGINLDRTLAAIFIVSINTGAYMTEVRRGILAVDKGQFE
AATALGMTHNQTMRKWLPQVVRNILPATGNEFVINIKDTSVLNVISVVEL
YFSGNTVATQTYQYFQTFRIIAVIYFVLTFTVTRILRFIERRMDMDTYTR
OANQMQTEDLKZ (SEQ. ID. NO. 130)
MTQAILEIKHLKKSYGQNEVLKDSLTHKGEVISIIGSSGSGKSTFRINL
LETPTDGQYHGQNVLEKGYDLTQYREKLGMVFQSFNLFENLNVLENTIVA
QTRVLKRERTEAEKIAKENLEKVGMGERYWQAKPKQLSGGQKQRVALARA
LSMNPDAILFDETSALDPEMVGEVLKIMQDLAQEGLTMIVVTHEMEFARD
VSHRVFMDKGVLAEEGKPEDLFTNPKEDRTKEFLQRYLKZ (SEQ. ID. NO. 131)
MKKYQLLFSAVFSYLFFVFSLSQTLIVQNYWQFSSQGNLPWIQNILSLL
FIGVMIVLVQHGYLFPJPPJCKWLWYSLTVLVLVQISFNVQTAKHVQS
TAEGWAVLIGYSGTNFAELGIYALFFLVPLMEELYRGLLQHAFFKRFGLD
LLLPSILFALPHFSSLPSLLDIFVFATVGIIFAGLTRYTKSIYPSYAVHV
INNIVATFPPFLLTFLHRVLGZ (SEQ. ID. NO. 132)
MNKKQWLGLGLVAVAAVGLAACGNRSSRNAASSSDVKTKIVTDTGGVDDK
SFNQSAWEGLQAWGKEHNKDNGFTYFQSTSEADYANNLQQAAGSYNLIFG
VGFALNNNAVKDAAKEHTDLNYYLIDDVIKDQKNVASVTFADNESGYLAGV
AAAKTTKTKQVGFVGGIESEVISRFEAGFKAGVASVDPISKVQVDYAGSF TABLE 2-continued GDAAKGKTIAAQYAAGADIVYQVAGGTGAGVFAEAKSLNESRPENEKVWI
GVDRDQEAEGKYTSKDGKESNFVLVSTLKQVGTTVKDISNKAERGEFPGG
QVIVYSLKDKGVDLAVTNLEEGKKAVEDAKAKILDGSVKPEKZ (SEQ. ID. NO. 133)
MSKKLQQISVPLISVFLGILLGAIVMWIFGYDAIWGYEELPYTAFGSLRG
IGEIFRAMGPLVLIGLGFAVASRAGFPNVGLPGQALAGWILSGWFALSHP
DMPRPLMILATIVIALIAGGIRAYLGTS2VIVTIMMNYIVLY
VGNAPIHAPPKDFMQSTDSTIRVGANATYQTPWLAELTGNSRMNIGIFFA
IIAVAVIWFMLKKTRLGFEIRAVGLNPMASEYAGISAKRTHLSMIISGAL
AGLGGAVEGLGTFQNVYVQGSSLAIGFNGMAVSLLAANSPIGILPAAFLF
GVLQVGAPGMNAAQVPSELVSIVTASIIFFVSVEYLIERPVKPKKQVKGG
KZ (SEQ. ID. NO. 134)
MGVKKLKLTSLLGSLLITACATNGVTSDITAESADWSKLVYPFAEIIRFL
SFDISIGVGuLFRVLIRTVLLPVQVQMVASRKMQEAQPRIKALREQYPGR
DMESRTKLEQEMRKVFKEMGVRQSDSLWPILIQMPVILALFQALSRVDFL
KTGHPLWINLGSVDTRLVLPILAAVFTFLSTWLSNKALSERNGATTAMMY
GIPVLIRPAVYAPGGVALYWTVSNAYQVLQTYFLNNPFKIIAEREAVVQA
QKDLENRKRKAKKKAQKTKZ (SEQ. ID. NO. 135)
MVIDPFANELDYYLVSHFHSDHIDPYTAAAILNNPKLHVKFIGPYHCGR
IWEGWGVKERFLVVKPGDTIELKDMKIHAVESFDRTCLVTLPVNGADETG
GELAGLAVTDEEMAQKAVNYIPETPGGTIYHGADSHFSNYFAJCHGKDFK
IDVALNNYGENPVGIQDKMTSIDLLRMAENLRTKVIIPVHYDIWSNFMAS
TNEILELwKMRKDRLQYDFHPFIwEVGGKYTYPQDQHLVEYHHPRGFDDC
FEQDSNIQFKALLZ (SEQ. ID. NO. 136)
MFLSGWLSFANYIHDLLVLFPDSPFLNAFESAIAAPLVEELSCVFVTM4P
VRXKSTLTGIASOLCFQMIKNGYIRTDLPEGFDFISRILERJISGIASHW
TFSGLAVVGVYLLYRAYKC3QKVGKKQGLIFLGLALGTHFLFNSPFVELE
TEIPLAIPVVTAIALYGFYMAYCFVEKHNELMTZ (SEQ. ID. NO. 137)
MKVEPRCDVLSRMSHFFIRILIMLQELVERSWAIRQAYHELEVKHHDSKV
RRVEEDLLALSNDIGNPQRLVMTKQGRYYDETPYTLEQKLSENIWWLLEL
SQRLDIDILTEMENFLSDKEKQLNVRTWKZ (SEQ. ID. NO. 138)
MLDWKQFFLAYLRSRSRLFIYLLSLAFLVLLFQFLASLGIYFLYFPPLCC
FVTILFRWDILVETQVYRQELLYGEREAKSPLEIALAEKLEAREMELYQQ
RSKAERKLTDLLDYYTLWVHQIKTPIAASQLLVAEVVDRQLKQQLEQEIF
ICIDSYTNLVLQYLRLESPHDDLVLKQVQIEDLVKEIIRKYALFRQKGLN
VNLHDDLKEIVTDKJCwLLVVIEQIISNSLKYTKEGGLEIYMDDQELCIK
DTGIGIKNSDVLRVFERGFSGYNGRLTQQSSGLGLYLSKKISEELGHQIR
IESEVGKGTRVRIQFAQVNLVLEZ (SEQ. ID. NO. 139)
MELNTHNAEILLSAANKSHYPQDELPEIALAGRSNVGKSSFINTMLNRXN
LARTSGKPGQLLNFFNIDDKMRFVDVPGYGYARVSKKEREKWGCMIEEYL
TRRENLAVVSLVDLRHDPSADDVQMYEFLKYYEIPVIRVATKADKIPRGK
WNKHESAIKKKLNFDPSDDFILFSSVSKAGMDEAWDAILEKLZ (SEQ. ID. NO. 140)
MTKKQLHLVVTGMSGAGKTVAIQSFBDLGYFEDNMPPALLPKFLQLVEIK
EDNPKLALVVDMRSRSFFSEIQAVLDELENQDGLDPKILLDAADKELVAR
YKETRRSHPLAADGRLDGIgLRELLAPLKNMSQNVVDRRELTPRELRITL
AEQFSDQEQAQSFPJEVMSFGIKYGIPIDADLVFDVRFLPNPYYLPELRN
QTGVDEPVYDYVMNHPESEDFYQHLLALIEPILPSYQKEGKSVLTIAMGC
TGGQMRSVAFAKRLAQDLSKNWSVNEGHPDKDRRKETVNRSZ (SEQ. ID. NO. 141)
MRKPKITVIGGGTGSPVTLKSLREKDVEAAIVTVADDGGSSGELRKNMQQ
LTPPGDLRNVLVAMSDMPKFYEKVFQYRFSEDAGAFAGHPLGNLUAGLEM
QGSTYNAMQLLSKFPHRGKYPSSDHPLTLVFQTEVAGHIVDMRGIIDNEV
LHRLRPFIDTVLVNEKVPEYMNSNRPDEYLVQVEHDFVGLCKQVSRVISS
NPLPENGGAIDLIVDELMRIQVKKZ (SEQ. ID. NO. 142)
MKNLIKLLIUVNLADSVFYIVALWHVSNNYSSSMFLGFIAVNYLPDLLLI
GPVDRVNPQKILIILVQLAVAVIFTLLLNQISFWVIMSLVFSVMASSISY
VIEDVLIQVVEYDKIVFANSLFSISYKVLDSPNSFFLQVAVGILLVKIDI
GIPLLALFILLLLKRTSNANIENFSFKYYKREVLQGTHFILNNGLLFTSI
SLTLINFFYSFQTVVVPFSIRYGPIJYGIPLTGLGGILGNMLAPIVIKYL
KSNQVGVFLFLNGSSWLVAIKDYTLSLILFFVCFMSKGVNIINSLYQQ (SEQ. ID. NO. 143)
IPPHQLLGRVNTTIDSIISFGMPIGSLVAGTLIDLNIELLVLIAISIPYF
LFSYLFYTDNGLKEFSIYZ MMSNKNKEILIFAILYTVLFMFDGVKLLASLMPSAIANYLVYVVLALYGS
FLFKDRLIQQWKEIRKTKRKFFFGVLTGWLFLILMTVVFEFVSEMLKQFV
GLDGQGLNQSNIQSTFQEQPLLIAVFACVIGPLVEELFFRQVLLHYLQER
LSGLLSIILVGLVFALTHMHSLALSEWIGAVGYLGGGLAFSIIYVKEKEN
IYYPLLVHMLSNSLSLIILAISIVKZ (SEQ. ID. NO. 144)
LKKPIIEFKNVSKVFEDSNTCVLKDNFELEEGICYTLLGASGSGKSTILN
HAGLLDATRGDIMLDGVRINDPTIKRDVHTVFQSYALFPHMNVFENVAFP
LRLRKIDKKEIEQRVAEVLKMVQLEGYEKRSLRKLSGGQRQRVAIARAII
NQPRVVLLDEPLSALDLKRTDMQYELRELQQRLGITFVFVTHDQEALAM
SDWTVMNDGETVQSGTPVDIYDEPINHFVATFGBSNILPGTMIEDYLVEF
NGKREAVDGGMKPNEPVEVVIRPEDLRTLPEEGKLQVKVDTQLFRGVHYE
UAYDELGNEWMIHSTRKAVGEEGLDFBPEDIHIMRLNETEEEFDAPJEEY
VEIEEQEAGLINAIEEERDEENKLZ (SEQ. ID. NO. 145)
MKSMRILFLLALIQISLSSCFLWKECILSFKQSTAFFIGSMVFVSGICAG
VNYLYTRKQEVHSVLASKKSVKLFYSMLLLNLLGAVLVLSDNLFKNLQQE
LVDFLLPSFFLFGLDLLIFLPLKKYVRDFLAMLDRXTVLVTILATLLFLR
NPMTVSLLIYIGLGLFFAAYLVPNSVKKEVSFYGHIRDLVLVIVTLIFFZ (SEQ. ID. NO. 146)
MVKKIIGMVLALLSVTVVGVGVFAYTIYQQGTETLAIZTYKKIGEETKVI
EATEPLTILLMGVURGNVERTETWVGRSDSMILMTVNPKTKRITMMSLER
DILTRIESGNGQAHEAKLNSAYADGGAELAIETIQKMMNIHIDRYVMVNM
RGLQKLVDAVGGRRVNNLGFPISSDQEENTSIGVGEQHIGGEEALVYARM
RYQDPEGDYGRQKRQREVIQKVMEKALSLNSIGHYQEILKALSDNMQTNI
DLSAKSPNLLGYPZDSFKTIETQQLQEGEEILQGVSYQIVSRAHMLEMQN
LLRRSLGQEEVTQLETNAVLFEDLFGRAPVGDEDNZ (SEQ. ID. NO. 147)
MKKQAYVUALTSFLFVFFFSHSLLEILDFDWSIFLHDVEKTEKFVFLLLV
FSMSMTCLLALFwRGIEEELSRKMQANLKRLLAGQEVVQVADPDLDASFK
SLSGKLNLLTEALQKAENQSLAQEEEIIEKERKRIARDLHDTVSQELFAA
HMILSGISQQALKLDREKMQTQLQSVTAILETAQKDLRVLLLHLRPVELE
QKSLIEGIQILLKELEDKSDLRVSLKQNMTKLPKKLEEHIFRJLQELSNT
LRHAQASCLDVYLYQTDVELQLKVVDR4GIGFQLGSLDDLSYGLRNIKER
VEDMAGTVQLLTAPKQGLAVDIRIPLLDKEZ (SEQ. ID. NO. 148)
MIVSIISQGFVWAILGLGIFMTFRILNFPDMTTEGSIPLGGAVAVTLITK
GVNPFLATLVAVGAGCLAGMAAGLLYTKGKIPTLLSGILVMTSCHSIMLL
IMGRANLGLLGTKQIQDVLPFDSDLNQLLTGLRFVSRVXALMLPLLDTKL
GQAYIATGDNPDMARSFGHTGRMELMGLVLSNGVIALAOALAQQEGYADV
SRGGVIVVGLASLIIGEVISLAEPVTIVVGSIAYQFLVWAVIAIOFNTSY
LRLYSALILAVCLMUTFKQTILKGAJCLSKZ (SEQ. ID. NO. 149)
MKKMKVWSTVLATGVALTRLAACSGGSNSTTASSSEEKADKSQELVIYSN
SVSNGRGDWLTAXAEAGFNIKMVDIAGAQLADRVLAEKNNAVADMVFGIG
AVDSNKIRDQKLVQYKPKWLDKIDQSLSDKDNYYNPVIVQPLVILQGAPD
VKEMPKDWTELGSKYKGKYSISGLQGGTGRALASILVRYLDDKGELGVSE
KGWEVAICEYLKNAYTLQKOESSIVKMLDKEDPIQYGMMWGSGALVGQKE
QNVVPKVMTPEIGVPFVTEQTMVLSTSKKQALAKEFIDWFGQSEIQVEYS
KNFGSIPANKDALKDLPEDTKKFVDQVKPQNIDWEAVGKHLDEWVEKAEL
EYVQZ (SEQ. ID. NO. 150)
MIKFDNIQIKYGDFVAIDNLNLDHEGEFTFLGPSGCGKSTLRALVGFLDP
SSGSIEVNGTDVTHLEPEKRGIGVFQSYALFPTMTVDNIAFGLKVKKVAP
DVIKAKVSAVAAKIKISDQLQRNVSELSGGQQQRVALARLVLEPKILCL
DEPLSNLDAKLRVDLRKELKRLQKELGRITLVTHDQEEALTLSDRIAVF
NNGYIEQVGTPVEIYHNSQTEVCDPIGDNVLTDETVHEVLLKNTSVFLED
KKGYIRLEKVRFNRETEQDFLKGTUDVEFSGVTEHYTIKVSESQILNVTS
IDSQAARSVGESVELFITPSDVLQFZ (SEQ. ID. NO. 151)
MRHKLNLKDWLRLGLRWFLVTRIYPNFDLVVNVFVKGGESLDAVHRVLKQ
PALQSMNSPSLIVNVVGILCVLFTEYFDIKGAKZLKLGYMTSLIYGGVVL
ATGYKFVYGPYGLITKFLQNVIPSLDPNWPIGYGAVFLIMTFSGTANHTL
FLTNTHSVDYTIEARNMGKPVFRICVVLPTITLFALTIMVFLSGLSAVA
APMIVGGKEFQTINPMIITFAGMGNSRDLAALLAIILGIATTILLTIMNK

TABLE 2-continued

```
IEKGGNYISISKTKAPLKKQKIASKPWNIIAHIVAYGLFTVFMLPLIFIV
LYSPTDPVVIALNFNSLLTDFDLSVFLYHPLAQPLGITIPSAGDETATSN
AQALVF\RYTIVLMIISGTVLYPTQPJGPJVPJ CZ
```

TABLE 3

ID201-4106.4

(SEQ. ID. NO. 168)
```
ATGATAAAAAATCCTAAATTATTAACCAAGTCTTTTTTAAGAAGTTTTGC
AATTCTAGGTGGTTGGTCTAGTCATTCATATAGCTATTTATTTGACCTTT
CCTTTTTATTATATTCAACTGGAGGGGGAAAAGTTTAATGAGAGCGCAAG
AGTGTTTACGGAGTATTTAAAGACTAAGACATCTGATGAAATTCCAAGCT
TACTCCAGTCTTATTCAAAGTCCTTGACCATATCTGCTCACCTTAAAAGA
GATATTGTAGATAAGCGGCTCCCTCTTGTGCATGACTTGGATATTAAAGA
TGGAAAGCTATCAAATTATATCGTGATGTTAGATATGTCTGTTAGTACAG
CAGATGGTAAACAOGTAACCGTGCAATTTGTTCACGGGGTGGATGTGTAC
AAAGAAGCAAAGAATATTTTGCTTTTGTATCTCCCATATACATTTTTGGT
TACAATTGCTTTTTCCTTTGTTTTTCTTATTTTTATACTAAACGCTTGC
TCAATCCTCTTTTTTACATTTCAGAAGTGACTAGTAAAATGCAAGATTTG
GATGACAATATTCGTTTTGATGAAAGTAGGAAAGATGAAGTTGGTGAAGT
TGGAAAACAGATTAATGGTATGTATGACACTTGTTGAAGGTTATTTATG
AGTTGGAAAGTCGTAATGAGCAAATTGTAAAATTGCAAAATCAAAAGGTT
TCCTTTGTCCGGGAGCATCACATGAGTTGAAAACCCCTTTAGCCAGTCT
TAGAATTATCCTAGAGAATATGCAGCATAATATTGGAGATTACAAAGATC
ATCCAAAATATATTGCAAAATCTATAAATAAGATTGACCAGATGAGCCAC
TTATTAGAAGAAGTACTGGAGTCTTCTAAATTCCAAGAGTGGACAGAGTG
TCGTGAGACCTTGACTGTTAAGCCAGTTTTAGTAGATATTTTATCACGTT
ATCAAGAATTAGCTCATTCAATAGGTGTTACAATTGAAAATCAATTGACA
GATGCTACCAGGGTCGTCATGAGTCTTAGGGCATTTAGGTAAGGTTTTGAC
AAACCTGATTAGTAATGCAATTAAATATTCAGATAAAAATGGGCGTGTAA
TCATATCCCAGCAAGATGGCTATCTCTATCAAAAATACATGTGCGCCT
CTAAGTGACCAAGAACTAGAACATTTATTTGATATATTCTATCATTCTCA
AATCGTGACAGATAAGGATGAAAGTTCCGGTTTGGGTCTTTACATTGTGA
ATAATATTTTAGAAAAGCTATCAAATGGATTATAGTTTTCTCCCTTATGAA
CACGGTATCGAATTTAAGATTACCTTATAG
```

(SEQ. ID. NO. 152)
```
MIKNPKLLTLSFLRSFAILGGVGLVIHIAIYLTFPFYYIQLEGEKFNESA
RVFTEYLKTKTSDEIPSLLQSYSKSLTISAHLKRDIVDKRLPLVHDLDIK
DGKLSNYIVMLDMSVSTADGKQVTVQFVHGVDVYKEAKNILLLYLPYTFL
VTIAFSFVFSYFYTKRLLNPLFYISEVTSKMQDLDDNIRFDESRKDEVGE
VGKQINGMYEHLLKVIYELESRNEQIVKLIQNQKVSFVRGASHELKTPLA
SLRILENMQHNIGDYKDHPKYIAKSINKIDQMSHLLEEVLESSKFQEWTE
CRETLTVKPVLVDILSRYQELAHSTGVTTENGLTDATRVVMSLRALDKVL
TNLTSNATTCYSDJGRVIISEQDGYLSIKNTCAPLSDQELEHLFDIFYHS
QIVTDKDESSGLGLYIVNNILESYQMDYSFLPYEHGMEFKISLZ
```

ID202-41069

(SEQ. ID. NO. 169)
```
ATGGATAAAATTATTAAAACTATATCAGAAAGCGGAGCCTTTCGTGCTTT
TGTCCTTGATAGCACTGAAACCGTCCGCACTGCTCAAGAAAAACATCAAA
CCCAAGCTAGCTCAACTGTAGCGCTTGGTCGAACTCTTATCGCTAGCCAG
ATTCTCGCAGCCAATGAAAAAGGAAATACCAAACTTACAGTTAAGGTGTT
GGGATCTAGCTCTCTAGGTGCTATTATCACCGTCGCTGATACCAAGGGGA
ACGTCAAAGGCTATGTTCAAAATCCTGGTGTTGACATCAAAAAGACTGCG
ACTGGTGAAGTCCTAGTCGGACCTTTTGTTGGAAATGGTCAATTCCTCGT
TATCACAGACTACGGTACTGGAAATCCTTACAACTCTATAACTCCCCTCA
TCTCTGGAGAAATCGGTGAAGACCTTGCCTTTTACCTTACTGAAAGTCAA
CAAACGCCTTCAGCGGTCGGCCTCAATGTCCTTTTGGACGAGGAAGACAA
GGTCAAGGTTGCAGGTGGTTTCCTAGTTCAAGTCTTGCCAGGAGCCAAGA
AAGAAGGATATTGCTCGCTTTGAAAAACGCATCCAAGAAATGCCAGCTATC
TCTACTCTTCTCGAAACGTTTCCAATGTGACTGTAGCCATGAACGCTTTA
TGAACGCTCTTGCCAGCCTTCCAAGCTCAGACTTACAGGAAATGAAAGAG
GAAGACCACGGGGCAGAAATCACTTGTCAATTCTGCCAAACTACTTACAA
CTTTGATGAAAAGGACCTGGAGGAACTCATTCGTGACAAATCTTAA
```

(SEQ. ID. NO. 153)
```
MDKIIKTISESGAFRAFVLDSTETVRTAQEKHQTQASSTVALGRTLIASQ
ILAANEKGNTKLTVKVLGSSSLGAIITVADTKCNV1CGYVQPCVDTKKTA
TGEVLVGPFVGNGQFLVTTDYGTG&PYNSTTPLTSGETGEDLAFYLTESQ
QTPSAVGLNLLDEEDKVKVAGGFLVQVLPGAKKEETARFETCRTQEMPAT
STLLESDDHIEALLKATYGDEAYKRLSEEEIRFQCDCSHERFMNALASLP
SSDLQEMKEEDHGAEITCQFCQTTYNFDEKDLEELIRDKSZ
```

ID203-4115

(SEQ. ID. NO. 170)
```
ATGAAATCAATAACTAAAAAGATTAAAGCAACTCTTGCAGGAGTAGCTGC
CTTGTTTGCAGTATTTGCTCCATCATTTGTATCTGCTCAAGAATCATCAA
CTTACACTGTTAAAGAAGGTGATACACTTTCAGAAATCGCTGAAACTCAC
AACACAACAGTTGAAAAATTGGCAGAAAACAACCACATTGATAACATTCA
TTTGATTTATGTTGATCAAGAGTTGGTTATCGATGGCCCTGTAGCGCCTG
TTGCAACACCAGCGCCAGCTACTTATGCGGCACCAGCCGCTCAAGATGAA
ACTGTTTCAGCTCCAGTAGCAGAAACTCCAGTAGTAAGTGAAACAGTTGT
TTCAACTGTAAGCGGATCTGAAGCAGAAGCCAAGAATGGATCGCTCAAA
AAGAATCAGGTGGTAGTATACAGCTACAAATGGACGTTATATCGGACGTT
ACCAATTAA
```

(SEQ. ID. NO. 154)
```
MKSITKKIKATLAGVAALFAVFAPSFVSAQESSTYTVKEGDTLSEIAETH
NTTVEKLAENNHTDNTHLTYVDQELVIDGPVAPVATPAPATYAAPAAQDE
TVSAPVAETPVVSETVVSTVSGSEAEAKEWIAQKESGGSIQLQMDVISDV
TNZ
```

ID204-4111.7

(SEQ. ID. NO. 171)
```
ATGAATTTAGGAGAATTTTGGTACAATAAAATAAATAAGAACAGAGGAAG
AAGGTTAATGAAGAAAGTAAGATTTATTTTTTTAGCTCTGCTATTTTTCT
TAGCTAATCCAGAGGGTGCAATGGCTAGTGATGGTACTTGGCAAGGAAAA
AGTATCTGAAAGAAGATGGCAGTCAAGCAGCAAATGAGTGGGTTTTTGAT
ACTCATTATCAATCTTGTTCTATATAAAAGCAGATGCTAACTATGCTGA
AAATGAATGGCTAAAGCAAGGTGACGACTATTTTTACCTCAAATCTGGTG
GCTATATGGCCAAATCAGAATGGGTAGAAGACAAGGGAGCCTTTTATTAT
CTTGACCAAGATGGAAAGATGAAAAGAAATGCTTGGGTAGGAACTTCCTA
TGTTGGTGCAACAGGTGCCAAAGTAATAGAAGACTGGGTCTATGATTCTC
AATACGATGCTTGGTTTTATATCAAAGCAGATGGACAGCACGCAGAGAAA
GAATGGCTCAAAGTTAAAGGGAAGGACTATTATTTCAAATCCGGTGGTTA
TCTACTGACAAGTCAGTGGATTAATCAAGCTTATGTGAATGCTAGTGGTG
CCAAAGTACAGCAAGGTTGGCTTTTTGACAAACAATACCAATCTTGGTTT
TACATCAAAGAAAATGGAAACTATGCTGATAAAGAATGGATTTTCGAGAA
TGGTCACTATTATTATCTAAAATCCGGTGGCTACATGGCAGCCAATGAAT
GGATTTGGGATAAGGAATCTTGGTTTTATCTCAAATTTGATGGGAAAATG
GCTGAAAAGAATGGGTCTACGATTCTCATAGTCAAGCTTGGTACTACTT
CAAATCCGGTGGTTACATGACAGCCAATGAATGGATTTGGGATAAGGAAT
CTTGGTTTTATCTCAAATCTGATGGGAAAATAGCTGAAAAGAATGGGTC
TACGATTCTCATAGTCAAGCTTGGTACTACTTCAAATCCGGTGGTTACAT
GACAGCCAATGAGGATTTGGGATAAGGAATCTTGGTTTTACCTCAAAT
CTGATGGGAAAATAGCTGAAAAGAATGGGTCTACGATTCTCATAGTCAA
GCTTGGTACTACTTCAAATCTGGTGGCTACATGGCAGAAAATGAGACAGT
AGATGGTTATCAGCTTGGAAGCGATGGTAAATGGCTTGGAGGAAAAACTA
CAAATGAAAATGCTGCTTACTATCAAGTAGTGCCTGTTACAGCCAATGTT
TATGATTCAGATGGTGAAAAGCTTTCCTATATATCGCAAGGTAGTGTCGT
ATGGCTAGATAAGGATAGAAAAAGTGATGACAAGCGCTTGGCTATTACTA
TTTCTGGTTTGTCAGGCTATATGAAAACAGAAGATTTACAAGCGCTAGAT
GCTAGTAAGGACTTTATCCCTTATTATGAGAGTGATGGCCACCGTTTTTA
TCACTATGTGGCTCAGAATGCTAGTATCCCAGTAGCTTCTCATCTTTCTG
ATATGGAAGTAGGCAAGAAATATTATTCGGCAGATGGCCTGCATTTTGAT
GGTTTTAAGCGTGAGAATCCCTTCCTTTTCAAAGATTTAACAGAGGCTAC
AAACTACAGTGCTGAAGAATTGGATAAGGTATTTAGTTTGCTAAACATTA
ACAATAGCCTTTTGGAGAACAAGGGCGCTACTTTTAAGGAAGCCGAAGAA
CATTACCATATCAATGCTCTTTATCTCCTTGCCCATAGTGCCCTAGAAAG
TAACTGGGGAAGAAGTAAAATTGCCAAAGATAAGAATAATTTCTTTGGCA
TTACAGCCTATGATACGACCCCTTACCTTTCTGCTAAGACATTTGATTGT
GTGGATAAGGGAATTTTAGGTGCAACCAAGTGGATTAAGGAAAATTATAT
CGATAGGGGAAGCTTTCCTTGAAACAAGGCTTCTGGTATGAATGTGG
AATATGCTTCAGACCCTTATTGGGCGAAAAAATTGCTAGTGTGATGATG
AAAATCAATGAAAGCTAGGTGGCAAAGATTAG
```

(SEQ. ID. NO. 155)
```
MNLGEFWYNKINKNRGRRLMKKVRFIFLALLFFLASPEGAMASDGTWQGK
QYLKEDGSQAANEWVFDTHYQSWFYIKADANYAENEWLKQGDDYFLKSG
GYMAKSEWVEDKGAFYYLDQDGKMKRNAWVGTSYVGATGAKVIEDWVYDS
QYDAWFYIKADGQHAEKEWLQIKGKDYYFKSGGYLLTSQWINQAYVNASG
AKVQQGWFDKQYQSWFYTKENGNYADKEWIFENGHYYYLKSGGYMAANEW
IWDKESWFYLKFDGKMAEKEWVYDSHSQAWYYFKSGGYMTANEWTWDKES
WFYLKSDGKIAEKEWVYDSHSQAWYYFKSGGYMTANEWIWDKESWFYLKS
DGKIAEKEWVYDSHSQAWYYFKSGGYMAKNETVDGYQLSDGKWLGGKTT
NENAAYYQVVPVTANVYDSDGEKLSYISQGSVVWLDKDRKSDDKRLAITI
SGLSGYMKTEDLQALDASKDFIPYYESDGHRFYHYVAQNASIPVASHLSD
```

TABLE 3-continued

MEVGKKYYSADGLHFDGFKLENPFLFKDLTEATNYSAEELDKVFSLLNIN
NSLLENKGATFKEAEEHYHINALYLLAHSALESNWGRSKIAKDKNNFFGI
TAYDTTPYLSAKTFDDVDKGILGATKWIKENYIDRGRTFLGNKASGMNVE
YASDPYWGEKIASVNNKINEKLGGKDZ

ID205-41181.1

(SEQ. ID. NO. 172)
ATGAAAAAATTAGGTACATTACTCGTTCTCTTTCTTTCTGCAATCATTCT
TGTAGCATGTGCTAGCGGAAAAAAGATACAACTTCTGGTCAAAAACTAA
AAGTTGTTGCTACAAACTCAATCATCGCTGATATTACTAAAAATATTGCT
GGTGCAAAATTGACCTTCATAGTATCGTTCCGATTGGGCAAGACCCACAC
GAATACGAACCACTTCCTGAAGACGTTAAGAAACTTCTGAGGCTAAATT
TGATTTTCTATAACGGTATCAACCTTGAAACAGGTGGCAATGCTTGGTTT
ACAAAATTGGTAGAAAATGCCAAGAAAACTGAAAACAAAGACTACTTCGC
AGTCAGCGACGGCGTTGATGTTATCTACCTTGAAGGTCAAAATGAAAAG
GAAAAGAAGACCCACACGCTTGGCTTAACCTTGAAAACGGTATTATTTTT
GCTAAAAATATCGCCAAACAATTGAGCGCAAAGACCCTAACAATAAAGA
ATTCTCATGAAAAAATCTCAAAGAATATACTGATAAGTTAGACAAACTT
GATAAAGAAAGTAAGGATAAATTTAATAAGATCCCTGCTGAAAAGAAAT
CCATTGTAACCAGCGAAAGGAGCATTCAAATACTTCTCTAAAGCCTATGG
TGTCCCAAGTGCTTTACATCTGGGAAATCAATACTGAAGAAGGAACT
CCTGAACAAATCAAGACCTTGGTTGAAAAACTTCGCCAAACAAAACTTCC
ATCACTCTTTGTAGAATCAAGTGTGGATGACCGTCCAATGAAAACTGTTT
CTCAAGACACAAACATCCCAATCTACGCTCAAATCTTTACTGACTCTATC
GCAGAACAAGGTCCCGAAGGCGACAGCTACTACAGCATGATGAAATACAA
CCTTGACAAGATTGCTGAAGGATTGGCAAAATAA (SEQ. ID. NO. 156)
MKKLGTLLVLFLSAIILVACASGKKDTTSGQKLKVVATNSIIADITKNIA
GDKIDLHSIVPIGQDPHEYEPLPEDVVKKTSEANLIFYNGINLETGGNAWF
TKLVENAKKTENKDYFAVSDGVDVIYLEGQNEKGKEDPHAWLNLENGIIF
AKNIAKQLSADPNNKEFYEKNLKEYTDKLDKLDKESKDKFNKIPAEKKL
IVTSEGAFKYFSKAYGVPSAYIWEINTEEEGTPEQIKTLVEKLRQTKVPS
LFVESSVDDRPMKTVSQDTNIPIYAQIFTDSIAEQGKEGDSYYSMMKYNL
DKIAEGLAKZ

ID206-41191.1

(SEQ. ID. NO. 173)
ATGGAATGGTATAAAAAAATCGGACTTCTTGCAACTACAGGTTTAGCTTT
GTTTGGGCTCGGCGCTTGCTCCAACTATGGTAAATCTGCGGATGGCACAG
TGACCATCGAGTATTTCAACCAGAAAAAGAAATGACCAAAACCTTGGAA
GAAATCACTCGTGATTTTGAGAAGGAAAACCCTAAGATCAAGGTCAAAGT
CGTCAATGTACCAAATGCTGGTGAAGTATTGAAGACACGCGTTCTCGAG
GAGATGTGCCTGATGTGGTCAATATTTACCCACAGTCCATCGAACTGCAA
GAATGGGCAAAAGCAGGTGTTTTTGAAGATTGACCAACAAAGACTACCTG
AAACGCGTGAAAATGGCTACGCTGAAAAATATGCTGTAAACGAAAAAGTT
TACAACGTTCCTTTTACAGCTAATGCTTATGGAATTTACTACAACAAAGA
TAAATTCGAAGAACTGGGCTTGAAGGTTCCTGAAACCTGGGATGAATTTG
AACAGTTAGTCAAAGATATCGTTGCTAAAGGACAAACACCATTTGGAATT
GCAGGTGCAGATGCTTGGACACTCAATGGTTACAATCAATTAGCCTTTGC
GACAGCAACAGGTGGAGGAAAAGAAGCAAATCAATACCTTCGTTATTCTC
AACCAAATGCCATTAAATTGTCGGATCCGATTATGAAAGATGATATCAAG
GTCATGGACATCCTTCGCATCAATGGATCTAAGCAAAAGAACTGGGAAGG
TGCTGGCTATACCGATGTTATCGGAGCCTTCGCACGTGGGGATGTCCTCA
TGACACCAATGGGTCTTGGGCGATCACAGCGATTAATGAACAAAAACCGA
ACTTTAAGATTGGGACCTTCATGATTCCAGGAAAGAAAAGGACAAAGC
TTAACCGTTGGTGCGGGAGACTTGGCATGGTCTATCTCAGCCACCACCAA
ACATCCAAAAGAAGCCAATGCCTTTGTGGAATATATGACCCGTCCAGAAG
TCATGCAAAAATACTATGATGGACGGATCTCCAACAGCGATCAAGGG
GTCAAACAAGCAGGAGAAGATTCACCGCCTTGCTGGTATGACCGAATATG
CCTTTACGGATCGTCACTTGGTCTGGTTGCAACAATACTGGACCAGTGAA
GCAGACTTCCATACCTTGACCATGAACTATGTCTTGACCGGTGATAAACA
AGGCATGGTCAATGATTTGAATGCCTTCTTTAACCCGATGAAAGCGGATG
TGGATTAG (SEQ. ID. NO. 157)
MEWYKKIGLLATTGLALFGLGACSNYGKSADGTVTIEYFNQKKEMTKTLE
EITRDFEKENPKIKVKVVNVPNAGEVLKTRVLAGDVPDVVNIYPQSIELQ
EWAKAGVFEDLSNKDYLKRVKNVAEKYAVNEKVYNVPFTANAYGIYYNK
DKFEELGLKVPETWDEFEQLVKDIVAKGQTPFGIAGADAWTLNGYNQLAF
ATATGGGKEANQYLRYSQPNAIKLSDPIMKDDIKVMDILRTNGSKQKNWE
GAGYTDVIGAFARGDVLMTPNGSWAITAINEQKPNDKIGTFMIPGKEKGQ
SLTVGAGDLAWSISATTKHPKEANAFVEYMTRPEVMQKYYDVDGSPTAIE
GVKQAGEDSPLAGMTEYAFTDRHLVWLQOYWTSEADFHTLTMNYVLTGDK
QGMVNDLNAFFNPMKADVDZ

ID207-4123.1

(SEQ. ID. NO. 174)
ATGAAGAAAATCAAACCGCATGGACCGTTACCAAGTCAGACTCAGCTAGC
TTATCTGGGAGATGAACTAGCAGCTTTTATCCACTTCGGTCCTAATACCT
TTTATGACCAAGAATGGGGACTGGACAGGAGGATCCTGAGCGCTTTAAC
CCGAGTCAGTTGGATGCGCGTGAGTGGGTTCGTGTGCTCAAGGAAACAGG
CTTCAAAAAGTTGATTTTGGTGGTCAAGCACCACGATGGCTTTGTCCTTT
ATCCGACAGCTCACACAGATTATTCGGTTAAGGTCAGTCCTTGGAGGAGA
GGAAAGGGCGAGTTGCTCCTTGAAGTATCCCAAGCTGCCACAGAGTTTGA
TATGGATATGGGGGTCTACCTGTCACCGTGGGATGCCCATAGTCCCCTCT
ATCATGTGCGCGAGAAGCGGACTACAATGCCTATTATCTGGCTCAGTTG
AAGGAAATCTTATCAAATCCTAACTATGGGAATGCTGGTAAGTTCGCTGA
GGTTTGGATGGATGGTGCCAGAGGAGAGGGCGCGCAAAAGGTTAATTATG
AATTTGAAAAATGGTTTGAAACCATTCGTGACCTGCAGGGCGATTGCTTG
ATTTTTTCAACAGAAGGCACCAGTATCCGCTGGATTGGCAATGAACGAGG
GTATGCAGGTGATCCACTGTGGCAAAAGGTGAATCCTGATAAACTAGGAA
CAGAAGCAGAGCTGAACTATCTTCAGCACGGGGATCCCTCGGGCACGATT
TTTTCAATCGGAGGAGCAGATGTTTCCATCCGTCCAGGCTGGTTCTACCA
TGAGGATCAGGATCCTAAGTCTCTCGAGGAGTTGGTCGAAATCTACTTTC
ACTCAGTAGGGCGAGGAACTCCACTCTTGCTTAATATTCCGCCGAATCAA
GCTGGGCTCTTTGATGCAAAGGATATTGAACGACTTTATGAATTTGCGAC
CTATCGCAATGAGCTCTATAAAGAAGATTTGGCTCTGGCAGAAGTCAGTG
GAGCAGCTCTCTTCCGACAGACTTTGCTTGTCGCATTTGACAGGAC
CTTGAGACCAGCTCTTGGGCAAGCGATGCAGACTTGCCCATCCAGTTAGA
ACTCGATTAGGTTCTCCTAAAACTTTTGATGTAATTGAGTTAAGAGAAG
ATTTGAAGCTAGGGCCCGAATCGCTGCTTTTCATGTGCAAGTAGAGGTGG
ATGGTGTCTGGCAGGAGTTTGGTCGGGCTCATACTGTTGGTTACAAACGT
CTCTTACGAGGAGCAGTTGTTGAGGCACAGAAGATACGTGTAGTCATTAC
AGAATCACAGGCCTTTGCCTTTGTTGACCAAGATTTCCCTTTATAAAACT
CCTGGATTATCAAAAAAGAAGTTGTTCAGGAACTAGCATTTGCAGAAAA
AAGCCTAGCTGTGGCAAAGGGAAATGCCTATTTTACAGTTAAGCGCA
GAGAATGTAGTGGTCCTTTAGAAGCTAAGATTTCGATTCAACCGGGACA
GGTGTCCATGGTGCGCCTATCAGGATGAGATTCAAGTCCTTGCGTTTCA
AACTGGTGAGACTGAAAAAGTCTGACGCTACCAACCTTGTATTTCGCAG
GAGATAAAACCTTGGATTTCTATCTGAACCTAACGGTGGATGGTCAGCTT
GTGGATCAACTTCAAGTCCAAGTTTCATAA (SEQ. ID. NO. 158)
MKKIKPHGPLPSQTQLAYLGDELAAFIHFGPNTFYDQEWGTGQEDPERFN
PSQLDAREWVRVLKETGFKKLILVVKHHDGFVLYPTAHTDYSVKVSPWRR
GKGDLLLEVSQAATEFDMDMGVYLSPWDAHSPLYHVDREADYNAYYLAQL
KEILSNPNYGNAGKFAEVWMDGARGEGAQKVNYEFEKWFETIRDLQGDCL
IFSTEGTSIRWIGNERGYAGDPLWQKVNPDKLGTEAELNYLQHGDPSGTI
FSIGEADVSIRPGWFYHEDQDPKSLEELVEIYFSHVGRVGTPLLLNIPPN
QAGLFDAKDIERLYEFATYRNELYKEDLALGAEVSGPALSADFACRHLTD
GLETSSWASDADLPIQLELDLGSPKTFDVIELREDLKLGQRIAAFHVQVE
VDGVWQEFGSGHTVGYKRLLRGAVVEAQKTRVVTTESQAPPLLTKTSLYK
TPGLSKKEVVQELAFAEKSLAVAKGENAYFTVKRRECSGPLEAKISIQPG
TGVHGVAYQDEIQVLAFQTGETEKSLTLPTLYFAGDKTLKFYLNLTVDGQ
LVDQLQVQVSV

ID208-4125.12

(SEQ. ID. NO. 175)
ATGCTTGAAAGACTGAAAAGAATACATTATATGTTTTGGATCAGTTTAAT
TTTTATGATTTTCCCCATCCTGTCTGTAGTGACTGGGTGGCTTTCTGCCT
GGCATTTATTGATTGATATTCTATTTGTAGTGGCATATTTGGGTGTTTTA
ACAACTAAGAGCCAGCGCCTATCTTGGCTATATTGGGCCTCATGCTGAC
TTATGTATTTGGGAATACTGCCTTTGTTGCTGTTAATTATATCTGGTTT
TCTTTTTCCTATCCAATCTCTTAAGTTATCATTTCAGCGTACGTAGTTTA
AAGTCTTTACATGTCTGGACTTTTCTTGCTCAAGTCCTTGTTGTGGG
GCAACTGTTGATTTTCAGAGAATCGAAGTTGAGTTCTATTCTATCTAC
TTGTAATTCTTACTTTTGTCGATTTAATGACTTTTGGATTGGTTCGGATT
CGTATTGTCGAGGATTTGAAAGAACGTCAAGGTCAAGAACAATGCTCAGAT
AAATTCATTGCTTGCTGAAAATGAACGTAGTCGTATCGGTCAGGATTGC
ATGATAGTCTGGGACATACCTTTGCTATGCTGAGTGTCAAGACAGATTTA
GCCTTGCAGTTATTTCAGATGGAGCTTATCCACAGGTGGAAAGGAATTAA
AGAAATTCACCAGATAGCAGGATCCATGA (SEQ. ID. NO. 159)
MLERLKRTHNYMFWTSLTFMTFPTLSVVTGWLSAWHLLTDFLFVVAYLGV
LTTKSQRLSWLYWGLMLTYVVGNTAFVAVNYIWFFFFLSNLLSYHFSVRS
LKSLHVWTFLLAQVLVVGQLLIFQRIEVEFLFYLVILTFVOLMTFGLVR
IRIVEDLKEAQVKQNAQINLLLAENERSRIGQDLHDSLGHTFAMLSVKTD
LALQLFQMEAYPQVEKELKEIHQISKDPZ

TABLE 3-continued

ID290-4126.3

(SEQ. ID. NO. 176)
ATGAATGATAAGTTAAAAATCTTCTTGTTGCTAGGAGTATTTTTTCTAGC
CATAACCGGTTTCTATGTTCTATTGATACGAAATGCAGGGCAGACAGATG
CCTCGCAAATTGAAAAGGCGGCAGTTAGCCAAGGAGGAAAAGCAGTGAAA
AAAACAGAAATTAGTAAAGACGCAGACTTGCACGAAATTTATCTAGCTGG
AGGTTGTTTCTGGGGAGTGGAGGAATATTTCTCACGTGTTCCCGGGGTGA
CGGATGCCGTTTCAGGCTATGCAAATGGTAGAGGAGAAACAACCAAGTAC
GAATTGATTAACCAAACAGGTCATGCAGAAACCGTCCATGTCACCTATGA
TGCCAAGCAAATTTCTCTCAAGGAAATCCTGCTTCACTATTTCCGCATTA
TCAATCCAACCAGCAAA)*ATAAACAAGGAAATGATGTGGGGACCCAGTA
CCGTACTGGTGTTTATTACACAGATGACAAGGATTTGGAAGTGATTAACC
AAGTCTTTGATGAGGTGGCTAAGAAATACGATCAACCTCTAGCAGTTGAA
AAGGAAACTTGAAGAATTTTGTGGTGGCTGAGGATTACCATCAAGACTA
TCTAAAGAAAAATCCAAATGGCTACTGCCATATCAATGTTAATCAGGCGG
CCTATCCTGTCATTGATGCCAGCAAATATCCAAAACCAAGTGATGAGGAA
TTGAAAAAGACCCTGTCACCTGAGGAGTATGCAGTTACCCAGGAAAATCA
AACAGAACGAGCTTTCTCAAACGTTACTGGGGATAAATTTGAATCCGGTA
TCTATGTGGATATAGCAACTGGGGAACCTCTCTTTTCATCAAAAGACAAA
TTTGAGTCTGGTTGTGGCTGGCCTAGTTTTACCCAACCCATCAGTCCAGA
TGTTGTCACCTACAAGGAAGATAAGTCCTACAATATGACGCGTATGGAAG
TGCCGGACCGAGTAGGAGATTCTCACCTTGGGCGTGTCTTTACGGATGGT
CCACAGGACAAGGGCGGCTTACGTTACTGTATCAATAGCCTCTCTATCCG
CTTTATTCCCAAAGACCAAATGGAAGAAAAAGgcTACGCTTATTTACTAG
ATTATGTTGATTAA (SEQ. ID. NO. 160)
MNDKLKIFLLLGVFFLAITGFYVLLIRNAGQTDASQIEKAAVSQGGKAVK
KTEISKDADLHETYTAGGCFWGVEEYFSRVPGVTDAVSGYANGRGETTKY
ELINQTGHAETVHVTYDAKQISLKEILLHYFRIINPTSKNKQGNDVGTQY
RTGVYYTDDKDLEVINQVFDEVAKKYDQPLAVEKENLKNFVVAEDYHQDY
LKKNPNGYCHINVNQAAYPVIDASKYPKPSDEELKKTLSPEEYAVTQENQ
TERAFSNRYWDKFESGIYVDIATGEPLFSSKDKFESGCGWPSFTQPISPD
VVTYKEDKSYNMTRMEVRSRVGDSHLGMVFTDGPQDKGGLRYCINSLSIR
FIPKDQMEEKGYAYLLDYVDZ

ID210-4127.1

(SEQ. ID. NO. 177)
ATGAAAAAGAAATGGATGTATTATGCTGCTTGTTCTTCTAATGAATCTGC
CGATGACAGTTCATCTGATAAGGAGACGGCGGTTCGCTAGTCGTTTATT
CACCAAACTCAGAGGGCTTAATTGGAGCAACTATTCCTGCCTTTGAAGAA
AAATATGGTATCAAAGTAGAACTGATTCAAGCTGGTACTGGAGAACTTTT
CAAAA)ACTAGAGTCAGAAAAAGAAGTTCCTGTAGCTGATGTTATCTTTG
GTGGTTCTTATACACAATATACTACCCACGGAGAACTCTTTGAAAACTAT
ACTTCAAAAGAAATGATAATGTTATCAAAGAATATCAAAACACAACTCG
CTACTCTACTCCTTATCACTAGATGGTAGTGTTTTAATCGTCAACCCTG
ATTTAACTAAAGGCATGAACATCGAAGGATATAACGATCTTTTCAAACCT
GAACTAAAAGGAAAAATCGCAACTGCTGACCCAGCAAACTCTTCTAGCGC
CTTTGCTCAATTAACAAATATGCTACAAGCTCAAGGTGGTTAACAAAGAT
GATAAGGCTTGGTCTTATGTAAAAGATCTTTTCACACTTATTGATGGTAA
AATCGGTTCAGTTCATCTAGTGTCTATAAAGTAGTCGCTAGTGGAGAAAT
GGCTGTTGGTCTCTCTTATGAAGATCCAGCAGTTAAACTCTTAAATGACG
GAGCTAACATTAAGGTAGTCTATCAAAAGAAGGAACCGTCTTCCTACCT
GCTAGTGCTGCTATCGTTAAAAAATCTAAAAATATGGAAAATGCCAAGAA
ATTTATCGATTTTATTATCTCAAGAAGTACAAGATACACTTGGTACAA
CCACTACTAACCGTCCTGTTCGTAAAAATGCTAAAACAAGCGAAAACATG
AAACCAATTGACAAAATCAAAACACTCACTGAAGATTATGATTATGTCAT
CAAGAATAAATCAGATATCGTTAAGAAATACAACGAAGTCTTTACAGATA
TCCAATCTAAACAGTAA (SEQ. ID. NO. 161)
MKKKWMYYAACSSNESADDSSSDKGDGGSLVVYSPNSEGLIGATIPAFEE
KYGIKVELIQAGTGELFKKLESEKEVPVADVIFGGSYTQYTTHGLFENY
TSKENDNVIKEYQNTTGYSTPYTLDGSVLIVNPDLTKGMNIEGYNDLFKP
ELKGKIATADPANSSSAFAQLTNMLQAQGGYKDDKAWSYVKDLFTLIDGK
IGSSSSVYKVVADGEMAVGLSYEDPAVKLLNDGANIKVVYPKEGTVFLPA
SAAIVKKSKNMENAKKFIDFIISQEVQDTLGTTTTNRPVRKAKTSENMKP
IDKIKTLTEDYDYVIKNKSDIVKKYNEVFTDIQSKQZ

ID211-4127.2

(SEQ. ID. NO. 178)
ATGAGTGAGATCAAAATTATTAACGCCAAAAAAATCTACCACGATGTCCC
TGTTATTGAGAATTTGAACATTACAATTCCAAAAGGAAGTCTCTTTACCC
TTCTTGGAGCTTCAGGATGTGGGAAAACGACCCTTCTTCGTATGATTGCA
GGTTTCAACAGTATCGAAGGTGGAGAATTTACTTCGATGATACAAAAAT

CAATAATATGGAACCCAGCAAACGCAATATCGGGATGGTTTTCCAAAACT
ACGCTATTTTCCCACATTTGACTGTCCGAGACAACGTTGCTTTTGGTCTT
ATGCAAAGAAGGTTCCAAAAGAAGAATTGATTCAACAGACCAACAAGTA
TCTTGAACTCATGCAAATTGCTCAATATGCGGATCGAAAGCCGATAAAC
TCAGTGGTGGACAACAACAACGTGTCACCTTGGCATGCGCCTTAGCGGTT
AATCCAAGTGTTCTCCTCATGGACGAGCCACTTAGTAATCTGGAGGCCAA
ACTTCGCTTGGATATGCGTCAAGCCATCGAGAAATCCAACACGAAGTGG
GAATTCAACTGTTTATGTAACCCACGACCAAGAAGAAGCCATGGCTATT
TCAGACCAAATTGCTGTTATGAAAGATGGGGTGATCCAACAAATCGGCCG
ACCAAAAGAACTCTATCATAAACCAGCTAATGAGTTTGTGGCAACCTTTA
TCGGACGCACAAATATTATCCCTGCCAATCTTGAAAAACGGAGCGACGGC
GCTTATCACTGTCTTTTCGAGATGGCTATGCCCTTCGAATGCCAGCTCTTG
ATCAGGTTGAGGAGCAAGCTATTCATGTAAGCATTCGTCCCGAAGAGTTT
ATCAAAGATGAATCTGGAGATATTGAAGGAACTATTAGAGATAGCGTCTA
TCTTGGACTAAATACGGATTATTTCATTGAGACAGGTTTTGCCTCAAAAA
TTCAAGTTAGTGAAGAATCAACTTTTGAAGAAGATCTACAAAAAGGCAAT
CGTATTCGTCTACGAATCAATACGCAAAAATTAAACATCTTTTCTGCAGA
TGGTTCCCAAAACCTGATAAAAAGGAGTCAACCATGAACGTAA (SEQ. ID. NO. 162)
MSEIKIINAKKIYHDVPVEINLNITIPKGSLFTLLGASGCGKTTLLRMIA
GFNSIEGGEFYFDDTKINNMEPSKRNIGMVFQNYAIFPHLTVRDNVAFGL
MQKKVPKEELIQQTNKYLELMQIAQYADRKPDKLSGGQRVTLACALAVN
PSVLLMDEPLSNLEAKLRLDMRQAIREIQHEVGITTVYVTHDQEEAMAIS
DQIAVMKDGVIQQIGRPKELYHKPANEFVATFIGRTNIIPANLEKRSDGA
YIVFSDGYALRMPALDQVEEQAIHVSIRPEEFIKDESGDIEGTIRDSVYL
GLNTDYFIETGFASKIQVSEESTFEEDLQKGNRIRLRINTQKLNIFSADG
SQNLIKGVNHGTZ

ID212-4136.1

(SEQ. ID. NO. 179)
ATGAAGAAAAAATTATTGGCAGGTGCCATCACACTATTACAGTAGCAA
TTTAGCACGTTGTTCGAAAGGGTCAGAAGGTGCAGACCTTATCAGCATGA
AGGGGATGTCATTACAGAACATCAATTTTATGAGCAAGTGAAAACGAAC
CCTTCAGCCCAACAAGTCTTGTTAAATATGACCATCCAAAAAGTTTTTGA
AAAACAATATGGCTCAGAGCTTGATGATAAAGAGGTTGATGATACTATTG
CCGAAGAAAAAAACAATATGGCGAAAATACCAACGTGTCTTGTCACAA
GCAGGTATGACTCTTGAAACACGTAAAGCTCAAATTCGTACAAGTAAATT
AGTTGAGTTGGCAGTTAAGAAGGTAGCAGAAGCTGAATTGACAGATGAAG
CCTATAAGAAGCCTTTGATGAGTACACTCCAGATGTAACGCTACAGGAA
ATCCGTCTTAATAATGAAGATAAGGCCAAAGAAGTTCTCGAAAAAGCCAA
GGCAGAAGGTGCTGATTTTGCTCAATTAGCCAAAGATAATTCAACTGATG
AAAAAACAAAAGAAAATGGTGAGAAATTACCTTTGATTCTGCTTCAACA
GAAGTACCTGACAAGTCAAAAAAGCCTTTCGCTTTAGATGTGGATGG
TGTTTGTGATGTGATTACGACAACTGGCACAGCCTACAGTAGCCAAT
ATTACATTGTAAAACTCACTAAGAAACAGAAAATCATCTAATATTGAT
GACTACAAAGAAAATTAAAAACTGTTATCTTGACTCAAAAACAAAATGA
TTCAACATTTGTTCAAAGCATTATCGGAAAAGAATTGCAAGCAGCCAATA
TCAAGGTTAAGGACCAAGCCTTCCAAAATATCTTTACCCAATATATCGGT
GGTGGAGATTCAAGCTCAAGCAGTAGTACATCAAACGAATAG (SEQ. ID. NO. 163)
MKKKLLAGAITLLSVATLAACSKGSEGADLISKMKGDVITEHQFYEQVKS
NPSAQQVLLNMTIQKVFEKQYGSELDDKEVDDTIAEEKKQYGENYQRVLS
QAGMTLETRKAQIRTSKLVELAVKKVAEAELTDEAYKKAFDEYTPDVTAQ
IIRLNNEDKAKEVLEKAKAEGADGAQLAKDNATDEKTKENGGEITFDSAS
TEVPEQVKKAAFALDVDGVSDVITATGTQAYAAQYYIVKLTKKTEKSSNI
DDYKEKLKTVILTQKQNDSTFVQSIIGKELQAANIKVKDQAFQNIFTQYI
GGGDSSSSSSTSNEZ

ID213-4137.3

(SEQ. ID. NO. 180)
ATGAAAAAAATATTAAACAATATGTAACCTTAGGTACTGTAGTGGTATT
ATCACATTTGTTGCTAACTCAGTTGCAGCTCAGGAGACTGAAACTTCTG
AAGTATCAACACCAAAGTTGGTGCAACCTGTTGCAACAACGACTCCGATT
TCGGAAGTACAACCTACATCGGATAACTCTTCGGAAGTTACTGTACAACC
TCGAACAGTTGAAACTACTGTTAAGGATCCATCTTCTACAGCGGAAGAAA
CTCCTGTCTTAGAAAAAATAATGTTACTTTAACAGGGGGCGGAAGAAAT
GTTACTAAAGAGTTAAAGGATAAATTTACTAGCGGTGACTTTTACTGTAGT
GATTAAGTACAATCAGTCAAGTGAGAAAGGCTTACAAGCTCTGTTTGGAA
TATCTAATTCCAAACCCGGTCAACAAAATAGTTATGTAGATGTGTTCCTT
AGAGACAATGGTAGTTGGGGATGGCGAAGCCGTGTACTTCTTCCAATAA
AAATAACCTAGTATCCAGACCTGCTTCAGTTTGGGGTAAGTACAAACAAG
AGGCTGTGACTAACACTGTTGCAGTAGTAGCAGATTCAGTCAAAAAACA
TATTCTTTATACGCAAATGGTACAAAAGTAGTAGAAAGAAAGTGGATAA
TTTCCTAAACATCAAGGATATTAAAGGTATTGATTACTATATGCTTGGGG
GAGTGAAACGTGCAGGAAAAACGGCGTTTGGTTTTAACGGAACACTAGAA

TABLE 3-continued

```
AATATCAAATTCTTTAATAGTGCATTGGATGAAGAAACTGTTAAAAAGAT
GACAACAAACGCTGTTACTGGACATTTAATTTATACGGCTAATGATACAA
CAGGTTCTAACTATTTCCGTATTCCAGTTCTGTATACTTTTAGCAATGGT
CGGGTATTTTCAACGATTGACGCTCGTTACGGTGGAACTCATGATTTCTT
GAATAAAATTAATATTGCTACAAGTTATAGTGATGATAATGGTAAGACAT
GGACTAAACCAAAATTAACATTGGCATTCGATGATTTTGCGCCAGTACCA
TTAGAATGGCCTCGTGAAGTTGGTGGACGTGACTTACAAATCAGCGGTGG
TGCAACCTATATTGACTCTGTTATTGTTGAAAAAAAGAACAAACAAGTAC
TCATGTTTGCTGATGTGATGCCTGCTGGAGTAAGTTTTAGAGAAGCAACT
AGAAAAGATTCAGGTGTATAAACAAATTGATGGTAATTATTACCTTAAATT
AAGGAAACAAGGTGATACTGATTACAATTATACTATTCGTGAGAATGGTA
CTGTATACGACGATCGTACCAACAGACCAACTGAATTTTCAGTAGATAAA
AATTTCGGTATTAAACAAAATGGTAATTATTTGACGGTAGAGCGG
```
               (SEQ. ID. NO. 164)

```
MKKNIKQYVTLGTVVVLSAFVANSVAAQETETSEVSTPKLVQPVAPTTPS
IEVQPTSDNSSEVTVQPRTVETTVKDPSSTAEETPVLEKNNVTLTGGGEN
VTKELKDKFTSGDFTVVIKYNQSSEKGLQALFGISNSKPGQQNSYVDVFL
RDNGELGMEARDTSSNKNNLVSRPASVWGKYKQEAVTNTVAVVADSVKKT
YSLYANGTKVVEKKVDNFLNIKDIKGIDYYMLGGVKRAGKTAFGFNGTLE
NIKFFNSALDEETVKKMTTNAVTGHLITYANDTTGSNYFRIPVLYTFSNG
RVFSSIDARYGGTHDFLNKINIATSYSDDNGKTWTKPKLTLAFDDFAPVP
LEWPREVGGRDLQISGGATYIDSVIVEKKNKQVLMFADVMPAGVSFREAT
RKDSGYKQIDGNYYLKLRKQGDTDYNYTIRENGTVYDDRTNRPTEFSVDK
NFGIKQNGNYLTVER
```

UD214-4185

```
ATGAAAAAATTTAGCCTATTACTAGCTATCCTACCATTTTTGGTTGCCTG
TGAGAATCAAGCTACACCCAAAGAGACTAGCGCTCAAAAGACAATCGTCC
TTGCTACAGCTGGCGACGTGCCACCATTTGACTACGAAGACAAGGGCAAT
CTGACAGGCTTTGATATCGAAGTTTTAAAGGCAGTAGATGAAAAACTCAG
CGACTACGAGATTCAATTCCAAAGAACCGCCTGGGAGAGCATCTTCCTAG
GACTTGATTCTGGTCACTATCAGGCTGCGGCCAATAACTTGAGTTACACA
AAAGAGCGTGCTGAAAAATACCTTTACTGCTTCAATTTCCAACAATCC
CCTCGTCCTTGTCAGCAACAAGAAAATCCTTTGACTTCTCTTGACCAGA
TCGCTGGTAAAACAACACAAGAGGATACCGGAACTTCTAACGCTCAATTC
ATCAATAACTGGAATCAGAAACACACTGATAATCCCGCTACAATTAATTT
TTCTGGTGAGGATATTGGTAAACGAATCCTAGACCTTGCTAACGGAGAGT
TTGATTTCCTAGTTTTTGACAAGGTATCCGTTCAAAAGATTATCAAGGAC
CGTGGTTTAGACCTCTCAGTCGTTGATTTACCTTCTGCAGATACGGGAAC
CAATTATATCATTTTCTCAAGCGACCAAAAAGAGTTTAAAGAGCAATTTG
ATAAAGCGCTCAAAGAACTCTATCAAGACGGAACCCTTGAAAACTCAGCA
ATACCCATCTAGGTGGTTCTTACCTCCCAGATCAATCTCAGTTACAATAA
```
               (SEQ. ID. NO. 165)

```
NKKFSLLLAILPFLVACENQATPKETSAQKTIVLATAGDVPPFDYEDKGN
LTGFDIEVLKAVDEKLSDYEIQFQRTAWESIFPGLDSGHYQAAANNLSYT
KERAEKYLYSLPISNNPLVLVSNKKNPLTSLDQIAGKTTQEDTGTSNAQF
INNWNQKHTDNPATINFSGEDIGKRILDLANGEFDFLVFDKVSVQKIIKD
RGLDLSVVDLPSADSPSNYIIFSSDQKEFKEQFDKALKELYQDGTLEKLS
NTYLGGSYLPDQSQLQZ
```

ID215-4211.1

(SEQ. ID. NO. 182)
```
ATGAAAAAAATAGTTTATATATCATATCCTCACTCTTTTTGCTTGTGT
CTTATTTGTCTATGCTACGGCGACGAATTTTCAAAACAGTACCAGTGCTA
GGCAGGTAAAAACGGAACCTATACTAATACAGTAACAAATGTCCCTATT
GACATACGCTATAATAGTGATAAGTATTTTATTAGCGGTTTTGCTTCAGA
AGTATCAGTGGTCTTGACTGGTGCAAATCGCCTATCGCTAGCTAGTGAAA
TGCAAGAAAGTACACGTAAATTCAAGGTTACTGCTGACCTAACAGATGCC
GGTGTTGGAACGATTGAAGTTCCTTTGAGCATTGAAGATTTTACCCAATGG
GCTGACCGCTGTGGCGACTCCGCAAAAAATTACAGTCAAGATTGGTAAGA
AGGCTCAGAAGGATAAGGTAAAGATTGTACCAGAGATTGACCCTAGTCAA
ATTGATAGTCGGGTACAAATTGAAAATGTCATGGTGTCAGATAAAGAAGT
GTCTATTACGAGTGACCAAGAGACATTGGATAGAATTGATAAGATTATCG
CTGTTTTGCCAACTAGCGAACGTATAACAGGTAATTACAGTGGTTCAGTA
CCTTTGCAGGCAATCGACCGCAATGGTGTTGTCTTACCGGCAGTTATCAC
TCCGTTTGATCAATAATGAAGGTGACTACAAAACCAGTAGCACCAAGTT
CAAGCACATCAAATTCAAGTACAAGCAGTTCATCGGAGACATCTTCGTCA
ACGAAACGAACTAGTTCAAAAACGAATTAA
```
               (SEQ. ID. NO. 166)
```
NKKNSLYIISSLFFACVLFVYATATNFQNSTSARQVKTETYNTVTNVPID
IRYNSDKYFISGFASEVSVVLTGANRLSLASEMQESTRKFKVTADLTDAG
VGTIEVPLSIEDLPNGLTAVATPQKITVKIGKKAQKDKVKIVPEIDPSQI
DSRVQIENVMVSDKEVSITSDQETLDRIDKIIAVLPTSERITGNYSGSVP
LQAIDRNGVVLPAVITPFDTIMKVTTKPVAPSSSTSNSSTSSSSETSSST
KATSSKTNZ
```

ID216-4127.3

```
ATGTTGATTGGCGAAGGGTATCGGACTTTCCCTGTCCTGATTTATACCCA
ATTTATTAGCGAGGTTGGAGGAAATTCTGCTTTTGCAATTATGGCGATTA
TCATTGCCCTGGCAATTTTCCTTATCCAAAAACACATTGCAAACCGCTAC
AGTTTCAGCATGAATCTGCTCCATCCAATTGAGCCTAAAAAAACTACAAA
AGGAAAAATGGCTGCCATTTATGCAACAGTCTACGGAATTATCTTTATCT
CTGTTTTACCTCAAATCTACTTAATTTATACCTCTTTCCTAAAAACATCA
GGTATGGTATCTGTTAAAGGTTATTCTCCAAACAGTTACAAGGTAGCTTT
CCATCGTATGGGATCTGCTATTTTCAATACCATTCGTATCCCTTTGATTG
CCTTAGTTCTAGTTGTTCTATTTGCGACATTTATCTCCTACCTAGCCGTT
AGAAAACGGAATTTGTTTACAAACTTAATTGACAGCCTCAGTATGGTACC
TTATATTGTACCAGGAACCGTTCTAGGGATTGCCTTCATTTCTTCCTTCA
ATACTGGTCTATTTGGAAGTGGATTTCTTATGATTACAGGGACTGCTTTC
ATCTTGATTATGTCTCTATCTGCCAGAAGATTACCTTATACTATTCGCTC
ATCTGTTGCTAGCTTACAACAAATAGCACCAAGTATTGAAGAAGCTGCTG
AAAGCTTAGGAAGTAGTCGTCTCAATACCTTTGCTAAGATTACAACTCCA
ATGATGCTATCTGGTATCATTTCTGGAGCCATCTTATCTTGA
```
               (SEQ. ID. NO. 167)

```
MLIGEGYRTFPVLIYTQFISEVGGNSAFAIMAIIIALAIFLIQKHIANRY
SFSMNLLHPEIPKKTTKGKMAAIYATVYGIIFISVLPQITLIYTSFLKTS
GMVSVKGYSPNSYKVAFHRMGSAIFNTIRIPLIALVLVVLFATFISYLAV
RKRNLFTNLIDSLSMVPYIVPGTVLGIAFISSFNTGLFGSGFLMITGTAF
ILIMSLSARRLPYTIRSSVASLQQIAPSIEEAAESLGSSRLNTFAKITTP
MMLSGIISGAILSZ
```

TABLE 4

ID301

(SEQ. ID. NO. 196)
```
ATGAATAAGAAAAAAGATTTTAACAAGTCTAGCCAGCGTCGATATCTTA
GGGGCTGGTTTTGTTACGTCTCAGCCTACTTTTGTAAGAGCAGAAGAATC
TCCCACAAGTTGTCGAAAAATCTTCATTAGAGAAGGAAATATGAGGAAGCA
AAAGCAAAAGCTGATACTGCCAAGAAAGATTACGAAACGGCTAAAAAGAA
AGCAGAAGACGCTCAGAAAAAGTATGAAGATGATCAGAAGAGAACTGAGG
AGAAAGCTCGAAAAGAAGCAGAAGCATCTCAAAAATTGAATGATGTGGCG
CTTGTTGTTCAAAATGCATATAAAGAGTACCGAGAAGTTCAAAATCAACG
TAGTAAATATAAATCTGACGCTGAATATCAGAAAGAATTAACAGAGGTCG
ACTCTAAAATAGAAGGCTAGGAAAGAGCAACAGGACTTGCAAATAAA
TTTAATGAAGTAAGAGCAGTTGTAGTTCCTGAACCAAATGCGTTGGCTGA
GACTAAGAAAAAAGCAGAAGAAGCTAAAGCAGAAGAAAATAGCTAAGA
GAAAATATGATTATGCAACTCTAAAGGTAGCACTAGCGAAGAAAGAAGTA
GAGGCTAAGGAACTTGAAATTGAAAAACTTCAATATGAAATTTCTACTTT
GGAACAAGAAGTTGCTACTGCTCAACATCAAGTAGATAATTTGAAAAAAC
TTCCTGCTGGTGCGGATCCTGATGATGGCACAGAAGTTATAGAAGCTAAA
TTAAAAAAAGGAGAACGTGAGCTAAACGCTAAACAAGCTGAGTTGCAAA
AAACAAACAGAACTTGAAAAACTTCTTGACAGCCTTGATCCTGAAGGTA
AGACTCAGGATGAATTAGATAAAGAAGCAGAAGAAGCTGAGTTGGATAAA
AAAGCTGATGAACTTCAAAATAAAGTTGCTGATTTAGAAAAAGAAATTAG
TAACCTTGAAATATTACTTGGAGGGCGTGATCCTGAAGATGATACTGTG
CTCTTCAAAATAAAATTAGCTGCTAAAAAGCTGAGTTAGCAAAAAACAA
ACAGAACTTGAAAAACTTCTTGACAGCCTTGATCCTGAAGGTAAGACTCA
GGATGAATTAGATAAAGAAGCAGAAGAAGCTGAGTTGGATAAAAAAGCTG
ATGAACTTCAAAATAAAGTTGCTGATTTAGAAAAAGAAATTAGTAACCTT
GAAATATTACTTGGAGGGCGTGATTCTGAAGATGATACTGCTGCTCTTCA
AAATAAATTAGCTACTAAAAAAGCTGAATTGAAAAAACTCAAAAGAAT
TAGATGCAGCTCTTAATGAGTTAGGCCCTGATGGAGATGAAGAAGAAACT
CCAGCGCCCGGCTCCTCAACCAGACAACCAGCTCCTGCACCAAAACCAGA
GCAACCAGCTCCAGCTCCAAAACCAGACAACCAGCTCCTGCACCAAAAC
CAGAGCAACCAGCTCCAGCTCCAAAACCAGAGCAACCAGCTCCAGCTCCA
AAACCAGAGCAACCAGCTAAGCCGGAGAAACCAGCTGAAGAGCCTACTCA
ACCAGAAAAACCAGCCACTCCAAAAACAGGCTGGAAACAAGAAAACGTA
TGTGGTATTTCTACAATACTGATGGTTCAATGGCAATAGGTTGGCTCCAA
AACAACGGTTCATGGTACTACCTAAACGCTAACGGCGCTATGGCAACAGG
TTGGGTGAAAGATGGAGATACCTGGTACTATCTTGAAGCATCAGGTGCTA
TGAAGACAAGCCAATGGTTCAAAGTATCAGATAAATGGTACTATGTCAAC
AGCAATGGCGCTATGGCGACAGGCTGGCTCCAATACAATGGCTCATGGTA
CTACCTCAACGCTAATGGTGATATGGCGACAGGATGGCTCCAATACAACG
GTTCATGGTATTACCTCAACGCTAATGGTGATATGGCGACAGGATGGGCT
AAAGTCAACGGTTCATGGTACTACCTAAACGCTAACGGTGCTATGGCTAC
AGGTTGGGCTAAAGTCAACGGTTCATGGTACTACCTAAACGCTAACGGTT
```

TABLE 4-continued

```
CAATGGCAACAGGTTGGGTGAAAGATGGAGATACCTGGTACTATCTTGAA
GCATCAGGTGCTATGAAAGCAAGCCAATGGTTCAAAGTATCAGATAAATG
GTACTATGTCAATGGCTTAGGTGCCCTTGCAGTCAACACAACTGTAGATG
GCTATAAAGTCAATGCCAATGGTGAATGGGTTTAA
```

(SEQ. ID. NO. 184)
```
MNKKKMILTSLASVAILGAGFVTSQPTFVRAEESPQVVEKSSLEKKYEEA
KAKADTAKKDYETAKKKAEDAQKKYEDDQRKTEEKARKEAEASQKLNDVA
LVVQNAYKEYREVQNQRSKYKSDAEYQKKLTEVDSKIEKARKEQQDLQNK
FNEVRAVVVPEPNALAETKKKAEEEAKAEEEVAKRKYDYATLKVALAKKEV
EAKELEIEKLQYEISTLEQEVATAQHQVDNLKKLLAGADPDDGTEVIEAK
LKKGEAELNAKQAELAKKQTELEKLLDSLDPEGKTQDELDKEAEEAELDK
KADELQNKVADLEKEISNLEILLGGADPEDDTAALQNKLAAKKAELAKKQ
TELEKLLDSLDPEGKTQDELDKEAEEAELDKKADELQNKVADLEKEISNL
EILLGGADSEDDTAALQNKLATKKAELEKTQKELDAALNELGPDGDEEET
PAPAPQPEQPAPAPKPEQPAPAPKPEQPAPAPKPEQPAPAPKPEQPAPAP
KPEQPAPKPEKPAEEPTQPEKPATPKTGWKQENGMWYFYNTDGSMAIGWLQ
NNGSWYYLNANGAMATGWNVKDGDTWYYLEASGAMKASQWFKVSDKWYYV
NSNGAMATGWLQYNGSWYYLNANGDMATGWLQYNGSWYYLNANGDMATGW
AKVNGSWYYLNANGAMATGWAKVNGSWYYLNANGSMARTGWVKEGDTWYY
LEASGAMKASQWFKVSDKWYYVNGLGALAVNTTVDGYKVNANGEWVZ
```

ID302

(SEQ. ID. NO. 197)
```
ATGTTTGCATCAAAAAGCGAAAGAAAAGTACATTATTCAATTCGTAAATT
TAGTGTTGGAGTAGCTAGTGTAGTTGTTGCCAGTCTTGTTATGGGAAGTG
TGGTTCATGCGACAGAGAACGAGGGAGCTACCCAAGTACCCACTTCTTCT
AATAGGGCAAATGAAAGTCAGGCAGAACAAGGAGAACAACCTAAAAAACT
CGATTCAGAACGAGATAAGGCAAGGAAAGAGGTCCAGGAGATAATGTAAAAA
AAATAGTGGGTGAGAGCTATGCAAAATCAACTAAAAAGCGACATACAATT
ACTGTAGCTGCCAGTCTTGTTATGGGAAGTGTGGTTCATGCGACAGAGAA
CGAGGGAGCTACCCAAGTACCCACTTCTTCTAATAAGATACTGATGATGG
AGAGTCGATCAAAAGTAGATGAAGCTGTGTCTAAGTTTGAAAAGGACTCA
TCTTCTTCGTCAAGTTCAGACTCTTCCACTAAACCGGAAGCTTCAGATAC
AGCGAAGCCAAACAAGCCGACAGAACCAGGAGAAAAGGTAGCAGAAGCTA
AGAAGAAGGTTGAAGAAGCTGAGAAAAAAGCCAAGGATCAAGAAGCAGAA
GATCGTCGTAACTACCCAACCATTACTTACAAAACGCTTGAACTTGAAAT
TGCTGAGTCCGATGTGGAAGTTAAAAAAGCGGAGCTTGAACTAGTAAAAG
TGAAAGCTAACGAACCTCGAGACGAGCAAAAAATTAAGCAAGCAGAAGCG
GAAGTTGAGAGTAAACAAGCTGAGGCTACAAGGTTAAAAAAATCAAGACA
GATCGTGAAGAAGCAGAAGAAGAAGCTAAACGAAGAGCAGATCGTAGATG
CGAAGTCTTCAGATTCTAGCTAGGTGAAGAAACTCTTCCAAGCCCATCC
CTGAAACCAGAAAAAAGGTAGCAGAAGCTGAGAAGAAGGTTGAAGAAGC
TAAGAAAAAAGCCGAGGATCAAAAAGAAGAAGATCGCCGTAACTACCCAA
CCAATACTTAGAAAACGCTTGAACTTGAAATTGCTGAGTCCGATGTGGAA
GTTAAAAAAGCGGAGCTTGAACTAGTAAAAGAGGAAGCTAAGGAACCTCG
AAACGAGGAAAAGTTAAGCAAGCAAAAGCGGAAGTTGAGAGTAAAAAAG
CTGAGGCTACAAGGTTAGAAAAAATCAAGACAGATCGTAAAAAGCAGAA
GAAGAAGCTAAACGAAAAGCAGCAGAAGAAGATAAAGTTAAAGAAAAACC
AGCTGAACAACCACAACCAGCGCCGGCTCCAAAAGCAGAAAAACCAGCTC
CAGCTCCAAAACCAGAGAATCCAGCTGAACAACCAAAAGCAGAAAAACCA
GCTGATCAACAAGCTGAAGAAGACTATGCTCGTAGATCAGAAGAAGAATA
TAATCGCTTGACTCAACAGCAACCGCCAAAAACTGAAAAACCAGCACAAC
CATCTACTCCAAAAACAGGCTGGAAACAAGAAAACGGTATGTGGTACTTC
TACAATACTGATGGTTCAATGGCGACAGGATGCTCCAAAACAATGGCTC
ATGGTACTACCTCAACAGCAATGGCGCTATGGCGACAGGATGGCTCCAAA
ACAATGGTTCATGGTACTATCTAAACGCTAATGGTTCATGGTACTACCAGGA
TGGCTCCAAAACAATGGTTCATGGTACTACCTAAACGCTAATGGTTCAAT
GGCGACAGGATGGCTCCAATACAATGGCTCATGGTACTACCTAAACGCTA
ATGGTTCAATGGCGACAGGATGGCTCCAATACAATGGCTCATGGTACTAC
CTAAACGCTAATGGTGATATGGCGACAGGTTGGGTGAAAGATGGAGATAC
CTGGTACTATCTTGAAGCATCAGGTGCTATGAAAGCAAGCCAATGGTTCA
AAGTATCAGATAAATGGTACTATGTCAATGGCTCAGGTGCCCTTGCAGTC
AACACAACTGTAGATGCTATGGAGTCAATGCCAATGGTGAATGGGTAAA
CTAA
```

(SEQ. ID. NO. 185)
```
MFASKSERKVHYSIRKFSVGVASVVVASLVMGSVVHATENEGATQVPTSS
NRANESQAEQGEQPKKLDSERDKARKEVEEYVKKIVGESYASKTKKRHTI
TVALVENELNNIKNEYLNKIVESTSESQLQILMMESRSKVDEABSGEKDS
SSSSSSDSSTKPEASDTAKPNKPTEPGEKVAEAKKKVEEAEKKAKDQKEE
DRRNYPTITYKTLELEIAESDVEVKKAELELVKVKANEPRDEQKIKQAEA
EVESKQAEATRLKIKTDREEAEEEAKRRADAKEQGKPKGRAKRGVPGELA
TPDKKENDAKSSDSSVGEETLSPSLKPEKKVAEAEKKVEEAKKKAEDQK
EEDRRNYPTNTYKTLELEIAESDVEVKKAELELVKEEAKEPRNEEKVKQA
KAEVESKKAEATRLEKIKTDRKKAEEEAKRKAAEEDKVKEKPAEQPQPAP
APKAEKPAPAPKPENPAEQPKAEKPADQQAEEDYARRSEEEYNRLTQQQP
PKTEKPAQPSTPKTGWKQENGMWYFYNTDGSMATGWLQNNGSWYYLNSNG
AMATGWLQNNGSWYYLNANGSMATGWLQNNGSWYYLNANGSMATGWLQYN
GSWYYLNANGSMATGWLQYNGSWYYLNANGDMATGWVKDGDTWYYLEASG
AMKASQWFKVSDKWYYVNGSGALAVNTTVDGYGVNANGEWVNZ
```

ID303

(SEQ. ID. NO. 198)
```
ATGGTAAAAAGACGTATAAGGAGAGGGACGAGAGGAACCTGAAAAAGTTGT
TGTTCCTGAGCAATCATCTATTCCTCGTATCCTGTATCTGTTACATCTAA
CCAAGGAACAGATGTAGCAGTAGAACCAGCTAAAGCAGTTGCTCCAACAA
CAGACTGGAAACAAGAAATGGTATGTGGTATTTTTATAATACTGATGGT
TCCATGGCAACAGGTTGGGTACAAGTTAATAGTTCATGGTACTACCTCAA
CAGCAACGGTTCTATGAAAGTCAATCAATGTTCCAAGTTGGTGGTAAAT
GGTATTATGTAAATACATCGGGTGAGTTAGCGGTCAATACAAGTATAGAT
GGCTATAGAGTCAATGATAATGGTGAATGGGTGCGTTAA
```

(SEQ. ID. NO. 186)
```
MVKRRIRRGRREPEKVVVPEQSSIPSYPVSVTSNQGTDVAVEPAKAVAPT
TDWKQENGMWYFYNTDGSMATGWVQVNSSWYYLNSNGMKVNQWFQVGGKW
YYVNTSGELEVNTSIDGYRVNDNGEWVRZ
```

ID304

(SEQ. ID. NO. 199)
```
CTGAATACAAGTTTTGTTCATGCTGCTGATGGGATTCAATATGTCAFAGA
TGATACTAGAGATAAAGAAGAGGGAATAGAGTATGATGACGCTGACAATG
GGGATATTATTGTAAAAGTAGCGACTAAACCTAAGGTAGTAACCAAGAAA
ATTTCAAGTACGCGAATTCGTTATGAAAAAGATGAAACAAAAGACCGTAG
TGAAAATCCTGTTACAATTGATGGAGAGGATGGCTATGTAACTACGACAA
GGACCTACGATGTTAATCCAGAGACTGGTTATGTACCGAACAGGTTACT
GTTGATAGAAAAGAAGCCACGGATACAGTTATCAAAGTTCCAGCTAAAAG
CAAGGTTGAAGAAGTTCTTGTTCCATTTGCTACTAAATATGAAGCAGACA
ATGACTTGTCAGGACAGGAGCCAAGAGATTACTTAGGAAAGAATGGG
AAAACAGTTACAACGATAACTTATAATGTAGATGGAAAGAGTGGACAAGT
AACTGAGAGTACTTTAAGTCAAAAAAAAGACTCTCAAACAAGAGTTGTTA
AAAAAAGAACCAAGCCCCAAGTTCTTGTCCAAGAAATTCCAATCGAAACA
GAATATCTCGATGGCCCAACTCTTGATAAAAGTCAAGAAGTAGAAGAAGT
AGGAGAAATTGGTAAATTACTCTTACTACAATCTATACTGTAG
```

(SEQ. ID. NO. 187)
```
LNTSFVHAADGIQYVRDDTRDKEEGIEYDDADNGDIIVKVATKPKVVTKK
ISSTRIRYEKDETKDRSENPVTIDGEDGYVTTTRTYDVNPETGYVTEQVT
VDRKEATDTVIKVPAKSKVEEVLVPFATKYEADNDLSAGQEQEITLGKNG
KTVTTITYNVDGKSGQVTESTLSQKKDSQTRVVKKRTKPQVLVQEIPIET
EYLDGPTLDKSQEVEEVGEIGKLLLLQSILZ
```

ID305

(SEQ. ID. NO. 200)
```
ATGAAGCTTTTGAAAAAAATGATGCAAATCGCACTAGCCACATTTTTCTT
CGGTTTGTTAGCGACAAATACAGTATTTGCAGATGATTCTGAAGGATGGC
AGTTTGTCCAAGAAAATGGTAGAACCTACTACAAAAAGGGGGATCTAAAA
GAAACCTACTGGAGAGTGATAGATGGGAAGTACTATTATTTTGATCCTTT
ATCCGGAGAGATGGTTGTCGGCTGACAATATATACCTGCTCCACACAAGG
GGGTTACGATTGGTCCTTCTCCAAGAATAGAGATTGCTCTTAGACCAGAT
TGGTTTTATTTTGGTCAAGATGGTGTATTACAAGAATTTGTTGGCAAGCA
AGTTTTAGAAGCAAAAACTGCTACGAATACCAACAAACATCATGGGGAAG
AATATGATGGCCAAGCAGAAAACAGTCTATTATTTTGAAGATCAGCGT
AGTTATCATACTTTAAAACTGGTTGGATTTATGAAGAGGGTCATTGGTA
TTATTTACAGAAGGATGGTGGCTTTGATTCGCGCATCAACAGATTCACGG
TTGGAGAGCTAGCACGTGTTGGGTTAAGGATTACCCTCTTACGTATGAT
GAAGAGAAGCTAAAAGCAGCTCCATGGTACTATCTAAATCCAGCAACTGG
CATTATGCAAACAGGTTGGCAATATCTAGGTAATAGATGGTACTACCTCC
ATTCGTCAGGAGCTATGGCAACTGGCTGGTATAAGGAAGGCTCAACTTGG
TACTATCTAGATGCTGAAAATGGTGATATGAGAACTGGCTGGCAAAACCT
TGGGAACAAATGGTACTATCTCCGTTCATCAGGACTCTAGGAATGGCTGTT
GGTATCAGGAAAGTTCGACTTGGTACTATCTAAATGCAAGTAATGGAGAT
ATGAAAACAGGCTGGTTCCAAGTCAATGGTAACTGGTACTATGCCTATGA
TTCAGGTGCTTTAGCTGTTAATACCACAGTAGGTGGTTACTACTTAAACT
ATAATGGTGAATGGGTTAAGTAA
```

(SEQ. ID. NO. 188)
```
MKLLKKMMQIALATFFFGLLATNTVFADDSEGWQFVQENGRTYYKKGDLK
ETYWRVIDGKYYYFDPLSGEMVVGWQYIPAPHKGVTIGPSPRIEIALRPD
WFYFGQDGVLQEFVGKQVLEAKTATNTNKHHGEEYDSQAEKRVYYFEDQR
SYHTYLHSSGAMATGWYKEGSTWYYLDAENGDMRTGWQNLGNKWYYLRSS
GAMATGWYQESSTWYYLNASNGDMKTGWFQVNGNWYYAYDSGALAVNTTV
GGYYLNYNGEWVKZ
```

TABLE 4-continued

ID306

(SEQ. ID. NO. 201)
TTGGCTGGTAGATATGGTTCTGCTGTTCAGTGTACAGAAGTGACTGCCTC
AAACCTTTCAACAGTTAAAACTAAAGCTACGGTTGTAGAAAAACCACTGA
AAGATTTTAGAGCGTCTACGTCTGATCAGTCTGGTTGGGTGGAATCTAAT
GGTAAATGGTATTTCTATGAGTCTGGTGATGTGAAGACAGGTTGGGTGAA
AACAGATGGTAAATGGTACTATTTGAATGACTTAGGTGTCATGCAGACTG
GATTTGTAAAATTTTCTGGTAGCTGGTATTACTTGAGCAATTCAGGTGCT
ATGTTTACAGGCTGGGGAACAGATGGTAGCAGATGGTTCTACTTTGACGG
CTCAGGAGCTATGAAGACAGGCTGGTACAAGGAAAATGGCACTTGGTATT
ACCTTGACGAAGCAGGTATCATGAAGACAGGTTGGTTTAAAGTCGGACCA
CACTGGTACTATGCCTACGGTTCAGGAGCTTTGGCTGTGAGCACAACAAC
ACCAGATGGTTACCGTGTAAATGGTAATGGTGAATGGGTAAACTAG (SEQ. ID. NO. 189)
LAGRYGSAVQCTEVTASNLSTVKTKATVVEKPLKDFRASTSDQSGWVESN
GKWYFYESGDVKTGWVKTDGKWYYLNDLGVMQTGFVKFSGSWYYLSNSGA
MFTGWGTDGSRWFYPDSGAMKTGWYKENGTWYYLDEAGIMKTGWFKVGP
HWYYAYGSGALAVSTTTPDGYRVNGNGEWVNZ

ID307

(SEQ. ID. NO. 200)
ATGAAAATTTTGAAAAAAACTATGCAAGTTGGACTGACAGTATTTTTCTT
TGGTTTGCTAGGGACCAGTACAGTATTTGCAGATGATTCTGAAGGATGGC
AGTTTGTCCAAGAAAACGGAAGAACCTACTACAAAAAGGGGGACCTCAAA
GAAACCTACTGGCGAGTGATTGATGGTAAGTACTATTATTTTGATTCTCT
ATCTGGAGAGATGGTTGTCGGCTGGCAATATATCCCGTTTCCATCTAAAG
GTAGTACAATTGGTCCTTACCCAAATGGTATCAGATTAGAAGGTTTTCCA
AAGTCAGAGTGGTACTACTTCGATAAAAATGGAGTGCTACAAGAGTTTGT
TGGTTGGAAAACATTAGAGATTAAAACTAAAGACAGTGTTGGAAGAAAGT
ACGGGGAAAAACGTGAAGATTCAGAAGATAAAGAAGAAGCGTTATTAT
ACGAACTATTACTTTAATCAAAATCATTCTTTAGACACACGTTCGCTTTA
TGATCAGTCTAACTCGTATTATCTAGCTAAGACGGAAATTAATGGAGAAA
ACTACCTTGGTGGTGAAAGACGTGCGGGGTGGATAAACGATGATTCGACT
TGGTACTACCTAGATCCAACAACTGGTATTATGCAAACAGGTTGGCAATA
TCTAGGTAATAAGTGGTACTACCTCCGTTCCTCAGGAGCAATGGCCACTG
GCTGGTATCAGGAAGGTACCACTTGGTATTATTTAGACCACCCAAATGGC
GATATGAAAACAGGTTGGCAAAACCTTGGGAACAAATGGTACTATCTCCG
TTCATCAGGAGCTATGGCAACTGGTTGGTATCAAGATGGTTCAACTTGGT
ACTACCTAAATGCAGGTAATGGAGACATGAAGACAGGTTGGTTCCAGGTC
AATGGCAACTGGTACTATGCTTAT (SEQ. ID. NO. 190)
MKILKKTMQVGLTVFFFGLLGTSTVFADDSEGWQFVQENGRTYYKKGDLK
ETYWRVIDGKYYYFDSLSGEMVVGWQYIPFPSKGSTIGPYPGIRLEGFPK
SEWYYFDIOGVLQEFVQWKTLEILKTISVGRKYGEKREDSEDKEEKRYYT
NYYFNQNHSLETGWLYSQSNWYYLAKTEINGENYLGGERRAGWINDDSTW
YYLDPTTGIMQTGWQYLGNKWYYLRSSGAMATGWYQEGTTWYYLDHPNGD
MKTGWQNLGNKWYYLRSSGAMATGWYQDGSTWYYLNAGNGDMKTGWFQVN
GNWYYAYSSGALAVNTTVDGYSVNYNGEWVRZ

ID308

(SEQ. ID. NO. 203)
ATGAAAAGAAATTAACTAGTTTAGCACTTGTAGGCGCTTTTTTAGGTTT
GTCATGGTATGGGAATGTTCAGGCTGAAGAAAGTTCAGGAAATAAAATCC
ACTTTATCAATGTTCAAGAAGGTGGCAGTGATGCGATTATTCTTGAAAGC
AATGGACATTTTGCCATGGTGGATACAGGAGAAGATTATGATTTCCCAGA
TGGAAGTGATTCTCGCTATCCATGGAGAGAAGGAATTGAAACGTCTTATA
AGCATGTTCTAACAGACCGTGTCTTTCGTCGTTTGAAGGAATTGGGTGTC
CAAAAACTTGATTTTATTTTGGTGACCCATACCCACAGTGATCATATTGG
AAATGTTGATGAATTACTGTCTACCTATCCAGTTGACCGAGTCTATCTTA
AGAAATATAGTGATAGTCGTATTACTAATTCTGAACGTCTATGGGATAAT
CTGTATGGCTATGATAAGGTTTTACAGACTGCTGCAGAAAAGATGGTGTTC
AGTTATTCAAAATATCACACAAGGGGATGCTCATTTTCAGTTTGGGGACA
TGGATATTCAGCTCTATAATTATGAAAATGAAACTGATTCATCGGGTGAA
TTAAAGAAAATTTGGGATGACAATTCCAATTCCTTGATThGCGTGGTGAA
AGTCAATGGCAGAAAATTTACCTTGGGGGCGATTTAGATAATGTTCATG
GAGCAGAAGACAAGTATGGTCCTCATTCATTGGAAAAGTTGATTTGATGAAG
TTTAATCATCACCATGATACCAACAATCAAATACCAAGGATTTCATTAA
AAATTTGAGTCCGAGTTTGATTGTTCAAACTTCGGATAGTCTACCTTGGA
AATGGTTTGTTTGATGAGTAGTGTTAATTGGCTCAAGAGAGGAAT
TGAGAGAATCACGCAGCCAGCAAAGACTATGATGCAACAGTTTTTGATAT
TCGAAAAGACGGTTTTGTCAATATTTCAACATCCTACAAGCCGATTCCAA
GTTTTCAAGCTGGTTGGCATAAGAGTGCATATGGGAACTGGTGGTATCAA
GCGCCTGATTCTACAGGAGAGTATGCTGTCGGTTGGAATGAAATCGAAGG
TGAATGGTATTACTTTAACCAAACGGGTATCTTGTTACAGAATCAATGGA

AAAAATGGAACAATCATTGGTTCTATITGACAGACTCTGGTGCTTCTGCT
AAAAATTGGAAGAAAATCGCTGGAATCTGGTATTATTTTAACAAAGAAAA
CCAGATGGAAATTGGTTGGATTCAAGATA)*AGAGCAGTGGTATTATTTG
GATGTTGATGGTTCTATGAAGACAGGATGGCTTCAATATATGGGGCAATG
GTATTACTTTGCTCCATCAGGGGAATGAAAATGGGCTGGGTAAAAGATA
AAGAAACCTGGTACTATATGGATTCTACTGGTGTCATGAAGACAGGTGAG
ATAGAAGTTGCTGGTCAACATTATTATCTGGAAGATTCAGGAGCTATGAA
GCAAGGCTGGCATAAAAAGGCAAATGATTTGGTATTTCTACAAGACAGACG
GTTCACGAGCTGTGGGTTGGATCAAGGACAAGGATAAATGGTACTTCTTG
AAAGAAAATGGTCAATTACTTGTGAACGGTAAGACACCAGAAGGTTATAC
TGTGGATTCAAGTGGTGCCTGGTTAGTGGATGTTTCGATCGAGAAATCTG
CTACAATTAAACATCAAGCTCATTCAGAAATAAAAGAATCCAAAGAAGTA
GTGAAAAAGGATCTTGAAAATAAAGAAACGAGTCAACATGAAAGTGTTAC
AAATTTTTTCAACTAGTCAAGATTTGACATCCTCAACTTCACAAAGCTCTG
AAACGAGTGTAAACAAATCGGAATCAGAACAGTAG (SEQ. ID. NO. 191)
MKKKLTSLALVGAFLGLSWYGNQAQESSGNKIHFINVQEGGSDAIILESN
GHFAMVDTGEDYDFPDGSDSRYPWREGIETSYKHVLTDRVFRRLKELGVQ
KLDFILVTHTHSDHIGNAHFQGDMDIQLYNYENETDSSGELKKIWDDNSN
LSISVVKVNGKKIYLGGDLDNVHGAHGQFGDMDIQLYNYENETDSSGELK
KIWDDNSNSLISVVKVNGKKIYLGGDLDNVHGAEDKYGPLIGKVDLMKFN
HHHDTNKSNTKDFIKNLSPSLIVQTSDSLPWJGVDDSRYVNWLKERGILE
RINAASKDYDATVFDIRKDGFVNISTSYKPIPSFQAGWHKSAYGNWWYQA
PDSTGEYAVGWNEIEGEWYYFNQTGILLQNQWKKWNNHWFYLTDSGASAK
NWKKIAGIWYYFNKENQMEIGWIQDKEQWYYLDVDGSMKTGWLQYMGQWY
YFAPSGEMKMGWVKDKETWYYMDSTGVMKTGEIEVAGQHYYLEDSGAMKQ
GWHKKANDWYFYKTDGSRAVGWIKDKDKWYFLKENGQLLVNGKTPEGYTV
DSSGAWLVDVSIEKSATIKTTSHSEIKESKEVVKKDLENKETSQHESVTM
FSTSQDLTSSTSQSSETSVNKSESEQZ

ID309

(SEQ. ID. NO. 204)
ATGGAAATTAATGTGAGTAAATTAAGAACAGATTTGCCTCAAGTCGGCGT
GCAACCCATATAGGCAAGTACACGCACACTCAACTGGGAATCCGCATTCAA
CCGTACAGAATGAAGCGGATTATCACTGGCGGAAGACCCAGAATTAGGT
TTTTTCTCGCACATTGTTGGGAACGGTTGCATCATGCAGGTAGGACCTGT
TGATAATGGTGCCTGGGACGTTGGGGGCGGTTGGAATGCTGAGACCTATG
CAGCGGTTGAACTGATTGAAAGCCATTCAACCAAAGAAGAGTTCATGACG
GACTACCGCCTTTATATCGAACTCTTACGCAATCTAGCAGATGAAGCAGG
TTTGCCGAAAACGCTTGATACAGGGAGTTTAGCTGGAATTAAAACGCACG
AGTATTGCACGAATACCAACCAAACAACCACTCAGACCACGTTGACCCT
TATCCATATCTTGCTAAATGGGGCATTAGCCGTGAGCAGTTTAAGCATGA
TATTGAAACGGCTTGACGATTGAAACAGGCTGGCAGAAGAATGACACTG
GCTACTGGTACGTACATTCAGACGGCTCTTATCCAAAAGACAAGTTTGAG
AAAATCAATGGCACTTGGTACTACTTTGACAGTTCAGGCTATATGCTTGC
AGACCGCTGGAGGAAGCACACAGACGGCAACTGGTACTGGTTCGACAACT
CAGGCGAAATGGCTACAGGCTGGAAGAAAATCGCTGATAAGTGGTACTAT
TTCAACGAAGAAGGTGCCATGAAGACAGGCTGGGTCAAGTACAAGGACAC
TTGGTACTACTTAGACGCTAAAGAAGGCGCCATGGTATCAAATGCCTTTA
TCCAGTCAGCGGACGGAACAGGCTGGTACTACCTCAAACCAGACGGAACA
CTGGCAGACAAGCCAGAATTCACAGTAGAGCCAGATGGCTTGATTACAGT
AAAATAA (SEQ. ID. NO. 192)
MEINVSKLRTDLPQVGVQPURQVHAHSTGNPHSTVQNEADYHWRKDPELG
FFSHIVGNGCIMQVGPVDGAWDVGGGWNAETYAAVELIESHSTKEEFMT
DYRLIELLRNLADEAGLPKTLDTGSLAGIKTHEYCTNNQPNNHSDHVDPY
PYLAKWGISREQFKHDIENGLTIETGWQKNDTGYWYVHSDGSYPKDKFEK
INGTWYYFDSSGYMLADRWRKHTDGNWYWFDNSGEMATGWKKIADKWYYF
NEEGAMKTGWVKYKDTWYYLDAKEGAMVSNAFIQSADGTGWYYLKPDGTL
ADKPEFTVEPDGLITVKZ

ID310

(SEQ. ID. NO. 205)
ATGGGCACAACAGGATTTACAATAATTGACTTAATTATCTTGATTGTTTA
TTTACTTGCGGTGTTGGTTGCAGGTATCTATTTCTCTAAAAAAGAGATGA
AAGGAAAAGAGTTCTTTAAAGGAGATGGTTCGGTTCTTCGGTATGTTACT
TCGGTATCCATTTTTGCCACAATGCTCAGTCCGATTTCCTTCTTGGGACT
CGCTGGTAGCTCTTATGCAGGTAGCTGGATTTTATGGTTTGCTCAATTAG
GGATGGTAGTAGCTATTCCACTGACAATTCGTTTTATCTTACCTATCTTT
GCACGATAGACATCGATGAGCAGATATCACAGCATATTACTTGGATAAACGTTTTAA
TTCTAAAGCACTTCGTATTATTTCAGCACTCTTTGTTTATTATTTTATCAAT
TGGGACTATGTCTATCATTATGTACCTCCCATCAGCTGGTTTATCAGTA
TTCAGAGGAATTGACATCAATATTTTGATTATTTTGATGGGTGTAGTTGC
AATTGTTTATTCTTATACTGGTGGTCTAAAATCCGTATTATGGACAGACT
TTATTCAAGGTGTGATTCTGATTAGTGGTGTCGTTTTAGCTTTATTTGTA

TABLE 4-continued

```
CTGATTGCTAATATTAAAGGTGGCTTTGGTGCAGTAGCAGAAACATTAGC
AAACGGGAAATTCCTTGCTGCAAATGAAAAACTTTTCGATCCTAACTTGC
TTTCAAACTCCATCTTTTTAATTGTGATGGGTTCAGGCTTTACAATCTTG
TCTTCCTATGCTTCATCTCAAGATTTGGTTCAACGTTTTACTACAACACA
AAATATTAAGAAACTTAATAAGATGTTGTTCACAAAGCCTGTTTTGTCAC
TTGCAACTGCAACAGTCTTTTACTTGATTGGTACAGGCTTGTACGTATTC
TATCAAGTACAAAATGCAGATAGTGCAGCTAGCAATATCCCTCAAGACCA
AATCTTTATGTACTTTATTGCATACCAGTTACCAGTAGGTATTACACAGGTT
TGATCTTGGCAGCGATTTATGCAGCATCTCAATCAACTATTTCAACAGGT
TTGAACTCTGRTGCAACTTCATGGACATTGGATATTCAAGATGTCATTTC
TAAAAATATGTCAGACAATCGTCGTACGAAAATTGCACAATTCGTATCTC
TAGCAGTAGGTTTATTCTCAATTGGTGTTTCCATTGTCATGGCTCACTCA
GATATTAAATCTGCATACGAATGGTTCAATAGTTTCATGGGACTTGTACT
TGGTCTACTTGGTGGTGTATTTATTCTTGGATTTGTTTCTAAAAAAGCAA
ATAAACAAGGTGCTTATGCAGCGCTGATTGTATCAACCATCGTCATGGTA
TTTATTAAATACTTCCTTCCTCCAACAGCTGTTAGCTACTGGGCATATTC
ATTGCATTTCAATCTCTGTATCAGTAGTTTCAGGTTATATTGTATCTGTTC
TTACTGGAAATAAAGTATCTGCACCTAAATATACAACGATRCATGATATT
ACAGAAATTAAAGCGGATTCAAGTTGGGAAGTTCGTCACTAA (SEQ. ID. NO. 193)
MGTTGFTIIDLIILIVYLLAVLVAGIYFSKKEMKGKEFFKGDGSVPWYVT
SVSIFATMLSPISFLGLAGSSYAGSWILWFAQLGMVVAIPLTIRFILPIF
ARIDIDRAYDYLDKRFNSKALRIISALLFIIYQLGRMSIIMYLPSAGLSV
LTGIDINILIILMGVVAIVYSYTGGLKSVLWTDFIQGVILISGVVLALFV
LIANIKGGFGAVAETLANGKFLAANEKLFDPNLLSNSIFLIVMGSGFTIL
SSYASSQDLVQRFTTTQNIKKLN14LFTNGVLSLATAIVFYLIGTGLYVF
YQVQNADSAASNIPQDQIFMYFIAYQLPVGITGLILAAIYAASQSTISTG
LNSVATSWTLDIQDVISKNMSDNRRTKIAQFVSLAVGLFSIGVSIVMAHS
DIKSAYEWFNSFNGLVLGLLGGVFILGFVSKKANKQGAYAALIVSTIVMV
FIKYFLPPTAVSYWAYSLISISVSVVSGYIVSVLTGNKVSAPKYTTIHDI
TEIKADSSWEVRHZ

ID311

(SEQ. ID. NO. 206)
ATGAAAATTAATAAAAAATATCTAGCAGGTTCAGTGGCAGTCCTTGCCCT
AAGTGTTTGTTCCTATGAGCTTGGTCGTCACCAAGCTGGTCAGGATAAGA
AAGAGTCTAATCGAGTTGCTTATATAGATGGTGATCAGGCTCGTCAAAAG
GCAGAAAACTTGACACCAGATGAAGTCAGTAAGAGGGAGGGGATCAACGC
CGAACAAATCCTCATCAAGATTACGGATCAAGGTTATGTGACCTCTCATG
GAGACCATTATCATTACTATAATGGCAAGCTCCCTTATGATGCCATCATC
AGTGAAGAGCTCCTCATGAAAGATCCGAATTATCAGTTGAAGGATTCAGA
CATTGTCAATGAAATCAAGGGTGGTTATGTCATCAAGGTAGACGGAAAAT
ACTATGTTThCCTTAAGGATGCAGCTCATGCGGATAATATTCGGACAAAA
GAAGAGATTAAACGTCAGAAGCAGGAACGCAGTCATAATCACGGGTCAGG
AGCTAACGATCATGCAGTAGCTGCAGCCAGAGCCCAAGGACGCTATACAA
CGGATGATGGGTATATCTTCAATGCATCTGATATCATTGAGGACACGGGT
GATGCTTATATCGTTCCTCACGGCGACCATTACCATTACATTCCTAAGAA
TGAGTTATCAGCTAGCGAGTTAGCTGCTGCAGAAOCCTATTGGAATGGGA
AGCAGGGATCTCGTCCTTCTTCAAGTTCTAGTTATAATGCAAATCCAGCT
CAACCAAGATTGTCAGAGAACCACAATCTGACTGTCACTCAAACTTATCA
TCAAATCAAGGGGAAACATTICAAGCCTTTTACGTGAATHGTATGCTA
AACCCTTATCAGAACGCCCATTGAACTCTGATGGCCTTATTTTCGACCCA
GCGCAAATCACAAGTCGAACCCCCAGAGGTGTAGCTGTCCCTCATGGTAA
CCATTACCACTTTATCCCTTATGAACAAATCTCTGAATTGGAAAACGAA
TTGCTCGTATTATTCCCCTTCGTTATCGTTCAAACCATTGGGTACCAGAT
TCAAGACCAGAACAACCAAGTCCACAATCGACTCCGGAACCTAGTCCAAG
TCCGCAACCTGCACCAAATCCTCAACCAGCTCCAAGCAATCCAATTGATG
AGAAATTGGTCAAAGAAGCTGTTCGAAAAGTAGGCGATGGTTATGTCTTT
GAGGAGAATGGAGTTTCTCGTTATATCCCAGCCAAGGATCTTTCAGCAGA
AACAGCAGCAGGCATTGATAGCAAACTGGCCAAGCAGGAAAGTTTATCTC
ATAAGCTAGGAGCTAAGAAAACTGACCTCCCATCTAGTGATCGAGAATT
TTACAATAAGGCTTATGACTTACTAGCAAGAATTCACCAAGATTTACTTG
ATAATAAAGGTCGACAAGTTGATTTGTAGACGTTTGGATAACCTGTTGGAA
CGACTCAAGGATGTCCCAAGTGATAAAGTCAAGTTAGTGGATGATATTCT
TGCCTTCTTAGCTCCGATTCGTCATCCAGAACGTTTAGGAAAACCAAATG
CGCAAATTACCTACACTGATGATGAGATTCAAGTAGCCAAGTTGGCAGGC
AAGTACACAACAGAAGACGGTTATATCTTTGATCCTCGTGATATAACCAG
TGATGAGGGGGATGCCTATGTAACTCCACATATGACCCATAGCCACTGGA
TTAAAAAAGATAGTTTGTCTGAAGCTGAGAGAGCGGCAGCCCAGGCTTAT
GCTAAAGAGAAAGGTTTGACCCCTCCTTCGACAGACCATCAGGATTCAGG
AAATACTGAGGCAAAAGGAGCAGAAGCTATCTACAACCGCGTGAAAGCAG
CTAAGAAGGTGCCACTTGATCGTATGCCTTACAATCTTCAATATACTGTA
GAAGTCAAAAACGGTAGTTTAATCATACCTCATTATGACCATTACAAA
CATCAAATTTGAGTGGTTTGACGAAGGCCTTTATGAGGCACCTAAGGGGT
ATACTCTTGAGGATCTTTTGGCGACTGTCAAGTACTATGTCGAACATCCA
AACGAACGTCCGCATTCAGATAATGGTTTTGGTAACGCTAGCGACCATGT
TCAAAGAAACAAAAATGGTCAAGCTGATACCAATCAAACGGAAAAACCAA
GCGAGGAGAAACCTCAGACAGAAAAACCTGAGGAAGAAACCCCTCGAGAA
GAGAAACCGCAAAGCGAGAAACCAGAGTCTCCAAAACCAACAGAGGAACC
AGAAGAATCACCAGAGGAATCAGAAGAACCTCAGGTCGAGACTGAAAAGG
TTGAAGAAAAACTGAGAGAGGCTGAAGATTTACTTGGAAAAATCCAGGAT
CCAATTATCAAGTCCAATGCCAAAGAGACTCTCACAGGATTAAAAAATAA
TTTACTATTTGGCACCCAGGACAACAATACTATTATGGCAGAAGCTGAAA
AACTATTGGCTTTATTAAAGGAGAGTAAGTAA (SEQ. ID. NO. 194)
MKINKKYLAGSVAVLALSVCSYELGRHQAGQDKKESNRVAYIDGDQAGQK
EANLTPDEVSKREGINAEQIVIKITDQGYVTSHGDHYHYYNGKVPYDAII
SEELLMKDPNYQLKDSDIVNEIKGGYVIKVDGKYYVYLKDAAHADNIRTK
EEIKRQKQERSHNHGSGANDHAVAAARAQGRYTTDDGTIFNASDIIEDTG
DAYIVPHGDHYHYIPKNELSASELAAAEAYWNGKQGSRPSSSSSYNANPA
QPRLSENWNTTVTPTYHQNQGENISSLLRELYAKPLSERJVESDGLIFDP
AOITSRTARGVAVPHGNHYHFIPYEQMSELEKRIARIIPLRYRSNHWVPD
SRPEQPSPQSTPEPSPSPQPAP4PQPAPSNPIDEKLVKEAVRKVGDGYVF
EENGVSRYIPAKDLSAETAAGIDSKLAKQESLSHKLGAKKTDLPSSDREF
YNKAYDLLARIHQDLLDNKGRQVDFEALDNLLERLKDVPSDKVKLVDDIL
AFLAPIRHPERLGKPNAQITYTDDEIQVAKLAGKYTTEDGYIFDPRDITS
DEGDAYVTPHMTHSHWIKKDSLSEAERAAAQAYAKEKGLTPPSTDHQDSG
NTEAKGAEIYNRNKAAKKVPLDRMPYNLQYTVEVKNGSLIIPHYDHYHNI
KFEWFDEGLYEAPKGYTLESLLATVKYYVEHPNERPHSDNGFGNASDHVQ
RNKNGQADTNQT3EKPSEEKPQTEKPEEETPREEKPQSEKPESPKPTEEP
EEPSPEESEEPQVETEKVEEKLREADEDLLGKIQDPIIKSNAKETLTGLK
NNLLFGTQDNNTIMAEAEKLLALLKESKZ

ID312

(SEQ. ID. NO. 307)
ATGGAGGGATTGGTTAGAGTGCATTTATTGCCTGTATTTGGCGATTACAA
GCTATCTAAACTTACTACGCCTATTCTTCAACAGCAAGTAAACAAATGGG
CTGACAAGGCAATAAAGGCGAAAAGGGGCATTTGCTAACTACTCTTTGC
TCCATAACATGAATAAGCGTATTTTGAAATATGGCGTAGCTATCCAGGTA
ATACAATACAACCCAGCTAATGATGTCATCGTTCCACGCAAACAGCAAAA
AGAAAAGGCTGCTGTCAAATACTTAGACAACAAAGAATTAAAACAGTTTC
TTGATTATTTAGATGCTCTGGATCAATCAAATTATGAGAACTTATTTGAT
GTTGTTCTGTATAAGACTTTATTGGCCACTGGTTGCCGTATTAGTGAGGC
TCTGGCTCTTGAATGGTCTGATATTGACCTAGAAAGCGGTGTTATCAGCA
TCAATAAGACACTAAACCGCTATCAGGAAATAAACTCACCTAAATCAAGC
GCTGGTTATCGTGATATACCAATAGACAAAGCCACATTACTTTTACTGAA
ACAATACAAAAACCGTCAACAATTCAGTCTTGGAATTAGGCCGATCTG
AAACAGTTGTATTCTCTGTATTTACGGAGAAATATGCTTATGCTTGTAAC
TTACGCAAACGCCTAAATAAGCATTTTGATGCTGCTGGAGTAACTAACGT
ATCATTTCATGGTTTCCGCCATACACATACTACTATGATGCTCTATGCTC
AGGTTAGCCCAAAAGATGTTCAGTATAGATTAGGCCACTCTAATTTAATG
ATCACTGAAAATACTTACTGGCATACTAACCAAGAGAATGCAAAAAAAGC
CGTCTCAAATTATGAAACAGCTATCAACAATTTATAA (SEQ. ID. NO. 195)
MEGLVRVHLLPVFGDYKLSKLTTPILQQQVNKWADKANKGEKGAFANYSL
LHNMNKRILKYGVAIQVIQYNPANDVIVPRKQQKEKAAVKYLDNKELKQF
LDYLDALDQSNYQNLFDVVLYKTLLATGCRISEALALEWSDIDLESGVIS
INKTLNRYQEINSPKSSAGYRDIPIDKATLLLLKQYKNRQQIQSWKLGRS
ETVVFSVFTEKYAYACNLRKRLNKHGDAAGVTVNSFHGFHTHTTMMLYAQ
VSPKDVQYRLGHSNLMITENTYWHTNQENAKKAVSNYETAINNLZ
```

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07713534B2). An electronic copy of the "Sequence Listing" will also be available from the USPTO upon request and payment of the fee set forth in 37 CFR 1.19(b)(3).

What is claimed is:

1. An isolated *Streptococcus pneumoniae* polypeptide comprising:
   (a) the amino acid sequence of SEQ ID NO: 194; or
   (b) the amino acid sequence at least 99% identical to SEQ ID NO: 194.

2. A fusion protein comprising
   (a) the amino acid sequence of SEQ ID NO: 194; or
   (b) the amino acid sequence at least 99% identical to SEQ ID NO: 194.

3. An immunogenic and/or antigenic composition comprising the polypeptide of claim 1 and one or more excipients, diluents, or adjuvants.

4. The composition of claim 3, wherein said composition is an antigenic composition.

5. The composition of claim 3, wherein said composition is an immunogenic composition.

* * * * *